United States Patent
Campana et al.

(10) Patent No.: US 11,709,164 B2
(45) Date of Patent: Jul. 25, 2023

(54) APPROACH FOR UNIVERSAL MONITORING OF MINIMAL RESIDUAL DISEASE IN ACUTE MYELOID LEUKEMIA

(71) Applicants: National University of Singapore, Singapore (SG); St. Jude Children's Research Hospital, Inc., Memphis, TN (US)

(72) Inventors: Dario Campana, Singapore (SG); Elaine Coustan-Smith, Singapore (SG)

(73) Assignees: National University of Singapore, Singapore (SG); St. Jude Children's Research Hospital, Inc., Memphis, TN (US)

( * ) Notice: Subject to any disclaimer, the term of this patent is extended or adjusted under 35 U.S.C. 154(b) by 388 days.

(21) Appl. No.: 16/757,137

(22) PCT Filed: Oct. 26, 2018

(86) PCT No.: PCT/US2018/057753
§ 371 (c)(1),
(2) Date: Apr. 17, 2020

(87) PCT Pub. No.: WO2019/084434
PCT Pub. Date: May 2, 2019

(65) Prior Publication Data
US 2020/0340995 A1    Oct. 29, 2020

Related U.S. Application Data

(60) Provisional application No. 62/577,673, filed on Oct. 26, 2017.

(51) Int. Cl.
*G01N 33/574*    (2006.01)

(52) U.S. Cl.
CPC . *G01N 33/57426* (2013.01); *G01N 2333/705* (2013.01)

(58) Field of Classification Search
CPC ............................................. G01N 33/57426
USPC ........................................................ 435/7.23
See application file for complete search history.

(56) References Cited

U.S. PATENT DOCUMENTS

| | | |
|---|---|---|
| 4,683,202 A | 7/1987 | Mullis |
| 4,843,155 A | 6/1989 | Chomczynski |
| 5,445,934 A | 8/1995 | Fodor et al. |
| 5,677,195 A | 10/1997 | Winkler et al. |
| 5,744,305 A | 4/1998 | Fodor et al. |
| 5,771,722 A | 6/1998 | DiVito et al. |
| 5,854,033 A | 12/1998 | Lizardi |
| 5,874,219 A | 2/1999 | Rava et al. |
| 9,833,466 B2 | 12/2017 | Jones et al. |
| 10,052,346 B2 | 8/2018 | Marcus |
| 10,137,130 B2 | 11/2018 | Amatangelo et al. |
| 2011/0015090 A1 | 1/2011 | Majeti et al. |
| 2014/0045843 A1 | 2/2014 | Schafer et al. |
| 2014/0274788 A1 | 9/2014 | Riken |
| 2014/0336942 A1 | 11/2014 | Pe Er et al. |
| 2017/0087190 A1 | 3/2017 | Walker et al. |
| 2017/0175197 A1 | 6/2017 | Gatalica et al. |

FOREIGN PATENT DOCUMENTS

WO    WO2011/068839 A1 *    6/2011

OTHER PUBLICATIONS

Araki et al., "Allogeneic Hematopoietic Cell Transplantation for Acute Myeloid Leukemia: Time to Move Toward a Minimal Residual Disease-Based Definition of Complete Remission?" Journal of Clin. Oncol., Feb. 1, 2016; 34(4); pp. 329-336.
Campana et al., "The Immunologic Detection of Minimal Residual Disease in Acute Leukemia," Blood, Jul. 1, 1990; 76(1); pp. 163-171.
Chung et al., "CD99 is a Therapeutic Target on Disease Stem Cells in Myeloid Malignancies," Sci. Transl. Med. 2017; 9; (374), pp. 1-27.
Cilloni et al., "Real-Time Quantitative Polymerase Chain Reaction Detection of Minimal Residual Disease by Standardized WT1 Assay to Enhance Risk Stratification in Acute Myeloid Leukemia: A European LeukemiaNet study," Journal of Clin. Oncol., Nov. 1, 2009; 27(31); pp. 5195-5201.
Corbacioglu et al., "Prognostic Impact of Minimal Residual Disease in CBFB-MYH11-Positive Acute Myeloid Leukemia," Journal of Clin. Oncol., Aug. 10, 2010; 28(23); pp. 3724-3729.
Coustan-Smith E., et al., "Clinical significance of residual disease during treatment in childhood acute myeloid leukaemia," British Journal of Haematol. 2003;123; pp. 243-252.
Coustan-Smith et al., "New markers for minimal residual disease detection in acute lymphoblastic leukemia," Blood, Apr. 12, 2011; 117(23); pp. 6267-6276.
Dohner et al., "Diagnosis and management of AML in adults: 2017 ELN recommendations from an international expert panel," Blood, Jan. 26, 2017; 129(4); pp. 424-447.
Falini et al., "Acute myeloid leukemia with mutated nucleophosmin (NPM1): is it a distinct entity?" Blood, 2010; 117(4); pp. 1109-1120.
Harrison et al., "Cytogenetics of Childhood Acute Myeloid Leukemia:United Kingdom Medical Research Council Treatment Trials AML 10 and 12," Journal of Clin. Oncol, Jun. 1, 2010; 28(16); pp. 2674-2681.
Hollink et al., "Favorable prognostic impact of NPM1 gene mutations in childhood acute myeloid leukemia, with emphasis on cytogenetically normal AML," Leukemia. 2009; 23(2); pp. 262-720.
Inaba et al., "Comparative Analysis of Different Approaches to Measure Treatment Response in Acute Myeloid Leukemia," Journal of Clin. Oncol, Oct. 10, 2012; 30(29); pp. 3625-3632.

(Continued)

*Primary Examiner* — Taofiq A Solola
(74) *Attorney, Agent, or Firm* — Hamilton, Brook, Smith & Reynolds, P.C.

(57) ABSTRACT

Methods for detecting the presence of proteins in a subject are described. The proteins detected can be indicative of acute myeloid leukemia (AML). The proteins can be particularly useful for monitoring minimal residual disease (MRD) in AML.

20 Claims, 22 Drawing Sheets

(56) References Cited

OTHER PUBLICATIONS

Inoue et al., "Long-Term Follow-Up of Minimal Residual Disease in Leukemia Patients by Monitoring WT1 (Wilms Tumor Gene) Expression Levels," Blood, 1996; 88(6); pp. 2267-2278.
Ivey et al., "Assessment of Minimal Residual Disease in Standard-Risk AML," The New England Journal of Medicine, 2016; 374(5); pp. 422-433.
Jin et al., "Monoclonal Antibody-Mediated Targeting of CD123, IL-3 Receptor α Chain, Eliminates Human Acute Myeloid Leukemic Stem Cells," Cell Stem Cell, 2009; 5(1); pp. 31-42.
Kayser et al., "Minimal residual disease-directed therapy in acute myeloid leukemia," Blood, 2015; 125(15); pp. 2331-2335.
Kikushige et al., "TIM-3 is a Promising Target to Selectively Kill Acute Myeloid Leukemia Stem Cells," Cell Stem Cell, 2010; 7(6); pp. 708-717.
Kronke et al., "Monitoring of Minimal Residual Disease in NPM1-Mutated Acute Myeloid Leukemia: A Study From the German-Austrian Acute Myeloid Leukemia Study Group," Journal of Clin. Oncol., 2011; 29(19); pp. 2709-2716.
Langebrake et al., "Residual Disease Monitoring in Childhood Acute Myeloid Leukemia by Multiparameter Flow Cytometry: The MRD-AML-BFM Study Group," Journal of Clin. Oncol., 2006; 24(22); pp. 3686-3692.
Levis, "FLT3 mutations in acute myeloid leukemia: what is the best approach in 2013?" Hematology 2013; 2013; pp. 220-226.
Majeti et al., "CD47 Is an Adverse Prognostic Factor and Therapeutic Antibody Target on Human Acute Myeloid Leukemia Stem Cells," Cell, 2009; 138(2); pp. 286-299.
Mardiros et al., "T cells expressing CD123 chimeric antigen receptors for treatment of acute myeloid leukemia," Curr. Opin. Hematol., 2015; 22(6); pp. 484-488.
Maurillo, et al., "Toward Optimization of Postremission Therapy for Residual Disease-Positive Patients With Acute Myeloid Leukemia," Journal of Clin. Oncol., 2008; 26(30); pp. 4944-4951.
Mirkowska et al., "Leukemia surfaceome analysis reveals new disease-associated features," Blood, 2013; 121(25); pp. 149-159.
PCT International Preliminary Report on Patentability and Written Opinion for International Application No. PCT/US2018/057753 entitled "A New Approach For Universal Monitoring Of Minimal Residual Disease In Acute Myeloid Leukemia," dated May 7, 2020.
PCT International Search Report and Written Opinion for International Application No. PCT/US2018/057753 entitled "A New Approach For Universal Monitoring Of Minimal Residual Disease In Acute Myeloid Leukemia," dated Feb. 14, 2019.
Rubnitz et al., "Minimal Residual Disease-Directed Therapy for Childhood Acute Myeloid Leukemia: Results of the AML02 Multicenter Trial," Lancet Oncol., Jun. 2010; 11(6); pp. 543-552.
Rubnitz et al., "Childhood acute myeloid leukaemia,". British Journal of Haematol., 2012 (159); pp. 259-276.
Saito et al., "Identification of Therapeutic Targets for Quiescent, Chemotherapy-Resistant Human Leukemia Stem Cells," Sci Transl Med., 2010; 2(17); pp. 1-22.
San Miguel et al., "Early immunophenotypical evaluation of minimal residual disease in acute myeloid leukemia identifies different patient risk groups and may contribute to postinduction treatment stratification," Blood, Sep. 15, 2001; 98(6); pp. 1746-1751.
Schnittger et al., "Minimal residual disease levels assessed by NPM1 mutation-specific RQ-PCR provide important prognostic information in AML," Blood, Sep. 10, 2009; 114(11) pp. 2220-2231.
Taub et al., "Improved outcomes for myeloid leukemia of Down syndrome: a report from the Children's Oncology Group AAML0431 trial," Blood, Jun. 22, 2017; 129(25) pp. 3304-3313.
Terstappen et al., "Flow Cytometric Characterization of Acute Myeloid Leukemia. Part II. Phenotypic Heterogeneity at Diagnosis," Leukemia, 1991; 6(1); pp. 757-767.
Terwijn et al., "High prognostic impact of flow cytometric minimal residual disease detection in acute myeloid leukemia: data from the HOVON/SAKK AML 42A study," Journal of Clin. Oncol., 2013; 31(31); pp. 3889-3897.
Van der Maaten et al.,"Visualizing Data Using t-SNE," Journal of Machine Learning Research, 2008; 9; pp. 2579-2605.
Van Rhenen et al., "The novel AML stem cell associated antigen CLL-1 aids in discrimination between normal and leukemic stem cells," Blood, Oct. 1, 2007; 110(7); pp. 2659-2666.
Venditti et al,. "Level of minimal residual disease after consolidation therapy predicts outcome in acute myeloid leukemia," Blood, Dec. 1, 2000; 96(12); pp. 3948-3952.
Walter et al., "Significance of minimal residual disease before myeloablative allogeneic hematopoietic cell transplantation for AML in first and second complete remission," Blood, Sep. 5, 2013; 122(10); pp. 1813-1821.
Walter, et al., "Impact of Pretransplantation Minimal Residual Disease, As Detected by Multiparametric Flow Cytometry, on Outcome of Myeloablative Hematopoietic Cell Transplantation for Acute Myeloid Leukemia,". Journal of Clin. Oncol., Mar. 20, 2011; 29(9); pp. 1190-1197.
Yin et al., "Minimal Residual Disease monitoring by RT-qPCR in Core-Binding Factor AML Allows Risk-Stratification and Predicts Relapse: Results of the United Kingdom MRC AML-15 trial," Blood, 2012; 120(14); pp. 2826-2835.
Zeijlemaker et al., "A simple one-tube assay for immunophenotypical quantification of leukemic stem cells in acute myeloid leukemia," Leukemia, Oct. 6, 2015; pp. 1-8.

\* cited by examiner

APPROACH FOR UNIVERSAL MONITORING OF MINIMAL RESIDUAL DISEASE IN ACUTE MYELOID LEUKEMIA

RELATED APPLICATION

This application is the U.S. National Stage of International Application No. PCT/US2018/057753, filed Oct. 26, 2018, which designates the U.S., published in English, and claims the benefit of U.S. Provisional Application No. 62/577,673, filed Oct. 26, 2017. The entire teachings of the above applications are incorporated herein by reference.

GOVERNMENT SUPPORT

This invention was made with government support under Grant Nos CA060419 and CA021765 awarded by the National Institutes of Health. The government has certain rights in the invention.

BACKGROUND

In most patients with acute myeloid leukemia (AML) receiving chemotherapy, leukemic cells initially become undetectable. Nevertheless, leukemia may subsequently relapse due to persisting chemo-resistant cells indistinguishable from normal hematopoietic progenitors by conventional morphologic analysis, i.e., minimal residual disease (MRD). In both childhood and adult AML, MRD is a powerful and independent prognostic factor. Despite compelling evidence supporting its clinical importance, MRD assays in AML have remained largely unchanged over the last decade.

MRD can be measured by either polymerase chain reaction (PCR) amplification of genetic abnormalities or flow cytometric detection of leukemia-associated cell marker profiles. In about 20% adult and 35% of pediatric AML cases, cells carry gene fusions, such as RUNX1-RUNX1T1, CBFB-MYH11, or MLL fusion transcripts; NPM1 mutations occur in about 30% of adult and <10% of pediatric cases. Detection of these molecular abnormalities during treatment correlates with relapse. Flow cytometric monitoring of MRD is also prognostically informative and, unlike PCR, is not limited to patients with specific genetic abnormalities. Nevertheless, standard flow cytometric monitoring of MRD has a sensitivity often not exceeding 0.1% (1 leukemic cell in 1,000 normal bone marrow cells), it requires considerable expertise to avoid unreliable results, and is still not applicable to all patients. The capacity of contemporary flow cytometers to detect 8 or more markers simultaneously can increase the discriminating power of MRD analysis. This potential, however, can be fulfilled only if sufficient leukemia-specific markers are available. Thus, the discovery of new markers differentially expressed in leukemic versus normal myeloid cells should increase applicability, sensitivity, and reliability of MRD monitoring by flow cytometry. In turn, this could widen the implementation of response-guided protocols in AML.

SUMMARY

Described herein are methods of detecting the quantity of one or more of proteins in a sample from a patient. The proteins quantified can include one or more of CD9, CD32, CD44, CD52, CD54, CD59, CD64, CD68, CD86, CD93, CD96, CD97, CD99, CD123, CX3CR1 and Tim-3. The method can further include detecting the quantity of one or more of CD18, CD25, CD47, CD200, CLEC12A and CD300a. As described herein, these proteins can be indicative of acute myeloid leukemia (AML), and are particularly useful for monitoring minimal residual disease (MRD) in AML.

Described herein are methods of detecting an expression level of a plurality of protein markers in a subject. The methods can include contacting a sample from the subject with a plurality of probes and detecting a complex formed between each probe and corresponding marker. A value is generated corresponding to an expression level of each of the markers. Described herein are methods of diagnosing acute myeloid leukemia, which can further involve diagnosing whether the subject has acute myeloid leukemia based on the generated values corresponding to the expression level of the markers. Also described are methods of treating acute myeloid leukemia, which can further involve administering to the subject diagnosed with acute myeloid leukemia an effective amount of a therapy for treating acute myeloid leukemia.

Each probe specifically binds to a single marker.

In some embodiments, the the markers are two or more of CD9, CD18, CD25, CD32, CD44, CD47, CD52, CD54, CD59, CD64, CD68, CD86, CD93, CD96, CD97, CD99, CD123, CD200, CD300a, CLEC12A, CX3CR1, and Tim-3. In some embodiments, the markers are two or more of CD9, CD32, CD44, CD52, CD54, CD59, CD64, CD68, CD86, CD93, CD96, CD97, CD99, CD123, CX3CR1, and Tim-3. In some embodiments, the markers are CD54, CD18, CD96, CD97, and CD99. In some embodiments, the markers are CD44, CD54, CD18, CD96, CD97 and CD99.

In some embodiments, the plurality of probes is a first set of probes that specifically bind to: a) CD52; b) CD59, CD96, or CD300a; c) TIM3; d) CD200; and e) CD123. There can be a second set of probes that specifically bind to: a) CD34; b) CD117; c) CD33; and d) CD45.

In some embodiments, the plurality of probes is a first set of probes that specifically bind to: a) CD9; b) CD93, CD99, or CLEC12A; c) CD44; d) CD32; and e) CD25. There can be a second set of probes that specifically bind to: a) CD34; b) CD117; c) CD33; and d) CD45.

In some embodiments, the plurality of probes is a first set of probes that specifically bind to: a) CD97; b) CD54, CD68, or CXCR1; c) CD64; d) CD86; and e) CD47. There can be a second set of probes that specifically bind to: a) CD34; b) CD117; c) CD33; and d) CD45.

In some embodiments, the plurality of probes is a first set of probes that specifically bind to: a) CD54; b) CD18; c) CD96; d) CD97; and e) CD99. There can be a second set of probes that specifically bind to: a) CD34; b) CD117; c) CD33; and d) CD45.

In some embodiments, the plurality of probes is a first set of probes that specifically bind to: a) CD44; b) CD54; c) CD18; d) CD96; and e) CD97 and CD99. There can be a second set of probes that specifically bind to: a) CD34; b) CD117; c) CD33; and d) CD45.

Also described herein is a method of detecting an expression level of a plurality of markers in a subject. The method can include contacting a sample from the subject with a first set of one or more probes and with a second set of one or probes, and detecting a complex formed between each probe and corresponding marker. A value is generated corresponding to an expression level of each of the markers.

In some embodiments, each probe of the first set of one or more probes specifically binds to a single marker. The markers to which the first set of probes binds are selected from the group consisting of CD9, CD18, CD25, CD32, CD44, CD47, CD52, CD54, CD59, CD64, CD68, CD86, CD93, CD96, CD97, CD99, CD123, CD200, CD300a, CLEC12A, CX3CR1, and Tim-3. Each probe of the second set of one or more probes specifically binds to a single marker. The markers to which the second set of probes binds are selected from the group consisting of CD45, CD34, CD33, and CD117.

In some embodiments, each probe of the first set of one or more probes specifically binds to a single marker. The markers to which the first set of probes binds are selected from the group consisting of CD9, CD18, CD25, CD32, CD44, CD47, CD52, CD54, CD59, CD64, CD68, CD86, CD93, CD96, CD97, CD99, CD123, CD200, CD300a, CLEC12A, CX3CR1, and Tim-3. Each probe of the second set of one or more probes specifically binds to a single marker. The markers to which the second set of probes binds are selected from the group consisting of CD34, CD13 and CD33.

In some embodiment, the first set of probes includes probes that specifically bind to: a) CD52; b) CD59, CD96, or CD300a; c) TIM3; d) CD200; and e) CD123. The second set of probes specifically bind to: a) CD34; b) CD117; c) CD33; and d) CD45.

In some embodiments, the first set of probes includes probes that specifically bind to: a) CD9; b) CD93, CD99, or CLEC12A; c) CD44; d) CD32; and e) CD25. The second set of probes includes probes that specifically bind to: a) CD34; b) CD117; c) CD33; and d) CD45.

In some embodiments, the first set of probes includes probes that specifically bind to: a) CD97; b) CD54, CD68, or CXCR1; c) CD64; d) CD86; and e) CD47. The second set of probes includes probes that specifically bind to: a) CD34; b) CD117; c) CD33; and d) CD45.

In some embodiments, the first set of probes includes probes that specifically bind to: a) CD54; b) CD18; c) CD96; d) CD97; and e) CD99. The second set of probes includes probes that specifically bind to: a) CD34; b) CD117; c) CD33; and d) CD45.

In some embodiments, the first set of probes includes probes that specifically bind to: a) CD44; b) CD54; c) CD18; d) CD96; and e) CD97 and CD99. The second set of probes specifically bind to: a) CD34; b) CD117; c) CD33; and d) CD45.

Also described are kits for detecting an expression level of a plurality of markers in a subject. The kits can include a plurality of probes. The plurality of probes can be according to any of the embodiments described herein.

Also described herein are devices for monitoring expression levels of a plurality of markers in a subject. The device can include an input member that receives digital representations of a subject sample. The digital representations can include flow cytometry outputs corresponding to a plurality of markers. The device can also include a processor engine coupled to receive from the input member the digital representations. The processor engine can be responsive to the digital representations and determine parameter values corresponding to an expression level of a marker in the subject sample. The device can also include a graphics memory module communicatively coupled to the processor engine and transforming the determined parameter values into a graphical representation indicative of expression levels of the plurality of markers in the subject. The device can also include a display monitor coupled to the graphics memory module rendering the graphical representation as generated by the graphics memory module. The processor engine can apply a t-Distributed Stochastic Neighbor Embedding (tSNE) machine learning algorithm to determine the parameter values in a manner enabling generation of the graphical representation.

Also described herein are processor-based methods for monitoring acute myeloid leukemia. The method can include receiving by a digital processor flow cytometry output representative of a plurality of markers of a subject sample. The method can also include, in the processor, in response to the flow cytometry output, determining parameter values corresponding to an expression level of a marker in the subject sample, and transforming the parameter values into a graphical representation. The method can also include outputting the graphical representation to a graphics memory module. The method can also include rendering on a display monitor the graphical representation by the graphics memory module. Determining parameter values can include applying a t-Distributed Stochastic Neighbor Embedding (tSNE) machine learning algorithm to transform the values corresponding to an expression level of a marker into a graphical representation.

In any of the embodiments described, one or more of the probes can be an antibody that specifically binds to a single marker. In any of the embodiments described, contacting the sample from the subject with a plurality of probes can include subjecting the sample to flow cytometry. In any of the embodiments described, the value generated can be fluorescence intensity. In any of the embodiments described, the value generated can be mean fluorescence intensity or median fluorescence intensity. In any of the embodiments described, the method can further include contacting the sample with an agent that permeabilizes a cell membrane prior to contacting the sample from the subject with a plurality of probes. In any of the embodiments described, the sample can include one or more of blood cells, bone marrow, and cellular products derived from blood cells or bone marrow cells. In any of the embodiments described, the sample can be a bone marrow sample. In any of the embodiments described, the subject can have been diagnosed previously with acute myeloid leukemia. In any of the embodiments described, the acute myeloid leukemia can be minimal residual disease in acute myeloid leukemia. In any of the embodiments described, the method can further include contacting the sample with one or more probes that specifically detect one or more genes of Table 2 or Table 3.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 3A is a chart showing expression of the new markers in paired samples collected at diagnosis ("D") and at relapse ("R"). Bars indicate the number of paired samples studied for each marker; gray bars denote samples with aberrant marker expression at both diagnosis and relapse, white bars samples in which the aberrantly expressed marker was present only at relapse, and black bars samples in which the aberrantly expressed marker at diagnosis was not detectable at relapse. FIG. 3B is a plot showing expression of new markers in AML blasts with the CD34+CD38 dim/neg immunophenotype ("leukemia stem cells"), in comparison with the more mature CD38 bright cell population. Each symbol is the percent median fluorescence intensity (MFI) of a new marker in the "stem cells" relative to that of the more mature AML cells in the same sample. Horizontal bar correspond to the median value; n=60). Data for individual markers/samples shown in FIG. 8. FIG. 3C is a set of flow cytometric histograms illustrate expression of selected marker on CD38 dim/neg (upper line) and CD38 bright AML cells (lower line).

FIG. 4A is a graph showing relation between MRD levels measured using the new markers versus those measured with standard markers (see Table 7). Spearman regression analysis of positive MRD results by both methods: r=0.9816, P<0.0001. FIG. 4B is a set of graphs showing median fluorescence intensity (MFI) of the indicated markers measured at diagnosis ("D") and during chemotherapy ("MRD"). Horizontal bars correspond to the median value in each group. Gray areas include MFI of normal CD34+ myeloid progenitors (CD13+ and/or CD33+).

FIG. 6A is a chart showing percentage of consecutive diagnostic (n=118) or relapse (n=11) AML samples with aberrant expression of the indicated markers. FIG. 6B is a chart showing sensitivity of MRD detection afforded by the new markers in comparison to standard MRD assays (see Table 7) in the 129 cases studied.

FIG. 6C is a set of graphs showing t-SNE analysis of the cell profile of normal bone marrow (NBM) CD34+CD33+ CD117+ mononucleated cells from 10 donors (shown in grey) containing various proportions of AML cells (shown in red). The histograms on the right show expression of the individual markers on the leukemia cell cluster (red) compared to the remaining cells (grey).

DETAILED DESCRIPTION

Figure 1:
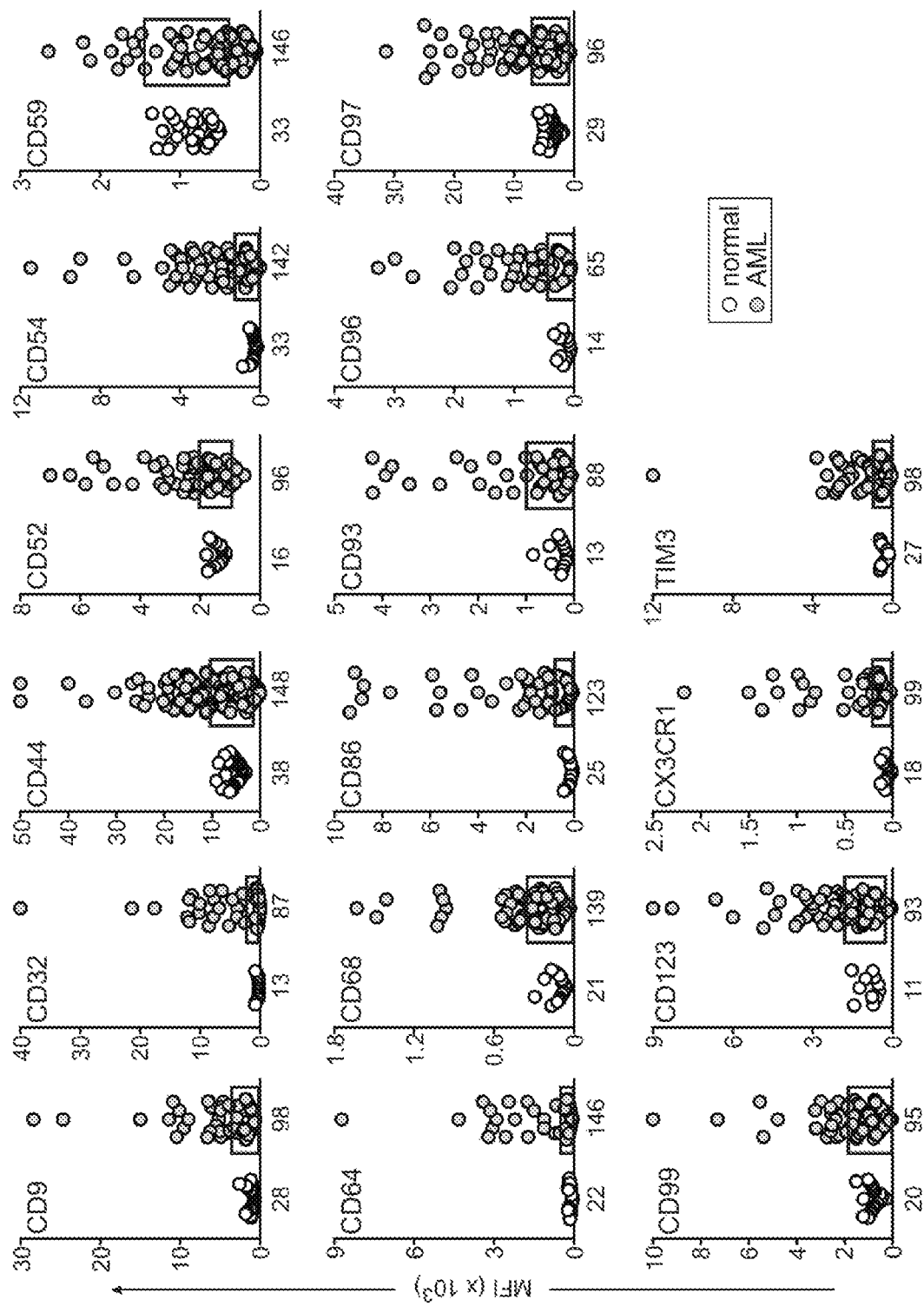
FIG. 1 is a set of graphs showing genes significantly over- and/or under-expressed in AML cells at the protein level as determined by flow cytometry. Plots indicate mean fluorescence intensity (MFI) of each marker in CD34+ cells expressing CD13 and/or CD33 from bone marrow aspirates of healthy donors or patients with ALL (white circles), and in diagnostic AML samples (gray circles). The box on the AML plots indicates the upper and lower normal limits. The number of samples studied is indicated under each plot. By unpaired t-test with Welch's correction, $P<0.0001$ for CD9, CD44, CD54, CD59, CD64, CD68, CD86, CD96, CD97, CD99, CD123, and CX3CR1; $P<0.001$ for CD32 and TIM3; $P<0.01$ for CD52 and CD93.

A description of example embodiments follows.

Optimal management of acute myeloid leukemia (AML) requires accurate monitoring of treatment response, but minimal residual disease (MRD) may escape detection. This study contrasts the genome-wide gene expression profiles of AML cells to those of their normal counterparts. The aberrant expression of selected genes was validated by flow cytometry, by analyzing their expression in large sets of normal and leukemic specimens. The findings led to the formulation of new marker panels and analytical algorithms for highly sensitive, clearly evident and universal monitoring of MRD in AML.

To identify distinctive features of AML cells for MRD monitoring, described herein is a comparison of genome-wide gene expression of leukemic myeloblasts from 157 patients with AML to that of $CD34^+$ myeloblasts from healthy donors. Aberrantly expressed genes, including some previously associated with "leukemia stem-cells", were studied by flow cytometry in 191 AML and 63 leukemia-free bone marrow samples. Sixteen (CD9, CD32, CD44, CD52, CD54, CD59, CD64, CD68, CD86, CD93, CD96, CD97, CD99, CD123, CX3CR1, and Tim-3) were significantly over- or under-expressed in AML, in agreement with gene array results. Six other markers (CD18, CD25, CD47, CD200, CD300a, and CLEC12A) were expressed at markedly abnormal levels in some AML cases. These 22 markers defined leukemia-associated profiles extending to cells with stem-cell phenotype; markers remained stable during treatment, and at relapse. In 208 samples from 52 patients undergoing chemotherapy, the new markers yielded MRD measurements matching those of standard methods (Spearman r=0.9816, P<0.0001), and also revealed MRD that was otherwise undetectable. Finally, the 22 new markers allowed MRD monitoring in 129 consecutive AML patients; using a machine learning algorithm to reduce the high-dimensional datasets to 2-dimensional data, 1 leukemic cell among more than 100,000 normal cells could be clearly visualized. This new approach to MRD studies should refine treatment of AML, and provide new eligibility and response criteria for studies of novel agents.

Acute Myeloid Leukemia (AML)

"Diagnosing acute myeloid leukemia (AML)" and/or "detecting minimal residual disease (MRD)" or "diagnosing minimal residual disease (MRD)" is intended to include, for example, diagnosing or detecting the presence of acute myeloid leukemia (AML) by identifying or detecting cells and/or cell products in samples or specimens that are indicative of AML, monitoring the progression of the disease, monitoring and/or detecting the recurrence of AML disease in patients who had been previously treated for AML, and monitoring and/or detecting minimal residual disease. The terms "diagnosing," "detecting," and "identifying" when used with acute myeloid leukemia or minimal residual disease (MRD) are used interchangeably herein to refer to the identifying or detecting cells and/or cell products in specimens that are indicative of disease.

One method disclosed herein is directed to monitoring remission of leukemia. Remission is defined as the absence of outward signs of cancer, or in the case of AML, the absence of detectable cancer cells in the body after a course of therapy. Remission in AML can be characterized, for example, as a lack of detectable abnormal cells in the blood, and/or cerebrospinal fluid, and less than 5% blast cells in the bone marrow. Embodiments seek to detect cancer cells in instances where there is a relatively minimal amount of disease (minimal residual disease (MDR)) by phenotypic analysis. Standard detection methods define minimal residual disease as an incidence of less than one leukemic cell in 10,000 normal bone marrow/blood cells. In some embodiments, the methods and compositions described herein can detect minimal residual disease with an incidence of less than one in 100,000 cells.

Most AML patients achieve at least an initial remission. However, some patients have residual leukemic cells in their marrow. Other patients achieve remission then "relapse" wherein they have a decrease in normal blood cells and a return of leukemia cells in the marrow. Embodiments can detect leukemia and can help evaluate the risk for relapse after initial treatment. In addition to the detection of evidence of minimal residual disease, embodiments can further help to evaluate treatment regimens. For example, the detection and characterization of MRD can be indicative of the efficacy of certain treatment regimes, e.g., stem cell transplant.

In other embodiments, detection or diagnosing MRD can help determine whether additional treatment may be necessary. One of skill in the art will recognize that in these methods the term "therapy" can include any therapy for treating AML, including but not limited to chemotherapy, radiation therapy, stem cell transplantation, and biological therapy (e.g., tyrosine kinase inhibitor therapy, monoclonal antibody therapy). Depending on the subtype, specific drugs or drug combinations, drug dosages, duration of treatment, and other types of treatment, may be indicated to achieve optimal results.

In still other embodiments, methods for evaluating the efficacy of a therapy for treating AML in a subject are provided. Embodiments can also be used to test specimens taken from a subject during the course of therapy to monitor the effects of treatment. Such methods typically comprise comparing the level of expression of a plurality of markers in a first specimen procured prior to the initiation of therapy with that from a second sample obtained following administration of at least a portion of the therapy. In some embodiments, a significantly lower and/or an undetectable level of expression of a marker in the second specimen relative to that of the first specimen obtained prior to the initiation of the therapy can be a positive indication of the efficacy of the therapy. In other embodiments, a significantly higher level of expression of a marker in the second sample can be a negative indication of the efficacy of the therapy. A positive indication of the efficacy of the therapy can mean that the therapy is producing beneficial results in the treatment of AML and no minimal residual disease is detected.

A negative indication of the efficacy of the therapy can mean that the therapy is not having beneficial effects with respect to treatment of AML, and minimal residual disease is detected.

Samples from Subjects

In embodiments, the method comprises obtaining a "specimen" from a subject. The term "specimen" is intended to include blood cells, bone marrow cells, and cellular products that are derived from blood and bone marrow cells. Cellular products can include, but are not limited to, expressed proteins, expressed RNA, and DNA. In embodiments, a specimen can include cells derived from a variety of sources including, but not limited to, single cells, a collection of cells, tissue, cell culture, bone marrow, blood, or other bodily fluids. A tissue or cell source may include a tissue biopsy sample, a cell sorted population, cell culture, or a single cell. Sources for the specimen include cells from peripheral blood or bone marrow, such as blast cells from peripheral blood or bone marrow. The term "specimen" can be used interchangeably with the term "sample" or "patient sample."

A specimen may be processed in another embodiment to release or otherwise make available a nucleic acid or a protein for detection as described herein. Such processing may include, in one embodiment, steps of nucleic acid manipulation, e.g., preparing a cDNA by reverse transcription of RNA from the specimen. Thus, the nucleic acid to be amplified in one embodiment by the methods described herein may be DNA or RNA. Isolation of protein, RNA, and DNA from the aforementioned sources is known to those of skill in the art, and is discussed herein.

In one embodiment, the method comprises obtaining a peripheral blood sample from a subject and analyzing the expression level of specific markers in leukocytes from the blood sample taken from the subject. To do blood tests, blood samples are generally taken from a vein in the subject's arm.

In another embodiment, the method comprises obtaining a bone marrow sample from a subject and analyzing the expression level of specific markers combinations in leukocytes from the blood sample taken from the subject. Specimens of marrow cells are obtained by bone marrow aspiration and biopsy.

The obtaining of a specimen uses methods well known in the art, as is the means to analyze leukocyte populations. For example, leukocyte populations can be prepared from whole blood by differential centrifugation, or for example, by density gradient centrifugation. The method can be conducted on leukocytes in blood samples which have not undergone any leukocyte enrichment, on whole blood samples, or where red blood cells have been lysed. In other embodiments the method can be conducted on enriched and purified subpopulations of cells, using methods well known in the art.

Analyzing Samples

In embodiments, the method comprises "contacting" the specimen with a plurality of probes. In one embodiment, the term "contacting" is in reference to probes that are antibodies and generally referring to methods of "cell staining." In an embodiment, an antibody is added to a specimen and the antibody recognizes and binds to a specific protein for example, on the surface of cells in the specimen. A complex is thereby formed between the probe and the expressed protein. The complex can be detected and visualized by various techniques, as will be discussed herein. Combinations of antibody probes can be collectively added to a specimen and thereby "stain" the cell for later analysis by visualization with a flow cytometer or microscope, for example. One of skill in the art could determine whether a cell expressed a specific protein based on the level of antibody that bound to the cell using standard methods.

In embodiments, the term "contacting" in reference to probes that are nucleic acids, refers to methods of detecting expression of an mRNA of interest in a specimen. A detectable complex can be formed when a nucleic acid probe specific to an expressed gene of interest hybridizes and binds an mRNA/cDNA expressed by cells in a specimen. One of skill in the art could determine whether a cell expressed a specific mRNA based on the level of detectable PCR product, for example, using standard methods.

Detecting Expression of Markers for Minimal Residual Disease

As used herein a "marker" can be any gene or protein whose level of expression in a tissue or cell is used comparatively to evaluate the level of expression to that of a normal or healthy cell or tissue. In particular embodiments, antibodies are used to detect marker expression at the protein level. In other aspects, marker expression is detected at the nucleic acid level.

Markers may be referred to herein interchangeably as "markers," "immunophenotypic markers," "leukemia-associated phenotypic markers," "phenotypic markers," or "cell markers." "Leukemia-associated markers" can refer to particular combinations of markers used to diagnosis a particular leukemia, for example, an expression profile of different combinations of markers may be particular to a patient with AML. In particular embodiments, markers can refer to "antigenic markers," "antigens," or "cell surface antigens," referring to proteins that are expressed on the cell surface. Combinations of markers are selective for AML, and specifically minimal residual disease.

The various markers employed in the methods and compositions disclosed herein, can have a modulated level of expression when compared to an appropriate control. Alternatively, a given marker need not show a modulated level of expression, but rather must only be expressed in the given sample. Specific expression profiles of the given marker combinations that are predictive of the various states disclosed herein are discussed in further detail elsewhere herein.

As used herein, a "modulated level" of a marker can comprise any statistically significant increase (overexpression) or decrease (underexpression) of the given marker when compared to an appropriate control. The modulated level can be assayed by monitoring either the concentration of and/or activity of the marker polypeptide and/or the level of the mRNA encoding the marker polypeptide. In general, a modulated level of marker can include either an increase or a decrease of at least 1%, 5%, 10%, 20%, 30%, 40%, 50%, 60%, 70%, 80%, 90% or higher relative to an appropriate control.

By "overexpressed" it is intended that the marker of interest is overexpressed in AML cells but is not overexpressed in conditions classified as nonmalignant, benign, and/or any conditions that are not considered to be indicative of clinical disease. In general, an overexpressed marker can include any statistically significant increase in expression when compared to an appropriate control, including for example, an increase of at least 1%, 5%, 10%, 20%, 30%, 40%, 50%, 60%, 70%, 80%, 90% or higher relative to an appropriate control.

By "underexpressed" it is intended that the marker of interest is underexpressed in AML cells but is not underexpressed in conditions classified as nonmalignant, benign, and/or any conditions that are not considered to be indicative of clinical disease. Thus, detection of various combinations of markers permit the differentiation of specimens indicative of an increased likelihood of minimal residual disease associated with AML as compared to those of normal control specimens that are indicative of nonmalignant and benign proliferation.

The level of expression of a particular marker that is sufficient to constitute "overexpression" will vary depending on the specific marker used. In particular embodiments, a "threshold level" of expression over a normal control is established for a particular marker, wherein expression levels above this value are deemed overexpression. Overexpression of a particular marker can refer to an increase in the percentage of a population detected as expressing a particular marker or marker combination. Overexpression can also refer to the level of expression on a population of cells as detected by an increase in the mean fluorescence intensity (MFI), though median fluorescence intensity can also be detected. For example, in one embodiment, "overexpression" may be determined if the marker MFI for the specimen is at least three-fold above the normal control, wherein a three-fold increase in MFI is the "threshold level." In other embodiments, an overexpressed marker can include any statistically significant decrease in expression when compared to an appropriate control, including for example, an increase of at least 1%, 5%, 10%, 20%, 30%, 40%, 50%, 60%, 70%, 80%, 90% or higher relative to an appropriate control or at least a 1 fold, 2 fold, 3 fold, 4 fold, 5 fold, 6 fold, 10 fold or higher expression level relative to an appropriate control.

The level of expression of a particular marker that is sufficient to constitute "underexpression" will vary depending on the specific marker used. In particular embodiments, a "threshold level" of expression is established for a particular marker, wherein expression levels below this value are deemed underexpression. Underexpression of a particular marker can refer to a decrease in the percentage of a population detected as expressing a particular marker or marker combination. Underexpression can also refer to the level of expression on a population of cells as detected by a decrease in the mean fluorescence intensity (MFI), though median fluorescence intensity can also be detected. For example, in one embodiment, "underexpression" may be determined for that particular marker if the marker MFI for the specimen is less than the normal control by at least half, wherein a 50% reduction MFI is the "threshold level". In other embodiments, an underexpressed marker can include any statistically significant decrease in expression when compared to an appropriate control, including for example, a decrease of at least 1%, 5%, 10%, 20%, 30%, 40%, 50%, 60%, 70%, 80%, 90% or lower relative to an appropriate control or at least a 1 fold, 2 fold, 3 fold, 4 fold, 5 fold, 6 fold, 10 fold or lower expression level relative to an appropriate control.

The methods described herein comprise diagnosing minimal residual disease in a sample taken from a subject by detecting the expression of a plurality of markers that are modulated in AML.

The methods described herein can comprise MRD detection by flow cytometry with preferred combinations of probes to specific markers. MRD detection can be combined with at least 4 different probes, and can include in some embodiments at least 5, 6, 7, 8, 9, 10, 11, and 12 different probes. When incorporated with at least 6-probes, the new marker combinations afford the detection of one leukemic cell amongst $10^5$ bone marrow cells.

Probes to Detect Markers of Minimal Residual Disease (MRD)

The term "probe" refers to any molecule that is capable of specifically binding to an intended target molecule, for example, a nucleotide transcript or a protein encoded by a marker gene. RNA/DNA probes can be synthesized by one of skill in the art, or derived from appropriate biological preparations. Likewise, antibody probes to specific targets can be generated by one of skill in the art, or derived from appropriate sources. Probes may be specifically designed to be labeled. Examples of molecules that can be utilized as probes include, but are not limited to, RNA, DNA, proteins, antibodies, and organic molecules.

By "specifically binds," it is generally meant that an antibody binds to an epitope via its antigen binding domain, and that the binding entails some complementarity between the antigen binding domain and the epitope. An epitope is a site on an antigen or marker where the antibody binds via its variable region. The epitope is therefore a part of the antigen or marker, but the epitope is only a portion of the marker recognized by the antibody. According to this definition, an antibody is said to "specifically bind" to an epitope or have "antigen specificity" when it binds to that epitope, via its antigen binding domain more readily than it would bind to a random, unrelated epitope. As used herein, therefore, "specifically binds" is used interchangeably with recognition of a defined epitope on an antigen or marker, or any epitope contained in the antigen or marker. For example, the term "specifically binds" when used in conjunction with a particular antibody is used to indicate that there is recognition of a certain epitope of the antigen and the interaction between the antibody and epitope is a non-random interaction indicative of the presence or "expression" of the certain epitope. The term "specifically binds" when used in conjunction with a particular marker is used to indicate that there is recognition of a certain antigen or marker and the interaction between the antibody and antigen or marker is a non-random interaction indicative of the presence or "expression" of the certain antigen or marker.

Embodiments include methods and kits comprising probes to detect markers and combinations of markers in Table 5 comprising genes overexpressed or underexpressed in AML.

Generating Expression Profiles

As used herein, an "expression profile" comprises one or more values corresponding to a measurement of the relative abundance of a gene expression product (e.g, a marker). Such values may include measurements of RNA levels or protein abundance. Thus, an expression profile can comprise values representing the measurement of the transcriptional state or the translational state of the gene. As is known to those of skill in the art, the transcriptional state and translational state are related.

In embodiments, an "expression profile" of a specimen can include the identities and relative abundance, or "expression level," of the RNA species, especially mRNAs present in populations of cells in the specimen. Preferably, a sufficient fraction or mRNA is used generate an expression profile using combinations of markers predictive of minimal residual disease. An expression profile can be conveniently determined by measuring transcript abundance by any of several existing gene expression technologies.

In embodiments, an "expression profile" of a specimen can include the identities and relative abundance, or "expression level", of the constituent protein species expressed in populations of cells in the specimen. Expression profiles of embodiments comprise one or more values representing the expression level of a gene having differential expression in minimal residual disease as compared to a normal control specimen. Each expression profile can contain a sufficient number of values such that the profile can be used to distinguish samples containing a minimal number of leukemic cells or minimal residual disease as compared to specimens taken from normal controls. In some embodiments, an expression profile can comprise four values. In other embodiments, an expression profile can comprise more than four values corresponding to differentially expressed genes, for example at least 5, 6, 7, 8, 9, 10, 11, or 12 values.

In other embodiments, an expression profile can comprise values corresponding to mRNA expression levels as detected by nucleic acid probes. In exemplary embodiments, it may be advantageous to use a greater number of probes and therefore analyze the expression of a greater number of genes simultaneously. Therefore, in other embodiments, 10, 20, 30, 40, 50, 60, 70, 80, 90, 100, 120, 130, 140, 150, 160, 170, 180, 190, 200, or >200 probes are reasonable. Embodiments can include, but are not limited to, the detection of mRNA expression with probe sets shown in Table 5 comprising genes overexpressed or underexpressed in AML.

Normal Controls

In one embodiment, a "normal control" used in the methods and kits are taken from a subject, or pool of subjects diagnosed and validated as "normal." As discussed elsewhere herein, the corresponding predictive markers which are assayed in these samples can include, but are not limited to, CD9, CD32, CD44, CD52, CD54, CD59, CD64, CD68, CD86, CD93, CD96, CD97, CD99, CD123, CX3CR1, Tim-3, CD18, CD25, CD47, CD200, CLEC12A, and CD300a or combinations thereof. In embodiments, specimens from normal controls correspond to blood or bone marrow specimens classified as nonmalignant, benign, and/or other conditions that are not considered to be indicative of clinical disease.

RNA Expression Profiling

The values in the expression profiles are measurements representing the absolute or the relative expression level of differentially expressed genes. The expression levels of marker genes may be determined by any method known in the art for assessing the expression level of an RNA molecule in a specimen. For example, expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are expressly incorporated herein by reference. Gene expression detection may also comprise nucleic acid probes in solution. Expression levels of RNA may also be monitored using the reverse transcriptase polymerase chain reaction (e.g., TaqMan®).

In one embodiment, microarrays are used to measure the values to be included in the expression profiles. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. High-density oligonucleotide arrays are particularly useful for determining the gene expression profile for a large number of RNA's in a sample.

In one approach, total mRNA isolated from cells taken from the subject is converted to labeled cDNA and then hybridized to an oligonucleotide array. Each specimen is hybridized to a separate array. Relative transcript levels are calculated by reference to appropriate controls present on the array and in the sample.

Embodiments can include, but are not limited to, the detection of mRNA expression with probes specific for genes described herein.

In embodiments an expression profile is generated by the detection of nucleic acid corresponding to the expression of mRNA from a specimen.

Protein Expression Profile and Antibody Detection

In other embodiments, the values in the expression profile are obtained by measuring the abundance of the protein products of the differentially-expressed genes. The abundance of these protein products can be determined, for example, using antibodies specific for the protein products of the differentially-expressed genes. The term "antibody" as used herein refers to an immunoglobulin molecule or immunologically active portion thereof, e.g., an antigen-binding portion. Examples of immunologically active portions of immunoglobulin molecules include F(ab) and F(ab')2 fragments, which can be generated by treating the antibody with an enzyme such as pepsin.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site (e.g., Fab', F(ab)2, Fv, single chain antibodies, diabodies). Antibody derivatives may comprise a protein or chemical moiety conjugated to the antibody.

In embodiments, the antibody can be a polyclonal, monoclonal, or recombinant, e.g., a chimeric or humanized, fully human, non-human (e.g., murine, or single chain antibody). The term "monoclonal antibody" as used herein refers to an antibody obtained from a population of substantially homogeneous antibodies, e.g., the individual antibodies comprising the population are identical except for possible naturally-occurring mutations that may be present in minor amounts.

The term "polyclonal antibody" as used herein refers to an antibody obtained from a population of heterogeneous antibodies derived from a multiple B cell response to an antigen which will recognize a variety of epitopes on the antigen. Polyclonal antibodies can be prepared by immunizing a suitable subject (e.g., rabbit, goat, mouse, or other mammal) with a marker protein immunogen. The antibody titer in the immunized subject can be monitored over time by standard techniques, such as with an enzyme linked immunosorbent assay (ELISA) using immobilized biomarker protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, C. (1975) Nature 256:495-497, the human B cell hybridoma technique (Kozbor, et al. (1983) Immunol. Today 4:72), the EBV-hybridoma technique (Cole, et al. (1985) in Monoclonal Antibodies and Cancer Therapy, ed. Reisfeld and Sell (Alan R. Liss, Inc., New York, N.Y.), pp. 77-96) or trioma techniques. The technology for producing hybridomas is well known (see generally Coligan, et al. eds. (1994) Current Protocols in Immunology (John Wiley & Sons, Inc., New York, N.Y.); Galfre et al. (1977) Nature 266:550-52; Kenneth (1980) in Monoclonal Antibodies: A New Dimension In Biological Analyses (Plenum Publishing Corp., NY); and Lerner (1981) Yale J. Biol. Med., 54:387 402).

As an alternative to preparing monoclonal antibody-secreting hybridomas, a monoclonal antibody can be identified and isolated by screening a recombinant combinatorial immunoglobulin library (e.g., an antibody phage display library) with a marker protein to thereby isolate immunoglobulin library members that bind the marker protein.

Antigen-binding fragments and variants of the monoclonal antibodies disclosed herein are contemplated. Such variants, for example, will retain the desired binding properties of the parent antibody. Methods for making antibody fragments and variants are generally available in the art. For example, amino acid sequence variants of a monoclonal antibody described herein can be prepared by mutations in the cloned DNA sequence encoding the antibody of interest. Methods for mutagenesis and nucleotide sequence alterations are well known in the art.

Preferably, variants of an antibody to a reference marker will have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody molecule, or to a shorter portion of the reference antibody molecule. More preferably, the molecules share at least 96%, 97%, 98% or 99% sequence identity.

In embodiments, an antibody can be used to detect the marker or protein product of a differentially expressed gene in order to evaluate the abundance and pattern of expression of the protein. These antibodies can also be used diagnostically to monitor protein expression levels over time as part of a clinical monitoring procedure, e.g., determine the efficacy of a given therapy and reoccurrence of disease.

Optical Detection Methods

Detection of antibodies can be facilitated by coupling (e.g., physically linking) the antibody to a detectable substance (e.g., antibody labeling). Examples of detectable substances include various enzymes, prosthetic groups, fluorescent materials (fluorophores, flurochromes), luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of fluorophores/flurochromes, include phycoerythrin (PE), fluorescein isothiocyanate (FITC), peridinin-chlorophyll (PerCP), allophycocyanin (APC), R-phycoerythrin conjugated with cyanine dye (PE-Cy7), allophycocyanin-cyanine tandem (APC-H7), coumarin dye (Horizon v450), sulphonyl chloride (Texas Red), cyanine (CY3, CY5, Cy7), FAM, JOE, TAMRA, TET, VIC, rhodamine; an example of a luminescent material includes luminol; examples of bioluminescent materials include luciferase, luciferin, and aequorin, and examples of suitable radioactive material include 125I, 131I, 35S or 3H. The skilled artisan will understand that additional moieties may be suitable.

A detectable moiety generally refers in one embodiment to a composition or moiety that is detectable by spectroscopic, photochemical, biochemical, immunochemical, electromagnetic, radiochemical or chemical means such as fluorescence, chemifluorescence, or chemiluminescence, or any other appropriate means. The terms "fluorophore" and "fluorochrome" are defined as a chemical group, or component of a molecule that causes a molecule to be fluorescent. It is a functional group in a molecule which will absorb energy of a specific wavelength and re-emit energy at a different (but equally specific) wavelength. A fluorophore/fluorochrome can refer to various fluorescent substances, including dyes, used in fluorescence microscopy or flow cytometry to stain specimens. The terms fluorophore" and "fluorochrome" are herein used interchangeably.

Fluorochromes may be conjugated to antibodies, proteins, polypeptides, peptides, or nucleotide probes which specifically bind to antigens, proteins, polypeptides, peptides, polysaccharides, DNA, or RNA sequences. Thus, binding of an antibody, protein, polypeptide, peptide, or nucleotide probe to an antigen, protein, polypeptide, peptide, polysaccharide, DNA, or RNA may be detected by measuring a signal generated from a fluorochrome by flow cytometry, or any suitable optical imaging technique. Detection of a signal may indicate binding, whereas lack of detection of a signal may indicate lack of binding.

Methods and compositions for detectably labeling nucleic acid probes, such as oligonucleotides, DNA-RNA hybrids, etc. are well known in the art.

The compositions further comprise monoclonal antibodies and variants and fragments thereof that specifically bind to marker proteins of interest, thereby forming a detectable complex. The monoclonal antibodies may be labeled with a detectable substance to facilitate marker protein detection in the sample. Such antibodies find use in practicing the methods described herein. Monoclonal antibodies having the binding characteristics of the antibodies disclosed herein are also contemplated. Compositions further comprise antigen-binding variants and fragments of the monoclonal antibodies.

In embodiments, a probe is an antibody, including but not limited to a whole antibody molecule, a F(ab')2, Fab', Fv, Fd', or Fd fragment. In yet other embodiments, an antibody can be conjugated with a detectable moiety, wherein the detectable moiety can be, for example, a fluorophore, a chromophore, a radionuclide, or an enzyme. In embodiments, a fluorophore can for example, can be, but is not limited to, phycoerythrin (PE), fluorescein isothiocyanate (FITC), peridinin-chlorophyll (PerCP), allophycocyanin (APC), R-phycoerythrin conjugated with cyanine dye (PE-Cy7), allophycocyanin-cyanine tandem (APC-H7), and coumarin dye (Horizon v450). Detection of complexes formed between an antibody probe and marker can be achieved by an optical detection technique, including, but not limited to flow cytometry and microscopy.

"Cell staining" when used in reference to an antibody means that the antibody recognizes an marker and binds to marker in the specimen forming a complex, thereby "labeling" or otherwise "staining" the cell expressing the marker to make it visible and/or detectable by microscopy or flow cytometry. Combinations of antibodies can be collectively added a specimen and thereby "stain the cell" for later analysis by visualization with a flow cytometer or microscope, for example. One of skill in the art could determine whether a cell expressed a specific protein based on the level of antibody that bound to the cell using standard methods.

The methods described herein can also be used in immunofluorescence histochemistry. This technique involves the use of antibodies labeled with various fluorophores to detect substances within a specimen. In exemplary embodiments a pathologist can derive a great deal of morphological information of diagnostic value by examining a specimen from a subject by microscope. Immunohistochemistry is particularly relevant to, for example, the early diagnosis of cancer or pre-acute states such as minimal residual disease in AML. Combinations of fluorophores or other detectable labels can be used by the methods described herein, thereby greatly increasing the number of distinguishable signals in multicolor protocols.

In another embodiment, the method employs flow cytometry. In another embodiment, in a peripheral blood sample or blood sample, lymphocyte, monocyte and granulocyte populations can be defined on the basis of forward and side scatter. Forward and side scatter are used in one embodiment to exclude debris and dead cells.

Flow cytometry is an optical technique that analyzes particles or cells in a fluid mixture based on their optical characteristics, via the use of a flow cytometer (See, for example, Shapiro, "Practical Flow Cytometry," Third Ed. (Alan R. Liss, Inc., 1995); and Melamed et al. "Flow Cytometry and Sorting," Second Ed. (Wiley-Liss 1990)). Flow cytometers hydrodynamically focus a fluid suspension of particles/cells into a thin stream so that they flow down the stream in substantially single file and pass through an examination zone. A focused light beam, such as a laser beam illuminates the particles as they flow through the examination zone. Optical detectors within the flow cytometer measure certain characteristics of the light as it interacts with the particles/cells. Commonly used flow cytometers such as the Becton-Dickinson Immunocytometry Systems "FACSCAN" (San Jose, Calif.) can measure forward light scatter (generally correlated with the refractive index and size of the particle/cell being illuminated), side light scatter (generally correlated with the cell granularity), and particle fluorescence at one or more wavelengths. Data acquisition and analysis can be done using FASCALIBER® LSRII flow cytometers (Becton Dickinson), and CELLQUEST Pro™, BD FACSDIVA™ software (both from Becton Dickinson), FLOWJO software (Tree Star, Ashland, Oreg.) and/or KALUZA™ software (Beckman Coulter, Miami, Fla.).

Cell Sorting and Selection of Subpopulations of Cells in a Specimen

Multiparameter flow cytometric cell analysis can be used as part of the methods described herein. The simultaneous analysis of multiple predictive parameters using flow cytometry is known to those of skill in the art. In one embodiment, the population of cells to be analyzed is contacted with a panel of antibodies directed against distinct cell surface markers, under conditions effective to allow antibody probe binding. The antibodies employed can be monoclonal antibodies, and can, in another embodiment, be labeled in a manner to allow their subsequent detection.

In embodiments, fluorochromes can be excited by at least two different lasers to give off light of at least four different wavelengths, with the potential, for simultaneous analysis of at least four different markers. An additional two parameters include two light scattering parameters; direct and orthogonal, or side-scattering capability which can be analyzed concurrently with antibody detection, thereby allowing for cell analysis on the basis of at least 6 parameters. In embodiments, at least five, six, seven, eight, nine, ten, eleven, or twelve different antibody probes, can be used simultaneously, thereby allowing for cell analysis on the basis of at least seven, eight, nine, ten, eleven, twelve, thirteen, or fourteen different parameters.

Multiparameter cell sorting can be used in an embodiment to isolate cells based on a specific expression profile. For example, in one embodiment cell sorting analysis can be achieved using fluorescence-activated flow cytometry, by methods well described in the art. In one embodiment cells can be sorted based on the co-expression of markers CD19 and CD10, wherein in combination with the expression of CD19 and CD10 the expression of other markers can be interrogated. In another embodiment, mRNA expression profiles can be generated from a purified population of CD19+ and CD10+ cells isolated from a subject specimen for the purpose of diagnosing minimal residual disease.

In yet other embodiments, enrichment of specific subpopulations of cells can be achieved by other methods as well. For example, a wide variety of magnetic bead separation and isolation procedures can be used to selectively negatively and positively enrich samples for specific subpopulations of cells. For example, in some embodiments a mixture of magnetic beads coupled to lineage specific antibodies can be used to deplete, T cells, NK cells, monocytes, platelets, dendritic cells, granulocytes and erythrocytes, thereby negatively isolating B cells. The skilled artisan will understand that combinations of different antibodies can be used alone or in combination, and in multiple successive rounds of isolation, to positively and/or negatively select for subpopulations of cells.

One of skill in the art will recognize that optimization of reagents and conditions, for example, antibody titer and parameters for detection of antigen-antibody binding, is needed to maximize the signal to noise ratio for a particular antibody. Antibody concentrations that maximize specific binding to the markers and minimize non-specific binding (or "background") will be determined. In particular embodiments, appropriate antibody titers are determined by initially testing various antibody dilutions on patient serum samples. The design of assays to optimize antibody titer and detection conditions is standard and well within the routine capabilities of those of ordinary skill in the art. Some antibodies require additional optimization to reduce background and/or to increase specificity and sensitivity.

The skilled artisan will recognize that optimization of multiparameter assays designed to detect a plurality of antibody probes simultaneously will be necessary. In embodiments, maximization of signal to noise ratio, as well an optimization of fluorochrome combinations will be necessary for each of the antibody probes combinations. Conjugated-antibody concentrations that maximize specific binding to the markers and minimize non-specific binding (or "background") will be determined with other such conjugated antibody probes as is known in the art. The design of assays to optimize and compensate the signals detected for the various conjugated antibodies is standard and well within the routine capabilities of those of ordinary skill in the art. Some antibodies require additional optimization to reduce background and/or to increase specificity and sensitivity.

Antibody and Nucleic Acid Probes to Target Genes The antibodies used to practice the methods described herein are selected to have high specificity for the marker proteins of interest. Methods for making antibodies and for selecting appropriate antibodies are known in the art. In some embodiments, commercial antibodies directed to specific marker proteins may be used to practice the methods described herein. The antibodies may be selected on the basis of desirable staining of cytological, rather than histological, samples. That is, in particular embodiments the antibodies are selected with the desired combination in mind and for binding specificity.

The markers and combinations of markers include genes or proteins that are selectively expressed, overexpressed or underexpressed in leukemia, and specifically in AML, as defined herein above, and may be combined with known markers as well as those presently unknown in the art. In particular embodiments, markers are intracellular proteins, secreted proteins or proteins that are predicted to encode membranous proteins with transmembrane segments and extracellular domains. In some embodiments, probes can detect markers that are polypeptides expressed at the surface of the cell. In other embodiments, probes can detect markers that are polypeptides expressed intracellularly. In still other embodiments, probes detect markers that are polynucleotides. In still other embodiments, kits and methods can comprise probes that can detect markers that include polypeptides and polynucleotide.

Intracellular Protein Targets

In some embodiments, the expression of intracellular proteins, for example, BCL2 and HSPB1, are detected using flow cytometry by first permeablizing the cell surface membrane to allow access of antibody through the membrane. In one embodiment a permeabilization reagent, such as those containing various surfactants (e.g., saponin, Triton X-100, Tween-20, N-acyl sarcosine, etc) or organic solvents (e.g., alcohols, acetone) or other similar solution, is used. A permeabilization reagent is optimally used in a sufficient amount enabling penetration of antibodies to the intercellular space, while substantially preserving the cellular membrane. Ideally, the permeabilizing agent creates apertures in the cell membrane without affecting the gross morphology of the cell such that flow cytometric light scattering characteristics of the cell are not affected. Such methods of permeabilizing cells are well known in the art.

In embodiments, the cell may be fixed prior to or during permeabilization to maintain the integrity of the cell. Methods of fixation are also well known in the art. In some embodiments, fixation and permeabilization can be combined. An example of a fixation/permeabilizing agent is INTRAPREP™ (Beckman Coulter, Inc.) which comprises 5.5% v/v formaldehyde as a fixation reagent and a phosphate buffered saline (PBS)-saponin-based permeabilization reagent.

RNA Expression Profiling

In other embodiments, the expression of a marker of interest is detected at the nucleic acid level. Nucleic acid-based techniques for assessing expression are well known in the art and include, for example, determining the level of marker mRNA in a specimen taken from a patient. Many expression detection methods use isolated RNA. Generally, blood, serum, or tissue samples can readily be processed using techniques well known to those of skill in the art, such as, for example, the single-step RNA isolation process of Chomczynski (1989, U.S. Pat. No. 4,843,155).

Isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a marker. Hybridization of an mRNA with the probe indicates that the marker in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers.

An alternative method for determining the level of marker mRNA in a sample involves the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al. U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects, marker expression is assessed by quantitative fluorogenic RT-PCR (e.g., the TaqMan® System). Such methods typically utilize pairs of oligonucleotide primers that are specific for the marker of interest. Methods for designing oligonucleotide primers specific for a known sequence are well known in the art.

Marker expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of marker expression may also comprise using nucleic acid probes in solution.

In one embodiment, microarrays are used to detect marker expression. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety for all purposes. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992, each of which is hereby incorporated in its entirety for all purposes. Arrays may be packaged in such a manner as to allow for diagnostics or other manipulation of an all-inclusive device. See, for example, U.S. Pat. Nos. 5,856,174 and 5,922,591.

In one approach, total mRNA isolated from a specimen is converted to labeled cRNA and then hybridized to an oligonucleotide array. Each specimen is hybridized to a separate array. Relative transcript levels may be calculated by reference to appropriate controls present on the array and in the sample. In one embodiment, RNA can be isolated from a subpopulation of cells with a characteristic expression profile.

In embodiments, an expression profile can comprise values corresponding to gene expression detected by mRNA expression levels where the expression of many genes can be analyzed simultaneously and interpreted in one sample.

Kits for Detection of Minimal Residual Disease

Kits for practicing the screening and diagnostic methods are further provided. The kits may also include methods for use in diagnosing minimal residual disease in AML, detecting or diagnosing AML, monitoring disease status in a patient for the recurrence of AML, or monitoring the efficacy of a treatment for AML. These methods are described elsewhere herein.

As used herein, "kit" refers to a set of reagents for the purpose of performing the method embodiments, more particularly, the detection of minimal residual disease in patient specimens. The term "kit" is intended to mean any manufacture (e.g., a package or a container) comprising at least one reagent, e.g., an antibody, a nucleic acid probe, etc. for specifically detecting the expression of a marker. The kit may be promoted, distributed, or sold as a unit for performing the methods described herein. Additionally, the kits may contain a package insert describing the kit and methods for its use.

In embodiments, expression of markers can be assessed at the protein level or nucleic acid level, or both in combination. In some embodiments, expression of protein expression is detected using specific antibody probes. Expression of identified markers can also be detected by nucleic acid based techniques, including, for example, hybridization and RT-PCR. Expression can be evaluated in a variety of specimens taken from the body including, but not limited to, blood cells or bone marrow cells, and cellular products extracted from blood and bone marrow cells, including, but not limited to protein and RNA extracted from blood and bone marrow cells.

Computer Implementation

Figure 16:
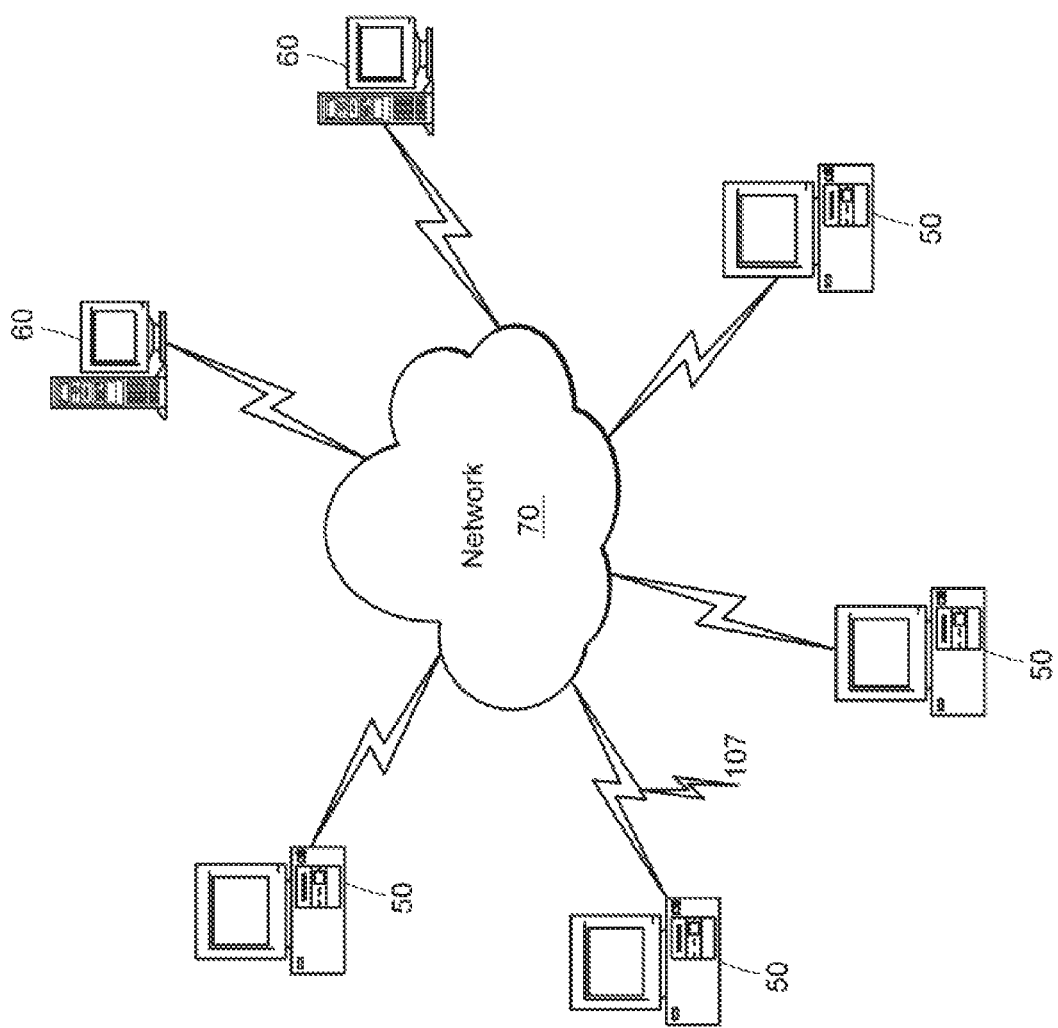
FIG. 16 is a schematic illustration of a computer network in which embodiments operate.

FIG. 16 illustrates a computer network or similar digital processing environment in which the present subject matter may be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), cloud computing servers or service, a worldwide collection of computers, Local area or Wide area networks, and gateways that currently use respective protocols (TCP/IP, Bluetooth, etc.) to communicate with one another. Other electronic device/computer network architectures are suitable.

Figure 17:
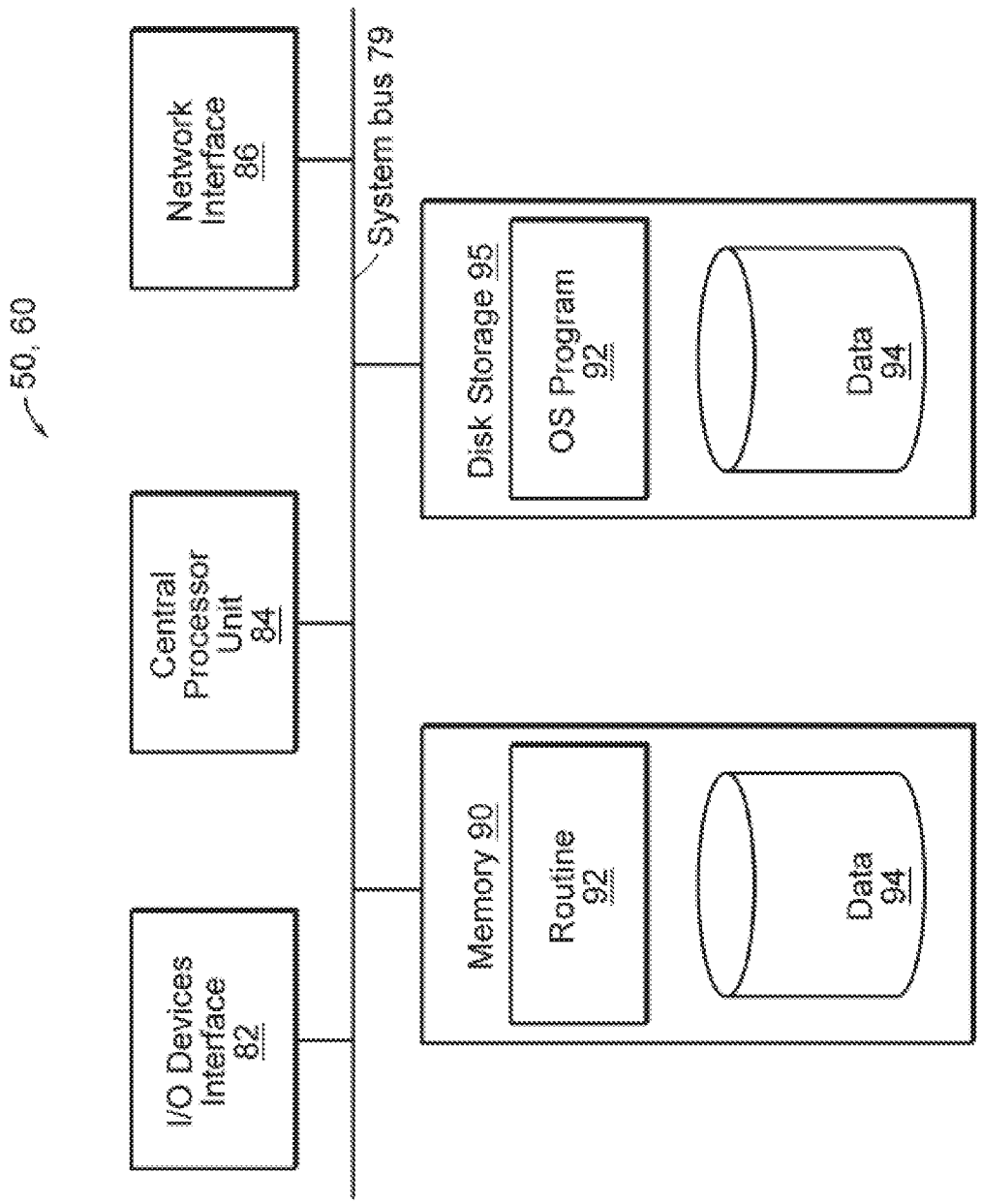
FIG. 17 is a block diagram of one computer node in the computer network of FIG. 16.

FIG. 17 is a diagram of the internal structure of a computer (e.g., client processor/device 50 or server computers 60) in the computer system of FIG. 16. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 16). Memory 90 provides volatile storage for computer software instructions 92 and data 94 used to implement an embodiment of the present subject matter (e.g., input module, processor engine, and graphics memory code detailed above). Disk storage 95 provides non-volatile storage for computer software instructions 92 and data 94 used to implement an embodiment of the present subject matter. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the system. Computer program product 92 can be installed by any suitable software installation procedure, as is well known in the art. In another embodiment, at least a portion of the software instructions may also be downloaded over a cable, communication and/or wireless connection. In other embodiments, the programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

In other embodiments, the program product 92 may be implemented as a so called Software as a Service (SaaS), or other installation or communication supporting end-users.

EXEMPLIFICATION

Materials and Methods

Patients and Cells

Bone marrow samples were collected at diagnosis from 370 patients with de novo or secondary AML, aged <1 to 63 years; patients with acute promyelocytic leukemia were not included in this study. Of the 370 samples, 157 from pediatric AML were used for genome-wide gene expression studies, and 213 from pediatric and adult AML for the studies by flow cytometry. Bone marrow (n=190) and peripheral blood (n=18) obtained from 52 patients with AML during therapy, and bone marrow samples collected from 27 patients at relapse were also studied. The diagnosis of AML was established according to morphology, cytochemistry and cell marker profile. Bone marrow samples from 30 healthy donors (7 included in the gene expression studies), and from 40 patients with acute leukemia during therapy were studied to determine marker expression in non-AML myeloid progenitors. These studies were approved by the St Jude Children's Research Hospital institutional review board and by the National University Hospital of Singapore Domain Specific Ethics Board, with informed consent obtained from donors, patients, their parents or their guardians, and assent from the patients, as appropriate.

Leukemic and normal mononucleated cells were obtained by centrifugation on a density gradient (AccuPrep, Nycomed, Oslo, Norway) and washed three times in phosphate-buffered saline (PBS). All samples used in the gene expression studies were cryopreserved. To obtain normal myeloid progenitor cells for gene expression analysis, CD19+ B-cells were removed from cryopreserved bone marrow mononucleated cells of 7 healthy donors using a MACS separation system (Miltenyi Biotec, Auburn, Calif.). The remaining cells were labeled with anti-CD34 conjugated to phycoerythrin (PE; BD Biosciences, San Jose, Calif.), anti-CD13 (from Dako, Carpinteria, Calif.) and anti-CD33 (BD Biosciences), both conjugated to fluorescein isothyocyanate (FITC). We then sorted CD34+ cells expressing CD13 and/or CD33 using a MoFlo fluorescence-activated cell sorter (Cytomation, Beckman Coulter, Brea, Calif.).

Gene Expression Arrays Studies

Gene expression array studies were performed as previously described (32). Briefly, after isolating total RNA from 157 AML samples and 7 normal myeloid progenitor cell samples using Trizol reagent (Invitrogen, Carlsbad, Calif.), we generated cDNA and prepared biotin-labeled cRNA hybridization solutions (Affymetrix; Santa Clara, Calif.). Three of the 7 normal myeloid progenitor cell preparation yielded low RNA and were pooled into one. The solutions were hybridized to HG-U133A oligonucleotide microarrays (Affymetrix), which were stained with phycoerythrin-conjugated streptavidin. The arrays were read with a laser confocal scanner (Agilent, Palo Alto, Calif.), with signal values computed using Affymetrix GeneChip Operating Software.

Flow Cytometric Analysis and MRD Studies

The antibodies used to determine marker expression by flow cytometry are listed in Table 1. These antibodies were used in combination with anti-CD34 peridinin chlorophyll protein (PerCP), CD117 conjugated to allophycocyanin (APC), CD45 conjugated to APC-H7, and CD33 phycoerythrin (PE)-Cy7 (all from BD Biosciences). Isotype-matched nonreactive antibodies were used as controls. For flow cytometric analysis, monunucleated cells were washed in PBS containing 0.5% bovine serum albumin and 0.5% sodium azide (PBSA), mixed with rabbit serum to block surface Fc receptors, incubated with the antibodies for 10 minutes at 20° C. in the dark, washed twice in PBSA and fixed with 0.5% formaldehyde. For intracellular markers, cells were permeabilized and fixed before exposure to antibodies using 8E, a reagent prepared in our laboratory from a proprietary formula. Measurements of antibody labeling were performed by multiparameter flow cytometry, using an LSRII flow cytometer (BD Biosciences).

Studies of MRD by flow cytometry were performed using combinations of monoclonal antibodies that identified leukemia-associated immunophenotypes determined at diagnosis. Cells staining was essentially performed as described above. Data acquisition and analysis was done as previously described, using an LSRII flow cytometer, and DIVA (BD Biosciences), and FlowJo (Tree Star, Ashland, Oreg.) software. At least 100,000 viable mononucleated cells (up to 1,000,000) were analyzed in each sample.

TABLE 1

Antibodies used in this study and cell types used to test their reactivity

| Specificity | Clone | Fluorochrome | Source | Catalog Number | Positive Control | Negative Control (negative or dim expression) |
|---|---|---|---|---|---|---|
| CD9 | M-L13 | FITC | BD Biosciences | 341646 | Monocytes | Lymphoid subset |
| ITGB2/CD18 | MEM-48 | PE | GeneTex | GTX79945 | All leukocytes | K562 cell line |
| IL2RA/CD25 | 2A3 | PE | BD Biosciences | 341010 | Activated lymphocytes | Resting lymphocytes |

TABLE 1-continued

Antibodies used in this study and cell types used to test their reactivity

| Specificity | Clone | Fluorochrome | Source | Catalog Number | Positive Control | Negative Control (negative or dim expression) |
|---|---|---|---|---|---|---|
| FCGR2A/CD32 | 2E1 | PE | Beckman Coulter | IM1935 | Monocytes | Lymphoid subset |
| CD44 | G44-26 | V450 | BD Biosciences | 561292 | All leukocytes | Jurkat cell line |
| CD47 | B6H12 | PE | BD Biosciences | 556046 | All leukocytes | Not known |
| CD52 | CF1D12 | FITC | Life Technologies | MHCD5201 | Lymphoid | NK subset, neutrophils |
| ICAM1/CD54 | LB-2 | PE | BD Biosciences | 347977 | Daudi cell line | Lymphoid subset |
| CD59 | P282 (H19) | PE | BD Biosciences | 555764 | K562 cell line | Lymphocytes |
| FCGR1A/CD64 | 10.1 | V450 | BD Biosciences | 561202 | Monocytes | Lymphocytes |
| CD68[1] | Y1/82A | PE | BD Biosciences | 556078 | Monocytes | Lymphocytes |
| CD86 | 2331 (FUN-1) | BV421 | BD Biosciences | 562432 | Monocytes | Resting lymphocytes |
| CD93 | VIMD2 | PE | Biolegend | 336108 | Monocytes | Lymphocytes |
| CD96 | 6F9 | PE | BD Biosciences | 562379 | Activated NK and T cells | Resting lymphocytes |
| CD97 | VIM3b | FITC | BD Biosciences | 555773 | Monocytes | Resting lymphocytes |
| CD99 | Tü12 | PE | BD Biosciences | 555689 | T cell lymphoblastic leukemia cells | Granulocytes |
| PVR/CD115 | 61708 | PE | R&D Systems | FAB329P | Monocytes | Lymphocytes |
| IL3RA/CD123 | 9F5 | PE | BD Biosciences | 340545 | Lymphoid subset, basophils, eosinophils | Lymphoid subset |
| CD163 | GHI/61 | PE | BD Biosciences | 556018 | Monocytes | Lymphocytes |
| PRV1/CD177 | MEM-166 | PE | AbD Serotec | MCA2045 | Granulocytes | Lymphoid |
| CX3CR1/CD181 | 2A9-1 | PE | Medical & Biological Laboratories | D070-5 | Monocytes | Lymphoid subset |
| CD200 | MRC OX-104 | V450 | BD Biosciences | 562126 | B lymphocytes | Monocytes |
| CD209 | DCN46 | V450 | BD Biosciences | 561275 | Peripheral blood dendritic cells | Lymphocytes |
| IL10RA/CD210 | 3F9 | PE | BD Biosciences | 556013 | Monocytes | Lymphoid subset |
| CD300a | E59.126 | PE | Beckman Coulter | A22328 | Monocytes, lymphoid subset | Lymphoid subset |
| CLEC12A | 50C1 | PE | Biolegend | 353604 | Monocytes | Lymphocytes |
| CCL5/Rantes[1] | 21445 | PE | R&D Systems | IC278P | Activated NK | Resting lymphocytes |
| HAVCR2/TIM3 | F38-2E2 | BV421 | Biolegend | 345008 | Monocytes | Lymphoid subset |

[1]Requires membrane permeabilization

Results

Genes Aberrantly Expressed in AML Cells and Normal Myeloid Progenitors

To identify genes aberrantly expressed in AML, we compared global gene expression of 157 AML diagnostic samples to that of normal CD34+ myeloid progenitor cells (CD13+ and/or CD33+) purified from the bone marrow of 7 healthy donors. We found 395 probe sets that were over-expressed in AML (e.g., at least 100% higher than the highest signal measured in normal myeloid cells) and 260 that were under-expressed (e.g., at least 50% lower than the lowest normal value) in 66% or more of AML cases. Widening the inclusion criterion to genes aberrantly expressed in at least 33% of AML cases raised the numbers to 1958 and 1271, respectively (Tables 2 and 3). Therefore, the genes of Table 2 and 3 can also be useful in identifying acute myeloid leukemia and minimal residual disease in acute myeloid leukemia.

TABLE 2

Genes over-expressed in AML

| probe | Gene | Unigene | Locus | % AML cases with overexpression |
|---|---|---|---|---|
| 216207_x_at | IGKV1D-13 | Hs.390427 | 28902 | 98.1 |
| 210972_x_at | TRA@ /// TRDV2 /// TRAV20 /// TRAJ17 /// TRAC | Hs.74647 | 28517 | 98.1 |
| 207529_at | DEFA5 | Hs.72887 | 1670 | 98.1 |
| 219710_at | SH3TC2 | Hs.483784 | 79628 | 98.1 |
| 217227_x_at | — | Hs.561078 | — | 97.5 |
| 215511_at | TCF20 | Hs.475018 | 6942 | 97.5 |
| 216341_s_at | GNRHR | Hs.407587 | 2798 | 96.8 |
| 215176_x_at | — | Hs.552522 | — | 96.2 |
| 209057_x_at | CDC5L | Hs.485471 | 988 | 96.2 |
| 62987_r_at | CACNG4 | Hs.514423 | 27092 | 95.5 |
| 201864_at | GDI1 | Hs.74576 | 2664 | 95.5 |
| 221239_s_at | FCRL2 | Hs.437393 | 79368 | 95.5 |
| 208013_s_at | ACRV1 | Hs.169222 | 56 | 95.5 |
| 203074_at | ANXA8 | Hs.463110 | 244 | 94.9 |
| 208460_at | GJA7 | Hs.532593 | 10052 | 94.9 |
| 31861_at | IGHMBP2 | Hs.503048 | 3508 | 94.3 |
| 71933_at | WNT6 | Hs.29764 | 7475 | 94.3 |
| 205758_at | CD8A | Hs.85258 | 925 | 94.3 |
| 206908_s_at | CLDN11 | Hs.31595 | 5010 | 94.3 |
| 209708_at | MOXD1 | Hs.6909 | 26002 | 94.3 |
| 211863_x_at | HFE | Hs.233325 | 3077 | 94.3 |
| 221943_x_at | RPL38 | Hs.380953 | 6169 | 93.6 |
| 217189_s_at | C1orf16 | Hs.270775 | 9887 | 93.6 |
| 206672_at | AQP2 | Hs.130730 | 359 | 93.6 |
| 396_f_at | EPOR | Hs.127826 | 2057 | 93.0 |
| 217378_x_at | LOC391427 | — | 391427 | 93.0 |
| 204006_s_at | FCGR3A /// FCGR3B | Hs.372679 | 2214 | 93.0 |
| 216576_x_at | — | Hs.552522 | — | 93.0 |
| 211339_s_at | ITK | Hs.558348 | 3702 | 93.0 |
| 207665_at | ADAM21 | Hs.178748 | 8747 | 93.0 |
| 217148_x_at | IGLV2-14 | — | 28815 | 92.4 |
| 214053_at | — | Hs.588182 | — | 92.4 |
| 206534_at | GRIN2A | Hs.567280 | 2903 | 92.4 |
| 211430_s_at | IGH@ /// IGHG1 /// IGHG2 /// IGHG3 /// IGHM | Hs.510635 | 3492 | 91.7 |
| 217022_s_at | IGHA1 /// IGHA2 /// MGC27165 | Hs.584764 | 283650 /// 3493 /// 3494 | 91.7 |
| 205456_at | CD3E | Hs.3003 | 916 | 91.7 |
| 217157_x_at | — | Hs.556743 | — | 91.7 |
| 206887_at | CCBP2 | Hs.24286 | 1238 | 91.7 |
| 206324_s_at | DAPK2 | Hs.237886 | 23604 | 91.1 |
| 211902_x_at | TRA@ | Hs.546375 | 6955 | 90.4 |
| 217430_x_at | COL1A1 | Hs.172928 | 1277 | 90.4 |
| 216025_x_at | CYP2C19 /// CYP2C9 | Hs.282409 | 1557 | 90.4 |
| 206948_at | NEU3 | Hs.191074 | 10825 | 90.4 |
| 210148_at | HIPK3 | Hs.201918 | 10114 | 90.4 |
| 208035_at | GRM6 | Hs.248131 | 2916 | 89.8 |
| 48030_i_at | C5orf4 | Hs.519694 | 10826 | 89.2 |
| 36564_at | IBRDC3 | Hs.128366 | 127544 | 89.2 |
| 203413_at | NELL2 | Hs.505326 | 4753 | 89.2 |
| 211231_x_at | CYP4A11 | Hs.1645 | 1579 | 89.2 |
| 208259_x_at | IFNA7 | Hs.282274 | 3444 | 89.2 |
| 213332_at | PAPPA2 | Hs.187284 | 60676 | 89.2 |
| 207269_at | DEFA4 | Hs.128581 | 1669 | 88.5 |
| 205445_at | PRL | Hs.1905 | 5617 | 88.5 |
| 211634_x_at | IGHM | Hs.538461 | 3507 | 88.5 |
| 211644_x_at | IGKC | Hs.449621 | 3514 | 88.5 |
| 209003_at | SLC25A11 | Hs.184877 | 8402 | 88.5 |
| 205291_at | IL2RB | Hs.474787 | 3560 | 88.5 |
| 212161_at | AP2A2 | Hs.19121 | 161 | 88.5 |
| 208540_x_at | S100A11 | Hs.417004 | 6282 | 87.9 |
| 38447_at | ADRBK1 | Hs.83636 | 156 | 87.9 |
| 211900_x_at | CD6 | Hs.502710 | 923 | 87.9 |
| 204443_at | ARSA | Hs.88251 | 410 | 87.9 |
| 209568_s_at | RGL1 | Hs.497148 | 23179 | 87.3 |

TABLE 2-continued

Genes over-expressed in AML

| probe | Gene | Unigene | Locus | % AML cases with overexpression |
|---|---|---|---|---|
| 211866_x_at | HFE | Hs.233325 | 3077 | 87.3 |
| 221370_at | LOC377064 | Hs.556877 | 377064 | 87.3 |
| 208544_at | ADRA2B | Hs.247686 | 151 | 87.3 |
| 219112_at | RAPGEF6 | — | 51735 | 86.6 |
| 211364_at | MTAP | Hs.193268 | 4507 | 86.6 |
| 207882_at | HSAJ2425 | Hs.194790 | 55566 | 86.6 |
| 221444_at | TAS2R16 | Hs.272395 | 50833 | 86.6 |
| 206765_at | KCNJ2 | Hs.1547 | 3759 | 86.6 |
| 202921_s_at | ANK2 | Hs.567235 | 287 | 86.6 |
| 1405_i_at | CCL5 | Hs.514821 | 6352 | 86.0 |
| 214777_at | — | Hs.551722 | — | 86.0 |
| 217480_x_at | LOC339562 | Hs.449972 | 339562 | 86.0 |
| 204804_at | TRIM21 | Hs.532357 | 6737 | 86.0 |
| 216292_at | PTPRM | Hs.49774 | 5797 | 86.0 |
| 208426_x_at | KIR2DL4 | Hs.166085 | 3805 | 86.0 |
| 60528_at | PLA2G4B | Hs.554815 | 8681 | 85.4 |
| 36907_at | MVK | Hs.130607 | 4598 | 85.4 |
| 213823_at | HOXA11 | Hs.249171 | 3207 | 85.4 |
| 216730_at | — | Hs.590753 | — | 85.4 |
| 211868_x_at | IGHA1 /// IGHG1 /// IGHG3 | Hs.558342 | 3493 | 85.4 |
| 211661_x_at | PTAFR | Hs.77542 | 5724 | 84.7 |
| 204647_at | HOMER3 | Hs.410683 | 9454 | 84.7 |
| 214470_at | KLRB1 | Hs.169824 | 3820 | 84.7 |
| 209365_s_at | ECM1 | Hs.81071 | 1893 | 84.7 |
| 204437_s_at | FOLR1 | Hs.73769 | 2348 | 84.7 |
| 208384_s_at | MID2 | Hs.12256 | 11043 | 84.7 |
| 216953_s_at | WT1 | Hs.408453 | 7490 | 84.7 |
| 221910_at | ETV1 | Hs.22634 | 2115 | 84.7 |
| 209138_x_at | IGLV3-25 /// DHRS4 /// IGLC2 | Hs.449585 /// Hs.528385 /// Hs.584765 | 10901 /// 28793 /// 3538 | 84.1 |
| 211645_x_at | — | Hs.554197 | — | 84.1 |
| 33768_at | DMWD | Hs.584752 | 1762 | 84.1 |
| 219095_at | PLA2G4B | Hs.554815 | 8681 | 84.1 |
| 204837_at | MTMR9 | Hs.528673 | 66036 | 84.1 |
| 214070_s_at | ATP10B | Hs.109358 | 23120 | 84.1 |
| 202638_s_at | ICAM1 | Hs.515126 | 3383 | 84.1 |
| 220017_x_at | CYP2C9 | Hs.282624 | 1559 | 84.1 |
| 209697_at | PPP3CC | Hs.149413 | 5533 | 84.1 |
| 221332_at | BMP15 | Hs.532692 | 9210 | 83.4 |
| 206227_at | CILP | Hs.442180 | 8483 | 83.4 |
| 216126_at | MGC39821 | Hs.351906 | 284440 | 83.4 |
| 215241_at | TMEM16C | Hs.91791 | 63982 | 83.4 |
| 209458_x_at | HBA1 /// HBA2 | Hs.449630 | 3039 /// 3040 | 82.8 |
| 205513_at | TCN1 | Hs.2012 | 6947 | 82.8 |
| 64064_at | GIMAP5 | Hs.412331 | 55340 | 82.8 |
| 218974_at | FLJ10159 | Hs.445244 | 55084 | 82.8 |
| 216046_at | PDE8A | Hs.9333 | 5151 | 82.8 |
| 221859_at | SYT13 | Hs.436643 | 57586 | 82.8 |
| 211813_x_at | DCN | Hs.156316 | 1634 | 82.8 |
| 215115_x_at | NTRK3 | Hs.410969 | 4916 | 82.8 |
| 209671_x_at | TRA@ /// TRAC | Hs.74647 | 28755 /// 6955 | 82.2 |
| 205821_at | KLRK1 | Hs.387787 | 22914 | 82.2 |
| 204533_at | CXCL10 | Hs.413924 | 3627 | 82.2 |
| 205277_at | PRDM2 | Hs.371823 | 7799 | 82.2 |
| 211590_x_at | TBXA2R | Hs.442530 | 6915 | 82.2 |
| 1494_f_at | CYP2A6 | Hs.439056 | 1548 | 82.2 |
| 215622_x_at | PHF7 | Hs.372719 | 51533 | 82.2 |
| 203958_s_at | ZBTB40 | Hs.418966 | 9923 | 82.2 |
| 217235_x_at | IGLC2 | Hs.449585 | 3538 | 81.5 |
| 217281_x_at | — | Hs.551925 | — | 81.5 |
| 35150_at | CD40 | Hs.472860 | 958 | 81.5 |
| 201598_s_at | INPPL1 | Hs.523875 | 3636 | 81.5 |
| 219697_at | HS3ST2 | Hs.115830 | 9956 | 81.5 |
| 207908_at | KRT2A | Hs.707 | 3849 | 81.5 |
| 221300_at | C15orf2 | Hs.451286 | 23742 | 81.5 |
| 216213_at | NEK1 | Hs.481181 | 4750 | 81.5 |
| 202500_at | DNAJB2 | Hs.77768 | 3300 | 81.5 |
| 211745_x_at | HBA1 | Hs.449630 | 3039 | 80.9 |
| 214677_x_at | IGL@ /// IGLC1 | Hs.449585 | 28793 /// 28815 /// | 80.9 |

TABLE 2-continued

Genes over-expressed in AML

| probe | Gene | Unigene | Locus | % AML cases with overexpression |
|---|---|---|---|---|
| | IGLC2 /// | | 28831 /// | |
| | IGLV3-25 /// | | 3535 /// | |
| | IGLV2-14 /// | | 3537 /// | |
| | IGLJ3 | | 3538 | |
| 213539_at | CD3D | Hs.504048 | 915 | 80.9 |
| 216510_x_at | IGHA1 /// | Hs.538461 | 3493 /// | 80.9 |
| | IGHD /// | | 3495 /// | |
| | IGHG1 /// | | 3500 /// | |
| | IGHM /// | | 3507 /// | |
| | LOC390714 | | 390714 | |
| 205879_x_at | RET | Hs.350321 | 5979 | 80.9 |
| 206666_at | GZMK | Hs.277937 | 3003 | 80.9 |
| 206181_at | SLAMF1 | Hs.523660 | 6504 | 80.9 |
| 204655_at | CCL5 | Hs.514821 | 6352 | 80.3 |
| 213629_x_at | MT1F | Hs.513626 | 4494 | 80.3 |
| 204858_s_at | ECGF1 | Hs.546251 | 1890 | 80.3 |
| 34846_at | CAMK2B | Hs.351887 | 816 | 80.3 |
| 210708_x_at | CASP10 | Hs.5353 | 843 | 80.3 |
| 205832_at | CPA4 | Hs.93764 | 51200 | 80.3 |
| 208241_at | NRG1 | Hs.453951 | 3084 | 80.3 |
| 204018_x_at | HBA1 /// | Hs.449630 | 3039 /// | 79.6 |
| | HBA2 | | 3040 | |
| 211699_x_at | HBA1 /// | Hs.449630 | 3039 /// | 79.6 |
| | HBA2 | | 3040 | |
| 207563_s_at | OGT | Hs.405410 | 8473 | 79.6 |
| 58900_at | LOC222070 | — | 222070 | 79.6 |
| 221041_s_at | SLC17A5 | Hs.485760 | 26503 | 79.6 |
| 206186_at | MPP3 | Hs.396566 | 4356 | 79.6 |
| 59433_at | LOC286434 | Hs.546700 | 286434 | 79.6 |
| 215100_at | C6orf105 | Hs.126409 | 84830 | 79.6 |
| 206225_at | ZNF507 | Hs.205392 | 22847 | 79.6 |
| 217414_x_at | HBA2 | Hs.398636 | 3040 | 79.0 |
| 204848_x_at | HBG1 /// | Hs.567283 | 3047 /// | 79.0 |
| | HBG2 | | 3048 | |
| 209287_s_at | CDC42EP3 | Hs.369574 | 10602 | 79.0 |
| 40359_at | RASSF7 | Hs.72925 | 8045 | 79.0 |
| 221929_at | RBM12B | Hs.192788 | 389677 | 79.0 |
| 219400_at | CNTNAP1 | Hs.408730 | 8506 | 79.0 |
| 33197_at | MYO7A | Hs.370421 | 4647 | 79.0 |
| 207192_at | DNASE1L2 | Hs.103503 | 1775 | 79.0 |
| 205081_at | CRIP1 | Hs.70327 | 1396 | 78.3 |
| 219962_at | ACE2 | Hs.178098 | 59272 | 78.3 |
| 41386_i_at | — | — | — | 78.3 |
| 203514_at | MAP3K3 | Hs.29282 | 4215 | 78.3 |
| 212400_at | C9orf132 | Hs.568044 | 399665 | 78.3 |
| 217342_x_at | FLJ11292 | Hs.586191 | 55338 | 78.3 |
| 204227_s_at | TK2 | Hs.512619 | 7084 | 78.3 |
| 215121_x_at | IGL@ /// | Hs.449585 | 28793 /// | 77.7 |
| | IGLC1 /// | | 28815 /// | |
| | IGLC2 /// | | 3535 /// | |
| | IGLV3-25 /// | | 3537 /// | |
| | IGLV2-14 | | 3538 | |
| 217179_x_at | — | Hs.586050 | — | 77.7 |
| 209670_at | TRAC | — | 28755 | 77.7 |
| 201087_at | PXN | Hs.446336 | 5829 | 77.7 |
| 210422_x_at | SLC11A1 | Hs.471393 | 6556 | 77.7 |
| 203234_at | UPP1 | Hs.488240 | 7378 | 77.7 |
| 206776_x_at | ACRV1 | Hs.169222 | 56 | 77.7 |
| 204813_at | MAPK10 | Hs.125503 | 5602 | 77.7 |
| 216055_at | PDGFB | Hs.1976 | 5155 | 77.7 |
| 216502_at | ISG20L2 | Hs.301904 | 81875 | 77.7 |
| 214768_x_at | — | Hs.534006 | — | 77.1 |
| 204891_s_at | LCK | Hs.470627 | 3932 | 77.1 |
| 207718_x_at | CYP2A6 /// | Hs.439056 | 1548 /// | 77.1 |
| | CYP2A7 /// | | 1549 /// | |
| | CYP2A7P1 /// | | 1550 /// | |
| | CYP2A13 | | 1553 | |
| 207217_s_at | NOX1 | Hs.132370 | 27035 | 77.1 |
| 206281_at | ADCYAP1 | Hs.531719 | 116 | 77.1 |
| 211488_s_at | ITGB8 | Hs.285724 | 3696 | 77.1 |
| 211606_at | — | — | — | 77.1 |
| 205925_s_at | RAB3B | Hs.123072 | 5865 | 77.1 |
| 210524_x_at | — | — | — | 76.4 |
| 211395_x_at | FCGR2C | — | 9103 | 76.4 |
| 203110_at | PTK2B | Hs.491322 | 2185 | 76.4 |

TABLE 2-continued

Genes over-expressed in AML

| probe | Gene | Unigene | Locus | % AML cases with overexpression |
|---|---|---|---|---|
| 203111_s_at | PTK2B | Hs.491322 | 2185 | 76.4 |
| 205019_s_at | VIPR1 | Hs.348500 | 7433 | 76.4 |
| 211947_s_at | BAT2D1 | Hs.494614 | 23215 | 76.4 |
| 219287_at | KCNMB4 | Hs.525529 | 27345 | 76.4 |
| 203370_s_at | PDLIM7 | Hs.533040 | 9260 | 76.4 |
| 214128_at | C11orf11 | Hs.241564 | 747 | 76.4 |
| 32699_s_at | PVR | Hs.171844 | 5817 | 76.4 |
| 213418_at | HSPA6 | Hs.3268 | 3310 | 75.8 |
| 214511_x_at | FCGR1A /// LOC440607 | Hs.534956 | 2209 /// 440607 | 75.8 |
| 209215_at | TETRAN | Hs.584848 | 10227 | 75.8 |
| 216984_x_at | IGLC2 | Hs.449585 | 3538 | 75.8 |
| 211643_x_at | IGKC | Hs.449621 | 3514 | 75.8 |
| 90265_at | CENTA1 | Hs.121593 | 11033 | 75.8 |
| 51774_s_at | LOC222070 | — | 222070 | 75.8 |
| 211067_s_at | GAS7 | Hs.462214 | 8522 | 75.8 |
| 212198_s_at | TM9SF4 | Hs.529360 | 9777 | 75.8 |
| 91920_at | BCAN | Hs.516904 | 63827 | 75.8 |
| 204574_s_at | MMP19 | Hs.154057 | 4327 | 75.8 |
| 217541_x_at | LOC125893 | Hs.446907 | 125893 | 75.8 |
| 203756_at | ARHGEF17 | Hs.533719 | 9828 | 75.8 |
| 207007_at | NR1I3 | Hs.349642 | 9970 | 75.8 |
| 206609_at | MAGEC1 | Hs.132194 | 9947 | 75.8 |
| 205960_at | PDK4 | Hs.8364 | 5166 | 75.8 |
| 204419_x_at | HBG1 /// HBG2 | Hs.567283 | 3047 /// 3048 | 75.2 |
| 204561_x_at | APOC2 | Hs.75615 | 344 | 75.2 |
| 204007_at | FCGR3B | — | 2215 | 75.2 |
| 36004_at | IKBKG | Hs.43505 | 8517 | 75.2 |
| 215766_at | GSTA1 | Hs.446309 | 2938 | 75.2 |
| 211826_s_at | AFFI | Hs.480190 | 4299 | 75.2 |
| 219685_at | TMEM35 | Hs.45140 | 59353 | 75.2 |
| 206168_at | ZC3H7B | Hs.474970 | 23264 | 75.2 |
| 216351_x_at | DAZ1 /// DAZ3 /// DAZ2 /// DAZ4 | Hs.558522 | 1617 /// 57054 /// 57055 /// 57135 | 75.2 |
| 37145_at | GNLY | Hs.105806 | 10578 | 74.5 |
| 221627_at | TRIM10 | Hs.274295 | 10107 | 74.5 |
| 56197_at | PLSCR3 /// MGC40107 | Hs.433154 | 254863 /// 57048 | 74.5 |
| 218805_at | GIMAP5 | Hs.412331 | 55340 | 74.5 |
| 221223_x_at | CISH | Hs.8257 | 1154 | 74.5 |
| 41657_at | STK11 | Hs.515005 | 6794 | 74.5 |
| 214205_x_at | TXNL2 | Hs.42644 | 10539 | 74.5 |
| 219716_at | APOL6 | Hs.257352 | 80830 | 74.5 |
| 216036_x_at | WDTC1 | Hs.469154 | 23038 | 74.5 |
| 221016_s_at | TCF7L1 | Hs.516297 | 83439 | 74.5 |
| 209988_s_at | ASCL1 | Hs.524672 | 429 | 74.5 |
| 221601_s_at | FAIM3 | Hs.58831 | 9214 | 73.9 |
| 209031_at | IGSF4 | Hs.370510 | 23705 | 73.9 |
| 204882_at | ARHGAP25 | Hs.531807 | 9938 | 73.9 |
| 38149_at | ARHGAP25 | Hs.531807 | 9938 | 73.9 |
| 201703_s_at | PPP1R10 | Hs.106019 | 5514 | 73.9 |
| 219613_s_at | SIRT6 | Hs.423756 | 51548 | 73.9 |
| 207979_s_at | CD8B1 | Hs.405667 | 926 | 73.9 |
| 220158_at | LGALS14 | Hs.24236 | 56891 | 73.9 |
| 205515_at | PRSS12 | Hs.445857 | 8492 | 73.9 |
| 209335_at | DCN | Hs.156316 | 1634 | 73.9 |
| 211560_s_at | ALAS2 | Hs.522666 | 212 | 73.2 |
| 205898_at | CX3CR1 | Hs.78913 | 1524 | 73.2 |
| 216950_s_at | FCGR1A | Hs.77424 | 2209 | 73.2 |
| 218335_x_at | TNIP2 | Hs.368551 | 79155 | 73.2 |
| 202197_at | MTMR3 | Hs.570462 | 8897 | 73.2 |
| 215761_at | DMXL2 | Hs.511386 | 23312 | 73.2 |
| 212154_at | SDC2 | Hs.1501 | 6383 | 73.2 |
| 211465_x_at | FUT6 | Hs.32956 | 2528 | 73.2 |
| 208591_s_at | PDE3B | Hs.445711 | 5140 | 73.2 |
| 214792_x_at | VAMP2 | Hs.25348 | 6844 | 73.2 |
| 206766_at | ITGA10 | Hs.158237 | 8515 | 73.2 |
| 216807_at | KIAA1751 | Hs.232092 | 85452 | 73.2 |
| 217120_s_at | CRSP2 | Hs.407604 | 9282 | 73.2 |
| 220991_s_at | RNF32 | Hs.490715 | 140545 | 73.2 |
| 215706_x_at | ZYX | Hs.490415 | 7791 | 72.6 |
| 206380_s_at | PFC | Hs.53155 | 5199 | 72.6 |

TABLE 2-continued

Genes over-expressed in AML

| probe | Gene | Unigene | Locus | % AML cases with overexpression |
|---|---|---|---|---|
| 218888_s_at | NETO2 | Hs.444046 | 81831 | 72.6 |
| 207554_x_at | TBXA2R | Hs.442530 | 6915 | 72.6 |
| 210301_at | XDH | Hs.250 | 7498 | 72.6 |
| 64899_at | LPPR2 | Hs.6846 | 64748 | 72.6 |
| 206278_at | PTAFR | Hs.77542 | 5724 | 72.6 |
| 64883_at | MOSPD2 | Hs.190043 | 158747 | 72.6 |
| 220009_at | LONRF3 | Hs.144266 | 79836 | 72.6 |
| 215775_at | THBS1 | Hs.164226 | 7057 | 72.6 |
| 214529_at | TSHB | Hs.406687 | 7252 | 72.6 |
| 210366_at | SLCO1B1 | Hs.449738 | 10599 | 72.6 |
| 213515_x_at | HBG1 /// HBG2 | Hs.567283 | 3047 /// 3048 | 72.0 |
| 202510_s_at | TNFAIP2 | Hs.525607 | 7127 | 72.0 |
| 221067_s_at | MGC10946 | Hs.130692 | 80763 | 72.0 |
| 217211_at | — | — | — | 72.0 |
| 215701_at | ZNF291 | Hs.458986 | 49855 | 72.0 |
| 217999_s_at | PHLDA1 | Hs.484885 | 22822 | 72.0 |
| 206121_at | AMPD1 | Hs.89570 | 270 | 72.0 |
| 205816_at | ITGB8 | Hs.285724 | 3696 | 72.0 |
| 207796_x_at | KLRD1 | Hs.524251 | 3824 | 72.0 |
| 216776_at | BCAP29 | Hs.303787 | 55973 | 72.0 |
| 204385_at | KYNU | Hs.470126 | 8942 | 71.3 |
| 219992_at | TAC3 | Hs.9730 | 6866 | 71.3 |
| 202637_s_at | ICAM1 | Hs.515126 | 3383 | 71.3 |
| 219020_at | HS1BP3 | Hs.531785 | 64342 | 71.3 |
| 209644_x_at | CDKN2A | Hs.512599 | 1029 | 71.3 |
| 202448_s_at | ZYG11BL | Hs.147950 | 10444 | 71.3 |
| 206209_s_at | CA4 | Hs.89485 | 762 | 71.3 |
| 209863_s_at | TP73L | Hs.137569 | 8626 | 71.3 |
| 205695_at | SDS | Hs.439023 | 10993 | 71.3 |
| 216755_at | OSBPL10 | Hs.150122 | 114884 | 71.3 |
| 206010_at | HABP2 | Hs.422542 | 3026 | 71.3 |
| 221399_at | EDA2R | Hs.302017 | 60401 | 71.3 |
| 206589_at | GFI1 | Hs.73172 | 2672 | 70.7 |
| 209117_at | WBP2 | Hs.514489 | 23558 | 70.7 |
| 78047_s_at | LOC400843 | — | 400843 | 70.7 |
| 204445_s_at | ALOX5 | Hs.89499 | 240 | 70.7 |
| 221421_s_at | ADAMTS12 | Hs.481865 | 81792 | 70.7 |
| 208495_at | TLX3 | Hs.249125 | 30012 | 70.7 |
| 214414_x_at | HBA2 | Hs.398636 | 3040 | 70.1 |
| 200660_at | S100A11 | Hs.417004 | 6282 | 70.1 |
| 214836_x_at | IGKC /// IGKV1-5 | Hs.449621 | 28299 /// 3514 | 70.1 |
| 217418_x_at | MS4A1 | Hs.438040 | 931 | 70.1 |
| 212975_at | DENND3 | Hs.18166 | 22898 | 70.1 |
| 121_at | PAX8 | Hs.469728 | 7849 | 70.1 |
| 205627_at | CDA | Hs.466910 | 978 | 70.1 |
| 210184_at | ITGAX | Hs.248472 | 3687 | 70.1 |
| 214054_at | DOK2 | Hs.71215 | 9046 | 70.1 |
| 211612_s_at | IL13RA1 | Hs.496646 | 3597 | 70.1 |
| 206178_at | PLA2G5 | Hs.319438 | 5322 | 70.1 |
| 207852_at | CXCL5 | Hs.89714 | 6374 | 70.1 |
| 208092_s_at | FAM49A | Hs.467769 | 81553 | 70.1 |
| 220429_at | NDST3 | Hs.480596 | 9348 | 70.1 |
| 210601_at | CDH6 | Hs.171054 | 1004 | 70.1 |
| 205818_at | DBC1 | Hs.532316 | 1620 | 70.1 |
| 212099_at | RHOB | Hs.502876 | 388 | 69.4 |
| 205899_at | CCNA1 | Hs.417050 | 8900 | 69.4 |
| 211649_x_at | IGHM | Hs.538461 | 3507 | 69.4 |
| 215253_s_at | DSCR1 | Hs.282326 | 1827 | 69.4 |
| 207044_at | THRB | Hs.187861 | 7068 | 69.4 |
| 203038_at | PTPRK | Hs.155919 | 5796 | 69.4 |
| 220533_at | — | — | — | 69.4 |
| 220194_at | FLJ14001 | Hs.570821 | 79730 | 69.4 |
| 211709_s_at | CLEC11A | Hs.512680 | 6320 | 68.8 |
| 214916_x_at | IGH@ /// IGHA1 /// IGHA2 /// IGHD /// IGHG1 /// IGHG2 /// IGHG3 /// IGHM /// MGC27165 /// LOC390714 | Hs.51063 5 | 283650 /// 3492 /// 3493 /// 3494 /// 3495 /// 3500 /// 3501 /// 3502 /// 3507 /// 390714 | 68.8 |

TABLE 2-continued

Genes over-expressed in AML

| probe | Gene | Unigene | Locus | % AML cases with overexpression |
|---|---|---|---|---|
| 200808_s_at | ZYX | Hs.490415 | 7791 | 68.8 |
| 219799_s_at | DHRS9 | Hs.179608 | 10170 | 68.8 |
| 214617_at | PRF1 | Hs.2200 | 5551 | 68.8 |
| 210966_x_at | LARP1 | Hs.292078 | 23367 | 68.8 |
| 220283_at | KIAA1822L | Hs.123515 | 79802 | 68.8 |
| 217263_x_at | RUNX1 | Hs.149261 | 861 | 68.8 |
| 220161_s_at | EPB41L4B | Hs.269180 | 54566 | 68.8 |
| 222005_s_at | GNG3 | Hs.179915 | 2785 | 68.8 |
| 214616_at | HIST1H3E | Hs.443021 | 8353 | 68.8 |
| 219761_at | CLEC1A | Hs.29549 | 51267 | 68.8 |
| 214225_at | PIN4 | Hs.118076 | 5303 | 68.8 |
| 206831_s_at | ARSD | Hs.528631 | 414 | 68.8 |
| 206022_at | NDP | Hs.522615 | 4693 | 68.8 |
| 221651_x_at | IGKC /// IGKV1-5 | Hs.449621 | 28299 /// 3514 | 68.2 |
| 64486_at | CORO1B | Hs.6191 | 57175 | 68.2 |
| 220326_s_at | FLJ10357 | Hs.35125 | 55701 | 68.2 |
| 207960_at | — | — | — | 68.2 |
| 218937_at | ZNF434 | Hs.123295 | 54925 | 68.2 |
| 207990_x_at | ACRV1 | Hs.169222 | 56 | 68.2 |
| 207477_at | — | — | — | 68.2 |
| 217020_at | RARB | Hs.436538 | 5915 | 68.2 |
| 37953_s_at | ACCN2 | Hs.274361 | 41 | 68.2 |
| 211741_x_at | PSG3 | Hs.555887 | 5671 | 68.2 |
| 205033_s_at | DEFA1 /// DEFA3 | Hs.294176 | 1667 /// 1668 | 67.5 |
| 208949_s_at | LGALS3 /// GALIG | Hs.531081 | 3958 /// 81625 | 67.5 |
| 213096_at | TMCC2 | Hs.6360 | 9911 | 67.5 |
| 206438_x_at | FLJ12975 | Hs.167165 | 79867 | 67.5 |
| 219892_at | TM6SF1 | Hs.513094 | 53346 | 67.5 |
| 209235_at | CLCN7 | Hs.459649 | 1186 | 67.5 |
| 221752_at | SSH1 | Hs.199763 | 54434 | 67.5 |
| 208514_at | KCNE1 | Hs.121495 | 3753 | 67.5 |
| 219741_x_at | ZNF552 | Hs.560727 | 79818 | 67.5 |
| 215479_at | SEMA6A | Hs.156967 | 57556 | 67.5 |
| 35147_at | MCF2L | Hs.170422 | 23263 | 67.5 |
| 204251_s_at | Cep164 | Hs.504009 | 22897 | 67.5 |
| 209437_s_at | SPON1 | Hs.445818 | 10418 | 67.5 |
| 207252_at | INE1 | Hs.534372 | 8552 | 67.5 |
| 215796_at | TRAV20 | Hs.512090 | 28663 | 67.5 |
| 205431_s_at | BMP5 | Hs.296648 | 653 | 67.5 |
| 210783_x_at | CLEC11A | Hs.512680 | 6320 | 66.9 |
| 205098_at | CCR1 | Hs.301921 | 1230 | 66.9 |
| 213446_s_at | IQGAP1 | Hs.430551 | 8826 | 66.9 |
| 206761_at | CD96 | Hs.142023 | 10225 | 66.9 |
| 206170_at | ADRB2 | Hs.2551 | 154 | 66.9 |
| 214746_s_at | ZNF467 | Hs.112158 | 168544 | 66.9 |
| 207704_s_at | GAS7 | Hs.462214 | 8522 | 66.9 |
| 211889_x_at | CEACAM1 | Hs.512682 | 634 | 66.9 |
| 215745_at | C4orf9 | Hs.398178 | 8602 | 66.9 |
| 36742_at | TRIM15 | Hs.309602 | 89870 | 66.9 |
| 209087_x_at | MCAM | Hs.511397 | 4162 | 66.9 |
| 205338_s_at | DCT | Hs.301865 | 1638 | 66.9 |
| 221252_s_at | GSG1 | Hs.240053 | 83445 | 66.9 |
| 217048_at | — | — | — | 66.9 |
| 221273_s_at | DKFZP761H1710 | Hs.512767 | 83459 | 66.9 |
| 214065_s_at | CIB2 | Hs.129867 | 10518 | 66.9 |
| 220378_at | TCP11 | Hs.435371 | 6954 | 66.9 |
| 207446_at | TLR6 | Hs.366986 | 10333 | 66.9 |
| 203911_at | RAP1GA1 | Hs.148178 | 5909 | 66.2 |
| 207636_at | SERPINI2 | Hs.445555 | 5276 | 66.2 |
| 216809_at | CYLC1 | Hs.444230 | 1538 | 66.2 |
| 219579_at | RAB3IL1 | Hs.13759 | 5866 | 66.2 |
| 207113_s_at | TNF | Hs.241570 | 7124 | 66.2 |
| 221866_at | TFEB | Hs.485360 | 7942 | 66.2 |
| 217629_at | — | Hs.446662 | — | 66.2 |
| 220944_at | PGLYRP4 | Hs.58356 | 57115 | 66.2 |
| 207919_at | ART1 | Hs.382188 | 417 | 66.2 |
| 215883_at | LOC401210 | Hs.534797 | 401210 | 66.2 |
| 216164_at | LRRN5 | Hs.26312 | 10446 | 66.2 |
| 217614_at | POLR2E | Hs.24301 | 5434 | 66.2 |
| 221394_at | TAAR2 | Hs.272382 | 9287 | 66.2 |
| 213880_at | LGR5 | Hs.172176 | 8549 | 66.2 |
| 221052_at | TDRKH | Hs.584859 | 11022 | 66.2 |

TABLE 2-continued

Genes over-expressed in AML

| probe | Gene | Unigene | Locus | % AML cases with overexpression |
|---|---|---|---|---|
| 215808_at | KLK10 | Hs.275464 | 5655 | 66.2 |
| 215477_at | DPY19L1P1 | Hs.331147 | 89231 | 66.2 |
| 208018_s_at | HCK | Hs.126521 | 3055 | 65.6 |
| 202812_at | GAA | Hs.1437 | 2548 | 65.6 |
| 203555_at | PTPN18 | Hs.516390 | 26469 | 65.6 |
| 49327_at | SIRT3 | Hs.555969 | 23410 | 65.6 |
| 211641_x_at | — | Hs.64568 | — | 65.6 |
| 205221_at | HGD | Hs.368254 | 3081 | 65.6 |
| 211977_at | GPR107 | Hs.512461 | 57720 | 65.6 |
| 220357_s_at | SGK2 | Hs.472793 | 10110 | 65.6 |
| 208593_x_at | CRHR1 | Hs.417628 | 1394 | 65.6 |
| 206713_at | NTNG1 | Hs.143707 | 22854 | 65.6 |
| 207991_x_at | ACRV1 | Hs.169222 | 56 | 65.6 |
| 44783_s_at | HEY1 | Hs.234434 | 23462 | 65.6 |
| 213732_at | TCF3 | Hs.371282 | 6929 | 65.6 |
| 214315_x_at | CALR | Hs.515162 | 811 | 65.0 |
| 202833_s_at | SERPINA1 | Hs.525557 | 5265 | 65.0 |
| 204446_s_at | ALOX5 | Hs.89499 | 240 | 65.0 |
| 204334_at | KLF7 | Hs.471221 | 8609 | 65.0 |
| 213622_at | COL9A2 | Hs.418012 | 1298 | 65.0 |
| 206337_at | CCR7 | Hs.370036 | 1236 | 65.0 |
| 218829_s_at | CHD7 | Hs.20395 | 55636 | 65.0 |
| 217580_x_at | ARL6IP2 | Hs.190440 | 64225 | 65.0 |
| 207973_x_at | ACRV1 | Hs.169222 | 56 | 65.0 |
| 219142_at | RASL11B | Hs.8035 | 65997 | 65.0 |
| 215126_at | — | Hs.537255 | — | 65.0 |
| 203700_s_at | DIO2 | Hs.202354 | 1734 | 65.0 |
| 206964_at | CML2 | Hs.458287 | 51471 | 65.0 |
| 212014_x_at | CD44 | Hs.502328 | 960 | 64.3 |
| 207152_at | NTRK2 | Hs.584783 | 4915 | 64.3 |
| 205686_s_at | CD86 | Hs.171182 | 942 | 64.3 |
| 210325_at | CD1A | Hs.1309 | 909 | 64.3 |
| 215822_x_at | MYT1 | Hs.279562 | 4661 | 64.3 |
| 210894_s_at | CEP2 | Hs.443976 | 11190 | 64.3 |
| 214759_at | WTAP | Hs.446091 | 9589 | 64.3 |
| 206032_at | DSC3 | Hs.41690 | 1825 | 64.3 |
| 202150_s_at | NEDD9 | Hs.37982 | 4739 | 64.3 |
| 216688_at | — | Hs.543737 | — | 64.3 |
| 216285_at | DGCR14 | Hs.517407 | 8220 | 64.3 |
| 211429_s_at | SERPINA1 | Hs.525557 | 5265 | 63.7 |
| 205131_x_at | CLEC11A | Hs.512680 | 6320 | 63.7 |
| 209906_at | C3AR1 | Hs.567242 | 719 | 63.7 |
| 206177_s_at | ARG1 | Hs.440934 | 383 | 63.7 |
| 204158_s_at | TCIRG1 | Hs.495985 | 10312 | 63.7 |
| 212193_s_at | LARP1 | Hs.292078 | 23367 | 63.7 |
| 216557_x_at | IGHA1 /// IGHG1 /// IGHG3 | Hs.558342 | 3493 /// 3500 /// 3502 | 63.7 |
| 214726_x_at | ADD1 | Hs.183706 | 118 | 63.7 |
| 200769_s_at | MAT2A | Hs.516157 | 4144 | 63.7 |
| 56829_at | NIBP | Hs.26814 | 83696 | 63.7 |
| 204650_s_at | APBB3 | Hs.529449 | 10307 | 63.7 |
| 217117_x_at | MUC3A | Hs.554764 | 4584 | 63.7 |
| 201341_at | ENC1 | Hs.104925 | 8507 | 63.7 |
| 201984_s_at | EGFR | Hs.488293 | 1956 | 63.7 |
| 209133_s_at | COMMD4 | Hs.351327 | 54939 | 63.7 |
| 214081_at | PLXDC1 | Hs.125036 | 57125 | 63.7 |
| 221060_s_at | TLR4 | Hs.174312 | 7099 | 63.1 |
| 213826_s_at | — | — | — | 63.1 |
| 209474_s_at | ENTPD1 | Hs.374230 | 953 | 63.1 |
| 211413_s_at | PADI4 | Hs.522969 | 23569 | 63.1 |
| 216774_at | — | — | — | 63.1 |
| 207716_at | KRTHA8 | Hs.248188 | 8687 | 63.1 |
| 207777_s_at | SP140 | Hs.471576 | 11262 | 63.1 |
| 206309_at | LECT1 | Hs.421391 | 11061 | 63.1 |
| 215167_at | CRSP2 | Hs.407604 | 9282 | 63.1 |
| 214034_at | ARTS-1 | Hs.436186 | 51752 | 63.1 |
| 205382_s_at | DF | Hs.155597 | 1675 | 62.4 |
| 214973_x_at | IGHD | Hs.560238 | 3495 | 62.4 |
| 211101_x_at | LILRA2 | Hs.534394 | 11027 | 62.4 |
| 209498_at | CEACAM1 | Hs.512682 | 634 | 62.4 |
| 209467_s_at | MKNK1 | Hs.371594 | 8569 | 62.4 |
| 209002_s_at | CALCOCO1 | Hs.156667 | 57658 | 62.4 |
| 211881_x_at | IGLJ3 | Hs.517453 | 28831 | 62.4 |
| 202723_s_at | FOXO1A | Hs.370666 | 2308 | 62.4 |

TABLE 2-continued

Genes over-expressed in AML

| probe | Gene | Unigene | Locus | % AML cases with overexpression |
|---|---|---|---|---|
| 210031_at | CD3Z | Hs.156445 | 919 | 62.4 |
| 217269_s_at | PRSS7 | Hs.149473 | 5651 | 62.4 |
| 204073_s_at | C11orf9 | Hs.473109 | 745 | 62.4 |
| 216446_at | GLIS1 | Hs.306691 | 148979 | 62.4 |
| 216377_x_at | ALPPL2 | Hs.333509 | 251 | 62.4 |
| 214735_at | PIP3-E | Hs.146100 | 26034 | 62.4 |
| 209371_s_at | SH3BP2 | Hs.167679 | 6452 | 62.4 |
| 222106_at | PRND | Hs.406696 | 23627 | 62.4 |
| 221119_at | FLJ20184 | Hs.272787 | 54848 | 62.4 |
| 214610_at | CYP11B1 | Hs.184927 | 1584 | 62.4 |
| 201852_x_at | COL3A1 | Hs.443625 | 1281 | 62.4 |
| 211471_s_at | RAB36 | Hs.369557 | 9609 | 62.4 |
| 205781_at | C16orf7 | Hs.164410 | 9605 | 62.4 |
| 211203_s_at | CNTN1 | Hs.567249 | 1272 | 62.4 |
| 211516_at | IL5RA | Hs.68876 | 3568 | 62.4 |
| 216539_at | ATXN3L | Hs.382641 | 92552 | 62.4 |
| 207759_s_at | DISC1 /// C1orf136 | Hs.13318 | 27185 /// 400574 | 62.4 |
| 205433_at | BCHE | Hs.420483 | 590 | 62.4 |
| 212587_s_at | PTPRC | Hs.192039 | 5788 | 61.8 |
| 203332_s_at | INPP5D | Hs.262886 | 3635 | 61.8 |
| 204972_at | OAS2 | Hs.584785 | 4939 | 61.8 |
| 207111_at | EMR1 | Hs.2375 | 2015 | 61.8 |
| 201482_at | QSCN6 | Hs.518374 | 5768 | 61.8 |
| 207643_s_at | TNFRSF1A | Hs.279594 | 7132 | 61.8 |
| 201673_s_at | GYS1 | Hs.386225 | 2997 | 61.8 |
| 207376_at | VENTX | Hs.125231 | 27287 | 61.8 |
| 211883_x_at | CEACAM1 | Hs.512682 | 634 | 61.8 |
| 211824_x_at | NALP1 | Hs.513902 | 22861 | 61.8 |
| 208452_x_at | MYO9B | Hs.123198 | 4650 | 61.8 |
| 206520_x_at | SIGLEC6 | Hs.397255 | 946 | 61.8 |
| 216034_at | SUHW1 | Hs.178665 | 129025 | 61.8 |
| 214903_at | — | Hs.25422 | — | 61.8 |
| 213756_s_at | HSF1 | Hs.530227 | 3297 | 61.8 |
| 219150_s_at | CENTA1 | Hs.121593 | 11033 | 61.8 |
| 221466_at | P2RY4 | Hs.533929 | 5030 | 61.8 |
| 220888_s_at | C20orf32 | Hs.473144 | 57091 | 61.8 |
| 207367_at | ATP12A | Hs.147111 | 479 | 61.8 |
| 41469_at | PI3 | Hs.112341 | 5266 | 61.8 |
| 203736_s_at | PPFIBP1 | Hs.172445 | 8496 | 61.8 |
| 203768_s_at | STS | Hs.522578 | 412 | 61.8 |
| 215234_at | — | Hs.66185 | — | 61.8 |
| 215489_x_at | HOMER3 | Hs.410683 | 9454 | 61.1 |
| 206881_s_at | LILRA3 | Hs.113277 | 11026 | 61.1 |
| 211100_x_at | LILRA2 | Hs.534394 | 11027 | 61.1 |
| 211650_x_at | — | Hs.448957 | — | 61.1 |
| 203828_s_at | IL32 | Hs.943 | 9235 | 61.1 |
| 201887_at | IL13RA1 | Hs.496646 | 3597 | 61.1 |
| 219717_at | FLJ20280 | Hs.518674 | 54876 | 61.1 |
| 210773_s_at | FPRL1 | Hs.99855 | 2358 | 61.1 |
| 207984_s_at | MPP2 | Hs.514208 | 4355 | 61.1 |
| 217024_x_at | PTPNS1 | Hs.128846 | 140885 | 61.1 |
| 202885_s_at | PPP2R1B | Hs.584790 | 5519 | 61.1 |
| 215525_at | — | — | — | 61.1 |
| 219792_at | AGMAT | Hs.567583 | 79814 | 61.1 |
| 217008_s_at | GRM7 | Hs.475336 | 2917 | 61.1 |
| 211039_at | CHRNA1 | Hs.434419 | 1134 | 61.1 |
| 204686_at | IRS1 | Hs.471508 | 3667 | 61.1 |
| 221671_x_at | IGKC /// IGKV1-5 | Hs.449621 | 28299 /// 3514 | 60.5 |
| 38487_at | STAB1 | Hs.301989 | 23166 | 60.5 |
| 205592_at | SLC4A1 | Hs.443948 | 6521 | 60.5 |
| 207459_x_at | GYPB | — | 2994 | 60.5 |
| 215498_s_at | MAP2K3 | Hs.514012 | 5606 | 60.5 |
| 217799_x_at | UBE2H | Hs.344165 | 7328 | 60.5 |
| 38710_at | OTUB1 | Hs.473788 | 55611 | 60.5 |
| 207691_x_at | ENTPD1 | Hs.374230 | 953 | 60.5 |
| 219991_at | SLC2A9 | Hs.444612 | 56606 | 60.5 |
| 219229_at | SLCO3A1 | Hs.311187 | 28232 | 60.5 |
| 211405_x_at | IFNA17 | Hs.282276 | 3451 | 60.5 |
| 202895_s_at | PTPNS1 | Hs.128846 | 140885 | 60.5 |
| 220951_s_at | ACF | Hs.499643 | 29974 | 60.5 |
| 213001_at | ANGPTL2 | Hs.521731 | 23452 | 60.5 |
| 215057_at | — | Hs.496916 | — | 60.5 |
| 207093_s_at | OMG | Hs.584786 | 4974 | 60.5 |

TABLE 2-continued

Genes over-expressed in AML

| probe | Gene | Unigene | Locus | % AML cases with overexpression |
|---|---|---|---|---|
| 211255_x_at | DEDD | Hs.517342 | 9191 | 60.5 |
| 204397_at | EML2 | Hs.24178 | 24139 | 60.5 |
| 214485_at | ODF1 | Hs.159274 | 4956 | 60.5 |
| 208346_at | PPBPL2 | Hs.3134 | 10895 | 60.5 |
| 209840_s_at | LRRN3 | Hs.3781 | 54674 | 60.5 |
| 204850_s_at | DCX | Hs.34780 | 1641 | 60.5 |
| 215379_x_at | IGL@ /// IGLC1 /// IGLC2 /// IGLV3-25 /// IGLV2-14 /// IGLJ3 | Hs.449585 | 28793 /// 28815 /// 28831 /// 3535 /// 3537 /// 3538 | 59.9 |
| 204745_x_at | MT1G | Hs.433391 | 4495 | 59.9 |
| 212588_at | PTPRC | Hs.192039 | 5788 | 59.9 |
| 216063_at | HBBP1 | Hs.20205 | 3044 | 59.9 |
| 221747_at | TNS1 | Hs.471381 | 7145 | 59.9 |
| 212969_x_at | EML3 | Hs.379785 | 256364 | 59.9 |
| 216542_x_at | IGHG1 /// MGC27165 | Hs.584764 | 283650 /// 3500 | 59.9 |
| 38340_at | HIP1R | Hs.524815 | 9026 | 59.9 |
| 213380_x_at | MSTP9 | Hs.475654 | 11223 | 59.9 |
| 160020_at | MMP14 | Hs.2399 | 4323 | 59.9 |
| 219538_at | WDR5B | Hs.567513 | 54554 | 59.9 |
| 217397_at | — | Hs.428848 | — | 59.9 |
| 216243_s_at | IL1RN | Hs.81134 | 3557 | 59.9 |
| 219316_s_at | C14orf58 | Hs.509966 | 55640 | 59.9 |
| 33323_r_at | SFN | Hs.523718 | 2810 | 59.9 |
| 216488_s_at | ATP11A | Hs.29189 | 23250 | 59.9 |
| 219702_at | PLAC1 | Hs.496811 | 10761 | 59.9 |
| 206044_s_at | BRAF | Hs.324250 | 673 | 59.9 |
| 205156_s_at | ACCN2 | Hs.274361 | 41 | 59.9 |
| 211287_x_at | CSF2RA | Hs.520937 | 1438 | 59.9 |
| 210127_at | RAB6B | Hs.2152 | 51560 | 59.9 |
| 221996_s_at | CLTB | Hs.484241 | 1212 | 59.9 |
| 216851_at | IGLJ3 | Hs.517453 | 28831 | 59.9 |
| 210219_at | SP100 | Hs.369056 | 6672 | 59.9 |
| 215480_at | KIAA0509 | Hs.554381 | 57242 | 59.9 |
| 211635_x_at | IGHV1-69 | Hs.449011 | 28461 | 59.2 |
| 54970_at | DKFZp761I2123 | Hs.77978 | 83637 | 59.2 |
| 216560_x_at | IGLC1 /// IGLC2 | Hs.449585 /// Hs.555877 | 3537 /// 3538 | 59.2 |
| 220954_s_at | PILRB | Hs.530084 | 29990 | 59.2 |
| 64942_at | GPR153 | Hs.531581 | 387509 | 59.2 |
| 219259_at | SEMA4A | Hs.408846 | 64218 | 59.2 |
| 214438_at | HLX1 | Hs.74870 | 3142 | 59.2 |
| 214329_x_at | TNFSF10 | Hs.478275 | 8743 | 59.2 |
| 211640_x_at | IGHV1-69 | Hs.449011 | 28461 | 59.2 |
| 209436_at | SPON1 | Hs.445818 | 10418 | 59.2 |
| 222329_x_at | ANKRD17 | Hs.518804 | 26057 | 59.2 |
| 220375_s_at | — | — | — | 59.2 |
| 207277_at | CD209 | Hs.278694 | 30835 | 59.2 |
| 202409_at | LOC492304 | Hs.568449 | 492304 | 59.2 |
| 34408_at | RTN2 | Hs.47517 | 6253 | 59.2 |
| 216106_at | LOC145678 | Hs.23777 | 145678 | 59.2 |
| 214454_at | ADAMTS2 | Hs.23871 | 9509 | 59.2 |
| 220230_s_at | CYB5R2 | Hs.414362 | 51700 | 59.2 |
| 202192_s_at | GAS7 | Hs.462214 | 8522 | 58.6 |
| 210706_s_at | RNF24 | Hs.114180 | 11237 | 58.6 |
| 215116_s_at | DNM1 | Hs.522413 | 1759 | 58.6 |
| 208978_at | CRIP2 | Hs.534309 | 1397 | 58.6 |
| 211822_s_at | NALP1 | Hs.513902 | 22861 | 58.6 |
| 205203_at | PLD1 | Hs.478230 | 5337 | 58.6 |
| 220475_at | SLC28A3 | Hs.584952 | 64078 | 58.6 |
| 202958_at | PTPN9 | Hs.445775 | 5780 | 58.6 |
| 221082_s_at | NDRG3 | Hs.437338 | 57446 | 58.6 |
| 213957_s_at | CAP350 | Hs.413045 | 9857 | 58.6 |
| 219190_s_at | EIF2C4 | Hs.471492 | 192670 | 58.6 |
| 220082_at | PPP1R14D | Hs.192927 | 54866 | 58.6 |
| 219746_at | DPF3 | Hs.162868 | 8110 | 58.6 |
| 215524_x_at | TRA@ /// TRDV2 /// TRAV20 /// TRAJ17 /// TRAC /// MGC40069 | Hs.369380 | 28517 /// 28663 /// 28738 /// 28755 /// 348035 /// 6955 | 58.6 |

TABLE 2-continued

Genes over-expressed in AML

| probe | Gene | Unigene | Locus | % AML cases with overexpression |
|---|---|---|---|---|
| 207706_at | USH2A | Hs.232072 | 7399 | 58.6 |
| 211456_x_at | LOC440737 | Hs.568244 | 440737 | 58.0 |
| 200872_at | S100A10 | Hs.143873 | 6281 | 58.0 |
| 201666_at | TIMP1 | Hs.522632 | 7076 | 58.0 |
| 200661_at | PPGB | Hs.517076 | 5476 | 58.0 |
| 218660_at | DYSF | Hs.252180 | 8291 | 58.0 |
| 205789_at | CD1D | Hs.1799 | 912 | 58.0 |
| 222218_s_at | PILRA | Hs.444407 | 29992 | 58.0 |
| 179_at | PMS2L11 | — | 441263 | 58.0 |
| 217493_x_at | NCR2 | Hs.194721 | 9436 | 58.0 |
| 77508_r_at | RABEP2 | Hs.555978 | 79874 | 58.0 |
| 221757_at | MGC17330 | Hs.26670 | 113791 | 58.0 |
| 207954_at | GATA2 | Hs.367725 | 2624 | 58.0 |
| 219194_at | SEMA4G | Hs.567556 | 57715 | 58.0 |
| 205294_at | BAIAP2 | Hs.128316 | 10458 | 58.0 |
| 35776_at | ITSN1 | Hs.160324 | 6453 | 58.0 |
| 205254_x_at | TCF7 | Hs.519580 | 6932 | 58.0 |
| 204237_at | GULP1 | Hs.470887 | 51454 | 58.0 |
| 221409_at | OR2S2 | Hs.553540 | 56656 | 58.0 |
| 201668_x_at | MARCKS | Hs.519909 | 4082 | 58.0 |
| 215639_at | SH2D3C | Hs.306412 | 10044 | 58.0 |
| 203703_s_at | — | — | — | 58.0 |
| 208121_s_at | PTPRO | Hs.160871 | 5800 | 58.0 |
| 207158_at | APOBEC1 | Hs.560 | 339 | 58.0 |
| 220910_at | FRAS1 | Hs.369448 | 80144 | 58.0 |
| 221339_at | OR10C1 | Hs.553838 | 442194 | 58.0 |
| 221034_s_at | TEX13B | Hs.333130 | 56156 | 58.0 |
| 211986_at | AHNAK | Hs.568948 | 79026 | 57.3 |
| 208248_x_at | APLP2 | Hs.370247 | 334 | 57.3 |
| 216491_x_at | IGHM | Hs.538461 | 3507 | 57.3 |
| 204086_at | PRAME | Hs.30743 | 23532 | 57.3 |
| 210889_s_at | FCGR2B | Hs.492655 | 2213 | 57.3 |
| 204498_s_at | ADCY9 | Hs.391860 | 115 | 57.3 |
| 211633_x_at | IGHG1 | Hs.578081 | 3500 | 57.3 |
| 206011_at | CASP1 | Hs.2490 | 834 | 57.3 |
| 212516_at | CENTD2 | Hs.503165 | 116985 | 57.3 |
| 203233_at | IL4R | Hs.513457 | 3566 | 57.3 |
| 201802_at | SLC29A1 | Hs.25450 | 2030 | 57.3 |
| 204981_at | SLC22A18 | Hs.50868 | 5002 | 57.3 |
| 209060_x_at | NCOA3 | Hs.382168 | 8202 | 57.3 |
| 213900_at | C9orf61 | Hs.118003 | 9413 | 57.3 |
| 215521_at | PHC3 | Hs.529592 | 80012 | 57.3 |
| 214421_x_at | CYP2C9 | Hs.282624 | 1559 | 57.3 |
| 220288_at | MYO15A | Hs.462390 | 51168 | 57.3 |
| 207303_at | PDE1C | Hs.487897 | 5137 | 57.3 |
| 220866_at | ADAMTS6 | Hs.344757 | 11174 | 57.3 |
| 213103_at | STARD13 | Hs.507704 | 90627 | 57.3 |
| 207345_at | FST | Hs.9914 | 10468 | 57.3 |
| 211469_s_at | CXCR6 | Hs.34526 | 10663 | 57.3 |
| 219331_s_at | FLJ10748 | Hs.10414 | 55220 | 57.3 |
| 215391_at | MAP1A | Hs.194301 | 4130 | 57.3 |
| 204515_at | HSD3B1 | Hs.364941 | 3283 | 57.3 |
| 211821_x_at | GYPA | Hs.434973 | 2993 | 56.7 |
| 200935_at | CALR | Hs.515162 | 811 | 56.7 |
| 206940_s_at | POU4F1 | Hs.211588 | 5457 | 56.7 |
| 202878_s_at | C1QR1 | Hs.97199 | 22918 | 56.7 |
| 210356_x_at | MS4A1 | Hs.438040 | 931 | 56.7 |
| 210119_at | KCNJ15 | Hs.411299 | 3772 | 56.7 |
| 37796_at | LRCH4 | Hs.125742 | 4034 | 56.7 |
| 203561_at | FCGR2A | Hs.352642 | 2212 | 56.7 |
| 211102_s_at | LILRA2 | Hs.534394 | 11027 | 56.7 |
| 208262_x_at | MEFV | Hs.173730 | 4210 | 56.7 |
| 201108_s_at | THBS1 | Hs.164226 | 7057 | 56.7 |
| 201332_s_at | STAT6 | Hs.524518 | 6778 | 56.7 |
| 205488_at | GZMA | Hs.90708 | 3001 | 56.7 |
| 216678_at | WDR10 | Hs.477537 | 55764 | 56.7 |
| 217377_x_at | NTRK3 | Hs.410969 | 4916 | 56.7 |
| 206954_at | WIT-1 | Hs.567499 | 51352 | 56.7 |
| 219333_s_at | CAPN10 | Hs.112218 | 11132 | 56.7 |
| 218554_s_at | ASH1L | Hs.491060 | 55870 | 56.7 |
| 205374_at | SLN | Hs.334629 | 6588 | 56.7 |
| 208292_at | BMP10 | Hs.158317 | 27302 | 56.7 |
| 219859_at | CLEC4E | Hs.236516 | 26253 | 56.7 |
| 205643_s_at | PPP2R2B | Hs.193825 | 5521 | 56.7 |
| 214632_at | NRP2 | Hs.471200 | 8828 | 56.7 |

TABLE 2-continued

Genes over-expressed in AML

| probe | Gene | Unigene | Locus | % AML cases with overexpression |
|---|---|---|---|---|
| 220544_at | TSKS | Hs.515858 | 60385 | 56.7 |
| 215049_x_at | CD163 | Hs.504641 | 9332 | 56.1 |
| 213733_at | MYO1F | Hs.408451 | 4542 | 56.1 |
| 209166_s_at | MAN2B1 | Hs.356769 | 4125 | 56.1 |
| 204774_at | EVI2A | Hs.567266 | 2123 | 56.1 |
| 210915_x_at | TRBV19 /// TRBC1 | Hs.567471 | 28568 /// 28639 | 56.1 |
| 218019_s_at | PDXK | Hs.284491 | 8566 | 56.1 |
| 58367_s_at | ZNF419 | Hs.98593 | 79744 | 56.1 |
| 205944_s_at | CLTCL1 | Hs.368266 | 8218 | 56.1 |
| 203184_at | FBN2 | Hs.519294 | 2201 | 56.1 |
| 213958_at | CD6 | Hs.502710 | 923 | 56.1 |
| 206723_s_at | EDG4 | Hs.122575 | 9170 | 56.1 |
| 206722_s_at | EDG4 | Hs.122575 | 9170 | 56.1 |
| 210197_at | ITPK1 | Hs.308122 | 3705 | 56.1 |
| 206586_at | CNR2 | Hs.73037 | 1269 | 56.1 |
| 214377_s_at | CTRL | Hs.405774 | 1506 | 56.1 |
| 216294_s_at | KIAA1109 | Hs.408142 | 84162 | 56.1 |
| 207330_at | PZP | Hs.480143 | 5858 | 56.1 |
| 213590_at | SLC16A5 | Hs.369554 | 9121 | 56.1 |
| 207188_at | CDK3 | Hs.584745 | 1018 | 56.1 |
| 212793_at | DAAM2 | Hs.436590 | 23500 | 56.1 |
| 215951_at | KIAA1055 | Hs.567426 | 23102 | 56.1 |
| 206199_at | CEACAM7 | Hs.74466 | 1087 | 56.1 |
| 214521_at | HES2 | Hs.118727 | 54626 | 56.1 |
| 213678_at | RP11-444E17.5 | Hs.12840 | 441151 | 56.1 |
| 206144_at | MAGI1 | Hs.567389 | 9223 | 56.1 |
| 209835_x_at | CD44 | Hs.502328 | 960 | 55.4 |
| 208438_s_at | FGR | Hs.1422 | 2268 | 55.4 |
| 203665_at | HMOX1 | Hs.517581 | 3162 | 55.4 |
| 216832_at | RUNX1T1 | Hs.368431 | 862 | 55.4 |
| 336_at | TBXA2R | Hs.442530 | 6915 | 55.4 |
| 211668_s_at | PLAU | Hs.77274 | 5328 | 55.4 |
| 210166_at | TLR5 | Hs.114408 | 7100 | 55.4 |
| 211599_x_at | MET | Hs.132966 | 4233 | 55.4 |
| 221112_at | IL1RAPL2 | Hs.188763 | 26280 | 55.4 |
| 210904_s_at | IL13RA1 | Hs.496646 | 3597 | 55.4 |
| 37831_at | SIPA1L3 | Hs.157259 | 23094 | 55.4 |
| 217563_at | CLOCK | Hs.436975 | 9575 | 55.4 |
| 209270_at | LAMB3 | Hs.497636 | 3914 | 55.4 |
| 216910_at | XPNPEP2 | Hs.170499 | 7512 | 55.4 |
| 212664_at | TUBB4 | Hs.110837 | 10382 | 55.4 |
| 206319_s_at | SPINLW1 | Hs.121084 | 57119 | 55.4 |
| 217479_at | FLJ45455 | Hs.441035 | 388336 | 55.4 |
| 204122_at | TYROBP | Hs.515369 | 7305 | 54.8 |
| 204588_s_at | SLC7A7 | Hs.513147 | 9056 | 54.8 |
| 218157_x_at | CDC42SE1 | Hs.22065 | 56882 | 54.8 |
| 203304_at | BAMBI | Hs.533336 | 25805 | 54.8 |
| 201412_at | LRP10 | Hs.525232 | 26020 | 54.8 |
| 209473_at | ENTPD1 | Hs.374230 | 953 | 54.8 |
| 202897_at | PTPNS1 | Hs.128846 | 140885 | 54.8 |
| 214366_s_at | ALOX5 | Hs.89499 | 240 | 54.8 |
| 212252_at | CAMKK2 | Hs.297343 | 10645 | 54.8 |
| 33304_at | ISG20 | Hs.459265 | 3669 | 54.8 |
| 222333_at | ALS2CL | Hs.517937 | 259173 | 54.8 |
| 212818_s_at | ASB1 | Hs.516788 | 51665 | 54.8 |
| 216252_x_at | FAS | Hs.244139 | 355 | 54.8 |
| 216971_s_at | PLEC1 | Hs.434248 | 5339 | 54.8 |
| 205975_s_at | HOXD1 | Hs.83465 | 3231 | 54.8 |
| 206574_s_at | PTP4A3 | Hs.43666 | 11156 | 54.8 |
| 210883_x_at | EFNB3 | Hs.26988 | 1949 | 54.8 |
| 210150_s_at | LAMA5 | Hs.473256 | 3911 | 54.8 |
| 219866_at | CLIC5 | Hs.485489 | 53405 | 54.8 |
| 220684_at | TBX21 | Hs.272409 | 30009 | 54.8 |
| 216196_at | LOC440366 | Hs.567926 | 440366 | 54.8 |
| 208585_at | BTN2A3 | Hs.370522 | 54718 | 54.8 |
| 213960_at | — | Hs.149024 | — | 54.8 |
| 219701_at | TMOD2 | Hs.513734 | 29767 | 54.8 |
| 204351_at | S100P | Hs.2962 | 6286 | 54.1 |
| 211799_x_at | HLA-C | Hs.534125 | 3107 | 54.1 |
| 205786_s_at | ITGAM | Hs.172631 | 3684 | 54.1 |
| 209892_at | FUT4 | Hs.390420 | 2526 | 54.1 |
| 206697_s_at | HP | Hs.513711 | 3240 | 54.1 |
| 203548_s_at | LPL | Hs.180878 | 4023 | 54.1 |
| 205929_at | GPA33 | Hs.437229 | 10223 | 54.1 |

TABLE 2-continued

Genes over-expressed in AML

| probe | Gene | Unigene | Locus | % AML cases with overexpression |
|---|---|---|---|---|
| 216152_at | PDZRN3 | Hs.434900 | 23024 | 54.1 |
| 211908_x_at | — | Hs.585642 | — | 54.1 |
| 219725_at | TREM2 | Hs.435295 | 54209 | 54.1 |
| 214767_s_at | HSPB6 | Hs.534538 | 126393 | 54.1 |
| 208156_x_at | EPPK1 | Hs.200412 | 83481 | 54.1 |
| 219365_s_at | CAMKV | Hs.145156 | 79012 | 54.1 |
| 207733_x_at | PSG9 | Hs.502092 | 5678 | 54.1 |
| 219318_x_at | MED31 | Hs.567493 | 51003 | 54.1 |
| 208004_at | PROL1 | Hs.479905 | 58503 | 54.1 |
| 218692_at | FLJ20366 | Hs.390738 | 55638 | 54.1 |
| 205719_s_at | PAH | Hs.325404 | 5053 | 54.1 |
| 221416_at | PLA2G2F | Hs.302034 | 64600 | 54.1 |
| 205625_s_at | CALB1 | Hs.65425 | 793 | 54.1 |
| 220870_at | — | — | — | 54.1 |
| 207950_s_at | ANK3 | Hs.499725 | 288 | 54.1 |
| 207010_at | GABRB1 | Hs.27283 | 2560 | 54.1 |
| 204150_at | STAB1 | Hs.301989 | 23166 | 53.5 |
| 206050_s_at | RNH1 | Hs.530687 | 6050 | 53.5 |
| 218232_at | C1QA | Hs.9641 | 712 | 53.5 |
| 218136_s_at | SLC25A37 | Hs.122514 | 51312 | 53.5 |
| 205312_at | SPI1 | Hs.502511 | 6688 | 53.5 |
| 208914_at | GGA2 | Hs.460336 | 23062 | 53.5 |
| 200785_s_at | LRP1 | Hs.162757 | 4035 | 53.5 |
| 205900_at | KRT1 | Hs.80828 | 3848 | 53.5 |
| 219243_at | GIMAP4 | Hs.30822 | 55303 | 53.5 |
| 41644_at | SASH1 | Hs.193133 | 23328 | 53.5 |
| 218114_at | GGA1 | Hs.499158 | 26088 | 53.5 |
| 214582_at | PDE3B | Hs.445711 | 5140 | 53.5 |
| 207734_at | LAX1 | Hs.272794 | 54900 | 53.5 |
| 220395_at | DNAJA4 | Hs.513053 | 55466 | 53.5 |
| 218030_at | GIT1 | Hs.514051 | 28964 | 53.5 |
| 205170_at | STAT2 | Hs.530595 | 6773 | 53.5 |
| 205708_s_at | TRPM2 | Hs.369759 | 7226 | 53.5 |
| 216739_at | — | Hs.589088 | — | 53.5 |
| 213236_at | SASH1 | Hs.193133 | 23328 | 53.5 |
| 209466_x_at | PTN | Hs.371249 | 5764 | 53.5 |
| 216973_s_at | HOXB7 | Hs.436181 | 3217 | 53.5 |
| 215178_x_at | ASAHL | Hs.437365 | 27163 | 53.5 |
| 214754_at | MGC22014 | Hs.516107 | 200424 | 53.5 |
| 204556_s_at | DZIP1 | Hs.157002 | 22873 | 53.5 |
| 207608_x_at | CYP1A2 | Hs.1361 | 1544 | 53.5 |
| 210789_x_at | CEACAM3 | Hs.11 | 1084 | 53.5 |
| 215092_s_at | NFAT5 | Hs.371987 | 10725 | 53.5 |
| 211916_s_at | MYO1A | Hs.5394 | 4640 | 53.5 |
| 216750_at | APBB2 | Hs.479602 | 323 | 53.5 |
| 216692_at | ZNF337 | Hs.213735 | 26152 | 53.5 |
| 202803_s_at | ITGB2 | Hs.375957 | 3689 | 52.9 |
| 205495_s_at | GNLY | Hs.105806 | 10578 | 52.9 |
| 201234_at | ILK | Hs.5158 | 3611 | 52.9 |
| 205838_at | GYPA | Hs.434973 | 2993 | 52.9 |
| 218920_at | FLJ10404 | Hs.484289 | 54540 | 52.9 |
| 202436_s_at | CYP1B1 | Hs.154654 | 1545 | 52.9 |
| 203668_at | MAN2C1 | Hs.26232 | 4123 | 52.9 |
| 210895_s_at | CD86 | Hs.171182 | 942 | 52.9 |
| 207270_x_at | CD300C | Hs.2605 | 10871 | 52.9 |
| 203516_at | SNTA1 | Hs.31121 | 6640 | 52.9 |
| 220898_at | — | — | — | 52.9 |
| 207051_at | SLC17A4 | Hs.282931 | 10050 | 52.9 |
| 208578_at | SCN10A | Hs.250443 | 6336 | 52.9 |
| 220577_at | GVIN1 | Hs.494757 | 387751 | 52.9 |
| 207705_s_at | KIAA0980 | Hs.472347 | 22981 | 52.9 |
| 221631_at | CACNA1I | Hs.125116 | 8911 | 52.9 |
| 212157_at | SDC2 | Hs.1501 | 6383 | 52.9 |
| 220881_at | LMO2 | Hs.34560 | 4005 | 52.9 |
| 217474_at | — | Hs.569826 | — | 52.9 |
| 210909_x_at | LPAL2 | Hs.439074 | 80350 | 52.9 |
| 203021_at | SLPI | Hs.517070 | 6590 | 52.2 |
| 38964_r_at | WAS | Hs.2157 | 7454 | 52.2 |
| 203281_s_at | UBE1L | Hs.16695 | 7318 | 52.2 |
| 216401_x_at | LOC400969 /// IGKC | Hs.429466 /// Hs.449621 /// Hs.516184 /// Hs.551722 | 3514 /// 400969 | 52.2 |
| 221565_s_at | FAM26B | Hs.241545 | 51063 | 52.2 |
| 210663_s_at | KYNU | Hs.470126 | 8942 | 52.2 |

TABLE 2-continued

Genes over-expressed in AML

| probe | Gene | Unigene | Locus | % AML cases with overexpression |
|---|---|---|---|---|
| 204632_at | RPS6KA4 | Hs.105584 | 8986 | 52.2 |
| 205926_at | IL27RA | Hs.132781 | 9466 | 52.2 |
| 215833_s_at | SPPL2B | Hs.330742 | 56928 | 52.2 |
| 217502_at | IFIT2 | Hs.437609 | 3433 | 52.2 |
| 1438_at | EPHB3 | Hs.2913 | 2049 | 52.2 |
| 201207_at | TNFAIP1 | Hs.76090 | 7126 | 52.2 |
| 206783_at | FGF4 | Hs.1755 | 2249 | 52.2 |
| 213713_s_at | LOC89944 | Hs.436178 | 89944 | 52.2 |
| 205144_at | FLJ22269 | Hs.567612 | 84179 | 52.2 |
| 221197_s_at | CHAT | Hs.302002 | 1103 | 52.2 |
| 218574_s_at | LMCD1 | Hs.475353 | 29995 | 52.2 |
| 37793_r_at | RAD51L3 | Hs.125244 | 5892 | 52.2 |
| 205503_at | PTPN14 | Hs.19281 | 5784 | 52.2 |
| 201976_s_at | MYO10 | Hs.481720 | 4651 | 52.2 |
| 220833_at | — | — | — | 52.2 |
| 221805_at | NEFL | Hs.521461 | 4747 | 52.2 |
| 203903_s_at | HEPH | Hs.31720 | 9843 | 52.2 |
| 204489_s_at | CD44 | Hs.502328 | 960 | 51.6 |
| 216268_s_at | JAG1 | Hs.224012 | 182 | 51.6 |
| 203666_at | CXCL12 | Hs.522891 | 6387 | 51.6 |
| 202687_s_at | TNFSF10 | Hs.478275 | 8743 | 51.6 |
| 210327_s_at | AGXT | Hs.144567 | 189 | 51.6 |
| 220404_at | GPR97 | Hs.383403 | 222487 | 51.6 |
| 221879_at | CALML4 | Hs.554828 | 91860 | 51.6 |
| 210872_x_at | GAS7 | Hs.462214 | 8522 | 51.6 |
| 201625_s_at | INSIG1 | Hs.520819 | 3638 | 51.6 |
| 40489_at | ATN1 | Hs.143766 | 1822 | 51.6 |
| 211440_x_at | CYP3A43 | Hs.306220 | 64816 | 51.6 |
| 215366_at | SNX13 | Hs.487648 | 23161 | 51.6 |
| 207445_s_at | CCR9 | Hs.225946 | 10803 | 51.6 |
| 219461_at | PAK6 | Hs.513645 | 56924 | 51.6 |
| 206132_at | MCC | Hs.483104 | 4163 | 51.6 |
| 208524_at | GPR15 | Hs.563128 | 2838 | 51.6 |
| 218892_at | DCHS1 | Hs.199850 | 8642 | 51.6 |
| 222166_at | C9orf16 | Hs.522412 | 79095 | 51.6 |
| 215959_at | PPFIBP2 | Hs.16019 | 8495 | 51.6 |
| 216663_s_at | ZMYND10 | Hs.526735 | 51364 | 51.6 |
| 221716_s_at | ACSBG2 | Hs.567599 | 81616 | 51.6 |
| 204309_at | CYP11A1 | Hs.303980 | 1583 | 51.6 |
| 219139_s_at | KIAA1922 | Hs.436604 | 114819 | 51.6 |
| 217023_x_at | TPSAB1 | — | 7177 | 51.0 |
| 211657_at | CEACAM6 | Hs.466814 | 4680 | 51.0 |
| 203104_at | CSF1R | Hs.483829 | 1436 | 51.0 |
| 219563_at | C14orf139 | Hs.41502 | 79686 | 51.0 |
| 209949_at | NCF2 | Hs.518604 | 4688 | 51.0 |
| 210244_at | CAMP | Hs.51120 | 820 | 51.0 |
| 218345_at | HCA112 | Hs.12126 | 55365 | 51.0 |
| 210032_s_at | SPAG6 | Hs.527698 | 9576 | 51.0 |
| 206057_x_at | SPN | Hs.461934 | 6693 | 51.0 |
| 210116_at | SH2D1A | Hs.349094 | 4068 | 51.0 |
| 211864_s_at | FER1L3 | Hs.500572 | 26509 | 51.0 |
| 214180_at | MAN1C1 | Hs.197043 | 57134 | 51.0 |
| 219257_s_at | SPHK1 | Hs.68061 | 8877 | 51.0 |
| 217507_at | SLC11A1 | Hs.471393 | 6556 | 51.0 |
| 201373_at | PLEC1 | Hs.434248 | 5339 | 51.0 |
| 210271_at | NEUROD2 | Hs.554765 | 4761 | 51.0 |
| 221643_s_at | RERE | Hs.463041 | 473 | 51.0 |
| 214928_at | OBSL1 | Hs.526594 | 23363 | 51.0 |
| 205132_at | ACTC | Hs.118127 | 70 | 51.0 |
| 207597_at | ADAM18 | Hs.127930 | 8749 | 51.0 |
| 219310_at | C20orf39 | Hs.124638 | 79953 | 51.0 |
| 216605_s_at | CEACAM21 | Hs.230424 | 90273 | 51.0 |
| 209946_at | VEGFC | Hs.435215 | 7424 | 51.0 |
| 211128_at | EDA | Hs.105407 | 1896 | 51.0 |
| 209621_s_at | PDLIM3 | Hs.85862 | 27295 | 51.0 |
| 217556_at | CLCN4 | Hs.495674 | 1183 | 51.0 |
| 202018_s_at | LTF | Hs.529517 | 4057 | 50.3 |
| 214407_x_at | GYPB | — | 2994 | 50.3 |
| 200931_s_at | VCL | Hs.500101 | 7414 | 50.3 |
| 211637_x_at | — | Hs.383169 | — | 50.3 |
| 216153_x_at | RECK | Hs.254269 | 8434 | 50.3 |
| 213915_at | NKG7 | Hs.10306 | 4818 | 50.3 |
| 205936_s_at | HK3 | Hs.411695 | 3101 | 50.3 |
| 200999_s_at | CKAP4 | Hs.74368 | 10970 | 50.3 |
| 212820_at | DMXL2 | Hs.511386 | 23312 | 50.3 |

TABLE 2-continued

Genes over-expressed in AML

| probe | Gene | Unigene | Locus | % AML cases with overexpression |
|---|---|---|---|---|
| 218380_at | NALP1 | Hs.104305 | 22861 | 50.3 |
| 211433_x_at | KIAA1539 | Hs.301696 | 80256 | 50.3 |
| 202896_s_at | PTPNS1 | Hs.128846 | 140885 | 50.3 |
| 212807_s_at | SORT1 | Hs.485195 | 6272 | 50.3 |
| 204436_at | pp9099 | Hs.458575 | 80301 | 50.3 |
| 215037_s_at | BCL2L1 | Hs.516966 | 598 | 50.3 |
| 212574_x_at | C19orf6 | Hs.515003 | 91304 | 50.3 |
| 211024_s_at | TITF1 | Hs.94367 | 7080 | 50.3 |
| 213633_at | SH3BP1 | Hs.584875 | 23616 | 50.3 |
| 204682_at | LTBP2 | Hs.512776 | 4053 | 50.3 |
| 217849_s_at | CDC42BPB | Hs.569310 | 9578 | 50.3 |
| 206248_at | PRKCE | Hs.97432 | 5581 | 50.3 |
| 206767_at | RBMS3 | Hs.221436 | 27303 | 50.3 |
| 217497_at | ECGF1 | Hs.546251 | 1890 | 50.3 |
| 210763_x_at | NCR3 | Hs.509513 | 259197 | 50.3 |
| 206226_at | HRG | Hs.1498 | 3273 | 50.3 |
| 205368_at | KIAA0773 | Hs.135343 | 9715 | 50.3 |
| 212679_at | TBL2 | Hs.52515 | 26608 | 50.3 |
| 206961_s_at | TRFP | Hs.278434 | 9477 | 50.3 |
| 207039_at | CDKN2A | Hs.512599 | 1029 | 50.3 |
| 206171_at | ADORA3 | Hs.281342 | 140 | 50.3 |
| 217163_at | ESR1 | Hs.208124 | 2099 | 50.3 |
| 219505_at | CECR1 | Hs.170310 | 51816 | 49.7 |
| 213193_x_at | TRBV19 /// TRBC1 | Hs.567471 | 28568 /// 28639 | 49.7 |
| 203973_s_at | CEBPD | Hs.440829 | 1052 | 49.7 |
| 219666_at | MS4A6A | Hs.523702 | 64231 | 49.7 |
| 207697_x_at | LILRB2 | Hs.534386 | 10288 | 49.7 |
| 211926_s_at | MYH9 | Hs.474751 | 4627 | 49.7 |
| 222217_s_at | SLC27A3 | Hs.438723 | 11000 | 49.7 |
| 210075_at | MARCH2 | Hs.445113 | 51257 | 49.7 |
| 220005_at | P2RY13 | Hs.546396 | 53829 | 49.7 |
| 204994_at | MX2 | Hs.926 | 4600 | 49.7 |
| 203065_s_at | CAV1 | Hs.74034 | 857 | 49.7 |
| 214040_s_at | GSN | Hs.522373 | 2934 | 49.7 |
| 207106_s_at | LTK | Hs.434481 | 4058 | 49.7 |
| 216689_x_at | ARHGAP1 | Hs.138860 | 392 | 49.7 |
| 212657_s_at | IL1RN | Hs.81134 | 3557 | 49.7 |
| 202877_s_at | C1QR1 | Hs.97199 | 22918 | 49.7 |
| 209156_s_at | COL6A2 | Hs.420269 | 1292 | 49.7 |
| 202801_at | PRKACA | Hs.194350 | 5566 | 49.7 |
| 212948_at | CAMTA2 | Hs.373952 | 23125 | 49.7 |
| 219534_x_at | CDKN1C | Hs.106070 | 1028 | 49.7 |
| 220066_at | CARD15 | Hs.135201 | 64127 | 49.7 |
| 202627_s_at | SERPINE1 | Hs.414795 | 5054 | 49.7 |
| 205479_s_at | PLAU | Hs.77274 | 5328 | 49.7 |
| 208360_s_at | — | Hs.578373 | — | 49.7 |
| 220290_at | AIM1L | Hs.128738 | 55057 | 49.7 |
| 209594_x_at | PSG9 | Hs.502092 | 5678 | 49.7 |
| 209747_at | TGFB3 | Hs.2025 | 7043 | 49.7 |
| 208314_at | RRH | Hs.352262 | 10692 | 49.7 |
| 208059_at | CCR8 | Hs.113222 | 1237 | 49.7 |
| 205343_at | SULT1C1 | Hs.436123 | 6819 | 49.7 |
| 58916_at | KCTD14 | Hs.17296 | 65987 | 49.7 |
| 206849_at | GABRG2 | Hs.7195 | 2566 | 49.7 |
| 215746_at | C4orf9 | Hs.398178 | 8602 | 49.7 |
| 217452_s_at | B3GALT2 | Hs.518834 | 8707 | 49.7 |
| 221365_at | MLNR | Hs.248126 | 2862 | 49.7 |
| 221451_s_at | OR2W1 | Hs.553526 | 26692 | 49.7 |
| 208704_x_at | APLP2 | Hs.370247 | 334 | 49.0 |
| 208703_s_at | APLP2 | Hs.370247 | 334 | 49.0 |
| 210629_x_at | LST1 | Hs.436066 | 7940 | 49.0 |
| 203518_at | LYST | Hs.532411 | 1130 | 49.0 |
| 207076_s_at | ASS | Hs.160786 | 445 | 49.0 |
| 212765_at | CAMSAP1L1 | Hs.23585 | 23271 | 49.0 |
| 203215_s_at | MYO6 | Hs.149387 | 4646 | 49.0 |
| 201940_at | CPD | Hs.446079 | 1362 | 49.0 |
| 218501_at | ARHGEF3 | Hs.476402 | 50650 | 49.0 |
| 214036_at | — | Hs.288741 | — | 49.0 |
| 206043_s_at | KIAA0703 | Hs.6168 | 9914 | 49.0 |
| 216606_x_at | LYPLA2 /// LYPLA2P1 /// LOC388499 | Hs.534075 | 11313 /// 285840 /// 388499 | 49.0 |
| 220483_s_at | RNF19 | Hs.292882 | 25897 | 49.0 |
| 202764_at | STIM1 | Hs.501735 | 6786 | 49.0 |

TABLE 2-continued

Genes over-expressed in AML

| probe | Gene | Unigene | Locus | % AML cases with overexpression |
|---|---|---|---|---|
| 215083_at | PSPC1 | Hs.213198 | 55269 | 49.0 |
| 201728_s_at | KIAA0100 | Hs.151761 | 9703 | 49.0 |
| 207343_at | LYZL6 | Hs.97477 | 57151 | 49.0 |
| 207936_x_at | RFPL3 | Hs.558455 | 10738 | 49.0 |
| 218822_s_at | NPEPL1 | Hs.528513 | 79716 | 49.0 |
| 201348_at | GPX3 | Hs.386793 | 2878 | 49.0 |
| 210169_at | SEC14L5 | Hs.512856 | 9717 | 49.0 |
| 221453_at | G6PC2 | Hs.283963 | 57818 | 49.0 |
| 217224_at | — | — | — | 49.0 |
| 205152_at | SLC6A1 | Hs.443874 | 6529 | 49.0 |
| 216368_s_at | COL4A3 | Hs.471525 | 1285 | 49.0 |
| 220537_at | MTMR8 | Hs.442892 | 55613 | 49.0 |
| 214236_at | CDC27 | Hs.463295 | 996 | 49.0 |
| 205030_at | FABP7 | Hs.26770 | 2173 | 49.0 |
| 220857_at | — | — | — | 49.0 |
| 205108_s_at | APOB | Hs.120759 | 338 | 49.0 |
| 209631_s_at | GPR37 | Hs.406094 | 2861 | 49.0 |
| 207741_x_at | TPSAB1 /// TPSB2 | Hs.405479 | 64499 /// 7177 | 48.4 |
| 210004_at | OLR1 | Hs.412484 | 4973 | 48.4 |
| 201350_at | FLOT2 | Hs.514038 | 2319 | 48.4 |
| 205227_at | IL1RAP | Hs.478673 | 3556 | 48.4 |
| 208624_s_at | EIF4G1 | Hs.433750 | 1981 | 48.4 |
| 203275_at | IRF2 | Hs.374097 | 3660 | 48.4 |
| 221335_x_at | FLJ12886 | Hs.466875 | 56006 | 48.4 |
| 211372_s_at | IL1R2 | Hs.25333 | 7850 | 48.4 |
| 203029_s_at | PTPRN2 | Hs.490789 | 5799 | 48.4 |
| 205467_at | CASP10 | Hs.5353 | 843 | 48.4 |
| 201893_x_at | DCN | Hs.156316 | 1634 | 48.4 |
| 213639_s_at | ZNF500 | Hs.513316 | 26048 | 48.4 |
| 206058_at | SLC6A12 | Hs.437174 | 6539 | 48.4 |
| 213078_x_at | LOC254531 | Hs.352614 | 254531 | 48.4 |
| 37022_at | PRELP | Hs.76494 | 5549 | 48.4 |
| 220511_s_at | DLC1 | Hs.134296 | 10395 | 48.4 |
| 205411_at | STK4 | Hs.472838 | 6789 | 48.4 |
| 219044_at | FLJ10916 | Hs.516179 | 55258 | 48.4 |
| 218700_s_at | RAB7L1 | Hs.115325 | 8934 | 48.4 |
| 217061_s_at | ETV1 | Hs.22634 | 2115 | 48.4 |
| 207393_at | HCRTR2 | Hs.151624 | 3062 | 48.4 |
| 213776_at | LOC157562 | Hs.27371 | 157562 | 48.4 |
| 208431_s_at | TUB | Hs.568986 | 7275 | 48.4 |
| 213413_at | SBLF | — | 11037 | 48.4 |
| 220908_at | FLJ32855 | Hs.383206 | 80125 | 48.4 |
| 214597_at | SSTR2 | Hs.514451 | 6752 | 48.4 |
| 210586_x_at | RHD | Hs.567331 | 6007 | 47.8 |
| 208891_at | DUSP6 | Hs.298654 | 1848 | 47.8 |
| 204834_at | FGL2 | Hs.520989 | 10875 | 47.8 |
| 211798_x_at | IGLJ3 | Hs.517453 | 28831 | 47.8 |
| 45749_at | FAM65A | Hs.152717 | 79567 | 47.8 |
| 221002_s_at | TSPAN14 | Hs.568777 | 81619 | 47.8 |
| 212443_at | NBEAL2 | Hs.437043 | 23218 | 47.8 |
| 204890_s_at | LCK | Hs.470627 | 3932 | 47.8 |
| 47069_at | PRR5 | — | 55615 | 47.8 |
| 216554_s_at | ENO1 | Hs.517145 | 2023 | 47.8 |
| 209241_x_at | MINK1 | Hs.443417 | 50488 | 47.8 |
| 211269_s_at | IL2RA | Hs.231367 | 3559 | 47.8 |
| 206513_at | AIM2 | Hs.281898 | 9447 | 47.8 |
| 219657_s_at | KLF3 | Hs.298658 | 51274 | 47.8 |
| 219788_at | PILRA | Hs.444407 | 29992 | 47.8 |
| 202485_s_at | MBD2 | Hs.25674 | 8932 | 47.8 |
| 221851_at | LOC90379 | Hs.443636 | 90379 | 47.8 |
| 204975_at | EMP2 | Hs.531561 | 2013 | 47.8 |
| 212272_at | LPIN1 | Hs.467740 | 23175 | 47.8 |
| 209182_s_at | C10orf10 | Hs.93675 | 11067 | 47.8 |
| 211460_at | TTTY9 /// TTY9 | Hs.567607 | 425057 /// 83864 | 47.8 |
| 209908_s_at | TGFB2 | Hs.133379 | 7042 | 47.8 |
| 217767_at | C3 | Hs.529053 | 718 | 47.8 |
| 212575_at | C19orf6 | Hs.515003 | 91304 | 47.8 |
| 207863_at | ADPRH | Hs.99884 | 141 | 47.8 |
| 220565_at | CCR10 | Hs.278446 | 2826 | 47.8 |
| 210644_s_at | LAIR1 | Hs.467288 | 3903 | 47.1 |
| 207809_s_at | ATP6AP1 | Hs.6551 | 537 | 47.1 |
| 216012_at | — | Hs.550193 | — | 47.1 |
| 210314_x_at | TNFSF13 | Hs.54673 | 407977 /// | 47.1 |

TABLE 2-continued

Genes over-expressed in AML

| probe | Gene | Unigene | Locus | % AML cases with overexpression |
|---|---|---|---|---|
| | TNFSF12-TNFSF13 | | 8741 | |
| 207509_s_at | LAIR2 | Hs.43803 | 3904 | 47.1 |
| 214298_x_at | SEPT6 | Hs.496666 | 23157 | 47.1 |
| 221484_at | B4GALT5 | Hs.370487 | 9334 | 47.1 |
| 219890_at | CLEC5A | Hs.446235 | 23601 | 47.1 |
| 203502_at | BPGM | Hs.198365 | 669 | 47.1 |
| 209403_at | TBC1D3 /// TBC1D3C | Hs.105891 | 414060 /// 84218 | 47.1 |
| 216052_x_at | ARTN | Hs.194689 | 9048 | 47.1 |
| 219359_at | FLJ22635 | Hs.353181 | 80162 | 47.1 |
| 209370_s_at | SH3BP2 | Hs.167679 | 6452 | 47.1 |
| 201798_s_at | FER1L3 | Hs.500572 | 26509 | 47.1 |
| 204425_at | ARHGAP4 | Hs.3109 | 393 | 47.1 |
| 209721_s_at | HOM-TES-103 | Hs.15243 | 25900 | 47.1 |
| 206772_at | PTHR2 | Hs.159499 | 5746 | 47.1 |
| 212355_at | KIAA0323 | Hs.558466 | 23351 | 47.1 |
| 204735_at | PDE4A | Hs.89901 | 5141 | 47.1 |
| 213006_at | CEBPD | Hs.440829 | 1052 | 47.1 |
| 221036_s_at | APH1B | Hs.511703 | 83464 | 47.1 |
| 220987_s_at | C11orf17 /// NUAK2 | Hs.131180 | 56672 /// 81788 | 47.1 |
| 210200_at | WWP2 | Hs.408458 | 11060 | 47.1 |
| 205742_at | TNNI3 | Hs.512709 | 7137 | 47.1 |
| 218950_at | CENTD3 | Hs.25277 | 64411 | 47.1 |
| 220032_at | FLJ21986 | Hs.189652 | 79974 | 47.1 |
| 214636_at | CALCB | Hs.534305 | 797 | 47.1 |
| 50965_at | RAB26 | Hs.3797 | 25837 | 47.1 |
| 209766_at | PRDX3 | Hs.523302 | 10935 | 47.1 |
| 204105_s_at | NRCAM | Hs.21422 | 4897 | 47.1 |
| 220874_at | — | — | — | 47.1 |
| 218272_at | FLJ20699 | Hs.435832 | 55020 | 47.1 |
| 217369_at | IGHG1 /// LOC440361 /// LOC440370 | Hs.512293 | 3500 /// 440361 /// 440370 | 47.1 |
| 214786_at | MAP3K1 | Hs.584779 | 4214 | 47.1 |
| 207732_s_at | DLG3 | Hs.522680 | 1741 | 47.1 |
| 208188_at | KRT9 | Hs.2783 | 3857 | 47.1 |
| 218959_at | HOXC10 | Hs.44276 | 3226 | 47.1 |
| 203180_at | ALDH1A3 | Hs.459538 | 220 | 47.1 |
| 220701_at | — | — | — | 47.1 |
| 206651_s_at | CPB2 | Hs.512937 | 1361 | 47.1 |
| 206228_at | PAX2 | Hs.155644 | 5076 | 47.1 |
| 202411_at | IFI27 | Hs.532634 | 3429 | 46.5 |
| 211284_s_at | GRN | Hs.514220 | 2896 | 46.5 |
| 202295_s_at | CTSH | Hs.148641 | 1512 | 46.5 |
| 211581_x_at | LST1 | Hs.436066 | 7940 | 46.5 |
| 218581_at | ABHD4 | Hs.445665 | 63874 | 46.5 |
| 219528_s_at | BCL11B | Hs.510396 | 64919 | 46.5 |
| 219332_at | MICAL-L2 | Hs.376617 | 79778 | 46.5 |
| 210944_s_at | CAPN3 | Hs.143261 | 825 | 46.5 |
| 220751_s_at | C5orf4 | Hs.519694 | 10826 | 46.5 |
| 217052_x_at | — | — | — | 46.5 |
| 206515_at | CYP4F3 | Hs.106242 | 4051 | 46.5 |
| 57082_at | LDLRAP1 | Hs.189782 | 26119 | 46.5 |
| 203168_at | CREBL1 | Hs.42853 | 1388 | 46.5 |
| 219358_s_at | CENTA2 | Hs.514063 | 55803 | 46.5 |
| 216791_at | TMEM92 | Hs.224630 | 162461 | 46.5 |
| 207601_at | SULT1B1 | Hs.129742 | 27284 | 46.5 |
| 219337_at | C1orf159 | Hs.235095 | 54991 | 46.5 |
| 201333_s_at | ARHGEF12 | Hs.24598 | 23365 | 46.5 |
| 213551_x_at | PCGF2 | Hs.371617 | 7703 | 46.5 |
| 211810_s_at | GALC | Hs.513439 | 2581 | 46.5 |
| 207216_at | TNFSF8 | Hs.494901 | 944 | 46.5 |
| 217359_s_at | NCAM1 | Hs.503878 | 4684 | 46.5 |
| 206677_at | KRTHA1 | Hs.41696 | 3881 | 46.5 |
| 208851_s_at | THY1 | Hs.134643 | 7070 | 46.5 |
| 204751_x_at | DSC2 | Hs.95612 | 1824 | 46.5 |
| 221303_at | PCDHB1 | Hs.278950 | 29930 | 46.5 |
| 220574_at | SEMA6D | Hs.511265 | 80031 | 46.5 |
| 206943_at | TGFBR1 | Hs.494622 | 7046 | 46.5 |
| 206888_s_at | ARHGDIG | Hs.534303 | 398 | 46.5 |
| 216474_x_at | TPSAB1 | — | 7177 | 45.9 |
| 207134_x_at | TPSAB1 | — | 7177 | 45.9 |
| 221269_s_at | SH3BGRL3 | Hs.109051 | 83442 | 45.9 |

TABLE 2-continued

Genes over-expressed in AML

| probe | Gene | Unigene | Locus | % AML cases with overexpression |
|---|---|---|---|---|
| 208450_at | LGALS2 | Hs.531776 | 3957 | 45.9 |
| 216320_x_at | MST1 | Hs.512587 | 4485 | 45.9 |
| 203882_at | ISGF3G | Hs.1706 | 10379 | 45.9 |
| 204320_at | COL11A1 | Hs.523446 | 1301 | 45.9 |
| 204103_at | CCL4 | Hs.75703 | 6351 | 45.9 |
| 207187_at | JAK3 | Hs.515247 | 3718 | 45.9 |
| 220240_s_at | TMCO3 | Hs.317593 | 55002 | 45.9 |
| 219428_s_at | PXMP4 | Hs.368717 | 11264 | 45.9 |
| 206150_at | TNFRSF7 | Hs.355307 | 939 | 45.9 |
| 212823_s_at | PLEKHG3 | Hs.509637 | 26030 | 45.9 |
| 210864_x_at | HFE | Hs.233325 | 3077 | 45.9 |
| 215672_s_at | KIAA0828 | Hs.195058 | 23382 | 45.9 |
| 204280_at | RGS14 | Hs.9347 | 10636 | 45.9 |
| 216635_at | — | Hs.492815 | — | 45.9 |
| 203769_s_at | STS | Hs.522578 | 412 | 45.9 |
| 216904_at | COL6A1 | Hs.474053 | 1291 | 45.9 |
| 211880_x_at | PCDHGA1 | — | 56114 | 45.9 |
| 205991_s_at | PRRX1 | Hs.283416 | 5396 | 45.9 |
| 221605_s_at | PIPOX | Hs.462585 | 51268 | 45.9 |
| 222324_at | OBSCN | Hs.231655 | 84033 | 45.9 |
| 222361_at | — | Hs.551805 | — | 45.9 |
| 210084_x_at | TPSAB1 | — | 7177 | 45.2 |
| 205557_at | BPI | Hs.529019 | 671 | 45.2 |
| 219371_s_at | KLF2 | Hs.107740 | 10365 | 45.2 |
| 201331_s_at | STAT6 | Hs.524518 | 6778 | 45.2 |
| 221824_s_at | MARCH8 | Hs.499489 | 220972 | 45.2 |
| 205831_at | CD2 | Hs.523500 | 914 | 45.2 |
| 209286_at | CDC42EP3 | Hs.369574 | 10602 | 45.2 |
| 213260_at | FOXC1 | Hs.348883 | 2296 | 45.2 |
| 218154_at | GSDMDC1 | Hs.118983 | 79792 | 45.2 |
| 211417_x_at | GGT1 | Hs.444164 | 2678 | 45.2 |
| 215364_s_at | KIAA0467 | Hs.301943 | 23334 | 45.2 |
| 218148_at | FLJ13111 | Hs.288382 | 80152 | 45.2 |
| 212682_s_at | BC002942 | Hs.150540 | 91289 | 45.2 |
| 205238_at | CXorf34 | Hs.496501 | 79979 | 45.2 |
| 210234_at | GRM4 | Hs.429018 | 2914 | 45.2 |
| 218818_at | FHL3 | Hs.57687 | 2275 | 45.2 |
| 221489_s_at | SPRY4 | Hs.323308 | 81848 | 45.2 |
| 209695_at | PTP4A3 | Hs.43666 | 11156 | 45.2 |
| 213010_at | PRKCDBP | Hs.434044 | 112464 | 45.2 |
| 208185_x_at | — | — | — | 45.2 |
| 216499_at | — | Hs.409816 | — | 45.2 |
| 210796_x_at | SIGLEC6 | Hs.397255 | 946 | 45.2 |
| 219873_at | COLEC11 | Hs.32603 | 78989 | 45.2 |
| 202198_s_at | MTMR3 | Hs.570462 | 8897 | 45.2 |
| 221405_at | LOC51190 | — | 51190 | 45.2 |
| 215056_at | — | Hs.498015 | — | 45.2 |
| 220984_s_at | SLCO5A1 | Hs.443609 | 81796 | 45.2 |
| 215246_at | HDCMA18P | Hs.278635 | 51574 | 45.2 |
| 207308_at | SLCO1A2 | Hs.46440 | 6579 | 45.2 |
| 217350_at | LOC160313 | Hs.527883 | 160313 | 45.2 |
| 202597_at | IRF6 | Hs.355827 | 3664 | 45.2 |
| 203649_s_at | PLA2G2A | Hs.466804 | 5320 | 45.2 |
| 212425_at | SCAMP1 | Hs.482587 | 9522 | 45.2 |
| 221266_s_at | TM7SF4 | Hs.208036 | 81501 | 45.2 |
| 206633_at | CHRNA1 | Hs.434419 | 1134 | 45.2 |
| 206021_at | SCAND2 | Hs.513102 | 54581 | 45.2 |
| 214079_at | DHRS2 | Hs.272499 | 10202 | 45.2 |
| 203535_at | S100A9 | Hs.112405 | 6280 | 44.6 |
| 215382_x_at | TPSAB1 | — | 7177 | 44.6 |
| 215806_x_at | TRGC2 /// TRGV9 /// LOC442532 /// LOC442670 /// TARP | Hs.534032 | 442532 /// 442670 /// 445347 /// 6967 /// 6983 | 44.6 |
| 200742_s_at | TPP1 | Hs.523454 | 1200 | 44.6 |
| 39854_r_at | PNPLA2 | Hs.118463 | 57104 | 44.6 |
| 201642_at | IFNGR2 | Hs.517240 | 3460 | 44.6 |
| 203385_at | DGKA | Hs.524488 | 1606 | 44.6 |
| 205614_x_at | MST1 | Hs.512587 | 4485 | 44.6 |
| 209047_at | AQP1 | Hs.76152 | 358 | 44.6 |
| 40829_at | WDTC1 | Hs.469154 | 23038 | 44.6 |
| 213348_at | CDKN1C | Hs.106070 | 1028 | 44.6 |
| 221541_at | CRISPLD2 | Hs.513779 | 83716 | 44.6 |
| 204773_at | IL11RA | Hs.558346 | 3590 | 44.6 |

TABLE 2-continued

Genes over-expressed in AML

| probe | Gene | Unigene | Locus | % AML cases with overexpression |
|---|---|---|---|---|
| 213093_at | PRKCA | Hs.531704 | 5578 | 44.6 |
| 61874_at | C9orf7 | Hs.62003 | 11094 | 44.6 |
| 202274_at | ACTG2 | Hs.516105 | 72 | 44.6 |
| 209948_at | KCNMB1 | Hs.484099 | 3779 | 44.6 |
| 203735_x_at | PPFIBP1 | Hs.172445 | 8496 | 44.6 |
| 206105_at | AFF2 | Hs.496911 | 2334 | 44.6 |
| 219255_x_at | IL17RB | Hs.558512 | 55540 | 44.6 |
| 215130_s_at | MGC35048 | Hs.460217 | 124152 | 44.6 |
| 205613_at | SYT17 | Hs.258326 | 51760 | 44.6 |
| 214320_x_at | CYP2A6 | Hs.439056 | 1548 | 44.6 |
| 206176_at | BMP6 | Hs.285671 | 654 | 44.6 |
| 220979_s_at | ST6GALNAC5 | Hs.303609 | 81849 | 44.6 |
| 219225_at | PGBD5 | Hs.520463 | 79605 | 44.6 |
| 207602_at | TMPRSS11D | Hs.132195 | 9407 | 44.6 |
| 210603_at | MGC10646 | Hs.330986 | 84779 | 44.6 |
| 217199_s_at | STAT2 | Hs.530595 | 6773 | 44.6 |
| 216472_at | ITSN1 | Hs.160324 | 6453 | 44.6 |
| 221013_s_at | APOL2 | Hs.474740 | 23780 | 44.6 |
| 205880_at | PRKD1 | Hs.508999 | 5587 | 44.6 |
| 210072_at | CCL19 | Hs.50002 | 6363 | 44.6 |
| 216230_x_at | SMPD1 | Hs.498173 | 6609 | 44.6 |
| 207712_at | BAGE | Hs.545789 | 574 | 44.6 |
| 214985_at | — | Hs.44690 | — | 44.6 |
| 204326_x_at | MT1X | Hs.374950 | 4501 | 43.9 |
| 204620_s_at | CSPG2 | Hs.443681 | 1462 | 43.9 |
| 216384_x_at | LOC440085 | Hs.568172 | 440085 | 43.9 |
| 208683_at | CAPN2 | Hs.350899 | 824 | 43.9 |
| 215633_x_at | LST1 | Hs.436066 | 7940 | 43.9 |
| 203562_at | FEZ1 | Hs.224008 | 9638 | 43.9 |
| 211426_x_at | GNAQ | Hs.269782 | 2776 | 43.9 |
| 217045_x_at | NCR2 | Hs.194721 | 9436 | 43.9 |
| 214475_x_at | CAPN3 | Hs.143261 | 825 | 43.9 |
| 206187_at | PTGIR | Hs.458324 | 5739 | 43.9 |
| 216981_x_at | SPN | Hs.461934 | 6693 | 43.9 |
| 209791_at | PADI2 | Hs.33455 | 11240 | 43.9 |
| 210660_at | LILRA1 | Hs.534393 | 11024 | 43.9 |
| 222155_s_at | GPR172A | Hs.6459 | 79581 | 43.9 |
| 217200_x_at | CYB561 | Hs.355264 | 1534 | 43.9 |
| 205865_at | ARID3A | Hs.501296 | 1820 | 43.9 |
| 207458_at | C8orf51 | Hs.245886 | 78998 | 43.9 |
| 209228_x_at | TUSC3 | Hs.426324 | 7991 | 43.9 |
| 220227_at | CDH4 | Hs.473231 | 1002 | 43.9 |
| 208322_s_at | ST3GAL1 | Hs.584803 | 6482 | 43.9 |
| 205285_s_at | FYB | Hs.370503 | 2533 | 43.9 |
| 203400_s_at | TF | Hs.518267 | 7018 | 43.9 |
| 217001_x_at | HLA-DOA | Hs.351874 | 3111 | 43.9 |
| 215687_x_at | PLCB1 | Hs.431173 | 23236 | 43.9 |
| 217552_x_at | CR1 | Hs.334019 | 1378 | 43.9 |
| 216762_at | ANKRD15 | Hs.306764 | 23189 | 43.9 |
| 214072_x_at | NENF | Hs.461787 | 29937 | 43.9 |
| 207347_at | ERCC6 | — | 2074 | 43.9 |
| 216132_at | ASTN2 | Hs.195633 | 23245 | 43.9 |
| 219720_s_at | C14orf118 | Hs.410231 | 55668 | 43.9 |
| 206426_at | MLANA | Hs.154069 | 2315 | 43.9 |
| 214388_at | PFAAP5 | Hs.507680 | 10443 | 43.9 |
| 219411_at | ELMO3 | Hs.377416 | 79767 | 43.9 |
| 210816_s_at | CYB561 | Hs.355264 | 1534 | 43.9 |
| 220322_at | IL1F9 | Hs.211238 | 56300 | 43.9 |
| 216280_s_at | DICER1 | Hs.87889 | 23405 | 43.9 |
| 213425_at | WNT5A | Hs.152213 | 7474 | 43.9 |
| 205683_x_at | TPSAB1 | — | 7177 | 43.3 |
| 212859_x_at | MT1E | Hs.534330 | 4493 | 43.3 |
| 214183_s_at | TKTL1 | Hs.102866 | 8277 | 43.3 |
| 203305_at | F13A1 | Hs.335513 | 2162 | 43.3 |
| 205859_at | LY86 | Hs.170081 | 9450 | 43.3 |
| 204490_s_at | CD44 | Hs.502328 | 960 | 43.3 |
| 209367_at | STXBP2 | Hs.534352 | 6813 | 43.3 |
| 211582_x_at | LST1 | Hs.436066 | 7940 | 43.3 |
| 208626_s_at | VAT1 | Hs.514199 | 10493 | 43.3 |
| 219559_at | C20orf59 | Hs.512686 | 63910 | 43.3 |
| 200862_at | DHCR24 | Hs.498727 | 1718 | 43.3 |
| 213350_at | RPS11 | Hs.433529 | 6205 | 43.3 |
| 207854_at | GYPE | Hs.371903 | 2996 | 43.3 |
| 202180_s_at | MVP | Hs.513488 | 9961 | 43.3 |
| 213198_at | ACVR1B | Hs.438918 | 91 | 43.3 |

TABLE 2-continued

Genes over-expressed in AML

| probe | Gene | Unigene | Locus | % AML cases with overexpression |
|---|---|---|---|---|
| 221602_s_at | FAIM3 | Hs.58831 | 9214 | 43.3 |
| 213110_s_at | COL4A5 | Hs.369089 | 1287 | 43.3 |
| 221080_s_at | DENND1C | Hs.236449 | 79958 | 43.3 |
| 203490_at | ELF4 | Hs.271940 | 2000 | 43.3 |
| 216042_at | TNFRSF25 | Hs.462529 | 8718 | 43.3 |
| 209889_at | SEC31L2 | Hs.18889 | 25956 | 43.3 |
| 207765_s_at | KIAA1539 | Hs.301696 | 80256 | 43.3 |
| 204921_at | GAS8 | Hs.431792 | 2622 | 43.3 |
| 206159_at | GDF10 | Hs.2171 | 2662 | 43.3 |
| 221895_at | MOSPD2 | Hs.190043 | 158747 | 43.3 |
| 204841_s_at | EEA1 | Hs.567367 | 8411 | 43.3 |
| 220162_s_at | CARD9 | Hs.528581 | 64170 | 43.3 |
| 215995_x_at | — | — | — | 43.3 |
| 209569_x_at | D4S234E | Hs.518595 | 27065 | 43.3 |
| 210185_at | CACNB1 | Hs.635 | 782 | 43.3 |
| 220485_s_at | SIRPB2 | Hs.22974 | 55423 | 43.3 |
| 215486_at | PRPS1L1 | Hs.169284 | 221823 | 43.3 |
| 219537_x_at | DLL3 | Hs.127792 | 10683 | 43.3 |
| 221367_at | MOS | Hs.533432 | 4342 | 43.3 |
| 216545_at | LOC441886 | — | 441886 | 43.3 |
| 202821_s_at | LPP | Hs.444362 | 4026 | 43.3 |
| 205206_at | KAL1 | Hs.521869 | 3730 | 43.3 |
| 203862_s_at | ACTN2 | Hs.498178 | 88 | 43.3 |
| 204944_at | PTPRG | Hs.146050 | 5793 | 43.3 |
| 202917_s_at | S100A8 | Hs.416073 | 6279 | 42.7 |
| 206461_x_at | MT1H | Hs.438462 | 4496 | 42.7 |
| 210746_s_at | EPB42 | Hs.368642 | 2038 | 42.7 |
| 211571_s_at | CSPG2 | Hs.443681 | 1462 | 42.7 |
| 219777_at | GIMAP6 | Hs.105468 | 474344 | 42.7 |
| 209919_x_at | GGT1 | Hs.444164 | 2678 | 42.7 |
| 202250_s_at | WDR42A | Hs.492236 | 50717 | 42.7 |
| 221011_s_at | LBH | Hs.567598 | 81606 | 42.7 |
| 219868_s_at | ANKFY1 | Hs.513875 | 51479 | 42.7 |
| 213716_s_at | SECTM1 | Hs.558009 | 6398 | 42.7 |
| 219620_x_at | FLJ20245 | Hs.495541 | 54863 | 42.7 |
| 220653_at | ZIM2 | — | 23619 | 42.7 |
| 213925_at | C1orf95 | Hs.116827 | 375057 | 42.7 |
| 217033_x_at | NTRK3 | Hs.410969 | 4916 | 42.7 |
| 201295_s_at | WSB1 | Hs.446017 | 26118 | 42.7 |
| 201982_s_at | PAPPA | Hs.494928 | 5069 | 42.7 |
| 219388_at | GRHL2 | Hs.161160 | 79977 | 42.7 |
| 203915_at | CXCL9 | Hs.77367 | 4283 | 42.7 |
| 208169_s_at | PTGER3 | Hs.445000 | 5733 | 42.7 |
| 215985_at | C6orf12 | Hs.302037 | 80862 | 42.7 |
| 204743_at | TAGLN3 | Hs.169330 | 29114 | 42.7 |
| 207687_at | INHBC | Hs.374664 | 3626 | 42.7 |
| 200795_at | SPARCL1 | Hs.62886 | 8404 | 42.7 |
| 218814_s_at | C1orf75 | Hs.445386 | 55248 | 42.7 |
| 204230_s_at | SLC17A7 | Hs.375616 | 57030 | 42.7 |
| 214944_at | PHLPPL | Hs.531564 | 23035 | 42.7 |
| 204272_at | LGALS4 | Hs.5302 | 3960 | 42.7 |
| 213783_at | MFNG | Hs.517603 | 4242 | 42.7 |
| 206704_at | CLCN5 | Hs.166486 | 1184 | 42.7 |
| 205638_at | BAI3 | Hs.13261 | 577 | 42.7 |
| 204955_at | SRPX | Hs.15154 | 8406 | 42.7 |
| 201028_s_at | CD99 | Hs.495605 | 4267 | 42.0 |
| 216833_x_at | GYPB /// GYPE | Hs.371903 | 2994 /// 2996 | 42.0 |
| 202497_x_at | SLC2A3 | Hs.419240 | 6515 | 42.0 |
| 203645_s_at | CD163 | Hs.504641 | 9332 | 42.0 |
| 212830_at | EGFL5 | Hs.494977 | 1955 | 42.0 |
| 207675_x_at | ARTN | Hs.194689 | 9048 | 42.0 |
| 204619_s_at | CSPG2 | Hs.443681 | 1462 | 42.0 |
| 211495_x_at | TNFSF13 /// TNFSF12-TNFSF13 | Hs.54673 | 407977 /// 8741 | 42.0 |
| 204088_at | P2RX4 | Hs.321709 | 5025 | 42.0 |
| 205798_at | IL7R | Hs.362807 | 3575 | 42.0 |
| 40850_at | FKBP8 | Hs.173464 | 23770 | 42.0 |
| 219104_at | RNF141 | Hs.44685 | 50862 | 42.0 |
| 211685_s_at | NCALD | Hs.492427 | 83988 | 42.0 |
| 209663_s_at | ITGA7 | Hs.524484 | 3679 | 42.0 |
| 219689_at | SEMA3G | Hs.59729 | 56920 | 42.0 |
| 202695_s_at | STK17A | Hs.268887 | 9263 | 42.0 |
| 204829_s_at | FOLR2 | Hs.433159 | 2350 | 42.0 |

TABLE 2-continued

Genes over-expressed in AML

| probe | Gene | Unigene | Locus | % AML cases with overexpression |
|---|---|---|---|---|
| 207184_at | SLC6A13 | Hs.504398 | 6540 | 42.0 |
| 219236_at | PAQR6 | Hs.235873 | 79957 | 42.0 |
| 205636_at | SH3GL3 | Hs.270055 | 6457 | 42.0 |
| 38766_at | SRCAP | Hs.584857 | 10847 | 42.0 |
| 208957_at | TXNDC4 | Hs.154023 | 23071 | 42.0 |
| 220785_at | UTS2 | Hs.162200 | 10911 | 42.0 |
| 212477_at | CENTB2 | Hs.478746 | 23527 | 42.0 |
| 206985_at | HSD17B3 | Hs.477 | 3293 | 42.0 |
| 208349_at | TRPA1 | Hs.137674 | 8989 | 42.0 |
| 209683_at | FAM49A | Hs.467769 | 81553 | 42.0 |
| 205064_at | SPRR1B | Hs.1076 | 6699 | 42.0 |
| 214245_at | RPS14 | Hs.381126 | 6208 | 42.0 |
| 216907_x_at | KIR3DL2 | Hs.567298 | 3812 | 42.0 |
| 210533_at | MSH4 | Hs.216639 | 4438 | 42.0 |
| 34063_at | RECQL5 | Hs.514480 | 9400 | 42.0 |
| 214287_s_at | CDC2L5 | Hs.233552 | 8621 | 42.0 |
| 210505_at | ADH7 | Hs.389 | 131 | 42.0 |
| 207501_s_at | FGF12 | Hs.584758 | 2257 | 42.0 |
| 216920_s_at | TRGC2 /// TRGV9 /// LOC442532 /// LOC442670 /// TARP | Hs.534032 | 442532 /// 442670 /// 445347 /// 6967 /// 6983 | 41.4 |
| 211144_x_at | TRGC2 | Hs.567345 | 6967 | 41.4 |
| 206978_at | CCR2 | Hs.511794 | 1231 | 41.4 |
| 204961_s_at | NCF1 | Hs.559477 | 4687 | 41.4 |
| 218473_s_at | GLT25D1 | Hs.418795 | 79709 | 41.4 |
| 214844_s_at | DOK5 | Hs.473133 | 55816 | 41.4 |
| 201276_at | RAB5B | Hs.567328 | 5869 | 41.4 |
| 200672_x_at | SPTBN1 | Hs.503178 | 6711 | 41.4 |
| 206067_s_at | WT1 | Hs.408453 | 7490 | 41.4 |
| 221511_x_at | CCPG1 | Hs.285051 | 9236 | 41.4 |
| 201525_at | APOD | Hs.522555 | 347 | 41.4 |
| 38521_at | MAG | Hs.515354 | 4099 | 41.4 |
| 210992_x_at | FCGR2C | — | 9103 | 41.4 |
| 220132_s_at | CLEC2D | Hs.268326 | 29121 | 41.4 |
| 205142_x_at | ABCD1 | Hs.159546 | 215 | 41.4 |
| 212705_x_at | PNPLA2 | Hs.118463 | 57104 | 41.4 |
| 202215_s_at | NFYC | Hs.233458 | 4802 | 41.4 |
| 206257_at | CCDC9 | Hs.227782 | 26093 | 41.4 |
| 201559_s_at | CLIC4 | Hs.440544 | 25932 | 41.4 |
| 203507_at | CD68 | Hs.246381 | 968 | 41.4 |
| 213471_at | NPHP4 | Hs.462348 | 261734 | 41.4 |
| 204819_at | FGD1 | Hs.522663 | 2245 | 41.4 |
| 210130_s_at | TM7SF2 | Hs.31130 | 7108 | 41.4 |
| 221857_s_at | TJAP1 | Hs.520145 | 93643 | 41.4 |
| 217198_x_at | IGH@ /// IGHD /// IGHG1 | Hs.567291 | 3492 /// 3495 /// 3500 | 41.4 |
| 221240_s_at | B3GNT4 | Hs.363315 | 79369 | 41.4 |
| 207835_at | FBLN1 | Hs.24601 | 2192 | 41.4 |
| 206663_at | SP4 | Hs.88013 | 6671 | 41.4 |
| 221097_s_at | KCNMB2 | Hs.478368 | 10242 | 41.4 |
| 211250_s_at | SH3BP2 | Hs.167679 | 6452 | 41.4 |
| 213609_s_at | SEZ6L | Hs.194766 | 23544 | 41.4 |
| 209951_s_at | MAP2K7 | Hs.531754 | 5609 | 41.4 |
| 201029_s_at | CD99 | Hs.495605 | 4267 | 40.8 |
| 214669_x_at | IGKC | Hs.449621 | 3514 | 40.8 |
| 215071_s_at | HIST1H2AC | Hs.484950 | 8334 | 40.8 |
| 210786_s_at | FLI1 | Hs.504281 | 2313 | 40.8 |
| 213894_at | KIAA0960 | Hs.120855 | 23249 | 40.8 |
| 215214_at | IGLV3-25 /// IGLC2 | Hs.449585 /// Hs.584765 | 28793 /// 3538 | 40.8 |
| 201389_at | ITGA5 | Hs.505654 | 3678 | 40.8 |
| 212097_at | CAV1 | Hs.74034 | 857 | 40.8 |
| 202459_s_at | LPIN2 | Hs.132342 | 9663 | 40.8 |
| 215449_at | BZRPL1 | Hs.357392 | 222642 | 40.8 |
| 204204_at | SLC31A2 | Hs.24030 | 1318 | 40.8 |
| 212464_s_at | FN1 | Hs.562079 | 2335 | 40.8 |
| 219452_at | DPEP2 | Hs.372633 | 64174 | 40.8 |
| 212974_at | DENND3 | Hs.18166 | 22898 | 40.8 |
| 210775_x_at | CASP9 | Hs.329502 | 842 | 40.8 |
| 210113_s_at | NALP1 | Hs.513902 | 22861 | 40.8 |
| 213119_at | SLC36A1 | Hs.269004 | 206358 | 40.8 |
| 205640_at | ALDH3B1 | Hs.523841 | 221 | 40.8 |

TABLE 2-continued

Genes over-expressed in AML

| probe | Gene | Unigene | Locus | % AML cases with overexpression |
|---|---|---|---|---|
| 206377_at | FOXF2 | Hs.484423 | 2295 | 40.8 |
| 201775_s_at | KIAA0494 | Hs.100874 | 9813 | 40.8 |
| 204059_s_at | ME1 | Hs.21160 | 4199 | 40.8 |
| 214885_at | MYST1 | Hs.533803 | 84148 | 40.8 |
| 213076_at | ITPKC | Hs.515415 | 80271 | 40.8 |
| 209983_s_at | NRXN2 | Hs.372938 | 9379 | 40.8 |
| 208124_s_at | SEMA4F | Hs.25887 | 10505 | 40.8 |
| 220112_at | FLJ11795 | Hs.436214 | 79722 | 40.8 |
| 207537_at | PFKFB1 | Hs.444304 | 5207 | 40.8 |
| 204465_s_at | INA | Hs.500916 | 9118 | 40.8 |
| 214152_at | CCPG1 | Hs.285051 | 9236 | 40.8 |
| 204987_at | ITIH2 | Hs.75285 | 3698 | 40.8 |
| 220334_at | RGS17 | Hs.166313 | 26575 | 40.8 |
| 205157_s_at | KRT17 | Hs.579174 | 3872 | 40.8 |
| 206840_at | AFM | Hs.168718 | 173 | 40.8 |
| 216530_at | — | Hs.552334 | — | 40.8 |
| 31835_at | HRG | Hs.1498 | 3273 | 40.8 |
| 206525_at | GABRR1 | Hs.437745 | 2569 | 40.8 |
| 217423_at | TTLL2 | Hs.520554 | 83887 | 40.8 |
| 207587_at | CRYGA | Hs.122566 | 1418 | 40.8 |
| 207907_at | TNFSF14 | Hs.129708 | 8740 | 40.8 |
| 214087_s_at | MYBPC1 | Hs.567306 | 4604 | 40.8 |
| 214069_at | LOC123876 /// ACSM2 | Hs.298252 | 123876 /// 348158 | 40.8 |
| 207583_at | ABCD2 | Hs.117852 | 225 | 40.8 |
| 201050_at | PLD3 | Hs.257008 | 23646 | 40.1 |
| 202902_s_at | CTSS | Hs.181301 | 1520 | 40.1 |
| 209813_x_at | TRGC2 /// TRGV9 /// LOC442532 /// LOC442670 /// TARP | Hs.534032 | 442532 /// 442670 /// 445347 /// 6967 /// 6983 | 40.1 |
| 200696_s_at | GSN | Hs.522373 | 2934 | 40.1 |
| 204885_s_at | MSLN | Hs.408488 | 10232 | 40.1 |
| 220416_at | ATP8B4 | Hs.511311 | 79895 | 40.1 |
| 201089_at | ATP6V1B2 | Hs.295917 | 526 | 40.1 |
| 1598_g_at | GAS6 | Hs.369201 | 2621 | 40.1 |
| 212509_s_at | MXRA7 | Hs.250723 | 439921 | 40.1 |
| 211890_x_at | CAPN3 | Hs.143261 | 825 | 40.1 |
| 203567_s_at | TRIM38 | Hs.584851 | 10475 | 40.1 |
| 205770_at | GSR | Hs.271510 | 2936 | 40.1 |
| 210423_s_at | SLC11A1 | Hs.471393 | 6556 | 40.1 |
| 220023_at | APOB48R | Hs.200333 | 55911 | 40.1 |
| 209098_s_at | JAG1 | Hs.224012 | 182 | 40.1 |
| 213296_at | PEX10 | Hs.567315 | 5192 | 40.1 |
| 202807_s_at | TOM1 | Hs.474705 | 10043 | 40.1 |
| 217600_at | SCUBE3 | Hs.12923 | 222663 | 40.1 |
| 205949_at | CA1 | Hs.23118 | 759 | 40.1 |
| 221670_s_at | LHX3 | Hs.148427 | 8022 | 40.1 |
| 214971_s_at | ST6GAL1 | Hs.207459 | 6480 | 40.1 |
| 203864_s_at | ACTN2 | Hs.498178 | 88 | 40.1 |
| 210640_s_at | GPR30 | Hs.20961 | 2852 | 40.1 |
| 216555_at | — | — | — | 40.1 |
| 209807_s_at | NFIX | Hs.257970 | 4784 | 40.1 |
| 213352_at | TMCC1 | Hs.477547 | 23023 | 40.1 |
| 218651_s_at | LARP6 | Hs.416755 | 55323 | 40.1 |
| 214912_at | — | — | — | 40.1 |
| 220805_at | HRH2 | Hs.247885 | 3274 | 40.1 |
| 220791_x_at | SCN11A | Hs.186877 | 11280 | 40.1 |
| 220524_at | EPB41L4B | Hs.269180 | 54566 | 40.1 |
| 215944_at | — | Hs.568545 | — | 40.1 |
| 213335_s_at | ST3GAL6 | Hs.148716 | 10402 | 40.1 |
| 201422_at | IFI30 | Hs.14623 | 10437 | 39.5 |
| 221479_s_at | BNIP3L | Hs.131226 | 665 | 39.5 |
| 204959_at | MNDA | Hs.153837 | 4332 | 39.5 |
| 203729_at | EMP3 | Hs.9999 | 2014 | 39.5 |
| 215819_s_at | RHCE /// RHD | Hs.567331 | 6006 /// 6007 | 39.5 |
| 205707_at | IL17R | Hs.129751 | 23765 | 39.5 |
| 211676_s_at | IFNGR1 | Hs.520414 | 3459 | 39.5 |
| 209970_x_at | CASP1 | Hs.2490 | 834 | 39.5 |
| 218589_at | P2RY5 | Hs.123464 | 10161 | 39.5 |
| 218035_s_at | FLJ20273 | Hs.518727 | 54502 | 39.5 |
| 220232_at | SCD5 | Hs.379191 | 79966 | 39.5 |

TABLE 2-continued

Genes over-expressed in AML

| probe | Gene | Unigene | Locus | % AML cases with overexpression |
|---|---|---|---|---|
| 209499_x_at | TNFSF13 /// TNFSF12-TNFSF13 | Hs.54673 | 407977 /// 8741 | 39.5 |
| 204669_s_at | RNF24 | Hs.114180 | 11237 | 39.5 |
| 202665_s_at | WASPIP | Hs.128067 | 7456 | 39.5 |
| 216541_x_at | IGHG1 /// IGHG3 /// IGHV1-69 /// MGC27165 | Hs.584764 | 283650 /// 28461 /// 3500 /// 3502 | 39.5 |
| 204653_at | TFAP2A | Hs.519880 | 7020 | 39.5 |
| 221530_s_at | BHLHB3 | Hs.177841 | 79365 | 39.5 |
| 219277_s_at | OGDHL | Hs.17860 | 55753 | 39.5 |
| 204099_at | SMARCD3 | Hs.444445 | 6604 | 39.5 |
| 211771_s_at | POU2F2 | Hs.515429 | 5452 | 39.5 |
| 203868_s_at | VCAM1 | Hs.109225 | 7412 | 39.5 |
| 216661_x_at | CYP2C9 | Hs.282624 | 1559 | 39.5 |
| 206900_x_at | ZNF253 /// LOC114977 | Hs.501796 | 114977 /// 56242 | 39.5 |
| 205819_at | MARCO | Hs.67726 | 8685 | 39.5 |
| 210239_at | IRX5 | Hs.435730 | 10265 | 39.5 |
| 214397_at | MBD2 | Hs.25674 | 8932 | 39.5 |
| 201265_at | — | — | — | 39.5 |
| 214762_at | ATP6V1G2 | Hs.249227 | 534 | 39.5 |
| 208337_s_at | NR5A2 | Hs.33446 | 2494 | 39.5 |
| 207034_s_at | GLI2 | Hs.111867 | 2736 | 39.5 |
| 206449_s_at | MASP1 | Hs.89983 | 5648 | 39.5 |
| 205954_at | RXRG | Hs.26550 | 6258 | 39.5 |
| 215060_at | — | Hs.512643 | — | 39.5 |
| 220929_at | GALNT8 | Hs.511985 | 26290 | 39.5 |
| 220108_at | GNA14 | Hs.62697 | 9630 | 39.5 |
| 214379_at | BMX | Hs.495731 | 660 | 39.5 |
| 207503_at | TCP10 | Hs.351 | 6953 | 39.5 |
| 219743_at | HEY2 | Hs.144287 | 23493 | 39.5 |
| 219973_at | ARSJ | Hs.22895 | 79642 | 39.5 |
| 206164_at | CLCA2 | Hs.241551 | 9635 | 39.5 |
| 200678_x_at | GRN | Hs.514220 | 2896 | 38.9 |
| 209101_at | CTGF | Hs.410037 | 1490 | 38.9 |
| 205119_s_at | FPR1 | Hs.753 | 2357 | 38.9 |
| 214574_x_at | LST1 | Hs.436066 | 7940 | 38.9 |
| 209806_at | HIST1H2BK | Hs.437275 | 85236 | 38.9 |
| 203388_at | ARRB2 | Hs.435811 | 409 | 38.9 |
| 216250_s_at | LPXN | Hs.125474 | 9404 | 38.9 |
| 117_at | HSPA6 | Hs.3268 | 3310 | 38.9 |
| 217388_s_at | KYNU | Hs.470126 | 8942 | 38.9 |
| 203508_at | TNFRSF1B | Hs.256278 | 7133 | 38.9 |
| 209288_s_at | CDC42EP3 | Hs.369574 | 10602 | 38.9 |
| 211535_s_at | FGFR1 | Hs.264887 | 2260 | 38.9 |
| 202621_at | IRF3 | Hs.75254 | 3661 | 38.9 |
| 212002_at | C1orf144 | Hs.252967 | 26099 | 38.9 |
| 221063_x_at | RNF123 | Hs.553723 | 63891 | 38.9 |
| 208463_at | GABRA4 | Hs.248112 | 2557 | 38.9 |
| 219946_x_at | MYH14 | Hs.467142 | 79784 | 38.9 |
| 47571_at | ZNF236 | Hs.189826 | 7776 | 38.9 |
| 207072_at | IL18RAP | Hs.158315 | 8807 | 38.9 |
| 41856_at | UNC5B | Hs.522997 | 219699 | 38.9 |
| 219628_at | WIG1 | Hs.386299 | 64393 | 38.9 |
| 221218_s_at | TPK1 | Hs.490454 | 27010 | 38.9 |
| 216936_at | — | — | — | 38.9 |
| 219557_s_at | NRIP3 | Hs.523467 | 56675 | 38.9 |
| 213448_at | GBA | Hs.511984 | 2629 | 38.9 |
| 218749_s_at | SLC24A6 | Hs.286194 | 80024 | 38.9 |
| 207185_at | SLC10A1 | Hs.952 | 6554 | 38.9 |
| 215848_at | ZNF291 | Hs.458986 | 49855 | 38.9 |
| 216892_at | IGHG2 | Hs.51063 5 | 3501 | 38.9 |
| 207400_at | NPY5R | Hs.519058 | 4889 | 38.9 |
| 210716_s_at | RSN | Hs.524809 | 6249 | 38.9 |
| 221128_at | ADAM19 | Hs.483944 | 8728 | 38.9 |
| 216622_at | LAMB4 | Hs.62022 | 22798 | 38.9 |
| 213596_at | CASP4 | Hs.138378 | 837 | 38.9 |
| 210702_s_at | PTGIS | Hs.302085 | 5740 | 38.9 |
| 216456_at | PCDH9 | Hs.407643 | 5101 | 38.9 |
| 210614_at | TTPA | Hs.69049 | 7274 | 38.9 |
| 213496_at | LPPR4 | Hs.13245 | 9890 | 38.9 |
| 203587_at | ARF4L | Hs.183153 | 379 | 38.9 |
| 205678_at | AP3B2 | Hs.199593 | 8120 | 38.9 |

TABLE 2-continued

Genes over-expressed in AML

| probe | Gene | Unigene | Locus | % AML cases with overexpression |
|---|---|---|---|---|
| 205764_at | — | — | — | 38.9 |
| 205620_at | F10 | Hs.361463 | 2159 | 38.9 |
| 221731_x_at | CSPG2 | Hs.443681 | 1462 | 38.2 |
| 216041_x_at | GRN | Hs.514220 | 2896 | 38.2 |
| 209193_at | PIM1 | Hs.81170 | 5292 | 38.2 |
| 214433_s_at | SELENBP1 | — | 8991 | 38.2 |
| 211820_x_at | GYPA | Hs.434973 | 2993 | 38.2 |
| 200001_at | CAPNS1 | Hs.515371 | 826 | 38.2 |
| 202688_at | TNFSF10 | Hs.478275 | 8743 | 38.2 |
| 208892_s_at | DUSP6 | Hs.298654 | 1848 | 38.2 |
| 209500_x_at | TNFSF13 /// TNFSF12-TNFSF13 | Hs.54673 | 407977 /// 8741 | 38.2 |
| 220570_at | RETN | Hs.283091 | 56729 | 38.2 |
| 212285_s_at | AGRN | Hs.273330 | 375790 | 38.2 |
| 212120_at | RHOQ | Hs.584872 | 23433 | 38.2 |
| 204328_at | EVER1 | Hs.16165 | 11322 | 38.2 |
| 212090_at | GRINA | Hs.339697 | 2907 | 38.2 |
| 209822_s_at | VLDLR | Hs.370422 | 7436 | 38.2 |
| 211639_x_at | — | Hs.556320 | — | 38.2 |
| 213367_at | LOC155060 | Hs.490512 | 155060 | 38.2 |
| 210237_at | ARTN | Hs.194689 | 9048 | 38.2 |
| 214551_s_at | CD7 | Hs.36972 | 924 | 38.2 |
| 211918_x_at | PAPPA2 | Hs.187284 | 60676 | 38.2 |
| 212527_at | D15Wsu75e | Hs.570455 | 27351 | 38.2 |
| 216301_at | — | Hs.449575 | — | 38.2 |
| 210081_at | AGER | Hs.184 | 177 | 38.2 |
| 212606_at | WDFY3 | Hs.480116 | 23001 | 38.2 |
| 219239_s_at | ZNF654 | Hs.27595 | 55279 | 38.2 |
| 204920_at | CPS1 | Hs.149252 | 1373 | 38.2 |
| 210513_s_at | VEGF | Hs.73793 | 7422 | 38.2 |
| 206087_x_at | HFE | Hs.233325 | 3077 | 38.2 |
| 211499_s_at | MAPK11 | Hs.57732 | 5600 | 38.2 |
| 208099_x_at | TTLL5 | Hs.200747 | 23093 | 38.2 |
| 222208_s_at | MGC13098 | Hs.584991 | 84820 | 38.2 |
| 207969_x_at | ACRV1 | Hs.169222 | 56 | 38.2 |
| 203892_at | WFDC2 | Hs.2719 | 10406 | 38.2 |
| 211527_x_at | VEGF | Hs.73793 | 7422 | 38.2 |
| 211241_at | ANXA2P3 | Hs.448622 | 305 | 38.2 |
| 211333_s_at | FASLG | Hs.2007 | 356 | 38.2 |
| 209851_at | KIAA0853 | Hs.136102 | 23091 | 38.2 |
| 220957_at | CTAGE1 | Hs.406709 | 64693 | 38.2 |
| 210861_s_at | WISP3 | Hs.558428 | 8838 | 38.2 |
| 222082_at | ZBTB7A | Hs.465623 | 51341 | 38.2 |
| 211891_s_at | ARHGEF4 | Hs.469935 | 50649 | 38.2 |
| 823_at | CX3CL1 | Hs.531668 | 6376 | 38.2 |
| 210302_s_at | MAB21L2 | Hs.584852 | 10586 | 38.2 |
| 220210_at | CHRNA10 | Hs.157714 | 57053 | 38.2 |
| 215469_at | — | Hs.137567 | — | 38.2 |
| 217744_s_at | PERP | Hs.520421 | 64065 | 38.2 |
| 50277_at | GGA1 | Hs.499158 | 26088 | 37.6 |
| 205922_at | VNN2 | Hs.293130 | 8875 | 37.6 |
| 46256_at | SPSB3 | Hs.7247 | 90864 | 37.6 |
| 208072_s_at | DGKD | Hs.471675 | 8527 | 37.6 |
| 202910_s_at | CD97 | Hs.466039 | 976 | 37.6 |
| 209099_x_at | JAG1 | Hs.224012 | 182 | 37.6 |
| 45526_g_at | FLJ14154 | Hs.513296 | 79903 | 37.6 |
| 202363_at | SPOCK | Hs.567340 | 6695 | 37.6 |
| 39248_at | AQP3 | Hs.234642 | 360 | 37.6 |
| 205568_at | AQP9 | Hs.104624 | 366 | 37.6 |
| 209395_at | CHI3L1 | Hs.382202 | 1116 | 37.6 |
| 221792_at | RAB6B | Hs.12152 | 51560 | 37.6 |
| 218211_s_at | MLPH | Hs.102406 | 79083 | 37.6 |
| 209295_at | TNFRSF10B | Hs.521456 | 8795 | 37.6 |
| 207700_s_at | NCOA3 | Hs.382168 | 8202 | 37.6 |
| 219669_at | CD177 | Hs.232165 | 57126 | 37.6 |
| 207224_s_at | SIGLEC7 | Hs.274470 | 27036 | 37.6 |
| 209164_s_at | CYB561 | Hs.355264 | 1534 | 37.6 |
| 204044_at | QPRT | Hs.513484 | 23475 | 37.6 |
| 204021_s_at | PETRA | Hs.443121 | 5813 | 37.6 |
| 206580_s_at | EFEMP2 | Hs.381870 | 30008 | 37.6 |
| 213182_x_at | CDKN1C | Hs.106070 | 1028 | 37.6 |
| 208466_at | RAB3D | Hs.567397 | 9545 | 37.6 |
| 221555_x_at | CDC14B | Hs.40582 | 8555 | 37.6 |
| 216432_at | SLC28A2 | Hs.367833 | 9153 | 37.6 |

TABLE 2-continued

Genes over-expressed in AML

| probe | Gene | Unigene | Locus | % AML cases with overexpression |
|---|---|---|---|---|
| 216748_at | PYHIN1 | Hs.224645 | 149628 | 37.6 |
| 203747_at | AQP3 | Hs.234642 | 360 | 37.6 |
| 206934_at | SIRPB1 | Hs.134565 | 10326 | 37.6 |
| 206261_at | ZNF239 | Hs.25040 | 8187 | 37.6 |
| 220284_at | DKKL1 | Hs.515855 | 27120 | 37.6 |
| 214064_at | TF | Hs.518267 | 7018 | 37.6 |
| 220873_at | REPS2 | Hs.186810 | 9185 | 37.6 |
| 221030_s_at | ARHGAP24 | Hs.444229 | 83478 | 37.6 |
| 221304_at | UGT1A10 | — | 54575 | 37.6 |
| 213952_s_at | ALOX5 | Hs.89499 | 240 | 37.6 |
| 221347_at | CHRM5 | Hs.584747 | 1133 | 37.6 |
| 215518_at | STXBP5L | Hs.477315 | 9515 | 37.6 |
| 205943_at | TDO2 | Hs.183671 | 6999 | 37.6 |
| 208281_x_at | DAZ1 /// DAZ3 /// DAZ2 /// DAZ4 | Hs.558522 | 1617 /// 57054 /// 57055 /// 57135 | 37.6 |
| 206801_at | NPPB | Hs.219140 | 4879 | 37.6 |
| 204895_x_at | MUC4 | Hs.369646 | 4585 | 37.6 |
| 217165_x_at | MT1F | Hs.513626 | 4494 | 36.9 |
| 201005_at | CD9 | Hs.114286 | 928 | 36.9 |
| 205147_x_at | NCF4 | Hs.474781 | 4689 | 36.9 |
| 205844_at | VNN1 | Hs.12114 | 8876 | 36.9 |
| 218627_at | FLJ11259 | Hs.525634 | 55332 | 36.9 |
| 206120_at | CD33 | Hs.83731 | 945 | 36.9 |
| 212472_at | MICAL2 | Hs.501928 | 9645 | 36.9 |
| 215535_s_at | AGPAT1 | Hs.409230 | 10554 | 36.9 |
| 214370_at | S100A8 | Hs.416073 | 6279 | 36.9 |
| 210854_x_at | SLC6A8 | Hs.540696 | 6535 | 36.9 |
| 217521_at | HAL | Hs.190783 | 3034 | 36.9 |
| 35626_at | SGSH | Hs.31074 | 6448 | 36.9 |
| 203559_s_at | ABP1 | Hs.521296 | 26 | 36.9 |
| 211178_s_at | PSTPIP1 | Hs.129758 | 9051 | 36.9 |
| 205566_at | ABHD2 | Hs.122337 | 11057 | 36.9 |
| 205409_at | FOSL2 | Hs.568265 | 2355 | 36.9 |
| 204043_at | TCN2 | Hs.417948 | 6948 | 36.9 |
| 221656_s_at | ARHGEF10L | Hs.443460 | 55160 | 36.9 |
| 220566_at | PIK3R5 | Hs.278901 | 23533 | 36.9 |
| 206388_at | PDE3A | Hs.386791 | 5139 | 36.9 |
| 215603_x_at | GGT2 | Hs.568255 | 2679 | 36.9 |
| 40020_at | CELSR3 | Hs.533070 | 1951 | 36.9 |
| 218420_s_at | C13orf23 | Hs.318526 | 80209 | 36.9 |
| 215557_at | SCD5 | Hs.379191 | 79966 | 36.9 |
| 221294_at | GPR21 | Hs.368372 | 2844 | 36.9 |
| 217428_s_at | COL10A1 | Hs.520339 | 1300 | 36.9 |
| 209701_at | ARTS-1 | Hs.436186 | 51752 | 36.9 |
| 204968_at | C6orf47 | Hs.247323 | 57827 | 36.9 |
| 205599_at | TRAF1 | Hs.531251 | 7185 | 36.9 |
| 204138_s_at | ZNF42 | Hs.399810 | 7593 | 36.9 |
| 220783_at | MMP27 | Hs.534479 | 64066 | 36.9 |
| 217683_at | HBE1 | Hs.117848 | 3046 | 36.9 |
| 210058_at | MAPK13 | Hs.178695 | 5603 | 36.9 |
| 211184_s_at | USH1C | Hs.502072 | 10083 | 36.9 |
| 214233_at | GGA2 | Hs.460336 | 23062 | 36.9 |
| 206684_s_at | ATF7 | Hs.12286 | 11016 | 36.9 |
| 216842_x_at | RBMY1A1 /// RBMY2FP /// RBMY1F /// RBMY1B /// RBMY1D /// RBMY1E /// RBMY1J | Hs.584735 | 159162 /// 159163 /// 378948 /// 378949 /// 378950 /// 378951 /// 5940 | 36.9 |
| 207663_x_at | GAGE3 | — | 2575 | 36.9 |
| 214520_at | FOXC2 | Hs.558329 | 2303 | 36.9 |
| 210918_at | — | — | — | 36.9 |
| 205931_s_at | CREB5 | Hs.437075 | 9586 | 36.9 |
| 216772_at | — | — | — | 36.9 |
| 209872_s_at | PKP3 | Hs.534395 | 11187 | 36.9 |
| 217537_x_at | — | — | — | 36.9 |
| 219115_s_at | IL20RA | Hs.445868 | 53832 | 36.9 |
| 211638_at | — | Hs.383169 | — | 36.9 |
| 217748_at | ADIPOR1 | Hs.5298 | 51094 | 36.3 |
| 203547_at | CD4 | Hs.17483 | 920 | 36.3 |
| 214875_x_at | APLP2 | Hs.370247 | 334 | 36.3 |
| 208890_s_at | PLXNB2 | Hs.3989 | 23654 | 36.3 |

TABLE 2-continued

Genes over-expressed in AML

| probe | Gene | Unigene | Locus | % AML cases with overexpression |
|---|---|---|---|---|
| 202191_s_at | GAS7 | Hs.462214 | 8522 | 36.3 |
| 200623_s_at | CALM3 | Hs.515487 | 808 | 36.3 |
| 209179_s_at | LENG4 | Hs.467279 | 79143 | 36.3 |
| 211719_x_at | FN1 | Hs.203717 | 2335 | 36.3 |
| 36030_at | HOM-TES-103 | Hs.15243 | 25900 | 36.3 |
| 204046_at | PLCB2 | Hs.355888 | 5330 | 36.3 |
| 213607_x_at | NADK | Hs.456572 | 65220 | 36.3 |
| 202650_s_at | KIAA0195 | Hs.514474 | 9772 | 36.3 |
| 204914_s_at | SOX11 | Hs.432638 | 6664 | 36.3 |
| 204970_s_at | MAFG | Hs.252229 | 4097 | 36.3 |
| 202761_s_at | SYNE2 | Hs.525392 | 23224 | 36.3 |
| 205804_s_at | TRAF3IP3 | Hs.147434 | 80342 | 36.3 |
| 32502_at | GDPD5 | Hs.503297 | 81544 | 36.3 |
| 208917_x_at | NADK | Hs.456572 | 65220 | 36.3 |
| 209947_at | UBAP2L | Hs.490551 | 9898 | 36.3 |
| 202572_s_at | DLGAP4 | Hs.249600 | 22839 | 36.3 |
| 215909_x_at | MINK1 | Hs.443417 | 50488 | 36.3 |
| 218441_s_at | RPAP1 | Hs.371045 | 26015 | 36.3 |
| 211391_s_at | ZNF278 | Hs.517557 | 23598 | 36.3 |
| 206313_at | HLA-DOA | Hs.351874 | 3111 | 36.3 |
| 219722_s_at | GDPD3 | Hs.289015 | 79153 | 36.3 |
| 205744_at | DOC2A | Hs.355281 | 8448 | 36.3 |
| 210247_at | SYN2 | Hs.445503 | 6854 | 36.3 |
| 211726_s_at | FMO2 | Hs.567271 | 2327 | 36.3 |
| 208237_x_at | ADAM22 | Hs.256398 | 53616 | 36.3 |
| 209738_x_at | PSG6 | Hs.466849 | 5675 | 36.3 |
| 220135_s_at | SLC7A9 | Hs.408567 | 11136 | 36.3 |
| 204400_at | EFS | Hs.24587 | 10278 | 36.3 |
| 208076_at | HIST1H4D | Hs.248179 | 8360 | 36.3 |
| 207764_s_at | HIPK3 | Hs.201918 | 10114 | 36.3 |
| 203963_at | CA12 | Hs.210995 | 771 | 36.3 |
| 206002_at | GPR64 | Hs.146978 | 10149 | 36.3 |
| 216086_at | SV2C | Hs.570933 | 22987 | 36.3 |
| 201105_at | LGALS1 | Hs.445351 | 3956 | 35.7 |
| 200871_s_at | PSAP | Hs.523004 | 5660 | 35.7 |
| 205237_at | FCN1 | Hs.440898 | 2219 | 35.7 |
| 219191_s_at | BIN2 | Hs.14770 | 51411 | 35.7 |
| 205987_at | CD1C | Hs.1311 | 911 | 35.7 |
| 211697_x_at | LOC56902 | Hs.262858 | 56902 | 35.7 |
| 205529_s_at | RUNX1T1 | Hs.368431 | 862 | 35.7 |
| 218231_at | NAGK | Hs.7036 | 55577 | 35.7 |
| 212890_at | MGC15523 | Hs.352240 | 124565 | 35.7 |
| 218251_at | MID1IP1 | Hs.522605 | 58526 | 35.7 |
| 202284_s_at | CDKN1A | Hs.370771 | 1026 | 35.7 |
| 214032_at | ZAP70 | Hs.234569 | 7535 | 35.7 |
| 213046_at | PABPN1 | Hs.117176 | 8106 | 35.7 |
| 206135_at | ST18 | Hs.147170 | 9705 | 35.7 |
| 213521_at | PTPN18 | Hs.516390 | 26469 | 35.7 |
| 219414_at | CLSTN2 | Hs.158529 | 64084 | 35.7 |
| 212171_x_at | VEGF | Hs.73793 | 7422 | 35.7 |
| 36019_at | STK19 | Hs.485102 | 8859 | 35.7 |
| 205059_s_at | IDUA | Hs.89560 | 3425 | 35.7 |
| 204194_at | BACH1 | Hs.154276 | 571 | 35.7 |
| 205021_s_at | CHES1 | Hs.567246 | 1112 | 35.7 |
| 37278_at | TAZ | Hs.409911 | 6901 | 35.7 |
| 202565_s_at | SVIL | Hs.499209 | 6840 | 35.7 |
| 205552_s_at | OAS1 | Hs.524760 | 4938 | 35.7 |
| 221155_x_at | SLC25A37 | Hs.122514 | 51312 | 35.7 |
| 206850_at | RRP22 | Hs.73088 | 10633 | 35.7 |
| 218963_s_at | KRT23 | Hs.9029 | 25984 | 35.7 |
| 212319_at | RUTBC1 | Hs.513861 | 9905 | 35.7 |
| 220390_at | AGBL2 | Hs.147377 | 79841 | 35.7 |
| 202928_s_at | PHF1 | Hs.166204 | 5252 | 35.7 |
| 216735_x_at | HRH1 | Hs.1570 | 3269 | 35.7 |
| 202509_s_at | TNFAIP2 | Hs.525607 | 7127 | 35.7 |
| 207859_s_at | CHRNB3 | Hs.96094 | 1142 | 35.7 |
| 214275_at | MED12 | Hs.409226 | 9968 | 35.7 |
| 214293_at | SEPT11 | Hs.128199 | 55752 | 35.7 |
| 218584_at | FLJ21127 | Hs.211511 | 79600 | 35.7 |
| 217102_at | MAG | Hs.348346 | 27307 | 35.7 |
| 206878_at | DAO | Hs.113227 | 1610 | 35.7 |
| 215189_at | KRTHB6 | Hs.278658 | 3892 | 35.7 |
| 221658_s_at | IL21R | Hs.210546 | 50615 | 35.7 |
| 205463_s_at | PDGFA | Hs.376032 | 5154 | 35.7 |
| 217375_at | — | — | — | 35.7 |

TABLE 2-continued

Genes over-expressed in AML

| probe | Gene | Unigene | Locus | % AML cases with overexpression |
|---|---|---|---|---|
| 210584_s_at | POLDIP3 /// dJ222E13.2 | Hs.387850 | 84271 /// 91695 | 35.7 |
| 220519_s_at | LIM2 | Hs.162754 | 3982 | 35.7 |
| 216437_at | EPC1 | Hs.167805 | 80314 | 35.7 |
| 207064_s_at | AOC2 | Hs.143102 | 314 | 35.7 |
| 217415_at | POLR2A | Hs.270017 | 5430 | 35.7 |
| 207214_at | SPINK4 | Hs.555934 | 27290 | 35.7 |
| 206194_at | HOXC4 /// FLJ12825 | Hs.350378 | 3221 /// 440101 | 35.7 |
| 220705_s_at | ADAMTS7 | Hs.16441 | 11173 | 35.7 |
| 214229_at | DNAH17 | Hs.464217 | 8632 | 35.7 |
| 215829_at | SHANK2 | Hs.268726 | 22941 | 35.7 |
| 217270_s_at | DYRK1B | Hs.130988 | 9149 | 35.7 |
| 204129_at | BCL9 | Hs.415209 | 607 | 35.7 |
| 206566_at | SLC7A1 | Hs.14846 | 6541 | 35.7 |
| 208581_x_at | MT1X | Hs.374950 | 4501 | 35.0 |
| 204232_at | FCER1G | Hs.433300 | 2207 | 35.0 |
| 203591_s_at | CSF3R | Hs.524517 | 1441 | 35.0 |
| 217977_at | SEPX1 | Hs.279623 | 51734 | 35.0 |
| 214084_x_at | NCF1 | Hs.559477 | 4687 | 35.0 |
| 204924_at | TLR2 | Hs.519033 | 7097 | 35.0 |
| 211133_x_at | LILRB2 /// LILRB3 | Hs.534386 | 10288 /// 11025 | 35.0 |
| 213065_at | MGC23401 | Hs.527874 | 196441 | 35.0 |
| 207857_at | LILRA2 | Hs.534394 | 11027 | 35.0 |
| 201364_s_at | OAZ2 | Hs.74563 | 4947 | 35.0 |
| 205837_s_at | GYPA | Hs.434973 | 2993 | 35.0 |
| 220956_s_at | EGLN2 | Hs.515417 | 112398 | 35.0 |
| 33322_i_at | SFN | Hs.523718 | 2810 | 35.0 |
| 211207_s_at | ACSL6 | Hs.14945 | 23305 | 35.0 |
| 213326_at | VAMP1 | Hs.20021 | 6843 | 35.0 |
| 209727_at | GM2A | Hs.483873 | 2760 | 35.0 |
| 203610_s_at | TRIM38 | Hs.584851 | 10475 | 35.0 |
| 208106_x_at | PSG6 | Hs.466849 | 5675 | 35.0 |
| 211295_x_at | CYP2A6 | Hs.439056 | 1548 | 35.0 |
| 208437_at | CLCN1 | Hs.121483 | 1180 | 35.0 |
| 221170_at | HRH4 | Hs.287388 | 59340 | 35.0 |
| 215019_x_at | ZNF528 | Hs.531612 | 84436 | 35.0 |
| 219509_at | MYOZ1 | Hs.238756 | 58529 | 35.0 |
| 203458_at | SPR | Hs.301540 | 6697 | 35.0 |
| 204368_at | SLCO2A1 | Hs.518270 | 6578 | 35.0 |
| 217147_s_at | TRAT1 | Hs.138701 | 50852 | 35.0 |
| 211332_x_at | HFE | Hs.233325 | 3077 | 35.0 |
| 214443_at | PVR | Hs.171844 | 5817 | 35.0 |
| 204051_s_at | SFRP4 | Hs.105700 | 6424 | 35.0 |
| 220853_at | GTDC1 | Hs.44780 | 79712 | 35.0 |
| 210799_at | HTR1B | Hs.123016 | 3351 | 35.0 |
| 212853_at | DCUN1D4 | Hs.221407 | 23142 | 35.0 |
| 210323_at | TEKT2 | Hs.127111 | 27285 | 35.0 |
| 217060_at | — | Hs.521251 | — | 35.0 |
| 206916_x_at | TAT | Hs.161640 | 6898 | 35.0 |
| 210345_s_at | DNAH9 | Hs.567259 | 1770 | 35.0 |
| 36499_at | CELSR2 | Hs.57652 | 1952 | 35.0 |
| 215562_at | C1orf34 | Hs.112949 | 22996 | 35.0 |
| 206280_at | CDH18 | Hs.317632 | 1016 | 35.0 |
| 204509_at | CA12 | Hs.210995 | 771 | 35.0 |
| 217360_x_at | IGHA1 /// IGHG1 /// IGHG3 /// MGC27165 | Hs.584764 | 283650 /// 3493 /// 3500 /// 3502 | 35.0 |
| 213169_at | — | Hs.27621 | — | 35.0 |
| 203477_at | COL15A1 | Hs.409034 | 1306 | 35.0 |
| 206165_s_at | CLCA2 | Hs.241551 | 9635 | 35.0 |
| 201510_at | ELF3 | Hs.67928 | 1999 | 35.0 |
| 202935_s_at | SOX9 | Hs.2316 | 6662 | 35.0 |
| 204688_at | SGCE | Hs.371199 | 8910 | 35.0 |
| 204471_at | GAP43 | Hs.134974 | 2596 | 35.0 |
| 206482_at | PTK6 | Hs.51133 | 5753 | 35.0 |
| 212843_at | NCAM1 | Hs.503878 | 4684 | 34.4 |
| 206687_s_at | PTPN6 | Hs.63489 | 5777 | 34.4 |
| 220088_at | C5R1 | Hs.2161 | 728 | 34.4 |
| 220532_s_at | LR8 | Hs.521295 | 28959 | 34.4 |
| 203615_x_at | SULT1A1 | Hs.567342 | 6817 | 34.4 |
| 215047_at | TRIM58 | Hs.323858 | 25893 | 34.4 |
| 221920_s_at | SLC25A37 | Hs.122514 | 51312 | 34.4 |

TABLE 2-continued

Genes over-expressed in AML

| probe | Gene | Unigene | Locus | % AML cases with overexpression |
|---|---|---|---|---|
| 38671_at | PLXND1 | Hs.301685 | 23129 | 34.4 |
| 221698_s_at | CLEC7A | Hs.143929 | 64581 | 34.4 |
| 209696_at | FBP1 | Hs.494496 | 2203 | 34.4 |
| 218876_at | CGI-38 | Hs.534458 | 51673 | 34.4 |
| 203718_at | NTE | Hs.511760 | 10908 | 34.4 |
| 218507_at | HIG2 | Hs.521171 | 29923 | 34.4 |
| 203206_at | FAM53B | Hs.129195 | 9679 | 34.4 |
| 57715_at | FAM26B | Hs.241545 | 51063 | 34.4 |
| 211610_at | KLF6 | Hs.4055 | 1316 | 34.4 |
| 209582_s_at | CD200 | Hs.79015 | 4345 | 34.4 |
| 211620_x_at | RUNX1 | Hs.149261 | 861 | 34.4 |
| 210129_s_at | TTLL3 | Hs.567445 | 26140 | 34.4 |
| 218655_s_at | FLJ20291 | Hs.406223 | 54883 | 34.4 |
| 214535_s_at | ADAMTS2 | Hs.23871 | 9509 | 34.4 |
| 219897_at | RNF122 | Hs.151237 | 79845 | 34.4 |
| 206590_x_at | DRD2 | Hs.73893 | 1813 | 34.4 |
| 215771_x_at | RET | Hs.350321 | 5979 | 34.4 |
| 220167_s_at | TP53TG3 | Hs.370561 | 24150 | 34.4 |
| 214923_at | ATP6V1D | Hs.272630 | 51382 | 34.4 |
| 205058_at | SLC26A1 | Hs.584858 | 10861 | 34.4 |
| 220363_s_at | ELMO2 | Hs.210469 | 63916 | 34.4 |
| 209086_x_at | MCAM | Hs.511397 | 4162 | 34.4 |
| 217654_at | CFLAR | Hs.390736 | 8837 | 34.4 |
| 214969_at | MAP3K9 | Hs.445496 | 4293 | 34.4 |
| 214650_x_at | MOG | Hs.141308 | 4340 | 34.4 |
| 211647_x_at | IGHM | Hs.538461 | 3507 | 34.4 |
| 212845_at | SAMD4 | Hs.98259 | 23034 | 34.4 |
| 201159_s_at | NMT1 | Hs.532790 | 4836 | 34.4 |
| 207394_at | ZNF137 | Hs.373648 | 7696 | 34.4 |
| 203942_s_at | MARK2 | Hs.567261 | 2011 | 34.4 |
| 220406_at | TGFB2 | Hs.133379 | 7042 | 34.4 |
| 207052_at | HAVCR1 | Hs.129711 | 26762 | 34.4 |
| 214618_at | CFLAR | Hs.390736 | 8837 | 34.4 |
| 215430_at | GK2 | Hs.98008 | 2712 | 34.4 |
| 210704_at | FEZ2 | Hs.258563 | 9637 | 34.4 |
| 209116_x_at | HBB | Hs.523443 | 3043 | 33.8 |
| 217232_x_at | HBB | Hs.523443 | 3043 | 33.8 |
| 201590_x_at | ANXA2 | Hs.511605 | 302 | 33.8 |
| 206676_at | CEACAM8 | Hs.41 | 1088 | 33.8 |
| 208690_s_at | PDLIM1 | Hs.368525 | 9124 | 33.8 |
| 212560_at | C11orf32 | — | 442871 | 33.8 |
| 202759_s_at | PALM2-AKAP2 | Hs.259461 | 445815 | 33.8 |
| 218559_s_at | MAFB | Hs.169487 | 9935 | 33.8 |
| 202241_at | TRIB1 | Hs.444947 | 10221 | 33.8 |
| 201040_at | GNAI2 | Hs.77269 | 2771 | 33.8 |
| 212307_s_at | OGT | Hs.405410 | 8473 | 33.8 |
| 203185_at | RASSF2 | Hs.379970 | 9770 | 33.8 |
| 202805_s_at | ABCC1 | Hs.391464 | 4363 | 33.8 |
| 202242_at | TSPAN7 | Hs.441664 | 7102 | 33.8 |
| 34206_at | CENTD2 | Hs.503165 | 116985 | 33.8 |
| 210069_at | CHKB /// CPT1B | Hs.439777 | 1120 /// 1375 | 33.8 |
| 213784_at | RABL4 | Hs.415172 | 11020 | 33.8 |
| 213338_at | RIS1 | Hs.35861 | 25907 | 33.8 |
| 205660_at | OASL | Hs.118633 | 8638 | 33.8 |
| 212344_at | SULF1 | Hs.409602 | 23213 | 33.8 |
| 34221_at | KIAA0194 | Hs.586219 | 22993 | 33.8 |
| 212521_s_at | PDE8A | Hs.9333 | 5151 | 33.8 |
| 221205_at | — | — | — | 33.8 |
| 217041_at | NPTXR | Hs.91622 | 23467 | 33.8 |
| 221010_s_at | SIRT5 | Hs.567431 | 23408 | 33.8 |
| 203461_at | CHD2 | Hs.220864 | 1106 | 33.8 |
| 208493_at | HOXA11 | Hs.249171 | 3207 | 33.8 |
| 213307_at | SHANK2 | Hs.268726 | 22941 | 33.8 |
| 208379_x_at | NPY2R | Hs.37125 | 4887 | 33.8 |
| 214468_at | MYH6 | Hs.278432 | 4624 | 33.8 |
| 205388_at | TNNC2 | Hs.182421 | 7125 | 33.8 |
| 50221_at | TFEB | Hs.485360 | 7942 | 33.8 |
| 211876_x_at | PCDHGA12 /// PCDHGA11 /// PCDHGA10 /// PCDHGA6 /// PCDHGA5 /// PCDHGA3 | | 26025 /// 56105 /// 56106 /// 56109 /// 56110 /// 56112 | 33.8 |

TABLE 2-continued

Genes over-expressed in AML

| probe | Gene | Unigene | Locus | % AML cases with overexpression |
|---|---|---|---|---|
| 213744_at | ATRNL1 | Hs.501127 | 26033 | 33.8 |
| 207351_s_at | SH2D2A | Hs.103527 | 9047 | 33.8 |
| 207642_at | HCRT | Hs.158348 | 3060 | 33.8 |
| 207096_at | SAA4 | Hs.512677 | 6291 | 33.8 |
| 213807_x_at | MET | Hs.132966 | 4233 | 33.8 |
| 216219_at | AQP6 | Hs.54505 | 363 | 33.8 |
| 210991_s_at | RIMS3 | Hs.434924 | 9783 | 33.8 |
| 213498_at | CREB3L1 | Hs.405961 | 90993 | 33.8 |
| 214598_at | CLDN8 | Hs.162209 | 9073 | 33.8 |
| 211019_s_at | LSS | Hs.517366 | 4047 | 33.8 |
| 221321_s_at | KCNIP2 | Hs.97044 | 30819 | 33.8 |
| 204845_s_at | ENPEP | Hs.435765 | 2028 | 33.8 |
| 208394_x_at | ESM1 | Hs.129944 | 11082 | 33.8 |
| 206007_at | PRG4 | Hs.432458 | 10216 | 33.8 |
| 217460_at | TNP2 | Hs.513349 | 7142 | 33.8 |
| 210427_x_at | ANXA2 | Hs.511605 | 302 | 33.1 |
| 218454_at | FLJ22662 | Hs.131933 | 79887 | 33.1 |
| 209604_s_at | GATA3 | Hs.524134 | 2625 | 33.1 |
| 218217_at | SCPEP1 | Hs.514950 | 59342 | 33.1 |
| 210817_s_at | NDP52 | Hs.514920 | 10241 | 33.1 |
| 204787_at | VSIG4 | Hs.8904 | 11326 | 33.1 |
| 204505_s_at | EPB49 | Hs.106124 | 2039 | 33.1 |
| 204912_at | IL10RA | Hs.504035 | 3587 | 33.1 |
| 221257_x_at | FBXO38 | Hs.483772 | 81545 | 33.1 |
| 217743_s_at | TMEM30A | Hs.108530 | 55754 | 33.1 |
| 207651_at | GPR171 | Hs.549152 | 29909 | 33.1 |
| 205076_s_at | MTMR11 | Hs.425144 | 10903 | 33.1 |
| 203549_s_at | LPL | Hs.180878 | 4023 | 33.1 |
| 202869_at | OAS1 | Hs.524760 | 4938 | 33.1 |
| 206522_at | MGAM | Hs.122785 | 8972 | 33.1 |
| 217184_s_at | LTK | Hs.434481 | 4058 | 33.1 |
| 211004_s_at | ALDH3B1 | Hs.523841 | 221 | 33.1 |
| 64440_at | IL17RC | Hs.129959 | 84818 | 33.1 |
| 204626_s_at | ITGB3 | Hs.218040 | 3690 | 33.1 |
| 219444_at | BCORL1 | Hs.496748 | 63035 | 33.1 |
| 201282_at | OGDH | Hs.488181 | 4967 | 33.1 |
| 201299_s_at | MOBK1B | Hs.196437 | 55233 | 33.1 |
| 216388_s_at | LTB4R | Hs.567248 | 1241 | 33.1 |
| 219308_s_at | AK5 | Hs.559718 | 26289 | 33.1 |
| 202609_at | EPS8 | Hs.316997 | 2059 | 33.1 |
| 201579_at | FAT | Hs.481371 | 2195 | 33.1 |
| 205685_at | CD86 | Hs.171182 | 942 | 33.1 |
| 204713_s_at | F5 | Hs.30054 | 2153 | 33.1 |
| 211330_s_at | HFE | Hs.233325 | 3077 | 33.1 |
| 207813_s_at | FDXR | Hs.69745 | 2232 | 33.1 |
| 44822_s_at | KIAA1193 | Hs.101891 | 54531 | 33.1 |
| 219707_at | CPNE7 | Hs.461775 | 27132 | 33.1 |
| 214647_s_at | HFE | Hs.233325 | 3077 | 33.1 |
| 209660_at | TTR | Hs.427202 | 7276 | 33.1 |
| 219883_at | KCNK4 | Hs.97174 | 50801 | 33.1 |
| 218234_at | ING4 | Hs.524210 | 51147 | 33.1 |
| 212960_at | KIAA0882 | Hs.480819 | 23158 | 33.1 |
| 211789_s_at | MONDOA | Hs.437153 | 22877 | 33.1 |
| 221460_at | OR2C1 | Hs.258574 | 4993 | 33.1 |
| 203910_at | ARHGAP29 | Hs.483238 | 9411 | 33.1 |
| 209758_s_at | MFAP5 | Hs.512842 | 8076 | 33.1 |
| 221828_s_at | C9orf28 | Hs.162659 | 89853 | 33.1 |
| 207506_at | TXNL2 | Hs.42644 | 10539 | 33.1 |
| 219745_at | C10orf77 | Hs.309069 | 79847 | 33.1 |
| 202920_at | ANK2 | Hs.567235 | 287 | 33.1 |
| 214967_at | — | — | — | 33.1 |
| 215476_at | — | Hs.159157 | — | 33.1 |
| 221033_s_at | RNF17 | Hs.333271 | 56163 | 33.1 |
| 209866_s_at | LPHN3 | Hs.411097 | 23284 | 33.1 |
| 208235_x_at | GAGE7 | — | 2579 | 33.1 |
| 220887_at | C14orf162 | Hs.458319 | 56936 | 33.1 |
| 216049_at | RHOBTB3 | Hs.445030 | 22836 | 33.1 |
| 207500_at | CASP5 | Hs.213327 | 838 | 33.1 |
| 215226_at | EXPH5 | Hs.269591 | 23086 | 33.1 |
| 222167_at | — | Hs.573405 | — | 33.1 |
| 217026_at | CFTR | Hs.489786 | 1080 | 33.1 |
| 222075_s_at | OAZ3 | Hs.144439 | 51686 | 33.1 |

TABLE 3

| | Genes under-expressed in AML | | | |
|---|---|---|---|---|
| probe | Gene | Unigene | Locus | % AML cases with under-expression |
| 203893_at | TAF9 | Hs.248941 | 6880 | 99.4 |
| 210666_at | IDS | Hs.460960 | 3423 | 98.7 |
| 217591_at | SKIL | Hs.536655 | 6498 | 96.8 |
| 201131_s_at | CDH1 | Hs.461086 | 999 | 95.5 |
| 221772_s_at | PPP2R2D | Hs.380372 | 55844 | 94.3 |
| 212224_at | ALDH1A1 | Hs.76392 | 216 | 94.3 |
| 204416_x_at | APOC1 | Hs.110675 | 341 | 93.6 |
| 219355_at | FLJ10178 | Hs.274267 | 55086 | 93.6 |
| 210281_s_at | ZNF198 | Hs.507433 | 7750 | 93.0 |
| 217975_at | WBP5 | Hs.533287 | 51186 | 93.0 |
| 205830_at | CLGN | Hs.86368 | 1047 | 93.0 |
| 205239_at | AREG | Hs.270833 | 374 | 92.4 |
| 202600_s_at | NRIP1 | Hs.155017 | 8204 | 92.4 |
| 203789_s_at | SEMA3C | Hs.269109 | 10512 | 92.4 |
| 213553_x_at | APOC1 | Hs.110675 | 341 | 91.7 |
| 209739_s_at | PNPLA4 | Hs.264 | 8228 | 91.7 |
| 205767_at | EREG | Hs.115263 | 2069 | 91.7 |
| 202591_s_at | SSBP1 | Hs.490394 | 6742 | 91.1 |
| 204749_at | NAP1L3 | Hs.21365 | 4675 | 91.1 |
| 210054_at | C4orf15 | Hs.584969 | 79441 | 90.4 |
| 209932_s_at | DUT | Hs.527980 | 1854 | 89.8 |
| 201323_at | EBNA1BP2 | Hs.346868 | 10969 | 89.8 |
| 36711_at | MAFF | Hs.517617 | 23764 | 89.8 |
| 210313_at | LILRA4 | Hs.406708 | 23547 | 89.8 |
| 209337_at | PSIP1 | Hs.493516 | 11168 | 88.5 |
| 209507_at | RPA3 | Hs.487540 | 6119 | 88.5 |
| 201465_s_at | JUN | Hs.525704 | 3725 | 88.5 |
| 206683_at | ZNF165 | Hs.55481 | 7718 | 88.5 |
| 203613_s_at | NDUFB6 | Hs.493668 | 4712 | 87.9 |
| 212151_at | PBX1 | Hs.493096 | 5087 | 87.9 |
| 212372_at | MYH10 | Hs.16355 | 4628 | 87.3 |
| 221894_at | ADCK2 | Hs.534141 | 90956 | 87.3 |
| 205429_s_at | MPP6 | Hs.533355 | 51678 | 87.3 |
| 208970_s_at | UROD | Hs.78601 | 7389 | 86.6 |
| 209226_s_at | TNPO1 | Hs.482497 | 3842 | 86.6 |
| 203496_s_at | PPARBP | Hs.462956 | 5469 | 86.6 |
| 209524_at | HDGFRP3 | Hs.513954 | 50810 | 86.6 |
| 216834_at | RGS1 | Hs.75256 | 5996 | 86.6 |
| 202620_s_at | PLOD2 | Hs.477866 | 5352 | 86.6 |
| 202949_s_at | FHL2 | Hs.443687 | 2274 | 86.0 |
| 219855_at | NUDT11 | Hs.200016 | 55190 | 86.0 |
| 208612_at | PDIA3 | Hs.308709 | 2923 | 85.4 |
| 220741_s_at | PPA2 | Hs.480452 | 27068 | 85.4 |
| 201138_s_at | SSB | Hs.546301 | 6741 | 85.4 |
| 205164_at | GCAT | Hs.54609 | 23464 | 85.4 |
| 217901_at | DSG2 | Hs.412597 | 1829 | 85.4 |
| 202766_s_at | FBN1 | Hs.146447 | 2200 | 85.4 |
| 213506_at | F2RL1 | Hs.154299 | 2150 | 85.4 |
| 215691_x_at | C1orf41 | Hs.525462 | 51668 | 84.7 |
| 202858_at | U2AF1 | Hs.365116 | 7307 | 84.7 |
| 204616_at | UCHL3 | Hs.162241 | 7347 | 84.7 |
| 203753_at | TCF4 | Hs.200285 | 6925 | 84.7 |
| 208580_x_at | HIST1H4K /// HIST1H4J | Hs.278483 | 8362 | 84.7 |
| 203917_at | CXADR | Hs.473417 | 1525 | 84.7 |
| 210986_s_at | TPM1 | Hs.133892 | 7168 | 84.7 |
| 213129_s_at | GCSH | Hs.546256 | 2653 | 84.1 |
| 218671_s_at | ATPIF1 | Hs.241336 | 93974 | 83.4 |
| 218493_at | C16orf33 | Hs.15277 | 79622 | 83.4 |
| 212282_at | MAC30 | Hs.199695 | 27346 | 83.4 |
| 204142_at | ENOSF1 | Hs.584931 | 55556 | 83.4 |
| 211148_s_at | ANGPT2 | Hs.553484 | 285 | 83.4 |
| 200748_s_at | FTH1 | Hs.524910 | 2495 | 82.8 |
| 201202_at | PCNA | Hs.147433 | 5111 | 82.8 |
| 205345_at | BARD1 | Hs.54089 | 580 | 82.8 |
| 205262_at | KCNH2 | Hs.188021 | 3757 | 82.8 |
| 204720_s_at | DNAJC6 | Hs.584843 | 9829 | 82.8 |
| 201586_s_at | SFPQ | Hs.355934 | 6421 | 82.2 |
| 39729_at | PRDX2 | Hs.432121 | 7001 | 82.2 |
| 206494_s_at | ITGA2B | Hs.411312 | 3674 | 82.2 |
| 215908_at | MARCH6 | Hs.432862 | 10299 | 82.2 |
| 216956_s_at | ITGA2B | Hs.411312 | 3674 | 82.2 |
| 204004_at | PAWR | Hs.406074 | 5074 | 82.2 |
| 210215_at | TFR2 | Hs.544932 | 7036 | 81.5 |

TABLE 3-continued

Genes under-expressed in AML

| probe | Gene | Unigene | Locus | % AML cases with under-expression |
|---|---|---|---|---|
| 202555_s_at | MYLK | Hs.477375 | 4638 | 81.5 |
| 203628_at | IGF1R | Hs.20573 | 3480 | 81.5 |
| 220418_at | UBASH3A | Hs.473912 | 53347 | 81.5 |
| 218883_s_at | MLF1IP | Hs.481307 | 79682 | 80.9 |
| 211569_s_at | HADHSC | Hs.438289 | 3033 | 80.9 |
| 202691_at | SNRPD1 | Hs.464734 | 6632 | 80.9 |
| 206493_at | ITGA2B | Hs.411312 | 3674 | 80.9 |
| 208029_s_at | LAPTM4B | Hs.492314 | 55353 | 80.9 |
| 220085_at | HELLS | Hs.463677 | 3070 | 80.9 |
| 221606_s_at | NSBP1 | Hs.282204 | 79366 | 80.9 |
| 211784_s_at | SFRS1 | Hs.68714 | 6426 | 80.3 |
| 217802_s_at | NUCKS1 | Hs.213061 | 64710 | 80.3 |
| 206207_at | CLC | Hs.889 | 1178 | 80.3 |
| 221884_at | EVI1 | Hs.165830 | 2122 | 80.3 |
| 201839_s_at | TACSTD1 | Hs.692 | 4072 | 80.3 |
| 202890_at | MAP7 | Hs.486548 | 9053 | 80.3 |
| 202988_s_at | RGS1 | Hs.75256 | 5996 | 80.3 |
| 206770_s_at | SLC35A3 | Hs.567432 | 23443 | 79.6 |
| 201690_s_at | TPD52 | Hs.368433 | 7163 | 79.6 |
| 221496_s_at | TOB2 | Hs.474978 | 10766 | 79.6 |
| 203680_at | PRKAR2B | Hs.433068 | 5577 | 79.6 |
| 204753_s_at | HLF | Hs.196952 | 3131 | 79.6 |
| 211734_s_at | FCER1A | Hs.897 | 2205 | 79.6 |
| 203138_at | HAT1 | Hs.470611 | 8520 | 79.0 |
| 211074_at | LOC441762 | Hs.532675 | 441762 | 79.0 |
| 214039_s_at | LAPTM4B | Hs.492314 | 55353 | 79.0 |
| 203856_at | VRK1 | Hs.422662 | 7443 | 79.0 |
| 203815_at | GSTT1 | Hs.268573 | 2952 | 79.0 |
| 204775_at | CHAF1B | Hs.75238 | 8208 | 79.0 |
| 211700_s_at | TRO | Hs.434971 | 7216 | 79.0 |
| 222258_s_at | SH3BP4 | Hs.516777 | 23677 | 79.0 |
| 208638_at | PDIA6 | Hs.212102 | 10130 | 78.3 |
| 200612_s_at | AP2B1 | Hs.514819 | 163 | 78.3 |
| 216449_x_at | TRA1 | Hs.192374 | 7184 | 78.3 |
| 221270_s_at | QTRT1 | Hs.323084 | 81890 | 78.3 |
| 218894_s_at | FLJ10292 | Hs.104650 | 55110 | 78.3 |
| 214682_at | PKD1 /// NPIP /// LOC339047 /// LOC399491 | Hs.546868 | 339047 | 78.3 |
| 222078_at | HCN3 | Hs.284171 | 57657 | 78.3 |
| 209388_at | PAPOLA | Hs.253726 | 10914 | 77.7 |
| 202340_x_at | NR4A1 | Hs.524430 | 3164 | 77.7 |
| 220377_at | C14orf110 | Hs.395486 | 29064 | 77.7 |
| 219550_at | ROBO3 | Hs.435621 | 64221 | 77.7 |
| 205691_at | SYNGR3 | Hs.435277 | 9143 | 77.7 |
| 202839_s_at | NDUFB7 | Hs.532853 | 4713 | 77.1 |
| 201599_at | OAT | Hs.523332 | 4942 | 77.1 |
| 221777_at | FLJ14827 | Hs.524762 | 84934 | 77.1 |
| 212382_at | TCF4 | Hs.200285 | 6925 | 77.1 |
| 206023_at | NMU | Hs.418367 | 10874 | 77.1 |
| 220520_s_at | FLJ20130 | Hs.163629 | 54830 | 77.1 |
| 202393_s_at | KLF10 | Hs.435001 | 7071 | 76.4 |
| 204071_s_at | TOPORS | Hs.535961 | 10210 | 76.4 |
| 207895_at | NAALADL1 | Hs.13967 | 10004 | 76.4 |
| 217617_at | PBX1 | Hs.493096 | 5087 | 76.4 |
| 218885_s_at | GALNT12 | Hs.47099 | 79695 | 76.4 |
| 215164_at | TCF4 | Hs.200285 | 6925 | 76.4 |
| 215203_at | GOLGA4 | Hs.344151 | 2803 | 75.8 |
| 212386_at | TCF4 | Hs.200285 | 6925 | 75.8 |
| 219555_s_at | BM039 | Hs.584937 | 55839 | 75.8 |
| 212291_at | HIPK1 | Hs.532363 | 204851 | 75.8 |
| 214295_at | KIAA0485 | — | 57235 | 75.8 |
| 203465_at | MRPL19 | Hs.44024 | 9801 | 75.8 |
| 210612_s_at | SYNJ2 | Hs.434494 | 8871 | 75.8 |
| 207469_s_at | PIR | Hs.495728 | 8544 | 75.8 |
| 201215_at | PLS3 | Hs.496622 | 5358 | 75.8 |
| 207335_x_at | ATP5I | Hs.85539 | 521 | 75.2 |
| 209267_s_at | SLC39A8 | Hs.288034 | 64116 | 75.2 |
| 205176_s_at | ITGB3BP | Hs.166539 | 23421 | 75.2 |
| 203099_s_at | CDYL | Hs.269092 | 9425 | 75.2 |
| 203565_s_at | MNAT1 | Hs.509523 | 4331 | 75.2 |
| 211743_s_at | PRG2 | Hs.512633 | 5553 | 75.2 |
| 201291_s_at | TOP2A | Hs.156346 | 7153 | 75.2 |
| 219201_s_at | TWSG1 | Hs.514685 | 57045 | 75.2 |

TABLE 3-continued

Genes under-expressed in AML

| probe | Gene | Unigene | Locus | % AML cases with under-expression |
|---|---|---|---|---|
| 214829_at | AASS | Hs.433075 | 10157 | 75.2 |
| 205967_at | HIST1H4C | Hs.46423 | 8364 | 74.5 |
| 221021_s_at | CTNNBL1 | Hs.472667 | 56259 | 74.5 |
| 205159_at | CSF2RB | Hs.285401 | 1439 | 74.5 |
| 218741_at | C22orf18 | Hs.208912 | 79019 | 74.5 |
| 213693_s_at | MUC1 | Hs.89603 | 4582 | 74.5 |
| 210387_at | HIST1H2BG | Hs.240135 | 8339 | 74.5 |
| 203497_at | PPARBP | Hs.462956 | 5469 | 73.9 |
| 201369_s_at | ZFP36L2 | Hs.503093 | 678 | 73.9 |
| 217408_at | MRPS18B | Hs.274417 | 28973 | 73.9 |
| 203347_s_at | MTF2 | Hs.31016 | 22823 | 73.9 |
| 202889_x_at | MAP7 | Hs.486548 | 9053 | 73.9 |
| 215296_at | CDC42BPA | Hs.35433 | 8476 | 73.9 |
| 213415_at | CLIC2 | Hs.54570 | 1193 | 73.9 |
| 213092_x_at | DNAJC9 | Hs.59125 | 23234 | 73.2 |
| 212190_at | SERPINE2 | Hs.38449 | 5270 | 73.2 |
| 202840_at | TAF15 | Hs.402752 | 8148 | 73.2 |
| 211828_s_at | TNIK | Hs.34024 | 23043 | 73.2 |
| 203577_at | GTF2H4 | Hs.485070 | 2968 | 73.2 |
| 214043_at | PTPRD | Hs.567325 | 5789 | 73.2 |
| 207332_s_at | TFRC | Hs.529618 | 7037 | 72.6 |
| 212855_at | DCUN1D4 | Hs.221407 | 23142 | 72.6 |
| 211596_s_at | LRIG1 | Hs.518055 | 26018 | 72.6 |
| 209167_at | GPM6B | Hs.495710 | 2824 | 72.6 |
| 205706_s_at | ANKRD26 | Hs.361041 | 22852 | 72.6 |
| 212281_s_at | MAC30 | Hs.199695 | 27346 | 72.0 |
| 209526_s_at | HDGFRP3 | Hs.513954 | 50810 | 72.0 |
| 206116_s_at | TPM1 | Hs.133892 | 7168 | 72.0 |
| 218320_s_at | NDUFB11 | Hs.521969 | 54539 | 71.3 |
| 215380_s_at | C7orf24 | Hs.530024 | 79017 | 71.3 |
| 209790_s_at | CASP6 | Hs.3280 | 839 | 71.3 |
| 219598_s_at | RWDD1 | Hs.532164 | 51389 | 71.3 |
| 216060_s_at | DAAM1 | Hs.19156 | 23002 | 71.3 |
| 203764_at | DLG7 | Hs.77695 | 9787 | 71.3 |
| 203382_s_at | APOE | Hs.515465 | 348 | 71.3 |
| 203381_s_at | APOE | Hs.515465 | 348 | 71.3 |
| 214769_at | CLCN4 | Hs.495674 | 1183 | 71.3 |
| 206693_at | IL7 | Hs.536926 | 3574 | 71.3 |
| 214464_at | CDC42BPA | Hs.35433 | 8476 | 71.3 |
| 203543_s_at | KLF9 | Hs.150557 | 687 | 71.3 |
| 200647_x_at | EIF3S8 | Hs.567374 | 8663 | 70.7 |
| 202887_s_at | DDIT4 | Hs.523012 | 54541 | 70.7 |
| 201904_s_at | CTDSPL | Hs.475963 | 10217 | 70.7 |
| 203203_s_at | HRB2 | Hs.584861 | 11103 | 70.7 |
| 208576_s_at | HIST1H3B | Hs.533292 | 8358 | 70.7 |
| 219479_at | KDELC1 | Hs.408629 | 79070 | 70.7 |
| 213241_at | PLXNC1 | Hs.584845 | 10154 | 70.1 |
| 215785_s_at | CYFIP2 | Hs.519702 | 26999 | 70.1 |
| 206310_at | SPINK2 | Hs.98243 | 6691 | 70.1 |
| 204126_s_at | CDC45L | Hs.474217 | 8318 | 70.1 |
| 221406_s_at | MSH5 | Hs.371225 | 4439 | 70.1 |
| 210487_at | DNTT | Hs.534206 | 1791 | 70.1 |
| 201242_s_at | ATP1B1 | Hs.291196 | 481 | 70.1 |
| 215096_s_at | ESD | Hs.432491 | 2098 | 69.4 |
| 202557_at | STCH | Hs.352341 | 6782 | 69.4 |
| 210802_s_at | HSA9761 | Hs.533222 | 27292 | 69.4 |
| 210180_s_at | SFRS10 | Hs.533122 | 6434 | 69.4 |
| 218694_at | ARMCX1 | Hs.9728 | 51309 | 69.4 |
| 203708_at | PDE4B | Hs.198072 | 5142 | 69.4 |
| 212148_at | PBX1 | Hs.493096 | 5087 | 69.4 |
| 201905_s_at | CTDSPL | Hs.475963 | 10217 | 69.4 |
| 217593_at | ZNF447 | Hs.235390 | 65982 | 69.4 |
| 204755_x_at | HLF | Hs.196952 | 3131 | 69.4 |
| 209160_at | AKR1C3 | Hs.78183 | 8644 | 69.4 |
| 205390_s_at | ANK1 | Hs.491558 | 286 | 68.8 |
| 218816_at | LRRC1 | Hs.485581 | 55227 | 68.8 |
| 209493_at | PDZK3 | Hs.481819 | 23037 | 68.8 |
| 201689_s_at | TPD52 | Hs.368433 | 7163 | 68.8 |
| 213954_at | KIAA0888 | Hs.91662 | 26049 | 68.8 |
| 214943_s_at | RBM34 | Hs.535224 | 23029 | 68.8 |
| 215230_x_at | EIF3S8 | Hs.567374 | 8663 | 68.2 |
| 205644_s_at | SNRPG | Hs.6454 | 6637 | 68.2 |
| 202427_s_at | BRP44 | Hs.517768 | 25874 | 68.2 |
| 201014_s_at | PAICS | Hs.518774 | 10606 | 68.2 |

TABLE 3-continued

Genes under-expressed in AML

| probe | Gene | Unigene | Locus | % AML cases with under-expression |
|---|---|---|---|---|
| 218585_s_at | DTL | Hs.126774 | 51514 | 68.2 |
| 214316_x_at | CALR | Hs.515162 | 811 | 68.2 |
| 206306_at | RYR3 | Hs.369250 | 6263 | 68.2 |
| 203352_at | ORC4L | Hs.558364 | 5000 | 68.2 |
| 212062_at | ATP9A | Hs.368002 | 10079 | 68.2 |
| 209994_s_at | ABCB1 /// ABCB4 | Hs.489033 | 5243 | 68.2 |
| 203053_at | BCAS2 | Hs.22960 | 10286 | 67.5 |
| 202705_at | CCNB2 | Hs.194698 | 9133 | 67.5 |
| 202388_at | RGS2 | Hs.78944 | 5997 | 67.5 |
| 203209_at | RFC5 | Hs.506989 | 5985 | 67.5 |
| 208657_s_at | SEPT9 | Hs.440932 | 10801 | 67.5 |
| 213668_s_at | SOX4 | Hs.357901 | 6659 | 67.5 |
| 221349_at | VPREB1 | Hs.247979 | 7441 | 67.5 |
| 207120_at | ZNF667 | Hs.433473 | 63934 | 67.5 |
| 208767_s_at | LAPTM4B | Hs.492314 | 55353 | 66.9 |
| 205677_s_at | DLEU1 | Hs.584850 | 10301 | 66.9 |
| 205178_s_at | RBBP6 | Hs.188553 | 5930 | 66.9 |
| 203448_s_at | TERF1 | Hs.584810 | 7013 | 66.9 |
| 202942_at | ETFB | Hs.74047 | 2109 | 66.9 |
| 213896_x_at | KIAA0974 | Hs.408577 | 317662 | 66.9 |
| 216620_s_at | ARHGEF10 | Hs.98594 | 9639 | 66.9 |
| 208790_s_at | PTRF | Hs.437191 | 284119 | 66.9 |
| 204709_s_at | KIF23 | Hs.270845 | 9493 | 66.9 |
| 222313_at | CNOT2 | Hs.133350 | 4848 | 66.9 |
| 207781_s_at | ZNF6 | Hs.326801 | 7552 | 66.9 |
| 218194_at | REXO2 | Hs.7527 | 25996 | 66.2 |
| 218611_at | IER5 | Hs.15725 | 51278 | 66.2 |
| 210504_at | KLF1 | Hs.37860 | 10661 | 66.2 |
| 221896_s_at | HIGD1A | Hs.7917 | 25994 | 66.2 |
| 213891_s_at | TCF4 | Hs.200285 | 6925 | 66.2 |
| 217963_s_at | NGFRAP1 | Hs.448588 | 27018 | 66.2 |
| 206660_at | IGLL1 | Hs.348935 | 3543 | 66.2 |
| 208789_at | PTRF | Hs.437191 | 284119 | 66.2 |
| 219237_s_at | DNAJB14 | Hs.512743 | 79982 | 66.2 |
| 203294_s_at | LMAN1 | Hs.465295 | 3998 | 66.2 |
| 219790_s_at | NPR3 | Hs.237028 | 4883 | 66.2 |
| 201466_s_at | JUN | Hs.525704 | 3725 | 66.2 |
| 204621_s_at | NR4A2 | Hs.165258 | 4929 | 66.2 |
| 207871_s_at | ST7 | Hs.368131 | 7982 | 66.2 |
| 202619_s_at | PLOD2 | Hs.477866 | 5352 | 66.2 |
| 215474_at | MGC39581 | Hs.130177 | 257062 | 66.2 |
| 212952_at | CALR | Hs.515162 | 811 | 65.6 |
| 206283_s_at | TAL1 | Hs.73828 | 6886 | 65.6 |
| 204057_at | IRF8 | Hs.137427 | 3394 | 65.6 |
| 205909_at | POLE2 | Hs.162777 | 5427 | 65.6 |
| 212385_at | TCF4 | Hs.200285 | 6925 | 65.6 |
| 41577_at | PPP1R16B | Hs.45719 | 26051 | 65.6 |
| 206470_at | PLXNC1 | Hs.584845 | 10154 | 65.6 |
| 200985_s_at | CD59 | Hs.278573 | 966 | 65.6 |
| 213684_s_at | PDLIM5 | Hs.480311 | 10611 | 65.6 |
| 202503_s_at | KIAA0101 | Hs.81892 | 9768 | 65.0 |
| 222103_at | ATF1 | Hs.435267 | 466 | 65.0 |
| 201890_at | RRM2 | Hs.226390 | 6241 | 65.0 |
| 207655_s_at | BLNK | Hs.444049 | 29760 | 65.0 |
| 205624_at | CPA3 | Hs.646 | 1359 | 65.0 |
| 213758_at | COX4I1 | Hs.433419 | 1327 | 65.0 |
| 201602_s_at | PPP1R12A | Hs.49582 | 4659 | 65.0 |
| 221024_s_at | SLC2A10 | Hs.305971 | 81031 | 65.0 |
| 202882_x_at | NOL7 | Hs.549161 | 51406 | 64.3 |
| 201274_at | PSMA5 | Hs.485246 | 5686 | 64.3 |
| 218350_s_at | GMNN | Hs.234896 | 51053 | 64.3 |
| 213229_at | DICER1 | Hs.87889 | 23405 | 64.3 |
| 214710_s_at | CCNB1 | Hs.23960 | 891 | 64.3 |
| 219819_s_at | MRPS28 | Hs.521124 | 28957 | 64.3 |
| 201043_s_at | ANP32A | Hs.458747 | 8125 | 64.3 |
| 204441_s_at | POLA2 | Hs.201897 | 23649 | 64.3 |
| 207883_s_at | TFR2 | Hs.544932 | 7036 | 64.3 |
| 206702_at | TEK | Hs.89640 | 7010 | 64.3 |
| 200891_s_at | SSR1 | Hs.114033 | 6745 | 63.7 |
| 208971_at | UROD | Hs.78601 | 7389 | 63.7 |
| 214214_s_at | C1QBP | Hs.555866 | 708 | 63.7 |
| 208078_s_at | SNF1LK | Hs.282113 | 150094 | 63.7 |
| 219311_at | C18orf9 | Hs.236940 | 79959 | 63.7 |

TABLE 3-continued

Genes under-expressed in AML

| probe | Gene | Unigene | Locus | % AML cases with under-expression |
|---|---|---|---|---|
| 214623_at | SHFM3P1 | — | 26226 | 63.7 |
| 209170_s_at | GPM6B | Hs.495710 | 2824 | 63.7 |
| 220900_at | FLJ12078 | Hs.584973 | 80042 | 63.7 |
| 219117_s_at | FKBP11 | Hs.438695 | 51303 | 63.1 |
| 219551_at | EAF2 | Hs.477325 | 55840 | 63.1 |
| 218762_at | ZNF574 | Hs.13323 | 64763 | 63.1 |
| 215471_s_at | MAP7 | Hs.486548 | 9053 | 63.1 |
| 213549_at | SLC18A2 | Hs.369009 | 6571 | 63.1 |
| 201462_at | SCRN1 | Hs.520740 | 9805 | 63.1 |
| 220432_s_at | CYP39A1 | Hs.387367 | 51302 | 63.1 |
| 221475_s_at | RPL15 | Hs.381219 | 6138 | 62.4 |
| 202268_s_at | APPBP1 | Hs.460978 | 8883 | 62.4 |
| 200596_s_at | EIF3S10 | Hs.523299 | 8661 | 62.4 |
| 202020_s_at | LANCL1 | Hs.13351 | 10314 | 62.4 |
| 214182_at | ARF6 | Hs.525330 | 382 | 62.4 |
| 207983_s_at | STAG2 | Hs.496710 | 10735 | 62.4 |
| 218339_at | MRPL22 | Hs.483924 | 29093 | 62.4 |
| 210028_s_at | ORC3L | Hs.410228 | 23595 | 62.4 |
| 219498_s_at | BCL11A | Hs.370549 | 53335 | 62.4 |
| 218609_s_at | NUDT2 | Hs.493767 | 318 | 62.4 |
| 203092_at | TIMM44 | Hs.465784 | 10469 | 62.4 |
| 219407_s_at | LAMC3 | Hs.201805 | 10319 | 62.4 |
| 220012_at | ERO1LB | Hs.558519 | 56605 | 62.4 |
| 201691_s_at | TPD52 | Hs.368433 | 7163 | 62.4 |
| 221691_x_at | NPM1 | Hs.557550 | 4869 | 61.8 |
| 200853_at | H2AFZ | Hs.119192 | 3015 | 61.8 |
| 201970_s_at | NASP | Hs.319334 | 4678 | 61.8 |
| 202345_s_at | FABP5 | Hs.408061 | 2171 | 61.8 |
| 215111_s_at | TSC22D1 | Hs.507916 | 8848 | 61.8 |
| 211727_s_at | COX11 | Hs.96530 | 1353 | 61.8 |
| 206102_at | PSF1 | Hs.360033 | 9837 | 61.8 |
| 202900_s_at | NUP88 | Hs.584784 | 4927 | 61.8 |
| 210036_s_at | KCNH2 | Hs.188021 | 3757 | 61.8 |
| 205097_at | SLC26A2 | Hs.302738 | 1836 | 61.8 |
| 219203_at | C14orf122 | Hs.271614 | 51016 | 61.8 |
| 204238_s_at | C6orf108 | Hs.109752 | 10591 | 61.8 |
| 202779_s_at | UBE2S | Hs.396393 | 27338 | 61.8 |
| 219258_at | FLJ20516 | Hs.426696 | 54962 | 61.8 |
| 204412_s_at | NEFH | Hs.198760 | 4744 | 61.8 |
| 203213_at | CDC2 | Hs.334562 | 983 | 61.8 |
| 208820_at | PTK2 | Hs.395482 | 5747 | 61.8 |
| 209922_at | BRAP | Hs.530940 | 8315 | 61.8 |
| 219651_at | DPPA4 | Hs.317659 | 55211 | 61.8 |
| 203667_at | TBCA | Hs.291212 | 6902 | 61.1 |
| 202854_at | HPRT1 | Hs.412707 | 3251 | 61.1 |
| 213535_s_at | UBE2I | Hs.302903 | 7329 | 61.1 |
| 205961_s_at | PSIP1 | Hs.493516 | 11168 | 61.1 |
| 202484_s_at | MBD2 | Hs.25674 | 8932 | 61.1 |
| 203097_s_at | RAPGEF2 | Hs.113912 | 9693 | 61.1 |
| 1053_at | RFC2 | Hs.139226 | 5982 | 61.1 |
| 209585_s_at | MINPP1 | Hs.121260 | 9562 | 61.1 |
| 200832_s_at | SCD | Hs.558396 | 6319 | 61.1 |
| 33767_at | NEFH | Hs.198760 | 4744 | 61.1 |
| 205731_s_at | NCOA2 | Hs.446678 | 10499 | 61.1 |
| 213194_at | ROBO1 | Hs.13640 | 6091 | 61.1 |
| 200826_at | SNRPD2 | Hs.515472 | 6633 | 60.5 |
| 209104_s_at | NOLA2 | Hs.27222 | 55651 | 60.5 |
| 201897_s_at | CKS1B | Hs.374378 | 1163 | 60.5 |
| 202983_at | SMARCA3 | Hs.3068 | 6596 | 60.5 |
| 213685_at | — | Hs.15535 | — | 60.5 |
| 211721_s_at | ZNF551 | Hs.184846 | 90233 | 60.5 |
| 211013_x_at | PML | Hs.526464 | 5371 | 60.5 |
| 209905_at | HOXA9 | Hs.127428 | 3205 | 60.5 |
| 202085_at | TJP2 | Hs.50382 | 9414 | 60.5 |
| 205472_s_at | DACH1 | Hs.129452 | 1602 | 60.5 |
| 206999_at | IL12RB2 | Hs.479347 | 3595 | 60.5 |
| 212981_s_at | KIAA0738 | Hs.406492 | 9747 | 60.5 |
| 204559_s_at | LSM7 | Hs.512610 | 51690 | 59.9 |
| 203721_s_at | WDR50 | Hs.463465 | 51096 | 59.9 |
| 201593_s_at | LEREPO4 | Hs.368598 | 55854 | 59.9 |
| 201263_at | TARS | Hs.481860 | 6897 | 59.9 |
| 212057_at | KIAA0182 | Hs.461647 | 23199 | 59.9 |
| 221520_s_at | CDCA8 | Hs.524571 | 55143 | 59.9 |
| 202201_at | BLVRB | Hs.515785 | 645 | 59.9 |

TABLE 3-continued

Genes under-expressed in AML

| probe | Gene | Unigene | Locus | % AML cases with under-expression |
|---|---|---|---|---|
| 221709_s_at | C14orf131 | Hs.106005 | 55778 | 59.9 |
| 218086_at | NPDC1 | Hs.105547 | 56654 | 59.9 |
| 219088_s_at | ZNF576 | Hs.11110 | 79177 | 59.9 |
| 205471_s_at | DACH1 | Hs.129452 | 1602 | 59.9 |
| 200602_at | APP | Hs.434980 | 351 | 59.9 |
| 211755_s_at | ATP5F1 | Hs.514870 | 515 | 59.2 |
| 214431_at | GMPS | Hs.546324 | 8833 | 59.2 |
| 213302_at | PFAS | Hs.370336 | 5198 | 59.2 |
| 203773_x_at | BLVRA | Hs.488143 | 644 | 59.2 |
| 214953_s_at | APP | Hs.434980 | 351 | 59.2 |
| 204300_at | PET112L | Hs.119316 | 5188 | 59.2 |
| 205769_at | SLC27A2 | Hs.11729 | 11001 | 59.2 |
| 211597_s_at | HOP | Hs.121443 | 84525 | 59.2 |
| 36830_at | MIPEP | Hs.507498 | 4285 | 59.2 |
| 219789_at | NPR3 | Hs.237028 | 4883 | 59.2 |
| 204304_s_at | PROM1 | Hs.479220 | 8842 | 59.2 |
| 214223_at | — | — | — | 59.2 |
| 219703_at | MNS1 | Hs.444483 | 55329 | 59.2 |
| 209781_s_at | KHDRBS3 | Hs.444558 | 10656 | 59.2 |
| 205572_at | ANGPT2 | Hs.553484 | 285 | 59.2 |
| 214469_at | HIST1H2AE | Hs.121017 | 3012 | 59.2 |
| 210574_s_at | NUDC | Hs.263812 | 10726 | 58.6 |
| 212943_at | KIAA0528 | Hs.271014 | 9847 | 58.6 |
| 211729_x_at | BLVRA | Hs.488143 | 644 | 58.6 |
| 205981_s_at | ING2 | Hs.107153 | 3622 | 58.6 |
| 206146_s_at | RHAG | Hs.120950 | 6005 | 58.6 |
| 208950_s_at | ALDH7A1 | Hs.483239 | 501 | 58.6 |
| 209485_s_at | OSBPL1A | Hs.370725 | 114876 | 58.6 |
| 214651_s_at | HOXA9 | Hs.127428 | 3205 | 58.6 |
| 202690_s_at | SNRPD1 | Hs.464734 | 6632 | 58.0 |
| 214700_x_at | RIF1 | Hs.536537 | 55183 | 58.0 |
| 218729_at | LXN | Hs.478067 | 56925 | 58.0 |
| 222146_s_at | TCF4 | Hs.200285 | 6925 | 58.0 |
| 203771_s_at | BLVRA | Hs.488143 | 644 | 58.0 |
| 215526_at | WWOX | Hs.461453 | 51741 | 58.0 |
| 213939_s_at | RIPX | Hs.7972 | 22902 | 58.0 |
| 213094_at | GPR126 | Hs.318894 | 57211 | 58.0 |
| 208956_x_at | DUT | Hs.527980 | 1854 | 57.3 |
| 202567_at | SNRPD3 | Hs.356549 | 6634 | 57.3 |
| 213097_s_at | ZRF1 | Hs.558476 | 27000 | 57.3 |
| 203351_s_at | ORC4L | Hs.558364 | 5000 | 57.3 |
| 210425_x_at | GOLGA8B | Hs.356225 | 440270 | 57.3 |
| 201948_at | GNL2 | Hs.75528 | 29889 | 57.3 |
| 212533_at | WEE1 | Hs.249441 | 7465 | 57.3 |
| 205419_at | EBI2 | Hs.784 | 1880 | 57.3 |
| 208352_x_at | ANK1 | Hs.491558 | 286 | 57.3 |
| 37986_at | EPOR | Hs.127826 | 2057 | 57.3 |
| 210115_at | RPL39L | Hs.478582 | 116832 | 57.3 |
| 216373_at | FLJ90013 | Hs.479223 | 202018 | 57.3 |
| 211955_at | RANBP5 | Hs.513057 | 3843 | 56.7 |
| 201846_s_at | RYBP | Hs.7910 | 23429 | 56.7 |
| 203690_at | TUBGCP3 | Hs.224152 | 10426 | 56.7 |
| 218529_at | CD320 | Hs.558499 | 51293 | 56.7 |
| 205193_at | MAFF | Hs.517617 | 23764 | 56.7 |
| 203228_at | PAFAH1B3 | Hs.466831 | 5050 | 56.7 |
| 210446_at | GATA1 | Hs.765 | 2623 | 56.7 |
| 208353_x_at | ANK1 | Hs.491558 | 286 | 56.7 |
| 213616_at | C18orf10 | Hs.558473 | 25941 | 56.7 |
| 220010_at | KCNE1L | Hs.522753 | 23630 | 56.7 |
| 209774_x_at | CXCL2 | Hs.75765 | 2920 | 56.7 |
| 203817_at | — | — | — | 56.7 |
| 202599_s_at | NRIP1 | Hs.155017 | 8204 | 56.7 |
| 214331_at | TSFM | Hs.505784 | 10102 | 56.7 |
| 203316_s_at | SNRPE | Hs.334612 | 6635 | 56.1 |
| 221452_s_at | TMEM14B | Hs.273077 | 81853 | 56.1 |
| 202467_s_at | COPS2 | Hs.369614 | 9318 | 56.1 |
| 208910_s_at | C1QBP | Hs.555866 | 708 | 56.1 |
| 218188_s_at | TIMM13 | Hs.75056 | 26517 | 56.1 |
| 206555_s_at | THUMPD1 | Hs.460232 | 55623 | 56.1 |
| 203794_at | CDC42BPA | Hs.35433 | 8476 | 56.1 |
| 219546_at | BMP2K | Hs.146551 | 55589 | 56.1 |
| 221286_s_at | PACAP | Hs.409563 | 51237 | 56.1 |
| 214045_at | LIAS | Hs.550502 | 11019 | 56.1 |
| 205984_at | CRHBP | Hs.115617 | 1393 | 56.1 |

TABLE 3-continued

Genes under-expressed in AML

| probe | Gene | Unigene | Locus | % AML cases with under-expression |
|---|---|---|---|---|
| 217538_at | RUTBC1 | Hs.513861 | 9905 | 56.1 |
| 217818_s_at | ARPC4 | Hs.323342 | 10093 | 56.1 |
| 203895_at | PLCB4 | Hs.472101 | 5332 | 56.1 |
| 217889_s_at | CYBRD1 | Hs.221941 | 79901 | 56.1 |
| 222348_at | — | — | — | 56.1 |
| 222378_at | FLJ43663 | Hs.150556 | 378805 | 56.1 |
| 209290_s_at | NFIB | Hs.370359 | 4781 | 56.1 |
| 219174_at | CCDC2 | Hs.145402 | 80173 | 56.1 |
| 204115_at | GNG11 | Hs.83381 | 2791 | 56.1 |
| 200750_s_at | RAN | Hs.10842 | 5901 | 55.4 |
| 219192_at | UBAP2 | Hs.493739 | 55833 | 55.4 |
| 217979_at | TSPAN13 | Hs.364544 | 27075 | 55.4 |
| 201569_s_at | SAMM50 | Hs.505824 | 25813 | 55.4 |
| 218711_s_at | SDPR | Hs.26530 | 8436 | 55.4 |
| 204030_s_at | SCHIP1 | Hs.134665 | 29970 | 55.4 |
| 205240_at | GPSM2 | Hs.584901 | 29899 | 55.4 |
| 208791_at | CLU | Hs.436657 | 1191 | 55.4 |
| 215779_s_at | HIST1H2BG | Hs.240135 | 8339 | 55.4 |
| 214815_at | TRIM33 | Hs.568681 | 51592 | 55.4 |
| 215402_at | APPBP2 | Hs.84084 | 10513 | 55.4 |
| 204005_s_at | PAWR | Hs.406074 | 5074 | 55.4 |
| 218981_at | ACN9 | Hs.42785 | 57001 | 55.4 |
| 200786_at | PSMB7 | Hs.213470 | 5695 | 54.8 |
| 208993_s_at | PPIG | Hs.470544 | 9360 | 54.8 |
| 201764_at | MGC5576 | Hs.103834 | 79022 | 54.8 |
| 202780_at | OXCT1 | Hs.278277 | 5019 | 54.8 |
| 219658_at | PTCD2 | Hs.126906 | 79810 | 54.8 |
| 219918_s_at | ASPM | Hs.121028 | 259266 | 54.8 |
| 215054_at | EPOR | Hs.127826 | 2057 | 54.8 |
| 213550_s_at | — | — | — | 54.8 |
| 209129_at | TRIP6 | Hs.534360 | 7205 | 54.8 |
| 210254_at | MS4A3 | Hs.99960 | 932 | 54.8 |
| 216022_at | WNK1 | Hs.504432 | 65125 | 54.8 |
| 207056_s_at | SLC4A8 | Hs.370636 | 9498 | 54.8 |
| 209669_s_at | SERBP1 | Hs.530412 | 26135 | 54.1 |
| 201459_at | RUVBL2 | Hs.515846 | 10856 | 54.1 |
| 203391_at | FKBP2 | Hs.227729 | 2286 | 54.1 |
| 212005_at | C1orf144 | Hs.252967 | 26099 | 54.1 |
| 205086_s_at | hCAP-H2 | Hs.180903 | 29781 | 54.1 |
| 209516_at | SMYD5 | Hs.516095 | 10322 | 54.1 |
| 207877_s_at | NVL | Hs.497867 | 4931 | 54.1 |
| 218856_at | TNFRSF21 | Hs.443577 | 27242 | 54.1 |
| 213844_at | HOXA5 | Hs.37034 | 3202 | 54.1 |
| 210758_at | PSIP1 | Hs.493516 | 11168 | 54.1 |
| 221841_s_at | KLF4 | Hs.376206 | 9314 | 54.1 |
| 217787_s_at | GALNT2 | Hs.567272 | 2590 | 54.1 |
| 208963_x_at | FADS1 | Hs.503546 | 3992 | 54.1 |
| 216813_at | — | — | — | 54.1 |
| 201427_s_at | SEPP1 | Hs.275775 | 6414 | 54.1 |
| 205711_x_at | ATP5C1 | Hs.271135 | 509 | 53.5 |
| 217774_s_at | HSPC152 | Hs.333579 | 51504 | 53.5 |
| 212780_at | SOS1 | Hs.278733 | 6654 | 53.5 |
| 210793_s_at | NUP98 | Hs.524750 | 4928 | 53.5 |
| 211302_s_at | PDE4B | Hs.198072 | 5142 | 53.5 |
| 209531_at | GSTZ1 | Hs.26403 | 2954 | 53.5 |
| 219961_s_at | C20orf19 | Hs.187635 | 55857 | 53.5 |
| 222154_s_at | DNAPTP6 | Hs.120323 | 26010 | 53.5 |
| 218435_at | DNAJC15 | Hs.438830 | 29103 | 53.5 |
| 213067_at | MYH10 | Hs.16355 | 4628 | 53.5 |
| 216248_s_at | NR4A2 | Hs.165258 | 4929 | 53.5 |
| 205372_at | PLAG1 | Hs.14968 | 5324 | 53.5 |
| 207879_at | — | — | — | 53.5 |
| 213224_s_at | LOC92482 | Hs.192249 | 92482 | 52.9 |
| 218049_s_at | MRPL13 | Hs.333823 | 28998 | 52.9 |
| 201292_at | TOP2A | Hs.156346 | 7153 | 52.9 |
| 202468_s_at | CTNNAL1 | Hs.58488 | 8727 | 52.9 |
| 201830_s_at | NET1 | Hs.25155 | 10276 | 52.9 |
| 203821_at | HBEGF | Hs.799 | 1839 | 52.9 |
| 202095_s_at | BIRC5 | Hs.514527 | 332 | 52.9 |
| 212263_at | QKI | Hs.510324 | 9444 | 52.9 |
| 214724_at | DIXDC1 | Hs.116796 | 85458 | 52.9 |
| 203532_x_at | CUL5 | Hs.440320 | 8065 | 52.9 |
| 217684_at | TYMS | Hs.369762 | 7298 | 52.9 |
| 206669_at | GAD1 | Hs.420036 | 2571 | 52.9 |

TABLE 3-continued

Genes under-expressed in AML

| probe | Gene | Unigene | Locus | % AML cases with under-expression |
|---|---|---|---|---|
| 214130_s_at | PDE4DIP | Hs.584841 | 9659 | 52.9 |
| 215330_at | FLJ43663 | Hs.150556 | 378805 | 52.9 |
| 214167_s_at | RPLP0 /// RPLP0-like | Hs.448226 | 220717 | 52.2 |
| 212694_s_at | PCCB | Hs.63788 | 5096 | 52.2 |
| 209049_s_at | PRKCBP1 | Hs.446240 | 23613 | 52.2 |
| 212368_at | ZNF292 | Hs.485892 | 23036 | 52.2 |
| 204976_s_at | AMMECR1 | Hs.211021 | 9949 | 52.2 |
| 203068_at | KLHL21 | Hs.7764 | 9903 | 52.2 |
| 205453_at | HOXB2 | Hs.514289 | 3212 | 52.2 |
| 205046_at | CENPE | Hs.75573 | 1062 | 52.2 |
| 204766_s_at | NUDT1 | Hs.534331 | 4521 | 52.2 |
| 216650_at | LOC283412 /// LOC442165 | Hs.531538 | 283412 | 52.2 |
| 215200_x_at | VIL2 | Hs.487027 | 7430 | 52.2 |
| 218128_at | NFYB | Hs.84928 | 4801 | 52.2 |
| 213122_at | TSPYL5 | Hs.173094 | 85453 | 52.2 |
| 219341_at | CLN8 | Hs.127675 | 2055 | 52.2 |
| 220602_s_at | FLJ22795 /// LOC388152 /// LOC388161 | Hs.405809 | 388152 | 52.2 |
| 201506_at | TGFBI | Hs.369397 | 7045 | 52.2 |
| 210691_s_at | CACYBP | Hs.508524 | 27101 | 52.2 |
| 200876_s_at | PSMB1 | Hs.352768 | 5689 | 51.6 |
| 221532_s_at | WDR61 | Hs.513055 | 80349 | 51.6 |
| 200783_s_at | STMN1 | Hs.209983 | 3925 | 51.6 |
| 203196_at | ABCC4 | Hs.508423 | 10257 | 51.6 |
| 218456_at | C1QDC1 | Hs.234355 | 65981 | 51.6 |
| 221685_s_at | FLJ20364 | Hs.368710 | 54908 | 51.6 |
| 219837_s_at | CYTL1 | Hs.13872 | 54360 | 51.6 |
| 202237_at | NNMT | Hs.503911 | 4837 | 51.6 |
| 201367_s_at | ZFP36L2 | Hs.503093 | 678 | 51.6 |
| 222326_at | PDE4B | Hs.198072 | 5142 | 51.6 |
| 209314_s_at | HBS1L | Hs.378532 | 10767 | 51.6 |
| 208646_at | RPS14 | Hs.381126 | 6208 | 51.0 |
| 201901_s_at | YY1 | Hs.388927 | 7528 | 51.0 |
| 202469_s_at | CPSF6 | Hs.369606 | 11052 | 51.0 |
| 219030_at | CGI-121 | Hs.157401 | 51002 | 51.0 |
| 202309_at | MTHFD1 | Hs.435974 | 4522 | 51.0 |
| 221932_s_at | C14orf87 | Hs.532683 | 51218 | 51.0 |
| 219067_s_at | C10orf86 | Hs.258798 | 54780 | 51.0 |
| 221652_s_at | C12orf11 | Hs.505077 | 55726 | 51.0 |
| 201377_at | UBAP2L | Hs.490551 | 9898 | 51.0 |
| 218025_s_at | PECI | Hs.15250 | 10455 | 51.0 |
| 202732_at | PKIG | Hs.472831 | 11142 | 51.0 |
| 212692_s_at | LRBA | Hs.480938 | 987 | 51.0 |
| 210762_s_at | DLC1 | Hs.134296 | 10395 | 51.0 |
| 202339_at | SYMPK | Hs.515475 | 8189 | 51.0 |
| 208792_s_at | CLU | Hs.436657 | 1191 | 51.0 |
| 208178_x_at | TRIO | Hs.130031 | 7204 | 51.0 |
| 201688_s_at | TPD52 | Hs.368433 | 7163 | 51.0 |
| 217876_s_at | GTF3C5 | Hs.495417 | 9328 | 51.0 |
| 212463_at | CD59 | Hs.278573 | 966 | 51.0 |
| 219264_s_at | PPP2R3B | Hs.124942 | 28227 | 51.0 |
| 210882_s_at | TRO | Hs.434971 | 7216 | 51.0 |
| 220298_s_at | SPATA6 | Hs.408467 | 54558 | 51.0 |
| 64900_at | CHST5 /// MGC15429 | Hs.420796 | 23563 | 51.0 |
| 221618_s_at | TAF9L | Hs.567505 | 51616 | 51.0 |
| 214143_x_at | RPL24 /// SLC36A2 | Hs.483877 | 153201 | 50.3 |
| 200642_at | SOD1 | Hs.443914 | 6647 | 50.3 |
| 219041_s_at | REPIN1 | Hs.521289 | 29803 | 50.3 |
| 205133_s_at | HSPE1 | Hs.1197 | 3336 | 50.3 |
| 201501_s_at | GRSF1 | Hs.309763 | 2926 | 50.3 |
| 212594_at | PDCD4 | Hs.232543 | 27250 | 50.3 |
| 221007_s_at | FIP1L1 | Hs.518760 | 81608 | 50.3 |
| 212629_s_at | PKN2 | Hs.440833 | 5586 | 50.3 |
| 219247_s_at | ZDHHC14 | Hs.187459 | 79683 | 50.3 |
| 212396_s_at | KIAA0090 | Hs.439200 | 23065 | 50.3 |
| 216804_s_at | PDLIM5 | Hs.480311 | 10611 | 50.3 |
| 206726_at | PGDS | Hs.128433 | 27306 | 50.3 |
| 214051_at | MGC39900 | Hs.496530 | 286527 | 50.3 |
| 203212_s_at | MTMR2 | Hs.181326 | 8898 | 50.3 |

TABLE 3-continued

Genes under-expressed in AML

| probe | Gene | Unigene | Locus | % AML cases with under-expression |
|---|---|---|---|---|
| 204307_at | KIAA0329 | Hs.195667 | 9895 | 50.3 |
| 203072_at | MYO1E | Hs.370392 | 4643 | 50.3 |
| 204979_s_at | SH3BGR | Hs.473847 | 6450 | 50.3 |
| 216027_at | TXNDC13 | Hs.169358 | 56255 | 50.3 |
| 207855_s_at | CLCC1 | Hs.554803 | 23155 | 50.3 |
| 215388_s_at | CFH /// CFHL1 | Hs.154224 | 3075 | 50.3 |
| 200679_x_at | HMGB1 | Hs.434102 | 3146 | 49.7 |
| 202589_at | TYMS | Hs.369762 | 7298 | 49.7 |
| 201273_s_at | SRP9 | Hs.511425 | 6726 | 49.7 |
| 208787_at | MRPL3 | Hs.205163 | 11222 | 49.7 |
| 218003_s_at | FKBP3 | Hs.509226 | 2287 | 49.7 |
| 201275_at | FDPS | Hs.335918 | 2224 | 49.7 |
| 202347_s_at | HIP2 | Hs.50308 | 3093 | 49.7 |
| 206061_s_at | DICER1 | Hs.87889 | 23405 | 49.7 |
| 217739_s_at | PBEF1 | Hs.489615 | 10135 | 49.7 |
| 203049_s_at | KIAA0372 | Hs.482868 | 9652 | 49.7 |
| 209340_at | UAP1 | Hs.492859 | 6675 | 49.7 |
| 202861_at | PER1 | Hs.445534 | 5187 | 49.7 |
| 201283_s_at | OIP106 | Hs.535711 | 22906 | 49.7 |
| 213789_at | — | — | — | 49.7 |
| 203542_s_at | KLF9 | Hs.150557 | 687 | 49.7 |
| 212813_at | JAM3 | Hs.150718 | 83700 | 49.7 |
| 210415_s_at | ODF2 | Hs.129055 | 4957 | 49.7 |
| 205673_s_at | ASB9 | Hs.19404 | 140462 | 49.7 |
| 204627_s_at | ITGB3 | Hs.218040 | 3690 | 49.7 |
| 213610_s_at | KLHL23 | — | 151230 | 49.7 |
| 215339_at | NKTR | Hs.529509 | 4820 | 49.7 |
| 211969_at | HSPCA | Hs.525600 | 3320 | 49.0 |
| 211713_x_at | KIAA0101 | Hs.81892 | 9768 | 49.0 |
| 222035_s_at | PAPOLA | Hs.253726 | 10914 | 49.0 |
| 218654_s_at | MRPS33 | Hs.83006 | 51650 | 49.0 |
| 206364_at | KIF14 | Hs.3104 | 9928 | 49.0 |
| 208935_s_at | LGALS8 | Hs.4082 | 3964 | 49.0 |
| 209318_x_at | PLAGL1 | Hs.444975 | 5325 | 49.0 |
| 204444_at | KIF11 | Hs.8878 | 3832 | 49.0 |
| 218886_at | PAK1IP1 | Hs.310231 | 55003 | 49.0 |
| 219251_s_at | WDR60 | Hs.389945 | 55112 | 49.0 |
| 221586_s_at | E2F5 | Hs.445758 | 1875 | 49.0 |
| 202855_s_at | SLC16A3 | Hs.500761 | 9123 | 49.0 |
| 208814_at | HSPA4 | Hs.90093 | 3308 | 49.0 |
| 215931_s_at | ARFGEF2 | Hs.62578 | 10564 | 49.0 |
| 211506_s_at | IL8 | Hs.624 | 3576 | 49.0 |
| 218656_s_at | LHFP | Hs.507798 | 10186 | 49.0 |
| 215016_x_at | DST | Hs.485616 | 667 | 49.0 |
| 215720_s_at | NFYA | Hs.10441 | 4800 | 49.0 |
| 216765_at | MAP2K5 | Hs.114198 | 5607 | 49.0 |
| 208672_s_at | SFRS3 | Hs.572089 | 6428 | 48.4 |
| 203133_at | SEC61B | Hs.191887 | 10952 | 48.4 |
| 211761_s_at | CACYBP | Hs.508524 | 27101 | 48.4 |
| 202911_at | MSH6 | Hs.445052 | 2956 | 48.4 |
| 221570_s_at | METTL5 | Hs.470553 | 29081 | 48.4 |
| 215780_s_at | SET /// LOC389168 | Hs.436687 | 389168 | 48.4 |
| 201464_x_at | JUN | Hs.525704 | 3725 | 48.4 |
| 202048_s_at | CBX6 | Hs.511952 | 23466 | 48.4 |
| 209299_x_at | PPIL2 | Hs.438587 | 23759 | 48.4 |
| 209196_at | WDR46 | Hs.520063 | 9277 | 48.4 |
| 209605_at | TST | Hs.474783 | 7263 | 48.4 |
| 204825_at | MELK | Hs.184339 | 9833 | 48.4 |
| 212750_at | PPP1R16B | Hs.45719 | 26051 | 48.4 |
| 205155_s_at | SPTBN2 | Hs.26915 | 6712 | 48.4 |
| 209406_at | BAG2 | Hs.55220 | 9532 | 48.4 |
| 215248_at | GRB10 | Hs.164060 | 2887 | 48.4 |
| 207057_at | SLC16A7 | Hs.439643 | 9194 | 48.4 |
| 213150_at | HOXA10 | Hs.110637 | 3206 | 48.4 |
| 212489_at | COL5A1 | Hs.210283 | 1289 | 48.4 |
| 222364_at | SLC44A1 | Hs.494700 | 23446 | 48.4 |
| 216278_at | KIAA0256 | Hs.9997 | 9728 | 48.4 |
| 207721_x_at | HINT1 | Hs.483305 | 3094 | 47.8 |
| 208691_at | TFRC | Hs.529618 | 7037 | 47.8 |
| 212036_s_at | PNN | Hs.409965 | 5411 | 47.8 |
| 200790_at | ODC1 | Hs.467701 | 4953 | 47.8 |
| 212055_at | C18orf10 | Hs.558473 | 25941 | 47.8 |
| 209662_at | CETN3 | Hs.128073 | 1070 | 47.8 |

TABLE 3-continued

Genes under-expressed in AML

| probe | Gene | Unigene | Locus | % AML cases with under-expression |
|---|---|---|---|---|
| 209759_s_at | DCI | Hs.403436 | 1632 | 47.8 |
| 213147_at | HOXA10 | Hs.110637 | 3206 | 47.8 |
| 219737_s_at | PCDH9 | Hs.407643 | 5101 | 47.8 |
| 205393_s_at | CHEK1 | Hs.24529 | 1111 | 47.8 |
| 221900_at | COL8A2 | Hs.353001 | 1296 | 47.8 |
| 220302_at | MAK | Hs.446125 | 4117 | 47.8 |
| 211136_s_at | CLPTM1 | Hs.444441 | 1209 | 47.8 |
| 207550_at | MPL | Hs.82906 | 4352 | 47.8 |
| 211549_s_at | HPGD | Hs.77348 | 3248 | 47.8 |
| 212182_at | NUDT4 | Hs.506325 | 11163 | 47.8 |
| 208368_s_at | BRCA2 | Hs.34012 | 675 | 47.8 |
| 215567_at | C14orl11 | Hs.343173 | 51077 | 47.8 |
| 214712_at | — | — | — | 47.8 |
| 208753_s_at | NAP1L1 | Hs.524599 | 4673 | 47.1 |
| 216237_s_at | MCM5 | Hs.517582 | 4174 | 47.1 |
| 221829_s_at | TNPO1 | Hs.482497 | 3842 | 47.1 |
| 208661_s_at | TTC3 | Hs.368214 | 7267 | 47.1 |
| 202947_s_at | GYPC | Hs.59138 | 2995 | 47.1 |
| 221847_at | LOC440123 | Hs.585252 | 440123 | 47.1 |
| 201123_s_at | EIF5A | Hs.534314 | 1984 | 47.1 |
| 211028_s_at | KHK | Hs.567297 | 3795 | 47.1 |
| 203264_s_at | ARHGEF9 | Hs.54697 | 23229 | 47.1 |
| 218976_at | DNAJC12 | Hs.260720 | 56521 | 47.1 |
| 206298_at | ARHGAP22 | Hs.435063 | 58504 | 47.1 |
| 207124_s_at | GNB5 | Hs.155090 | 10681 | 47.1 |
| 215992_s_at | RAPGEF2 | Hs.113912 | 9693 | 47.1 |
| 206698_at | XK | Hs.78919 | 7504 | 47.1 |
| 211840_s_at | PDE4D | Hs.117545 | 5144 | 47.1 |
| 207798_s_at | ATXN2L | Hs.460499 | 11273 | 47.1 |
| 214422_at | RAD23B /// LOC131185 | Hs.521640 | 131185 | 47.1 |
| 203913_s_at | HPGD | Hs.77348 | 3248 | 47.1 |
| 208805_at | PSMA6 | Hs.446260 | 5687 | 46.5 |
| 211936_at | HSPA5 | Hs.522394 | 3309 | 46.5 |
| 200806_s_at | HSPD1 | Hs.567290 | 3329 | 46.5 |
| 213655_at | YWHAE | Hs.513851 | 7531 | 46.5 |
| 215416_s_at | STOML2 | Hs.3439 | 30968 | 46.5 |
| 210983_s_at | MCM7 | Hs.438720 | 4176 | 46.5 |
| 209153_s_at | TCF3 | Hs.371282 | 6929 | 46.5 |
| 219076_s_at | PXMP2 | Hs.430299 | 5827 | 46.5 |
| 215223_s_at | SOD2 | Hs.487046 | 6648 | 46.5 |
| 203061_s_at | MDC1 | Hs.433653 | 9656 | 46.5 |
| 213593_s_at | TRA2A | Hs.445652 | 29896 | 46.5 |
| 203114_at | SSSCA1 | Hs.534388 | 10534 | 46.5 |
| 204833_at | ATG12 | Hs.264482 | 9140 | 46.5 |
| 212070_at | GPR56 | Hs.513633 | 9289 | 46.5 |
| 204162_at | KNTC2 | Hs.414407 | 10403 | 46.5 |
| 212229_s_at | FBXO21 | Hs.159699 | 23014 | 46.5 |
| 222180_at | — | — | — | 46.5 |
| 212529_at | FLJ30656 | Hs.355570 | 124801 | 46.5 |
| 204717_s_at | SLC29A2 | Hs.32951 | 3177 | 46.5 |
| 215440_s_at | BEXL1 | Hs.184736 | 56271 | 46.5 |
| 209488_s_at | RBPMS | Hs.334587 | 11030 | 46.5 |
| 207850_at | CXCL3 | Hs.89690 | 2921 | 46.5 |
| 206864_s_at | HRK | Hs.87247 | 8739 | 46.5 |
| 215846_at | CDC42SE2 | Hs.508829 | 56990 | 46.5 |
| 219148_at | PBK | Hs.104741 | 55872 | 46.5 |
| 210662_at | KYNU | Hs.470126 | 8942 | 46.5 |
| 211987_at | TOP2B | Hs.475733 | 7155 | 45.9 |
| 200969_at | SERP1 | Hs.518326 | 27230 | 45.9 |
| 202078_at | COPS3 | Hs.6076 | 8533 | 45.9 |
| 202396_at | TCERG1 | Hs.443465 | 10915 | 45.9 |
| 218450_at | HEBP1 | Hs.294133 | 50865 | 45.9 |
| 201540_at | FHL1 | Hs.435369 | 2273 | 45.9 |
| 206478_at | KIAA0125 | Hs.584844 | 9834 | 45.9 |
| 218452_at | SMARCAL1 | Hs.516674 | 50485 | 45.9 |
| 202478_at | TRIB2 | Hs.467751 | 28951 | 45.9 |
| 216614_at | ITPR2 | Hs.512235 | 3709 | 45.9 |
| 204881_s_at | UGCG | Hs.304249 | 7357 | 45.9 |
| 212758_s_at | TCF8 | Hs.124503 | 6935 | 45.9 |
| 221071_at | — | — | — | 45.9 |
| 206847_s_at | HOXA7 | Hs.446318 | 3204 | 45.9 |
| 201044_x_at | DUSP1 | Hs.171695 | 1843 | 45.9 |
| 219990_at | E2F8 | Hs.523526 | 79733 | 45.9 |

TABLE 3-continued

Genes under-expressed in AML

| probe | Gene | Unigene | Locus | % AML cases with under-expression |
|---|---|---|---|---|
| 215002_at | LOC23117 /// DKFZp547E087 /// LOC348162 /// LOC388221 /// LOC440345 /// LOC440354 /// LOC613037 | Hs.444600 | 23117 | 45.9 |
| 206637_at | P2RY14 | Hs.2465 | 9934 | 45.9 |
| 222320_at | CDC73 | Hs.378996 | 79577 | 45.9 |
| 204386_s_at | MRP63 | Hs.458367 | 78988 | 45.2 |
| 208758_at | ATIC | Hs.90280 | 471 | 45.2 |
| 200658_s_at | PHB | Hs.514303 | 5245 | 45.2 |
| 208843_s_at | GORASP2 | Hs.431317 | 26003 | 45.2 |
| 209014_at | MAGED1 | Hs.5258 | 9500 | 45.2 |
| 217848_s_at | PPA1 | Hs.437403 | 5464 | 45.2 |
| 217814_at | GK001 | Hs.202011 | 57003 | 45.2 |
| 212508_at | MOAP1 | Hs.24719 | 64112 | 45.2 |
| 213227_at | PGRMC2 | Hs.507910 | 10424 | 45.2 |
| 204299_at | FUSIP1 | Hs.3530 | 10772 | 45.2 |
| 59644_at | BMP2K | Hs.146551 | 55589 | 45.2 |
| 203989_x_at | F2R | Hs.482562 | 2149 | 45.2 |
| 207194_s_at | ICAM4 | Hs.386467 | 3386 | 45.2 |
| 204962_s_at | CENPA | Hs.1594 | 1058 | 45.2 |
| 221690_s_at | NALP2 | Hs.369279 | 55655 | 45.2 |
| 218430_s_at | RFXDC2 | Hs.282855 | 64864 | 45.2 |
| 205391_x_at | ANK1 | Hs.491558 | 286 | 45.2 |
| 207232_s_at | DZIP3 | Hs.409210 | 9666 | 45.2 |
| 214255_at | ATP10A | Hs.128041 | 57194 | 45.2 |
| 203533_s_at | CUL5 | Hs.440320 | 8065 | 45.2 |
| 204195_s_at | PKNOX1 | Hs.431043 | 5316 | 45.2 |
| 207532_at | CRYGD | Hs.546247 | 1421 | 45.2 |
| 212715_s_at | MICAL3 | Hs.528024 | 57553 | 45.2 |
| 221187_s_at | FLJ22688 | Hs.288800 | 80199 | 45.2 |
| 220171_x_at | KIAA1704 | Hs.507922 | 55425 | 45.2 |
| 214637_at | OSM | Hs.248156 | 5008 | 45.2 |
| 202371_at | TCEAL4 | Hs.194329 | 79921 | 45.2 |
| 203987_at | FZD6 | Hs.292464 | 8323 | 45.2 |
| 205122_at | TMEFF1 | Hs.336224 | 8577 | 45.2 |
| 202144_s_at | ADSL | Hs.75527 | 158 | 44.6 |
| 202001_s_at | NDUFA6 | Hs.274416 | 4700 | 44.6 |
| 201931_at | ETFA | Hs.39925 | 2108 | 44.6 |
| 217745_s_at | MAK3 | Hs.269528 | 80218 | 44.6 |
| 210093_s_at | MAGOH | Hs.421576 | 4116 | 44.6 |
| 209680_s_at | KIFC1 | Hs.436912 | 3833 | 44.6 |
| 222209_s_at | FLJ22104 | Hs.188591 | 65084 | 44.6 |
| 204622_x_at | NR4A2 | Hs.165258 | 4929 | 44.6 |
| 209035_at | MDK | Hs.82045 | 4192 | 44.6 |
| 202336_s_at | PAM | Hs.369430 | 5066 | 44.6 |
| 222375_at | PPIG | Hs.470544 | 9360 | 44.6 |
| 203865_s_at | ADARB1 | Hs.474018 | 104 | 44.6 |
| 204524_at | PDPK1 | Hs.459691 | 5170 | 44.6 |
| 205628_at | PRIM2A | Hs.485640 | 5558 | 44.6 |
| 203325_s_at | COL5A1 | Hs.210283 | 1289 | 44.6 |
| 202760_s_at | AKAP2 /// PALM2-AKAP2 | Hs.259461 | 11217 | 44.6 |
| 219650_at | FLJ20105 | Hs.47558 | 54821 | 44.6 |
| 218087_s_at | SORBS1 | Hs.38621 | 10580 | 44.6 |
| 201134_x_at | COX7C | Hs.430075 | 1350 | 43.9 |
| 201277_s_at | HNRPAB | Hs.248746 | 3182 | 43.9 |
| 203345_s_at | MTF2 | Hs.31016 | 22823 | 43.9 |
| 209330_s_at | HNRPD | Hs.480073 | 3184 | 43.9 |
| 217028_at | CXCR4 | Hs.421986 | 7852 | 43.9 |
| 202232_s_at | hfl-B5 | Hs.502244 | 10480 | 43.9 |
| 201197_at | AMD1 | Hs.159118 | 262 | 43.9 |
| 203048_s_at | KIAA0372 | Hs.482868 | 9652 | 43.9 |
| 205964_at | ZNF426 | Hs.567574 | 79088 | 43.9 |
| 209865_at | SLC35A3 | Hs.567432 | 23443 | 43.9 |
| 206655_s_at | GP1BB | Hs.517410 | 2812 | 43.9 |
| 204317_at | GTSE1 /// LOC440834 | Hs.386189 | 440834 | 43.9 |
| 209081_s_at | COL18A1 | Hs.517356 | 80781 | 43.9 |
| 205857_at | — | — | — | 43.9 |
| 220593_s_at | FLJ20753 | Hs.202542 | 55036 | 43.9 |
| 205413_at | MPPED2 | Hs.289795 | 744 | 43.9 |

TABLE 3-continued

Genes under-expressed in AML

| probe | Gene | Unigene | Locus | % AML cases with under-expression |
|---|---|---|---|---|
| 208826_x_at | HINT1 | Hs.483305 | 3094 | 43.3 |
| 202857_at | TMEM4 | Hs.8752 | 10330 | 43.3 |
| 202431_s_at | MYC | Hs.202453 | 4609 | 43.3 |
| 201880_at | ARIH1 | Hs.268787 | 25820 | 43.3 |
| 200965_s_at | ABLIM1 | Hs.438236 | 3983 | 43.3 |
| 205051_s_at | KIT | Hs.479754 | 3815 | 43.3 |
| 211464_x_at | CASP6 | Hs.3280 | 839 | 43.3 |
| 214579_at | NPAL3 | Hs.523442 | 57185 | 43.3 |
| 219188_s_at | LRP16 | Hs.502814 | 28992 | 43.3 |
| 204558_at | RAD54L | Hs.523220 | 8438 | 43.3 |
| 213566_at | RNASE6 | Hs.23262 | 6039 | 43.3 |
| 219661_at | RANBP17 | Hs.410810 | 64901 | 43.3 |
| 206871_at | ELA2 | Hs.99863 | 1991 | 43.3 |
| 208937_s_at | ID1 | Hs.504609 | 3397 | 43.3 |
| 205937_at | CGREF1 | Hs.159525 | 10669 | 43.3 |
| 208499_s_at | DNAJC3 | Hs.59214 | 5611 | 43.3 |
| 212775_at | OBSL1 | Hs.526594 | 23363 | 43.3 |
| 204141_at | TUBB2 | Hs.512712 | 7280 | 43.3 |
| 213714_at | CACNB2 | Hs.59093 | 783 | 43.3 |
| 203434_s_at | MME | Hs.307734 | 4311 | 43.3 |
| 215578_at | — | — | — | 43.3 |
| 213619_at | HNRPH1 | Hs.202166 | 3187 | 42.7 |
| 209492_x_at | ATP5I | Hs.85539 | 521 | 42.7 |
| 40189_at | SET | Hs.436687 | 6418 | 42.7 |
| 209118_s_at | TUBA3 | Hs.524395 | 7846 | 42.7 |
| 210097_s_at | NOL7 | Hs.549161 | 51406 | 42.7 |
| 203362_s_at | MAD2L1 | Hs.559215 | 4085 | 42.7 |
| 203373_at | SOCS2 | Hs.485572 | 8835 | 42.7 |
| 200983_x_at | CD59 | Hs.278573 | 966 | 42.7 |
| 201067_at | PSMC2 | Hs.437366 | 5701 | 42.7 |
| 222186_at | ZA20D3 | Hs.306329 | 54469 | 42.7 |
| 218237_s_at | SLC38A1 | Hs.533770 | 81539 | 42.7 |
| 205653_at | CTSG | Hs.421724 | 1511 | 42.7 |
| 204917_s_at | MLLT3 | Hs.493585 | 4300 | 42.7 |
| 219094_at | ARMC8 | Hs.266826 | 25852 | 42.7 |
| 213012_at | NEDD4 | Hs.1565 | 4734 | 42.7 |
| 203467_at | PMM1 | Hs.75835 | 5372 | 42.7 |
| 219922_s_at | LTBP3 | Hs.289019 | 4054 | 42.7 |
| 204112_s_at | HNMT | Hs.42151 | 3176 | 42.7 |
| 204468_s_at | TIE1 | Hs.78824 | 7075 | 42.7 |
| 214804_at | FSHPRH1 | Hs.348920 | 2491 | 42.7 |
| 202269_x_at | GBP1 | Hs.62661 | 2633 | 42.7 |
| 210466_s_at | SERBP1 | Hs.530412 | 26135 | 42.0 |
| 218462_at | BXDC5 | Hs.481202 | 80135 | 42.0 |
| 217836_s_at | YY1AP1 | Hs.584927 | 55249 | 42.0 |
| 212160_at | XPOT | Hs.85951 | 11260 | 42.0 |
| 201737_s_at | MARCH6 | Hs.432862 | 10299 | 42.0 |
| 218662_s_at | HCAP-G | Hs.567567 | 64151 | 42.0 |
| 203787_at | SSBP2 | Hs.102735 | 23635 | 42.0 |
| 221599_at | PTD015 | Hs.503357 | 28971 | 42.0 |
| 208501_at | GFI1B | Hs.118539 | 8328 | 42.0 |
| 218930_s_at | FLJ11273 | Hs.396358 | 54664 | 42.0 |
| 205521_at | ENDOGL1 | Hs.517897 | 9941 | 42.0 |
| 205997_at | ADAM28 | Hs.174030 | 10863 | 42.0 |
| 217259_at | MTMR7 | Hs.584834 | 9108 | 42.0 |
| 221027_s_at | PLA2G12A | Hs.480519 | 81579 | 42.0 |
| 213478_at | KIAA1026 | Hs.368823 | 23254 | 42.0 |
| 209914_s_at | NRXN1 | Hs.468505 | 9378 | 42.0 |
| 218801_at | UGCGL2 | Hs.193226 | 55757 | 42.0 |
| 215392_at | MINPP1 | Hs.121260 | 9562 | 42.0 |
| 213088_s_at | DNAJC9 | Hs.59125 | 23234 | 41.4 |
| 200984_s_at | CD59 | Hs.278573 | 966 | 41.4 |
| 203560_at | GGH | Hs.78619 | 8836 | 41.4 |
| 207165_at | HMMR | Hs.72550 | 3161 | 41.4 |
| 207828_s_at | CENPF | Hs.497741 | 1063 | 41.4 |
| 220040_x_at | KIAA1166 | Hs.28249 | 55906 | 41.4 |
| 218397_at | FANCL | Hs.411433 | 55120 | 41.4 |
| 212949_at | BRRN1 | Hs.308045 | 23397 | 41.4 |
| 217858_s_at | ARMCX3 | Hs.172788 | 51566 | 41.4 |
| 213420_at | DHX57 | Hs.468226 | 90957 | 41.4 |
| 210139_s_at | PMP22 | Hs.372031 | 5376 | 41.4 |
| 214126_at | MCART1 | Hs.118394 | 92014 | 41.4 |
| 207892_at | CD40LG | Hs.652 | 959 | 41.4 |
| 209204_at | LMO4 | Hs.436792 | 8543 | 41.4 |

TABLE 3-continued

Genes under-expressed in AML

| probe | Gene | Unigene | Locus | % AML cases with under-expression |
|---|---|---|---|---|
| 211267_at | HESX1 | Hs.171980 | 8820 | 41.4 |
| 218045_x_at | PTMS | Hs.504613 | 5763 | 41.4 |
| 207110_at | KCNJ12 | Hs.200629 | 3768 | 41.4 |
| 220004_at | DDX43 | Hs.125507 | 55510 | 41.4 |
| 218395_at | ACTR6 | Hs.115088 | 64431 | 40.8 |
| 201565_s_at | ID2 | Hs.180919 | 3398 | 40.8 |
| 220007_at | FLJ13984 | Hs.135146 | 79828 | 40.8 |
| 212599_at | AUTS2 | Hs.21631 | 26053 | 40.8 |
| 219733_s_at | SLC27A5 | Hs.309583 | 10998 | 40.8 |
| 221922_at | GPSM2 | Hs.584901 | 29899 | 40.8 |
| 208788_at | ELOVL5 | Hs.520189 | 60481 | 40.8 |
| 204306_s_at | CD151 | Hs.512857 | 977 | 40.8 |
| 209094_at | DDAH1 | Hs.379858 | 23576 | 40.8 |
| 211182_x_at | RUNX1 | Hs.149261 | 861 | 40.8 |
| 219497_s_at | BCL11A | Hs.370549 | 53335 | 40.8 |
| 206877_at | MXD1 | Hs.468908 | 4084 | 40.8 |
| 204430_s_at | SLC2A5 | Hs.530003 | 6518 | 40.8 |
| 209764_at | MGAT3 | Hs.276808 | 4248 | 40.8 |
| 209372_x_at | TUBB2 /// TUBB-PARALOG | Hs.512712 | 347733 /// 7280 | 40.8 |
| 205352_at | SERPINI1 | Hs.478153 | 5274 | 40.8 |
| 208403_x_at | MAX | Hs.285354 | 4149 | 40.8 |
| 209763_at | CHRDL1 | Hs.496587 | 91851 | 40.8 |
| 207341_at | PRTN3 | Hs.928 | 5657 | 40.8 |
| 202110_at | COX7B | Hs.522699 | 1349 | 40.1 |
| 201381_x_at | CACYBP | Hs.508524 | 27101 | 40.1 |
| 201143_s_at | EIF2S1 | Hs.151777 | 1965 | 40.1 |
| 201829_at | NET1 | Hs.25155 | 10276 | 40.1 |
| 218710_at | FLJ20272 | Hs.468125 | 55622 | 40.1 |
| 204146_at | RAD51AP1 | Hs.504550 | 10635 | 40.1 |
| 204028_s_at | RABGAP1 | Hs.271341 | 23637 | 40.1 |
| 215338_s_at | NKTR | Hs.529509 | 4820 | 40.1 |
| 209304_x_at | GADD45B | Hs.110571 | 4616 | 40.1 |
| 205394_at | CHEK1 | Hs.24529 | 1111 | 40.1 |
| 219054_at | FLJ14054 | Hs.13528 | 79614 | 40.1 |
| 210377_at | ACSM3 | Hs. 160976 | 6296 | 40.1 |
| 201996_s_at | SPEN | Hs.558463 | 23013 | 40.1 |
| 204069_at | MEIS1 | Hs.526754 | 4211 | 40.1 |
| 208813_at | GOT1 | Hs.500756 | 2805 | 40.1 |
| 210868_s_at | ELOVL6 | Hs.412939 | 79071 | 40.1 |
| 205190_at | PLS1 | Hs.203637 | 5357 | 40.1 |
| 219135_s_at | FLJ12681 | Hs.71912 | 64788 | 40.1 |
| 218051_s_at | FLJ12442 | Hs.84753 | 64943 | 40.1 |
| 203836_s_at | MAP3K5 | Hs.186486 | 4217 | 40.1 |
| 219785_s_at | FBXO31 | Hs.567582 | 79791 | 40.1 |
| 215850_s_at | NDUFA5 | Hs.83916 | 4698 | 40.1 |
| 210734_x_at | MAX | Hs.285354 | 4149 | 40.1 |
| 201334_s_at | ARHGEF12 | Hs.24598 | 23365 | 40.1 |
| 205253_at | PBX1 | Hs.493096 | 5087 | 40.1 |
| 219976_at | HOOK1 | Hs.378836 | 51361 | 40.1 |
| 205407_at | RECK | Hs.388918 | 8434 | 40.1 |
| 219871_at | FLJ13197 | Hs.29725 | 79667 | 40.1 |
| 219688_at | BBS7 | Hs.58974 | 55212 | 40.1 |
| 209803_s_at | PHLDA2 | Hs.154036 | 7262 | 40.1 |
| 201947_s_at | CCT2 | Hs.189772 | 10576 | 39.5 |
| 200085_s_at | TCEB2 | Hs.172772 | 6923 | 39.5 |
| 202501_at | MAPRE2 | Hs.532824 | 10982 | 39.5 |
| 206052_s_at | SLBP | Hs.298345 | 7884 | 39.5 |
| 211653_x_at | AKR1C2 | Hs.567256 | 1646 | 39.5 |
| 202391_at | BASP1 | Hs.201641 | 10409 | 39.5 |
| 201397_at | PHGDH | Hs.487296 | 26227 | 39.5 |
| 213008_at | FLJ10719 | Hs.513126 | 55215 | 39.5 |
| 207000_s_at | PPP3CC | Hs.149413 | 5533 | 39.5 |
| 207949_s_at | ICA1 | Hs.487561 | 3382 | 39.5 |
| 212891_s_at | GADD45GIP1 | Hs.515164 | 90480 | 39.5 |
| 203960_s_at | C1orf41 | Hs.525462 | 51668 | 39.5 |
| 221908_at | TMEM118 | Hs.437195 | 84900 | 39.5 |
| 202711_at | EFNB1 | Hs.144700 | 1947 | 39.5 |
| 201923_at | PRDX4 | Hs.83383 | 10549 | 39.5 |
| 205389_s_at | ANK1 | Hs.491558 | 286 | 39.5 |
| 217486_s_at | ZDHHC17 | Hs.4014 | 23390 | 39.5 |
| 214966_at | GRIK5 | Hs.367799 | 2901 | 39.5 |
| 216228_s_at | WDHD1 | Hs.385998 | 11169 | 39.5 |

TABLE 3-continued

Genes under-expressed in AML

| probe | Gene | Unigene | Locus | % AML cases with under-expression |
|---|---|---|---|---|
| 210012_s_at | EWSR1 | Hs.374477 | 2130 | 39.5 |
| 215653_at | GPC5 | Hs.567269 | 2262 | 39.5 |
| 200840_at | KARS | Hs.3100 | 3735 | 38.9 |
| 201584_s_at | DDX39 | Hs.311609 | 10212 | 38.9 |
| 202824_s_at | TCEB1 | Hs.554594 | 6921 | 38.9 |
| 208795_s_at | MCM7 | Hs.438720 | 4176 | 38.9 |
| 201478_s_at | DKC1 | Hs.4747 | 1736 | 38.9 |
| 203137_at | WTAP | Hs.446091 | 9589 | 38.9 |
| 209181_s_at | RABGGTB | Hs.78948 | 5876 | 38.9 |
| 201326_at | CCT6A | Hs.82916 | 908 | 38.9 |
| 218680_x_at | SERF2 /// HYPK | Hs.424126 | 10169 /// 25764 | 38.9 |
| 212279_at | MAC30 | Hs.199695 | 27346 | 38.9 |
| 209219_at | RDBP | Hs.423935 | 7936 | 38.9 |
| 217956_s_at | MASA | Hs.18442 | 58478 | 38.9 |
| 205339_at | SIL | Hs.525198 | 6491 | 38.9 |
| 215215_s_at | LOC81691 | Hs.177926 | 81691 | 38.9 |
| 221521_s_at | Pfs2 | Hs.433180 | 51659 | 38.9 |
| 219000_s_at | DCC1 | Hs.315167 | 79075 | 38.9 |
| 202283_at | SERPINF1 | Hs.532768 | 5176 | 38.9 |
| 209750_at | NR1D2 | Hs.37288 | 9975 | 38.9 |
| 219213_at | JAM2 | Hs.517227 | 58494 | 38.9 |
| 202806_at | DBN1 | Hs.130316 | 1627 | 38.9 |
| 202479_s_at | TRIB2 | Hs.467751 | 28951 | 38.9 |
| 216983_s_at | ZNF224 | Hs.549077 | 7767 | 38.9 |
| 213556_at | LOC390940 | Hs.22049 | 390940 | 38.9 |
| 214146_s_at | PPBP | Hs.2164 | 5473 | 38.9 |
| 207087_x_at | ANK1 | Hs.491558 | 286 | 38.9 |
| 220221_at | VPS13D | Hs.439381 | 55187 | 38.9 |
| 204149_s_at | GSTM4 | Hs.348387 | 2948 | 38.9 |
| 205808_at | ASPH | Hs.332422 | 444 | 38.9 |
| 210368_at | PCDHGB4 /// PCDHGA8 | — | 8641 /// 9708 | 38.9 |
| 214405_at | CUGBP2 | Hs.309288 | 10659 | 38.9 |
| 209967_s_at | CREM | Hs.200250 | 1390 | 38.9 |
| 209900_s_at | SLC16A1 | Hs.75231 | 6566 | 38.9 |
| 214393_at | LOC284062 | Hs.436395 | 284062 | 38.9 |
| 210997_at | HGF | Hs.396530 | 3082 | 38.9 |
| 213591_at | ALDH7A1 | Hs.483239 | 501 | 38.9 |
| 207717_s_at | PKP2 | Hs.164384 | 5318 | 38.9 |
| 200705_s_at | EEF1B2 | Hs.421608 | 1933 | 38.2 |
| 208808_s_at | HMGB2 | Hs.434953 | 3148 | 38.2 |
| 207585_s_at | RPL36AL | Hs.444749 | 6166 | 38.2 |
| 201892_s_at | IMPDH2 | Hs.476231 | 3615 | 38.2 |
| 201317_s_at | PSMA2 | Hs.333786 | 5683 | 38.2 |
| 217725_x_at | SERBP1 | Hs.530412 | 26135 | 38.2 |
| 206445_s_at | HRMT1L2 | Hs.20521 | 3276 | 38.2 |
| 217679_x_at | — | Hs.573462 | — | 38.2 |
| 219105_x_at | ORC6L | Hs.49760 | 23594 | 38.2 |
| 209122_at | ADFP | Hs.3416 | 123 | 38.2 |
| 203224_at | RFK | Hs.37558 | 55312 | 38.2 |
| 216212_s_at | DKC1 | Hs.4747 | 1736 | 38.2 |
| 218857_s_at | ASRGL1 | Hs.535326 | 80150 | 38.2 |
| 213007_at | FLJ10719 | Hs.513126 | 55215 | 38.2 |
| 208158_s_at | OSBPL1A | Hs.370725 | 114876 | 38.2 |
| 220688_s_at | C1orf33 | Hs.463797 | 51154 | 38.2 |
| 203590_at | DNCLI2 | Hs.369068 | 1783 | 38.2 |
| 205667_at | WRN | Hs.567358 | 7486 | 38.2 |
| 213899_at | METAP2 | Hs.444986 | 10988 | 38.2 |
| 219242_at | Cep63 | Hs.443301 | 80254 | 38.2 |
| 212387_at | — | — | — | 38.2 |
| 216591_s_at | SDHC | Hs.444472 | 6391 | 38.2 |
| 204928_s_at | SLC10A3 | Hs.522826 | 8273 | 38.2 |
| 203069_at | SV2A | Hs.516153 | 9900 | 38.2 |
| 203662_s_at | TMOD1 | Hs.404289 | 7111 | 38.2 |
| 209528_s_at | KIAA0683 | Hs.271044 | 9894 | 38.2 |
| 218663_at | HCAP-G | Hs.567567 | 64151 | 38.2 |
| 218707_at | ZNF444 | Hs.24545 | 55311 | 38.2 |
| 220183_s_at | NUDT6 | Hs.558459 | 11162 | 38.2 |
| 219742_at | PRR7 | Hs.534492 | 80758 | 38.2 |
| 203891_s_at | DAPK3 | Hs.233308 | 1613 | 38.2 |
| 214764_at | KIAA0507 | Hs.552801 | 57241 | 38.2 |
| 204113_at | CUGBP1 | Hs.530727 | 10658 | 38.2 |
| 214452_at | BCAT1 | Hs.438993 | 586 | 38.2 |
| 218901_at | PLSCR4 | Hs.477869 | 57088 | 38.2 |

TABLE 3-continued

Genes under-expressed in AML

| probe | Gene | Unigene | Locus | % AML cases with under-expression |
|---|---|---|---|---|
| 213793_s_at | HOMER1 | Hs.129051 | 9456 | 38.2 |
| 215457_at | ARPC1A | Hs.124126 | 10552 | 38.2 |
| 219380_x_at | POLH | Hs.439153 | 5429 | 38.2 |
| 201226_at | NDUFB8 | Hs.523215 | 4714 | 37.6 |
| 208796_s_at | CCNG1 | Hs.79101 | 900 | 37.6 |
| 218447_at | DC13 | Hs.388255 | 56942 | 37.6 |
| 204023_at | RFC4 | Hs.518475 | 5984 | 37.6 |
| 203675_at | NUCB2 | Hs.128686 | 4925 | 37.6 |
| 204516_at | ATXN7 | Hs.476595 | 6314 | 37.6 |
| 201055_s_at | HNRPA0 | Hs.96996 | 10949 | 37.6 |
| 222240_s_at | ISYNA1 | Hs.405873 | 51477 | 37.6 |
| 209704_at | MTF2 | Hs.31016 | 22823 | 37.6 |
| 219217_at | FLJ23441 | Hs.503389 | 79731 | 37.6 |
| 204531_s_at | BRCA1 | Hs.194143 | 672 | 37.6 |
| 202859_x_at | IL8 | Hs.624 | 3576 | 37.6 |
| 222303_at | — | — | — | 37.6 |
| 217776_at | RDH11 | Hs.226007 | 51109 | 37.6 |
| 202747_s_at | ITM2A | Hs.17109 | 9452 | 37.6 |
| 212186_at | ACACA | Hs.160556 | 31 | 37.6 |
| 205008_s_at | CIB2 | Hs.129867 | 10518 | 37.6 |
| 201841_s_at | HSPB1 | Hs.520973 | 3315 | 37.6 |
| 218756_s_at | MGC4172 | Hs.462859 | 79154 | 37.6 |
| 214095_at | SHMT2 | Hs.75069 | 6472 | 37.6 |
| 215224_at | RPL23 | Hs.406300 | 9349 | 37.6 |
| 204182_s_at | ZNF297B | Hs.355581 | 23099 | 37.6 |
| 219386_s_at | SLAMF8 | Hs.438683 | 56833 | 37.6 |
| 214472_at | HIST1H3D | Hs.532144 | 8351 | 37.6 |
| 210506_at | FUT7 | Hs.457 | 2529 | 37.6 |
| 207808_s_at | PROS1 | Hs.64016 | 5627 | 37.6 |
| 205292_s_at | HNRPA2B1 | Hs.487774 | 3181 | 36.9 |
| 200807_s_at | HSPD1 | Hs.567290 | 3329 | 36.9 |
| 212426_s_at | YWHAQ | Hs.74405 | 10971 | 36.9 |
| 220647_s_at | CHCHD8 | Hs.475387 | 51287 | 36.9 |
| 201091_s_at | CBX3 | Hs.381189 | 11335 | 36.9 |
| 222266_at | C19orf2 | Hs.466391 | 8725 | 36.9 |
| 209795_at | CD69 | Hs.208854 | 969 | 36.9 |
| 203285_s_at | HS2ST1 | Hs.48823 | 9653 | 36.9 |
| 203189_s_at | NDUFS8 | Hs.90443 | 4728 | 36.9 |
| 204947_at | E2F1 | Hs.96055 | 1869 | 36.9 |
| 217919_s_at | MRPL42 | Hs.199579 | 28977 | 36.9 |
| 202536_at | CHMP2B | Hs.476930 | 25978 | 36.9 |
| 208269_s_at | ADAM28 | Hs.174030 | 10863 | 36.9 |
| 213989_x_at | C21orf18 | Hs.473727 | 54093 | 36.9 |
| 210157_at | C19orf2 | Hs.466391 | 8725 | 36.9 |
| 206233_at | B4GALT6 | Hs.464848 | 9331 | 36.9 |
| 219412_at | RAB38 | Hs.283148 | 23682 | 36.9 |
| 202871_at | TRAF4 | Hs.8375 | 9618 | 36.9 |
| 215509_s_at | BUB1 | Hs.469649 | 699 | 36.9 |
| 209213_at | CBR1 | Hs.88778 | 873 | 36.9 |
| 209917_s_at | TP53AP1 | Hs.274329 | 11257 | 36.9 |
| 220038_at | SGK3 | Hs.380877 | 23678 | 36.9 |
| 217071_s_at | MTHFR | Hs.214142 | 4524 | 36.9 |
| 209576_at | GNAI1 | Hs.134587 | 2770 | 36.9 |
| 203803_at | PCYOX1 | Hs.567502 | 51449 | 36.9 |
| 207030_s_at | CSRP2 | Hs.530904 | 1466 | 36.9 |
| 221802_s_at | KIAA1598 | Hs.501140 | 57698 | 36.9 |
| 208515_at | HIST1H2BM | Hs.182432 | 8342 | 36.9 |
| 203222_s_at | TLE1 | Hs.197320 | 7088 | 36.9 |
| 209487_at | RBPMS | Hs.334587 | 11030 | 36.9 |
| 202244_at | PSMB4 | Hs.89545 | 5692 | 36.3 |
| 215171_s_at | TIMM17A | Hs.20716 | 10440 | 36.3 |
| 217845_x_at | HIGD1A | Hs.7917 | 25994 | 36.3 |
| 217933_s_at | LAP3 | Hs.479264 | 51056 | 36.3 |
| 201093_x_at | SDHA | Hs.440475 | 6389 | 36.3 |
| 218708_at | NXT1 | Hs.516933 | 29107 | 36.3 |
| 202416_at | DNAJC7 | Hs.500156 | 7266 | 36.3 |
| 201614_s_at | RUVBL1 | Hs.272822 | 8607 | 36.3 |
| 209543_s_at | CD34 | Hs.374990 | 947 | 36.3 |
| 218285_s_at | DHRS6 | Hs.567972 | 56898 | 36.3 |
| 208886_at | H1F0 | Hs.226117 | 3005 | 36.3 |
| 212183_at | NUDT4 | Hs.506325 | 11163 | 36.3 |
| 81737_at | LOC388221 /// LOC440345 | Hs.348979 /// Hs.444600 /// Hs.587880 | 388221 /// 440345 | 36.3 |

TABLE 3-continued

Genes under-expressed in AML

| probe | Gene | Unigene | Locus | % AML cases with under-expression |
|---|---|---|---|---|
| 218264_at | BCCIP | Hs.370292 | 56647 | 36.3 |
| 202648_at | RPS19 | Hs.438429 | 6223 | 36.3 |
| 201640_x_at | CLPTM1 | Hs.444441 | 1209 | 36.3 |
| 213638_at | PHACTR1 | Hs.436996 | 221692 | 36.3 |
| 204794_at | DUSP2 | Hs.1183 | 1844 | 36.3 |
| 221224_s_at | FLJ22955 | Hs.463148 | 79877 | 36.3 |
| 206500_s_at | C14orf106 | Hs.437941 | 55320 | 36.3 |
| 215757_at | PRKDC | Hs.491682 | 5591 | 36.3 |
| 202773_s_at | SFRS8 | Hs.308171 | 6433 | 36.3 |
| 207521_s_at | ATP2A3 | Hs.513870 | 489 | 36.3 |
| 213082_s_at | SLC35D2 | Hs.494556 | 11046 | 36.3 |
| 211200_s_at | EFCAB2 | Hs.134857 | 84288 | 36.3 |
| 211085_s_at | STK4 | Hs.472838 | 6789 | 36.3 |
| 206906_at | ICAM5 | Hs.465862 | 7087 | 36.3 |
| 203165_s_at | SLC33A1 | Hs.478031 | 9197 | 36.3 |
| 214918_at | HNRPM | Hs.465808 | 4670 | 36.3 |
| 219166_at | C14orf104 | Hs.231761 | 55172 | 36.3 |
| 212466_at | SPRED2 | Hs.59332 | 200734 | 36.3 |
| 202270_at | GBP1 | Hs.62661 | 2633 | 36.3 |
| 215212_at | — | Hs.127737 | — | 36.3 |
| 203830_at | NJMU-R1 | Hs.462754 | 64149 | 36.3 |
| 214715_x_at | ZNF160 | Hs.467236 | 90338 | 35.7 |
| 218334_at | NIF3L1BP1 | Hs.288151 | 80145 | 35.7 |
| 208662_s_at | TTC3 | Hs.368214 | 7267 | 35.7 |
| 218039_at | NUSAP1 | Hs.511093 | 51203 | 35.7 |
| 203011_at | IMPA1 | Hs.492120 | 3612 | 35.7 |
| 201036_s_at | HADHSC | Hs.438289 | 3033 | 35.7 |
| 201017_at | EIF1AX | Hs.522590 | 1964 | 35.7 |
| 218858_at | DEPDC6 | Hs.303788 | 64798 | 35.7 |
| 213357_at | GTF2H5 | Hs.356224 | 404672 | 35.7 |
| 201083_s_at | BCLAF1 | Hs.486542 | 9774 | 35.7 |
| 218620_s_at | HEMK1 | Hs.517987 | 51409 | 35.7 |
| 218236_s_at | PRKD3 | Hs.173536 | 23683 | 35.7 |
| 204695_at | CDC25A | Hs.1634 | 993 | 35.7 |
| 221248_s_at | WHSC1L1 | Hs.32099 | 54904 | 35.7 |
| 210547_x_at | ICA1 | Hs.487561 | 3382 | 35.7 |
| 203955_at | KIAA0649 | Hs.533260 | 9858 | 35.7 |
| 203919_at | TCEA2 | Hs.505004 | 6919 | 35.7 |
| 45633_at | FLJ13912 | Hs.47125 | 64785 | 35.7 |
| 203627_at | IGF1R | Hs.20573 | 3480 | 35.7 |
| 215288_at | TRPC2 | Hs.131910 | 7221 | 35.7 |
| 203715_at | TBCE | Hs.498143 | 6905 | 35.7 |
| 219327_s_at | GPRC5C | Hs.44643 8 | 55890 | 35.7 |
| 212019_at | RSL1D1 | Hs.401842 | 26156 | 35.7 |
| 211548_s_at | HPGD | Hs.77348 | 3248 | 35.7 |
| 215942_s_at | GTSE1 | Hs.386189 | 51512 | 35.7 |
| 211280_s_at | NRF1 | Hs.298069 | 4899 | 35.7 |
| 216254_at | PARVB | Hs.475074 | 29780 | 35.7 |
| 205063_at | SIP1 | Hs.533862 | 8487 | 35.7 |
| 201951_at | ALCAM | Hs.150693 | 214 | 35.7 |
| 210875_s_at | TCF8 | Hs.124503 | 6935 | 35.7 |
| 220474_at | SLC25A21 | Hs.134544 | 89874 | 35.7 |
| 201922_at | TINP1 | Hs.482526 | 10412 | 35.0 |
| 201432_at | CAT | Hs.502302 | 847 | 35.0 |
| 200959_at | FUS | Hs.513522 | 2521 | 35.0 |
| 203538_at | CAMLG | Hs.529846 | 819 | 35.0 |
| 218256_s_at | NUP54 | Hs.430435 | 53371 | 35.0 |
| 209678_s_at | PRKCI | Hs.478199 | 5584 | 35.0 |
| 203177_x_at | TFAM | Hs.559835 | 7019 | 35.0 |
| 209250_at | DEGS1 | Hs.299878 | 8560 | 35.0 |
| 204504_s_at | HIRIP3 | Hs.567370 | 8479 | 35.0 |
| 213134_x_at | BTG3 | Hs.473420 | 10950 | 35.0 |
| 219553_at | NME7 | Hs.567487 | 29922 | 35.0 |
| 202188_at | NUP93 | Hs.276878 | 9688 | 35.0 |
| 211962_s_at | ZFP36L1 | Hs.85155 | 677 | 35.0 |
| 221809_at | RANBP10 | Hs.368569 | 57610 | 35.0 |
| 219156_at | SYNJ2BP | Hs.443661 | 55333 | 35.0 |
| 205398_s_at | SMAD3 | Hs.555881 | 4088 | 35.0 |
| 213701_at | DKFZp434N2030 | Hs.494204 | 91298 | 35.0 |
| 219769_at | INCENP | Hs.142179 | 3619 | 35.0 |
| 207206_s_at | ALOX12 | Hs.422967 | 239 | 35.0 |
| 210830_s_at | PON2 | Hs.530077 | 5445 | 35.0 |
| 221760_at | MAN1A1 | Hs.102788 | 4121 | 35.0 |
| 212013_at | PXDN | Hs.332197 | 7837 | 35.0 |

TABLE 3-continued

Genes under-expressed in AML

| probe | Gene | Unigene | Locus | % AML cases with under-expression |
|---|---|---|---|---|
| 216850_at | SNRPN | Hs.564847 | 6638 | 35.0 |
| 204439_at | IFI44L | Hs.389724 | 10964 | 35.0 |
| 205768_s_at | SLC27A2 | Hs.11729 | 11001 | 35.0 |
| 212979_s_at | KIAA0738 | Hs.406492 | 9747 | 35.0 |
| 207996_s_at | C18orf1 | Hs.149363 | 753 | 35.0 |
| 220809_at | FLJ14327 | — | 79972 | 35.0 |
| 216113_at | ABI2 | Hs.471156 | 10152 | 35.0 |
| 214807_at | — | Hs.99472 | — | 35.0 |
| 207286_at | CEP4 | Hs.518767 | 9662 | 35.0 |
| 200022_at | RPL18 | Hs.515517 | 6141 | 34.4 |
| 217724_at | SERBP1 | Hs.530412 | 26135 | 34.4 |
| 217809_at | BZW2 | Hs.487635 | 28969 | 34.4 |
| 200818_at | ATP5O | Hs.409140 | 539 | 34.4 |
| 208246_x_at | TK2 | Hs.512619 | 7084 | 34.4 |
| 202330_s_at | UNG | Hs.191334 | 7374 | 34.4 |
| 207405_s_at | RAD17 | Hs.16184 | 5884 | 34.4 |
| 212677_s_at | KIAA0582 | Hs.146007 | 23177 | 34.4 |
| 218349_s_at | ZWILCH | Hs.21331 | 55055 | 34.4 |
| 214048_at | MBD4 | Hs.35947 | 8930 | 34.4 |
| 40472_at | LOC254531 | Hs.352614 | 254531 | 34.4 |
| 202894_at | EPHB4 | Hs.437008 | 2050 | 34.4 |
| 204663_at | ME3 | Hs.199743 | 10873 | 34.4 |
| 208146_s_at | CPVL | Hs.233389 | 54504 | 34.4 |
| 220589_s_at | MDS028 | Hs.446098 | 55846 | 34.4 |
| 220266_s_at | KLF4 | Hs.376206 | 9314 | 34.4 |
| 218899_s_at | BAALC | Hs.533446 | 79870 | 34.4 |
| 218927_s_at | CHST12 | Hs.213088 | 55501 | 34.4 |
| 217555_at | SMC1L1 | Hs.211602 | 8243 | 34.4 |
| 202260_s_at | STXBP1 | Hs.288229 | 6812 | 34.4 |
| 215630_at | — | — | — | 34.4 |
| 205215_at | RNF2 | Hs.124186 | 6045 | 34.4 |
| 210024_s_at | UBE2E3 | Hs.470804 | 10477 | 34.4 |
| 209480_at | HLA-DQB1 | Hs.409934 | 3119 | 34.4 |
| 207115_x_at | MBTD1 | Hs.369586 | 54799 | 34.4 |
| 220549_at | FSBP | — | 10646 | 34.4 |
| 201171_at | ATP6V0E | Hs.484188 | 8992 | 34.4 |
| 207737_at | — | — | — | 34.4 |
| 209067_s_at | HNRPDL | Hs.527105 | 9987 | 33.8 |
| 212593_s_at | PDCD4 | Hs.232543 | 27250 | 33.8 |
| 213649_at | SFRS7 | Hs.309090 | 6432 | 33.8 |
| 204905_s_at | EEF1E1 | Hs.88977 | 9521 | 33.8 |
| 205353_s_at | PBP | Hs.433863 | 5037 | 33.8 |
| 204949_at | ICAM3 | Hs.353214 | 3385 | 33.8 |
| 202534_x_at | DHFR | Hs.83765 | 1719 | 33.8 |
| 201139_s_at | SSB | Hs.546301 | 6741 | 33.8 |
| 206111_at | RNASE2 | Hs.728 | 6036 | 33.8 |
| 207769_s_at | PQBP1 | Hs.534384 | 10084 | 33.8 |
| 214349_at | LOC388388 | Hs.464404 | 388388 | 33.8 |
| 48808_at | DHFR | Hs.83765 | 1719 | 33.8 |
| 203095_at | MTIF2 | Hs.149894 | 4528 | 33.8 |
| 213311_s_at | KIAA1049 | Hs.415342 | 22980 | 33.8 |
| 205548_s_at | BTG3 | Hs.473420 | 10950 | 33.8 |
| 217370_x_at | FUS | Hs.513522 | 2521 | 33.8 |
| 219037_at | CGI-115 | Hs.408101 | 51018 | 33.8 |
| 219212_at | HSPA14 | Hs.534169 | 51182 | 33.8 |
| 221582_at | HIST3H2A | Hs.26331 | 92815 | 33.8 |
| 202918_s_at | PREI3 | Hs.205173 | 25843 | 33.8 |
| 201767_s_at | ELAC2 | Hs.434232 | 60528 | 33.8 |
| 207011_s_at | PTK7 | Hs.90572 | 5754 | 33.8 |
| 213599_at | OIP5 | Hs.567421 | 11339 | 33.8 |
| 207104_x_at | LILRB1 | Hs.149924 | 10859 | 33.8 |
| 213286_at | ZFR | Hs.435231 | 51663 | 33.8 |
| 217974_at | TM7SF3 | Hs.438641 | 51768 | 33.8 |
| 207574_s_at | GADD45B | Hs.110571 | 4616 | 33.8 |
| 212497_at | C14orf32 | Hs.437831 | 93487 | 33.8 |
| 201425_at | ALDH2 | Hs.436437 | 217 | 33.8 |
| 214757_at | — | Hs.533128 | — | 33.8 |
| 204643_s_at | COVA1 | Hs.171458 | 10495 | 33.8 |
| 201876_at | PON2 | Hs.530077 | 5445 | 33.8 |
| 219254_at | FLJ22222 | Hs.567578 | 79701 | 33.8 |
| 212254_s_at | DST | Hs.485616 | 667 | 33.8 |
| 212478_at | FLJ13910 | Hs.75277 | 64795 | 33.8 |
| 201743_at | CD14 | Hs.163867 | 929 | 33.8 |
| 205762_s_at | DUS4L | Hs.97627 | 11062 | 33.8 |

TABLE 3-continued

Genes under-expressed in AML

| probe | Gene | Unigene | Locus | % AML cases with under-expression |
|---|---|---|---|---|
| 204083_s_at | TPM2 | Hs.300772 | 7169 | 33.8 |
| 210299_s_at | FHL1 | Hs.435369 | 2273 | 33.8 |
| 211407_at | NDUFB7 | Hs.532853 | 4713 | 33.8 |
| 206112_at | ANKRD7 | Hs.371820 | 56311 | 33.8 |
| 212287_at | SUZ12 | Hs.462732 | 23512 | 33.1 |
| 212773_s_at | TOMM20 | Hs.533192 | 9804 | 33.1 |
| 203346_s_at | MTF2 | Hs.31016 | 22823 | 33.1 |
| 215438_x_at | GSPT1 | Hs.528780 | 2935 | 33.1 |
| 217266_at | RPL15 /// LOC136321 /// LOC402694 | Hs.381219 | 136321 /// 402694 /// 6138 | 33.1 |
| 203474_at | IQGAP2 | Hs.291030 | 10788 | 33.1 |
| 208822_s_at | DAP3 | Hs.516746 | 7818 | 33.1 |
| 218011_at | UBL5 | Hs.534477 | 59286 | 33.1 |
| 203358_s_at | EZH2 | Hs.444082 | 2146 | 33.1 |
| 220668_s_at | DNMT3B | Hs.251673 | 1789 | 33.1 |
| 217841_s_at | PME-1 | Hs.503251 | 51400 | 33.1 |
| 200894_s_at | FKBP4 | Hs.524183 | 2288 | 33.1 |
| 210829_s_at | SSBP2 | Hs.102735 | 23635 | 33.1 |
| 212060_at | SR140 | Hs.529577 | 23350 | 33.1 |
| 218487_at | ALAD | Hs.1227 | 210 | 33.1 |
| 218865_at | MOSC1 | Hs.497816 | 64757 | 33.1 |
| 215587_x_at | DHRS8 | Hs.282984 | 51170 | 33.1 |
| 218957_s_at | WDR71 | Hs.525017 | 80227 | 33.1 |
| 211855_s_at | SLC25A14 | Hs.194686 | 9016 | 33.1 |
| 204824_at | ENDOG | Hs.224137 | 2021 | 33.1 |
| 203341_at | CEBPZ | Hs.135406 | 10153 | 33.1 |
| 210298_x_at | FHL1 | Hs.435369 | 2273 | 33.1 |
| 205136_s_at | NUFIP1 | Hs.525006 | 26747 | 33.1 |
| 209811_at | CASP2 | Hs.368982 | 835 | 33.1 |
| 201906_s_at | CTDSPL | Hs.475963 | 10217 | 33.1 |
| 208719_s_at | DDX17 | Hs.528305 | 10521 | 33.1 |
| 215029_at | — | — | — | 33.1 |
| 213479_at | NPTX2 | Hs.3281 | 4885 | 33.1 |
| 218404_at | SNX10 | Hs.520714 | 29887 | 33.1 |
| 206145_at | RHAG | Hs.120950 | 6005 | 33.1 |
| 214930_at | SLITRK5 | Hs.508337 | 26050 | 33.1 |
| 219663_s_at | MGC4659 | Hs.157527 | 80757 | 33.1 |
| 220348_at | KBTBD9 | Hs.130593 | 114818 | 33.1 |
| 32088_at | BLZF1 | Hs.130746 | 8548 | 33.1 |

Among the differentially expressed genes, some has been previously shown to be aberrantly expressed in AML. These included WT1 (over-expressed in 84.7% of cases) (33, 34), CD56 (46.5%) (35), CD7 (38.2%) (36, 37), CD33 (36.9%) (38), CD4 (36.3%) (39), CD14 (30.6%) (38), and CD19 (28.0%) (39), while CD34 was under-expressed (36.3%) (40). Interestingly, genes previously reported to be "leukemia stem cell-specific" had also been shortlisted in our screening. This included 18 of the 25 genes reported by Saito et al. (41) to be over-expressed in CD34+CD38-AML cells; the remaining 7 were either over-expressed in <25% of cases (n=4) or not probed by the HG-U133A array (n=3). Similarly, we identified 16 of the 21 genes associated with AML stem cells by Kikushige et al. (42); the remaining 5 were either over-expressed in <25% of cases (n=3) or not probed by our array (n=2). In sum, of the 35 probed genes previously found to be over-expressed in "leukemia stem cells" (6 were listed by both Saito and Kikushige), 28 were also found to be over-expressed in our analysis (including all 6 common genes) (Table 4).

TABLE 4

Genes overexpressed in AML "stem cells" according to previous studies and their overexpression in AML according to the present analysis

| Gene overexpressed in AML stem cells according to Saito et al. (41) | Gene overexpressed in AML stem cells according to Kikushige et al. (42) | AML cases with overexpression in this study (%) |
|---|---|---|
| WT1 | | 84.7 |
| FCGR2C, CD32 | FCGR2C, CD32 | 76.4 |
| DOK2 | | 70.1 |
| | CD96 | 66.9 |
| HCK | | 65.6 |
| CD86 | CD86 | 64.3 |
| | CD44 | 64.3 |
| C1QR1, CD93 | | 56.7 |
| ITGB2, CD18 | ITGB2, CD18 | 52.9 |
| | CSF1R, CD115 | 51.0 |
| IL2RA, CD25 | IL2RA, CD25 | 47.8 |
| LY86 | | 43.3 |
| IL7R, CD127 | | 42.0 |
| | CD99 | 42.0 |
| | IL17R | 39.5 |

TABLE 4-continued

Genes overexpressed in AML "stem cells" according to previous studies and their overexpression in AML according to the present analysis

| Gene overexpressed in AML stem cells according to Saito et al. (41) | Gene overexpressed in AML stem cells according to Kikushige et al. (42) | AML cases with overexpression in this study (%) |
|---|---|---|
| CD97 | CD97 | 37.6 |
| CD33 | CD33 | 36.9 |
|  | CD9 | 36.9 |
| CD1C |  | 35.7 |
| AK5 |  | 33.1 |
| BIK |  | 31.2 |
|  | CD47 | 30.6 |
| TNFRSF4, CD134 |  | 29.3 |
|  | CD84 | 29.3 |
| IL2RG, CD132 |  | 27.4 |
|  | ITGB7 | 27.4 |
| CEACAM6, CD66c |  | 26.8 |
|  | FLT3 | 25.5 |
| CD180 |  | <25 |
| CTSC |  | <25 |
| PDE9A |  | <25 |
| CD24 |  | <25 |
|  | CD36 | <25 |
|  | CD123 | <25 |
|  | ITGAE | <25 |
| LRG1 |  | Not on HG-U133A array |
| SUCNR1 |  | Not on HG-U133A array |
| TNFSF13B |  | Not on HG-U133A array |
|  | CLL-1 | Not on HG-U133A array |
|  | TIM-3 | Not on HG-U133A array |

[a]Gene expression was studied by HG-U133A oligonucleotide microarrays in157 AML samples and 7 samples of normal CD34+ myeloid progenitors. Shown is the percentage of AML cases with expression signals higher than 2-fold of the highest value obtained among normal CD34+ myeloid cells Flow Cytometric Analysis of Proteins Encoded by Aberrantly Expressed Genes Some of genes differentially expressed by gene array analysis (e.g., CD7, CD19, CD56) encoded proteins already used as flow cytometric markers for MRD studies (8, 20, 21, 24, 25, 28, 31, 35, 43, 44), suggesting that mining the microarray data might uncover other useful markers. For further studies, we prioritized genes that were a) differentially expressed in at least 33% of cases of AML; b) over-expressed by at least 5-fold of the maximum value in normal cells, or under-expressed by at least 5-fold of the minimum value; c) targetable by commercially available, fluorochrome-conjugated, antibodies. We selected 24 genes (22 over-expressed in AML, 1 under-expressed, and 1 over-expressed in some cases and under-expressed in others) (Table 5). To these, we added CD47, CD123, TIM3, and CLEC12A (CLL-1), which had been previously associated with AML stem-cells (42, 45-47). In our gene expression analysis, CD47 and CD123 were overexpressed in <33% of cases and had not met our selection criteria; TIM3 and CLEC12A (CLL-1) were not probed by the HG-U133A oligonucleotide microarray.

TABLE 5

Differentially expressed markers according to gene array analysis selected for further studies

| Probe | Symbol and/or common name | % of AML cases with differential expression[a] |
|---|---|---|
| Overexpressed in AML | | |
| 202638_s_at | ICAM1, CD54 | 84.1 |
| 204655_at | CCL5, RANTES | 80.3 |
| 211395_x_at | FCGR2C, CD32 | 76.4 |
| 214511_x_at | FCGR1A, CD64 | 75.8 |
| 205898_at | CX3CR1 | 73.2 |
| 206761_at | CD96 | 66.9 |
| 205686_s_at | CD86 | 64.3 |
| 212014_x_at | CD44 | 64.3 |
| 207277_at | CD209 | 59.2 |
| 202878_s_at | C1QR1, CD93 | 56.7 |
| 215049_x_at | CD163 | 56.1 |
| 202803_s_at | ITGB2, CD18 | 52.9 |
| 207270_x_at | CD300C | 52.9 |
| 203104_at | CSF1R, CD115 | 51.0 |
| 211269_s_at | IL2RA, CD25 | 47.8 |
| 201028_s_at | CD99 | 42.0 |
| 203507_at | CD68 | 41.4 |
| 202910_s_at | CD97 | 37.6 |
| 219669_at | CD177 | 37.6 |
| 201005_at | CD9 | 36.9 |
| 209582_s_at | CD200 | 34.4 |
| 204912_at | IL10RA, CD210 | 33.1 |
| 204661_at | CD52 | 28.7 |
| Underexpressed in AML | | |
| 200985_s_at | CD59 | 65.6 |
| 34210_at | CD52 | 28.0 |

[a]Gene expression was studied by HG-U133A oligonucleotide microarrays in 157 AML samples and 7 samples of normal CD34+ myeloid progenitors. Shown is the percentage of AML cases with expression signals higher than 2-fold of the highest value obtained among normal CD34+ myeloid cells ("overexpressed in AML") or at least 50% lower than the lowest signal among the normal CD34+ myeloid cells ("underexpressed in AML").

Figure 2:
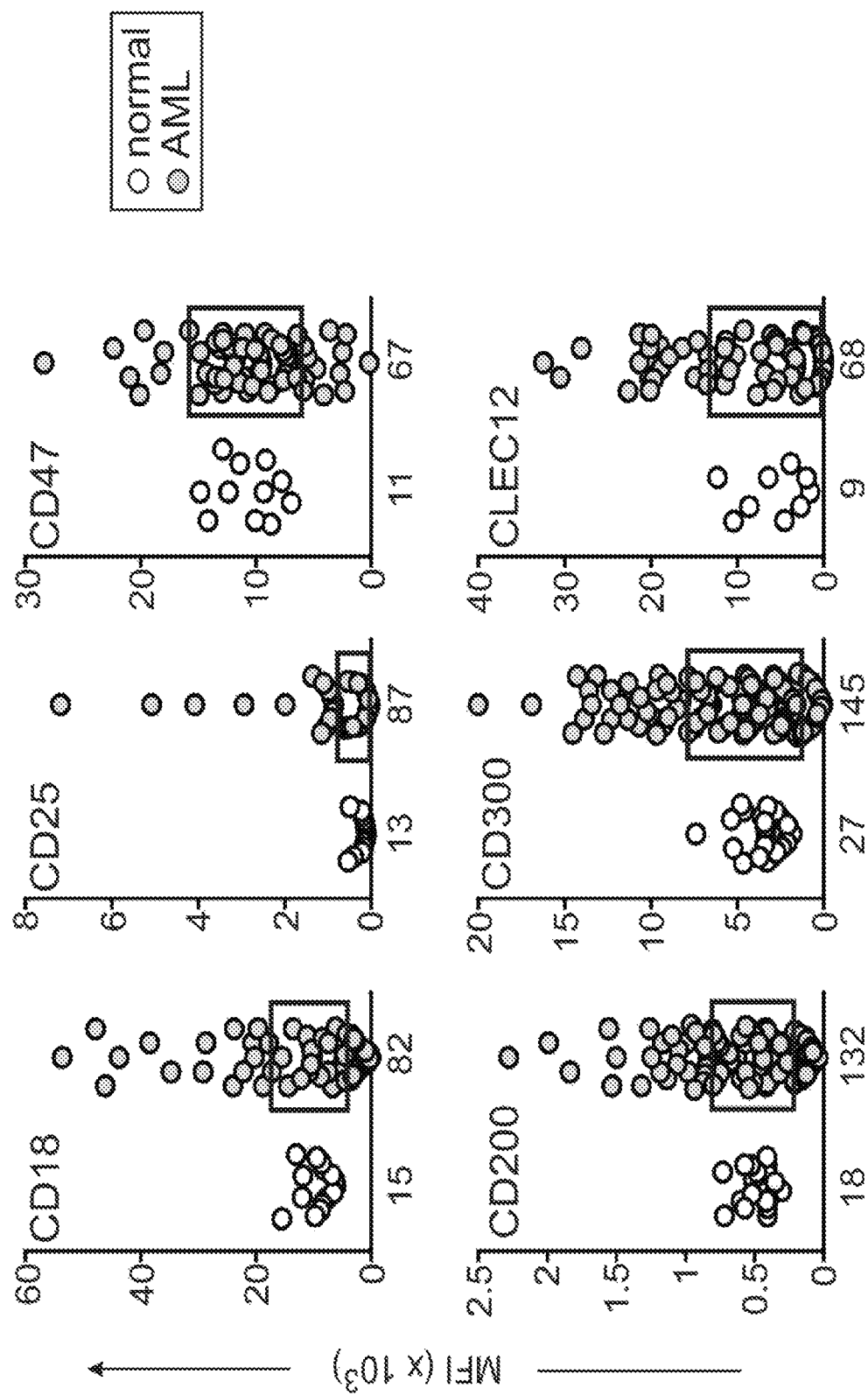
FIG. 2 is a set of graphs showing genes whose expression in AML cells by flow cytometry was not statistically different than that of their normal counterparts. Plots indicate mean fluorescence intensity (MFI) of each marker in CD34+ cells expressing CD13 and/or CD33 from bone marrow aspirates of healthy donors or patients with ALL (white circles), and in diagnostic AML samples (gray circles). The box on the AML plots indicates the upper and lower normal limits. The number of samples studied is indicated under each plot. By unpaired t-test with Welch's correction, P>0.05 for all markers, except CD25 (P=0.049) and CD300a (P=0.020). Some AML samples show considerable over- or under-expression.

After confirming the specificity of the antibodies with positive and negative target cells (Table 1), we tested the expression of the 28 selected markers in 191 AML and 63 leukemia-free bone marrow samples. These were from either healthy donors (n=23) or children with leukemia on therapy and MRD-negative (n=40); many of the latter samples contained high proportions of regenerating $CD34^+$ myeloid progenitors. Six of the 28 markers (CD115, CD163, CD177, CD209, CD210, and CCL5/Rantes) were expressed in AML cells at levels too low to allow reliable MRD studies and were excluded from further studies. Among the remaining 22 markers, expression in AML was significantly different (P<0.01) for 16: CD9, CD32, CD44, CD52, CD54, CD64, CD68, CD86, CD93, CD96, CD97, CD99, CD123, CX3CR1, and Tim-3 were predominantly over-expressed, while CD59 was predominantly under-expressed, in agreement with the gene array result (FIG. 1). For the other 6 markers, differences between leukemic and normal cells were either not statistically significant (CD18, CD47, CD200, and CLEC12A; P>0.1), or yielded a higher P value (CD25, P=0.049; CD300a, P=0.020). Regardless, some AML cases had clear over- or under-expression (FIG. 2), suggesting their potential as markers for MRD studies.

For each of the 22 markers, we determined the number of AML cases that expressed them at a median fluorescence intensity (MFI) higher than the maximum level seen among normal CD34+ myeloid cells plus 1 standard deviation (SD), or lower than the lowest value minus 1 SD. By these criteria, the 22 markers were differentially expressed in 14.8%-57.3% (median, 36.5%) of cases (Table 6). Interestingly, several (CD18, CD44, CD47, CD52, CD59, CD97, CD123, CD200, and CD300a) were over-expressed in some cases and under-expressed in others.

TABLE 6

Expression of the new markers in AML cells relative to their expression in non-leukemia bone marrow CD34+ cells expressing CD13 and/or CD33 as determined by flow cytometry

| Marker | Number of AML cases studied | Number of non-leukemic bone marrow studied | Number of AML cases with over-expression [a] | Number of AML cases with under-expression [b] | % AML cases with over- or under-expression |
|---|---|---|---|---|---|
| CD18 | 82 | 15 | 15 | 32 | 57.3 |
| CD54 | 142 | 33 | 79 | 0 | 55.6 |
| CD52 | 96 | 16 | 34 | 17 | 53.1 |
| CD97 | 96 | 29 | 50 | 0 | 52.1 |
| CD96 | 65 | 14 | 32 | 0 | 49.2 |
| CD59 | 146 | 33 | 7 | 63 | 47.9 |
| CD200 | 132 | 18 | 25 | 35 | 45.5 |
| CD44 | 148 | 38 | 53 | 12 | 43.9 |
| CX3CR1 | 99 | 18 | 43 | 0 | 43.4 |
| TIM-3 | 98 | 27 | 40 | 0 | 40.8 |
| CD300a | 145 | 27 | 26 | 28 | 37.2 |
| CD86 | 123 | 25 | 44 | 0 | 35.8 |
| CD123 | 93 | 11 | 29 | 4 | 35.5 |
| CD32 | 87 | 13 | 27 | 0 | 31.0 |
| CD9 | 98 | 28 | 28 | 0 | 28.6 |
| CD99 | 95 | 20 | 25 | 0 | 26.3 |
| CD64 | 146 | 22 | 43 | 0 | 29.5 |
| CLEC12A | 68 | 9 | 15 | 0 | 22.1 |
| CD47 | 67 | 11 | 7 | 7 | 20.9 |
| CD68 | 139 | 21 | 24 | 0 | 17.3 |
| CD25 | 87 | 13 | 14 | 0 | 16.1 |
| CD93 | 88 | 13 | 13 | 0 | 14.8 |

[a] Number of AML cases that expressed the indicated marker at levels higher than the highest mean fluorescence intensity (MFI) value (+1 SD) recorded among normal CD34+ myeloid progenitors.
[b] Number of AML cases that expressed the indicated marker at levels lower than the lowest MFI (−1 SD) measured in normal CD34+ myeloid progenitors.

Figure 3A:
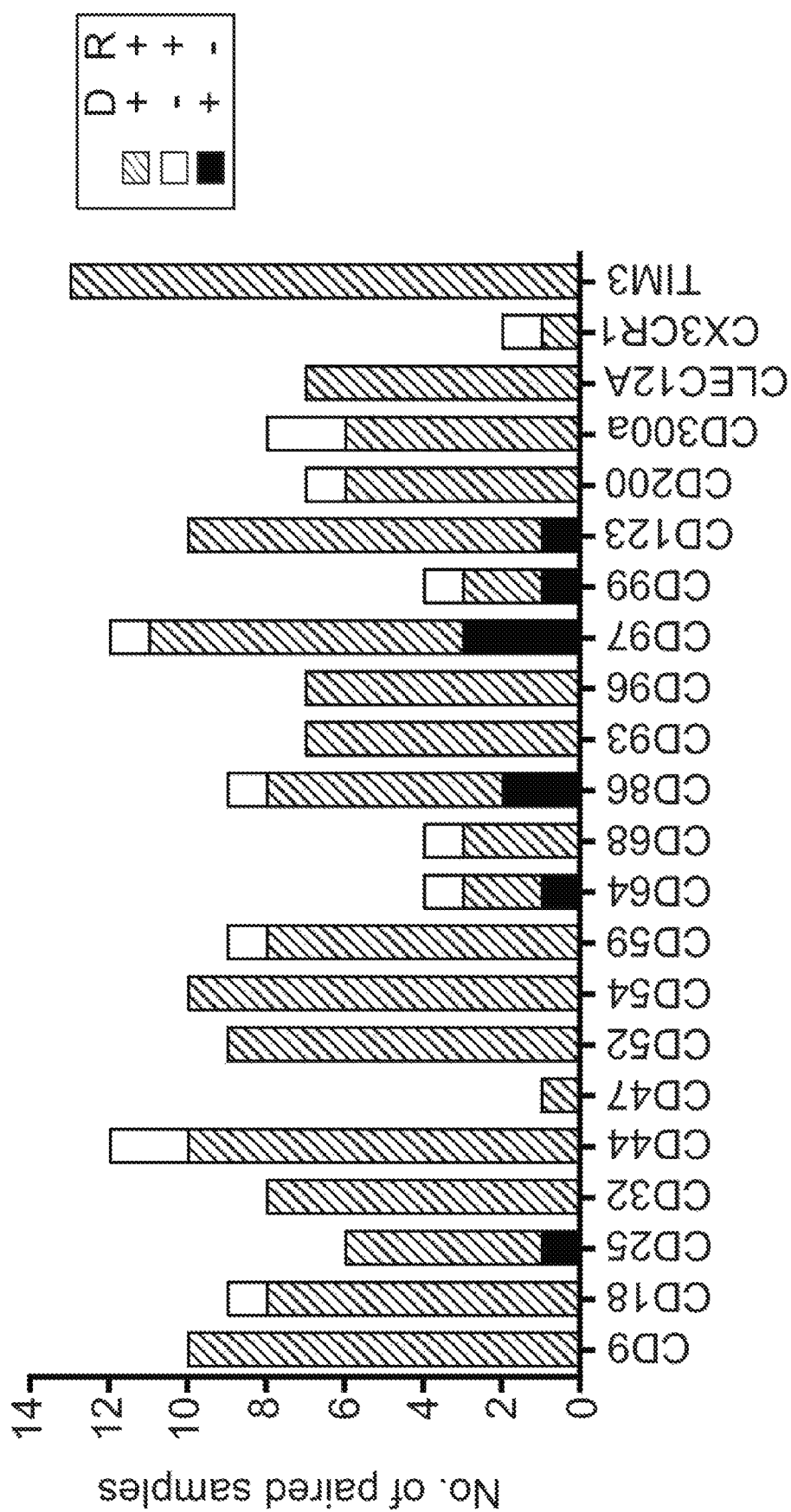
FIGS. 3A-C show that the new markers persist at relapse and are expressed on AML cells with stem cell features.
Figure 7:
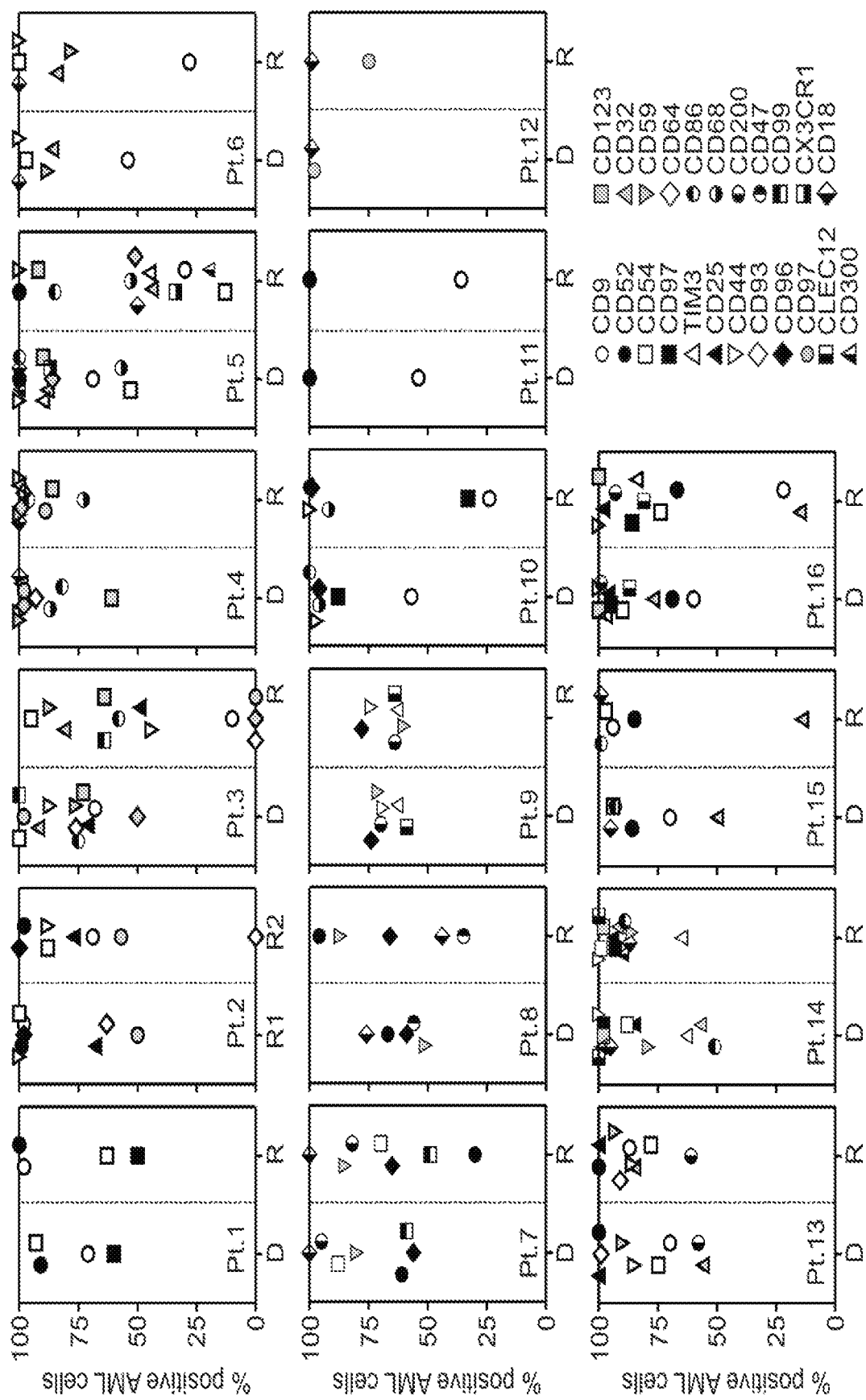
FIG. 7 is a set of plots showing expression of new markers at relapse. Plots show percentage of AML cells expressing the indicated marker at diagnosis ("D") and relapse ("R), or at first ("R1") and second relapse ("R2") in 16 patients with AML. Each marker studied is indicated by a symbol.

The New Markers Persist at Relapse and are Expressed on AML with Stem Cell Features Leukemia subclones at diagnosis may become predominant at relapse, resulting in immunophenotypic shifts (25). We determined the prevalence of expression shifts using paired samples collected at diagnosis and relapse from 16 AML patients, for a total of 168 tests. As shown in FIG. 3A, in 146 of the 168 (86.9%) tests, a new marker was aberrantly expressed at diagnosis and remained aberrantly expressed at relapse. In an additional 13 (7.7%) tests, a new marker not present at diagnosis was detected at relapse. In only 9 (5.4%) tests, an aberrantly expressed marker at diagnosis reverted to normal range at relapse. Importantly, in all 16 patients studied, markers aberrantly expressed at diagnosis in more than 50% of blasts remained abnormally expressed at relapse (FIG. 7). Thus, the new markers remained prevalently expressed at relapse, indicating that their aberrant expression extended to virtually all sub-clones within the leukemic cell populations.

Figure 3B:
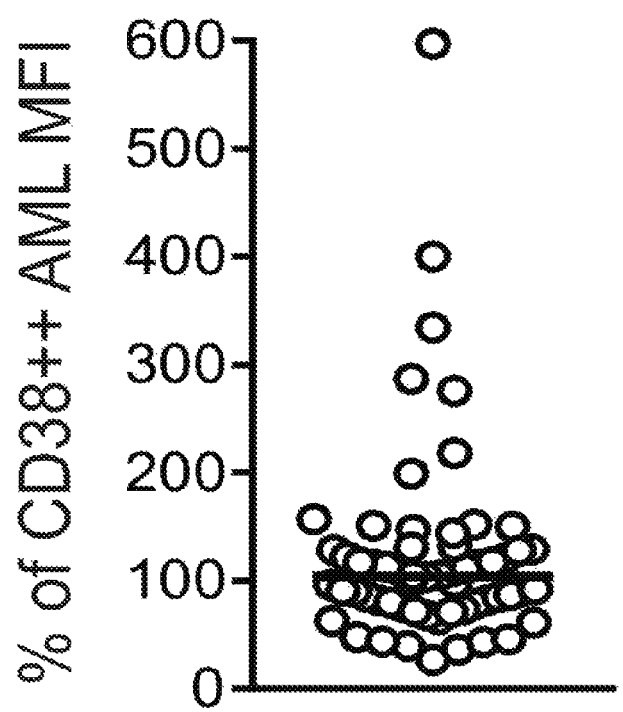
Figure 3C:
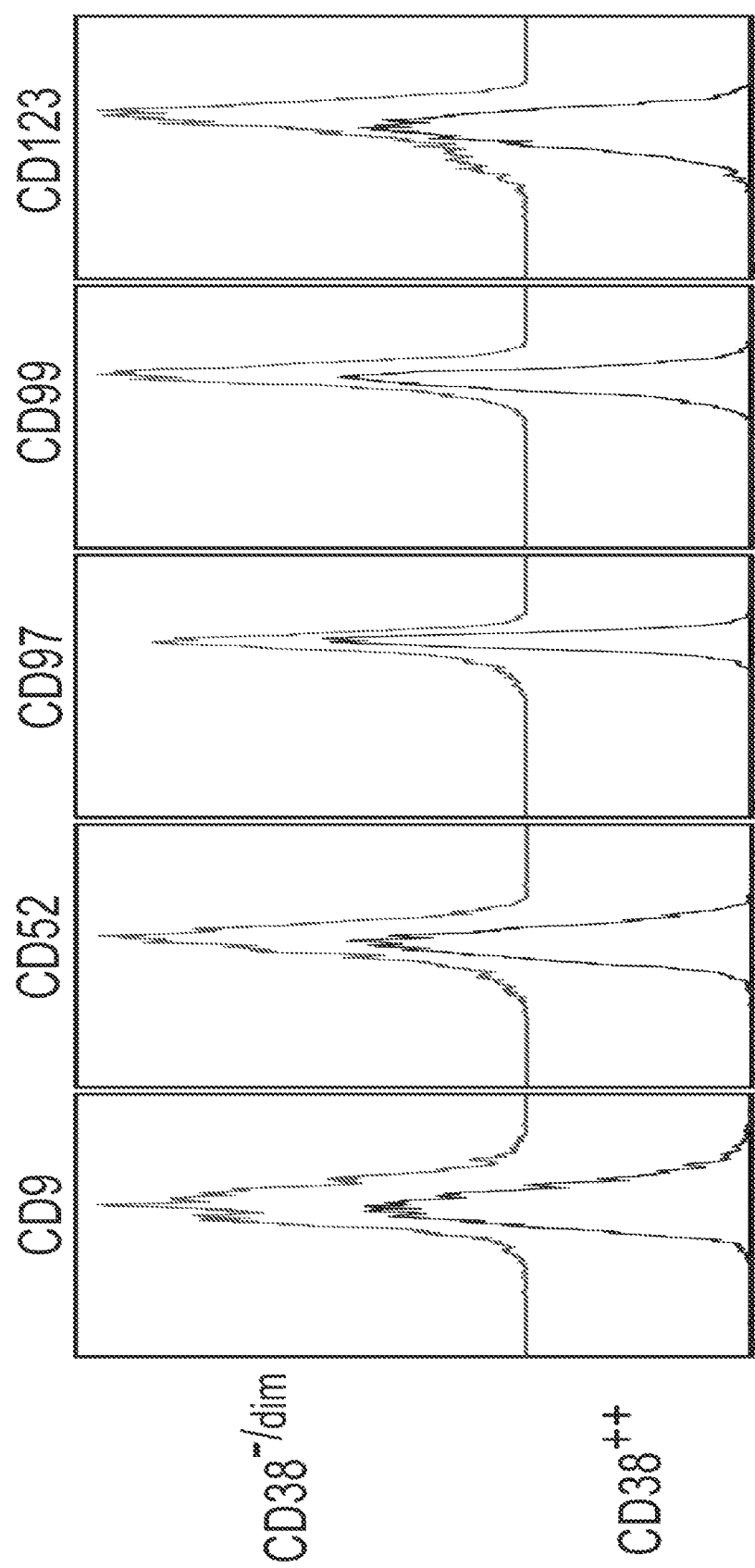
Figure 8:
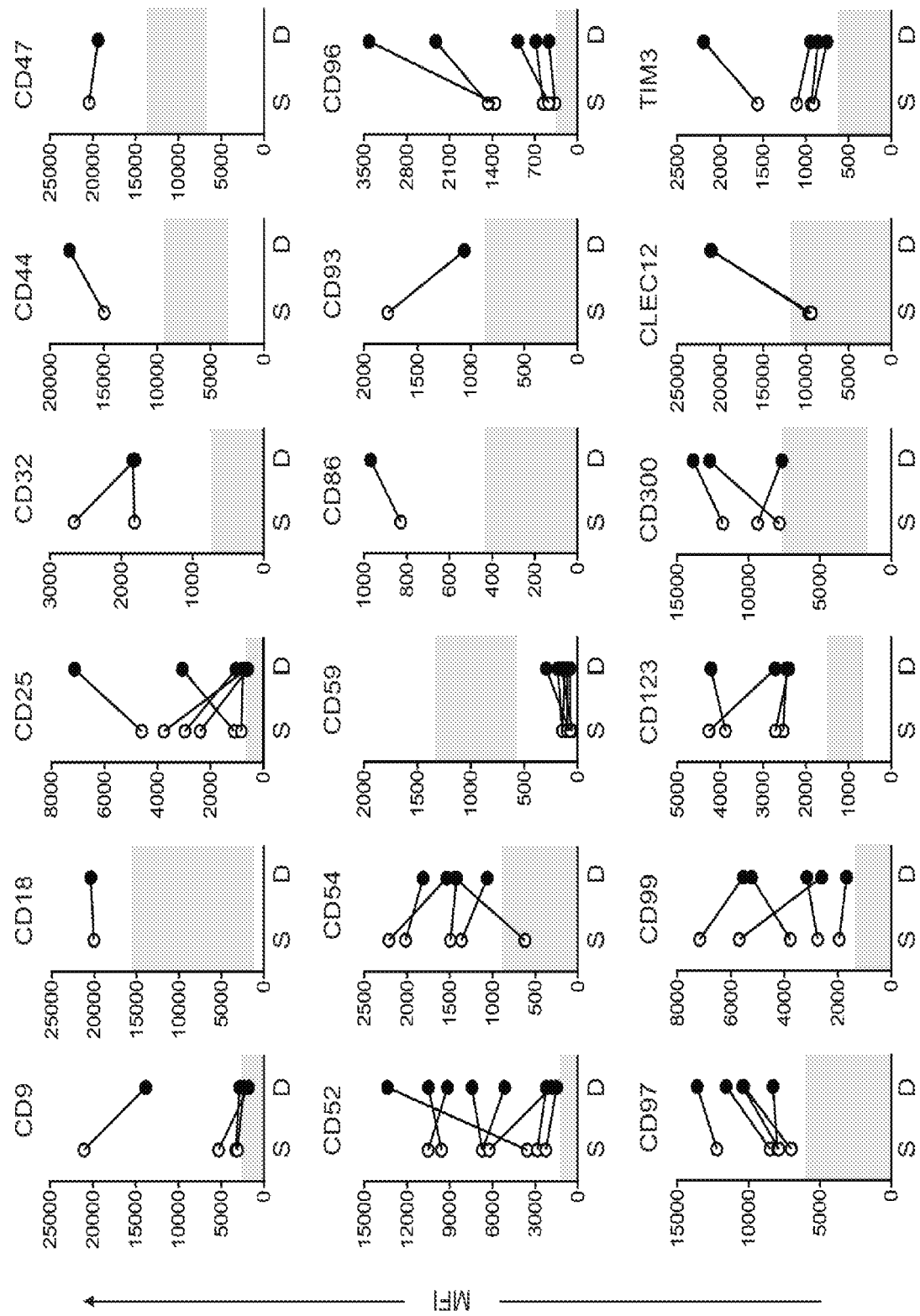
FIG. 8 is a set of plots showing expression of new markers in AML blasts with the CD34+CD38 dim/neg immunophenotype ("S"), in comparison with the more mature CD38 bright cell population ("D"). Each symbol is the percent mean fluorescence intensity (MFI) of a new marker in the "stem cells" relative to that of the more mature AML cells in the same sample. Gray areas indicate limits of expression in normal CD34+CD13 and/or CD33+ cells.

The potential usefulness of the new markers was further corroborated by studies of marker expression in AML cells with phenotypic features associated with leukemia stem-cells, e.g., CD34-positive, CD38-dim/negative. We studied 12 diagnostic samples containing 13% to 65% (median, 27%) AML stem cells. Collectively, the new markers were aberrantly expressed in these cells and in the more mature CD38-bright cells in 48 tests (43 over-expressed in both subsets, 5 under-expressed in both subsets) while in an additional 12, clear aberrant expression was confined to the stem cell subset. In only 5 tests, the markers were aberrantly expressed in the more mature cells but were within the normal range in the stem cell population. Although variations in expression intensity among AML subsets with different maturity features were observed, marker expression largely overlapped: median MFI for the overexpressed markers in AML stem cells was 104% (27% to 597%) of that in more mature cells (FIGS. 3B, 3C, and 8).

Validation of the New Markers for MRD Detection

The above results indicated that the new markers should allow reliable detection of MRD. This assumption was tested in 190 bone marrow and 18 peripheral blood samples which were collected from 52 patients with AML (35 children and 17 adults) during treatment (68 at the end of the first or second cycle of remission induction therapy, and 140 collected subsequently), for a total of 720 tests. In all 52 patients, at least one of the new markers had been found to be abnormally expressed at diagnosis. We used 8-marker panels including CD34, CD117, CD45 and CD33 in addition to the new markers.

Figure 4A:
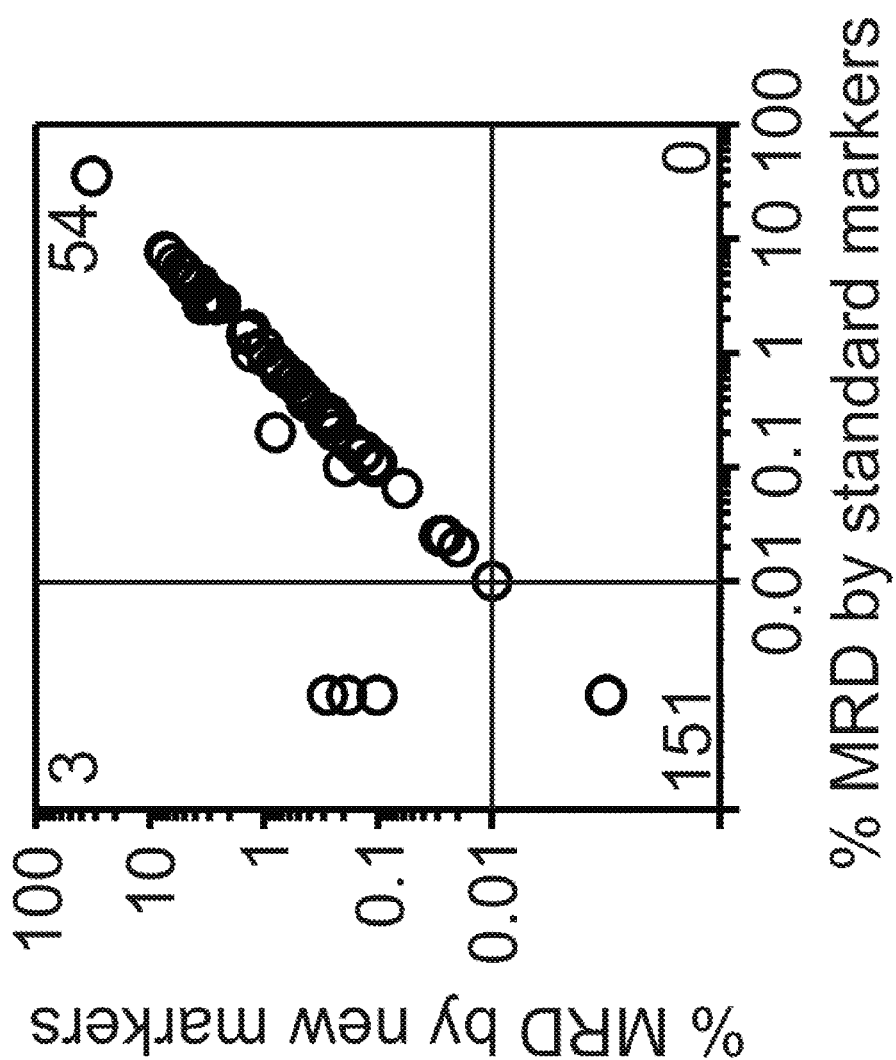
FIGS. 4A-B shows that the new markers allow detection of MRD and remain aberrantly expressed during chemotherapy.

By standard flow cytometric methods (Table 7) (24, 27), 54 of the 208 samples studied had 0.01% or more leukemic cells (0.01% to <0.1%, 7; ≥0.1%, 47), and 154 had no detectable leukemic cells. There was an excellent correlation between these results and those obtained with the new marker combinations (FIG. 4A). All 54 specimens with MRD according to the standard method also had MRD by the new markers, with levels of MRD estimated by the two sets of markers generally matching (Spearman r=0.9816, P<0.0001). Moreover, in 3 samples where the standard MRD markers failed to detect residual leukemic cells, the new markers revealed the presence of 0.10%, 0.19% and 0.28% leukemic cells (FIG. 4A).

Figure 4B:
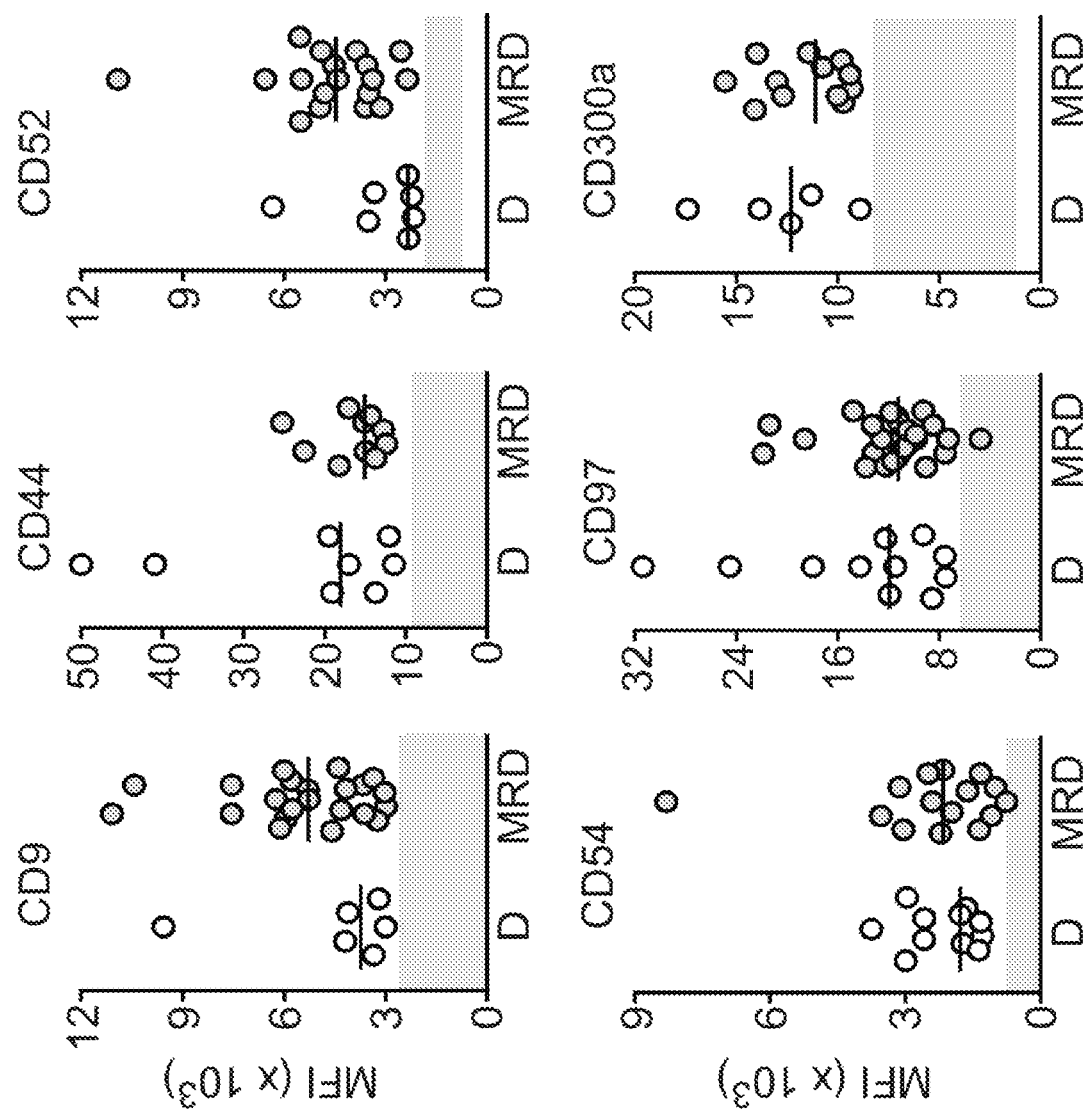
Figure 9:
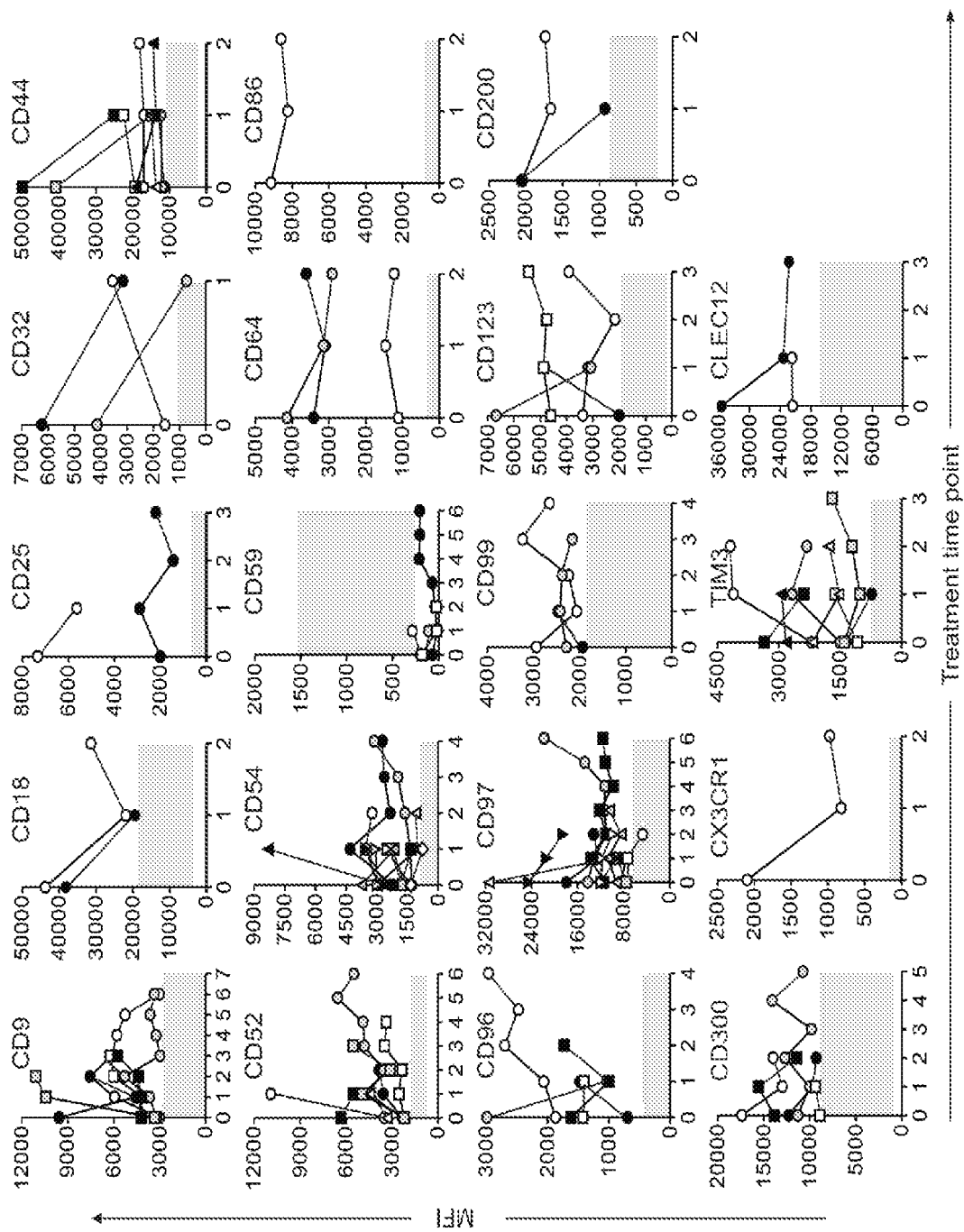
FIG. 9 is a set of plots showing expression of the new markers on residual AML cells during treatment. Mean fluorescence intensity ("MFI") of the indicated new markers as measured at diagnosis ("0") and in subsequent follow-up samples ("1, 2, etc."). Each symbol represents results obtained in samples from one patient. Gray areas indicate limits of expression in normal CD34+CD13 and/or CD33+ cells.

To be useful for MRD studies, leukemia markers should persist despite exposure to chemotherapy. To this end, we measured levels of expression in leukemic cells of 27 patients who had MRD≥0.1% during treatment according to standard flow cytometric methods (Table 7). FIG. 4B shows data obtained for 6 markers; data for 13 additional markers are shown in FIG. 9. Overall, expression levels remained beyond the threshold of the maximum normal value (or minimum for CD59) plus 1 SD; in only 4 of 175 (2.3%) MRD tests (one each for CD54, CD59, CD97 and TIM3), the marker's mean fluorescence intensity crossed that threshold. Thus, exposure to chemotherapy is unlikely to cause false-negative results in MRD studies with these markers.

TABLE 7

Standard marker panel for MRD studies in AML

| FITC | PE | PerCP | APC | PECy7 | APCH7 | BV421 | BV510 or v500 |
|---|---|---|---|---|---|---|---|
| CD13 | CD133 | CD34 | CD117 | CD33 | CD45 | CD38 | anti-HLA-Dr |
| CD15 | CD56 | CD34 | CD117 | CD33 | CD45 | CD19 | CD4 |
| CD7 | NG2 (7.1) | CD34 | CD117 | CD33 | CD45 | CD11b | anti-HLA-Dr |
| IgG2a | IgG1 | CD34 | CD117 | CD33 | CD45 | CD41a | IgG2a |

The following antibodies were used: CD13 (WM-47) from Merck; CD15 (MMA), CD56 (NCM16.2), CD34 (8G12), CD33 (P67.6), CD41a (HIPS), CD19 (HIB19), anti-HLA-Dr (G46-6), Mouse IgG1 (X40), Mouse IgG2a (X39), Mouse IgG2a (G155-178), from BD Biosciences; CD38 (HIT2), CD11b (ICRF44), CD4 (OKT4) from Biolegend; CD133 (AC133/1), CD117 (A3C6E2) from Miltenyi Biotec; CD7 (4H9) from eBioscience; NG2 (7.1) from Beckman Coulter.

Association of the New Markers with AML Subtypes

Figure 5:
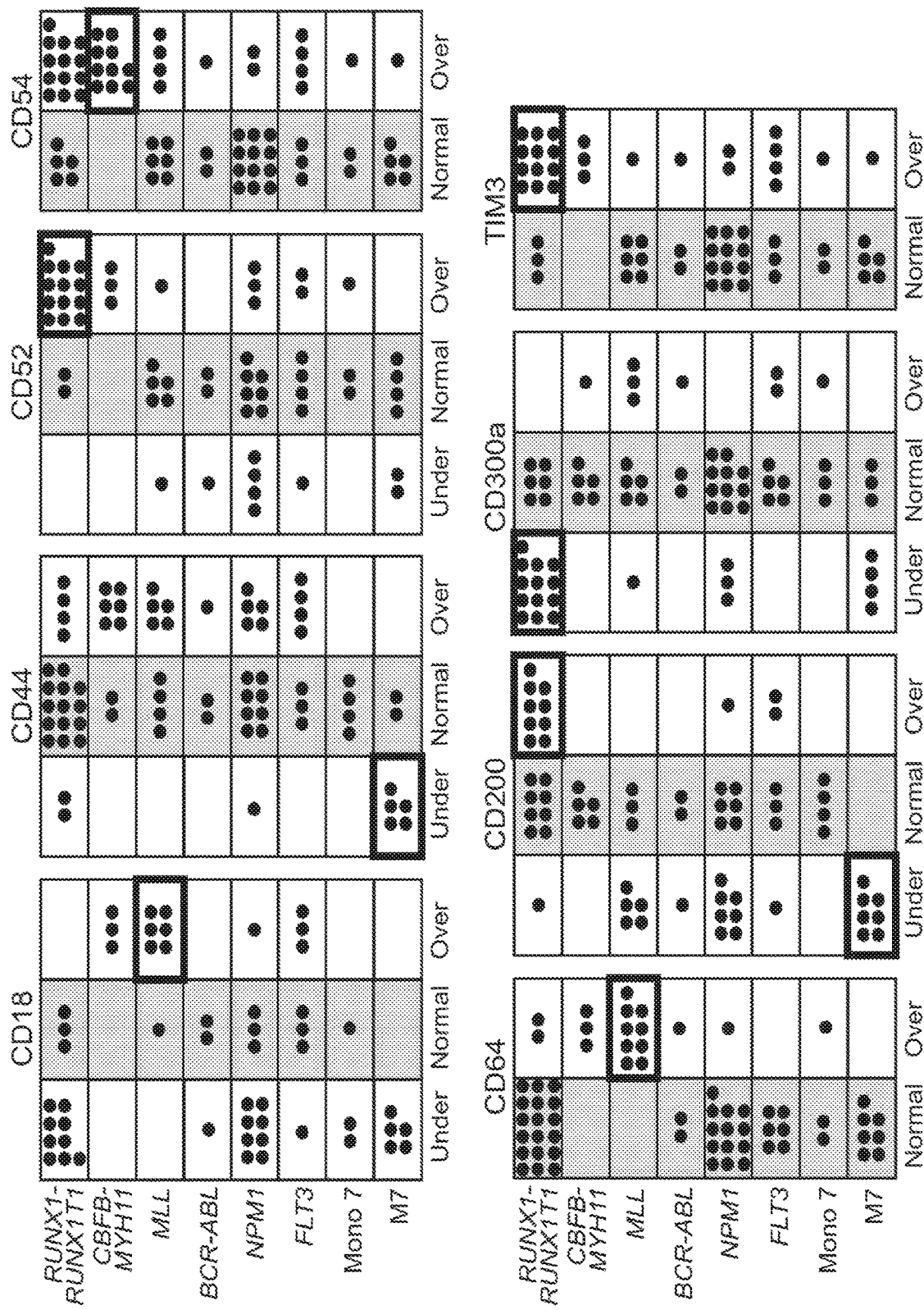
FIG. 5 is a set of plots showing preferential expression of the new markers in subgroups of AML. Each symbol corresponds to an AML diagnostic sample studied with the indicated marker. Markers significantly over- or underexpressed are in boxes with a thicker frame (all P<0.001 by Fischer's exact test). Additional data shown in FIG. 10.
Figure 10:
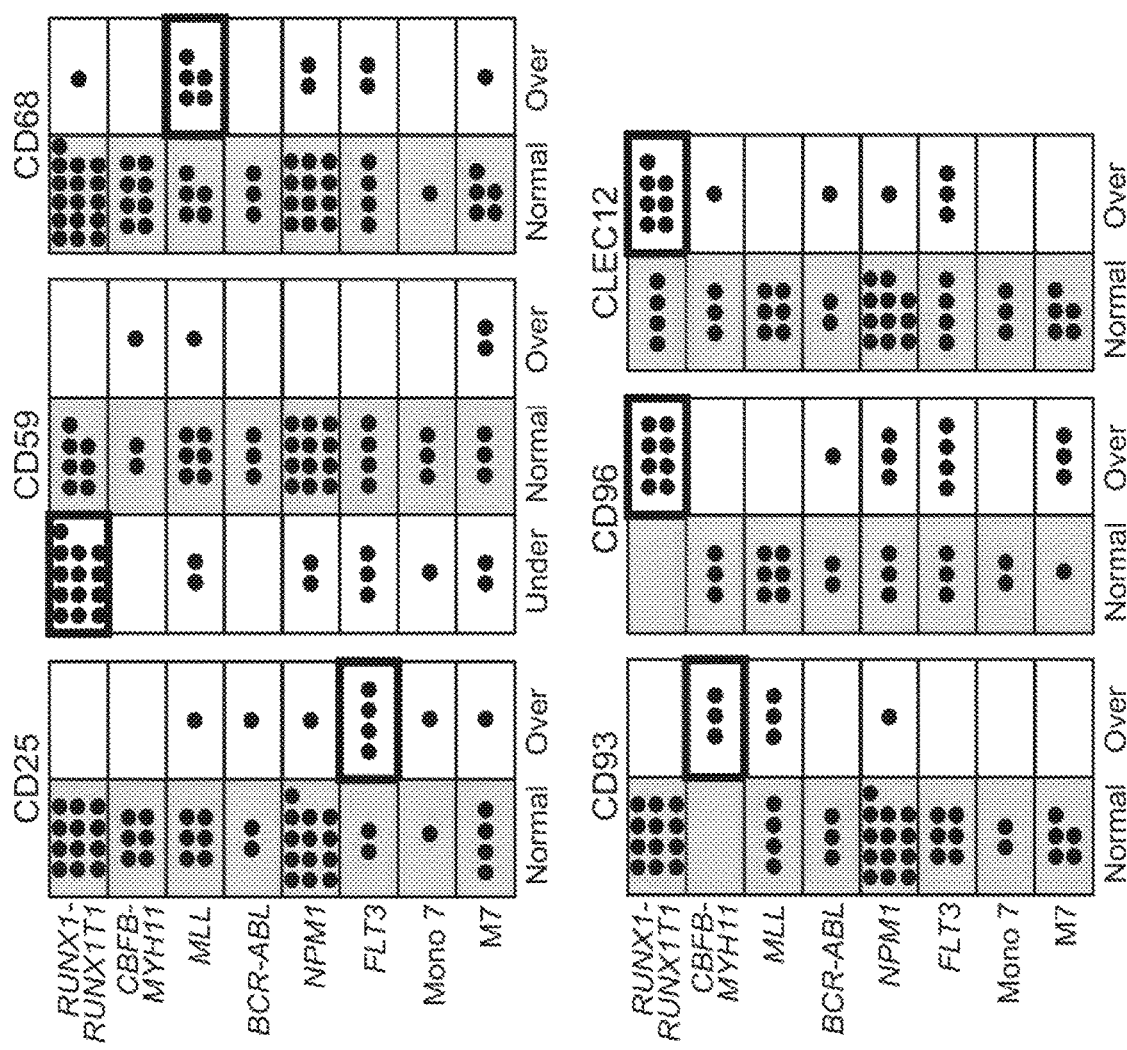
FIG. 10 is a set of plots showing preferential expression of the new markers in subgroups of AML. Each symbol corresponds to an AML diagnostic sample studied with the indicated marker. Markers significantly over- or underexpressed are in boxes with a thicker frame (all P<0.001 by Fischer's exact test). Additional data shown in FIG. 5.

We determined whether expression of the new markers identified in this study was associated with clinically relevant features of AML, including RUNX1-RUNX1T1, CBFB-MYH11, MLL gene rearrangements, BCR-ABL, NPM1 mutations, FLT3 internal tandem duplications (ITD), monosomy 7, or M7 morphology with or without t(1;22) (p13;q13). We found that aberrant expression of some of the markers was more prevalent in some AML subtypes (FIGS. 5 and 10). Thus, among RUNX1-RUNX1T1 cases there was a significantly higher prevalence of CD52 (P<0.0001 by Fisher's exact test), CD96 (P=0.0012), CD200 (P=0.0002), CLEC12A (P=0.0029) and TIM3 (P=0.0018) over-expression, while CD59 (P=0.0015) and CD300a (P<0.0001) were particularly under-expressed. Cases with CBFB-MYH11 commonly over-expressed CD54 (P=0.0009), and CD93 (P=0.0016), those with MLL gene rearrangements CD18 (P=0.0009), CD64 (P<0.0001) and CD68 (P=0.0090), and those with FLT3 ITD CD25 (P=0.0047). Finally, AML M7 cases show a higher prevalence of CD44 (P<0.0001) and CD200 (P=0.0002) under-expression, regardless of whether the t(1;22)(p13;q13) was present or not.

Application of the New Markers for MRD Monitoring

Figure 11:
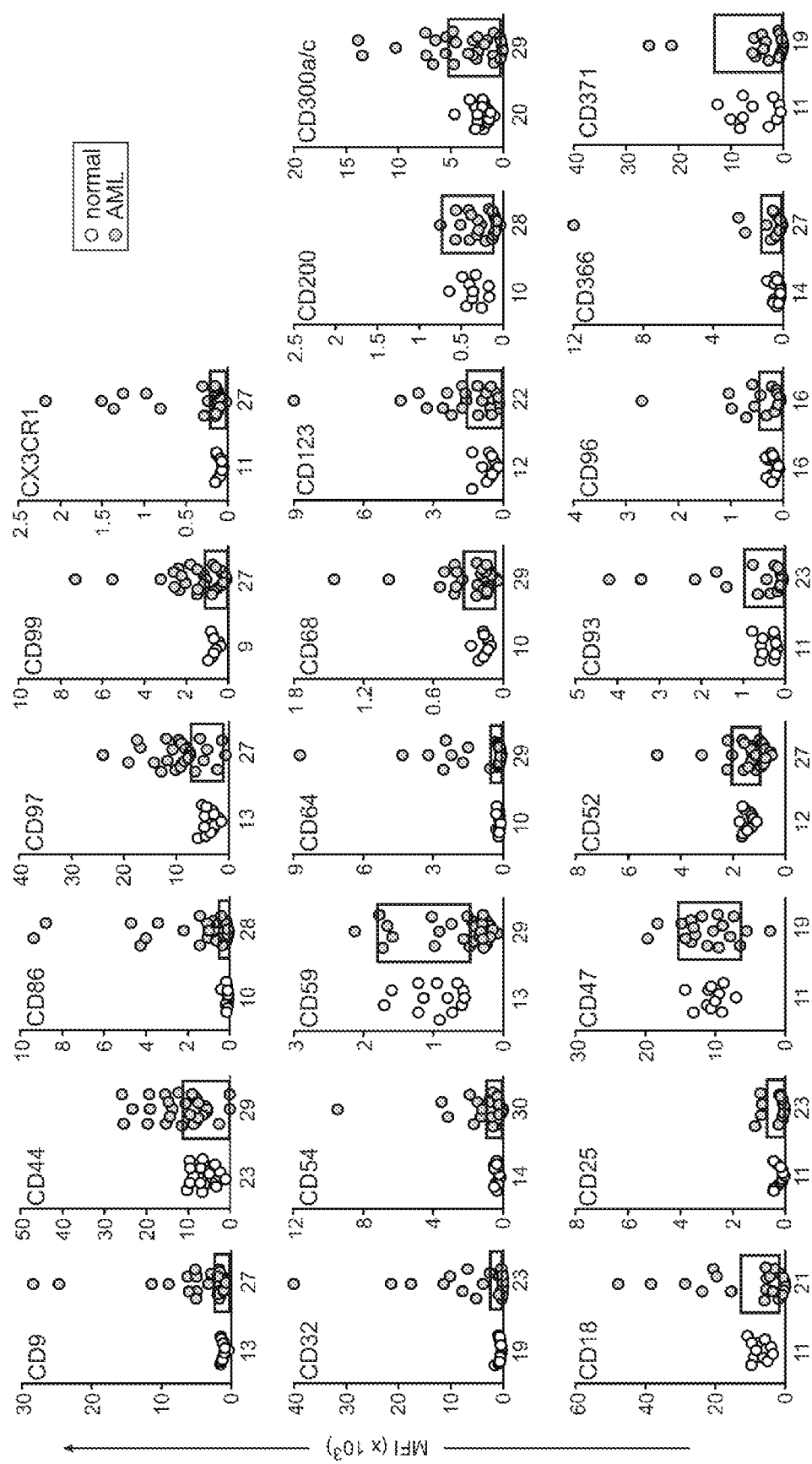
FIG. 11 shows marker expression in AML cases with <25% CD34+ cells. Markers were tested by flow cytometry in 34 cases of AML with low/absent CD34 and compared to that of CD117+CD33+ cells from non-leukemic bone marrow samples, including maturing myeloid cells, monoblasts and erythroblasts, and excluding mature monocytes and granulocytes. Plots indicate median fluorescence intensity (MFI) of each marker in normal cells (white circles), and AML cells (gray circles). Boxes on the AML plots indicate upper and lower normal limits. Number of samples studied is shown under each plot. Top row, P<0.001; middle row, P<0.05 but >0.01; bottom row, P>0.05.

Among the 191 AML cases studied for marker expression, 34 (17.8%) had less than 25% leukemic cells expressing CD34. A sub-analysis of the 22 selected markers in these cases was performed, comparing their expression to that of CD117+CD33+ cells from non-leukemic bone marrow samples, including maturing myeloid cells, monoblasts and erythroblasts, and excluding mature monocytes and granulocytes. As shown in FIG. 11, expression in this subset of AML was significantly different (P<0.001) for 6 of the markers (CD9, CD44, CD86, CD97, CD99, and CX3CR1). For another 8 markers (CD32, CD54, CD59, CD64, CD68, CD123, CD200, CD300a/c) comparisons yielded a higher P value (<0.05 but >0.01). For the remaining 8 markers, the differences were not significant (P>0.05), although some AML cases had clear over- or under-expression.

Figure 6A:
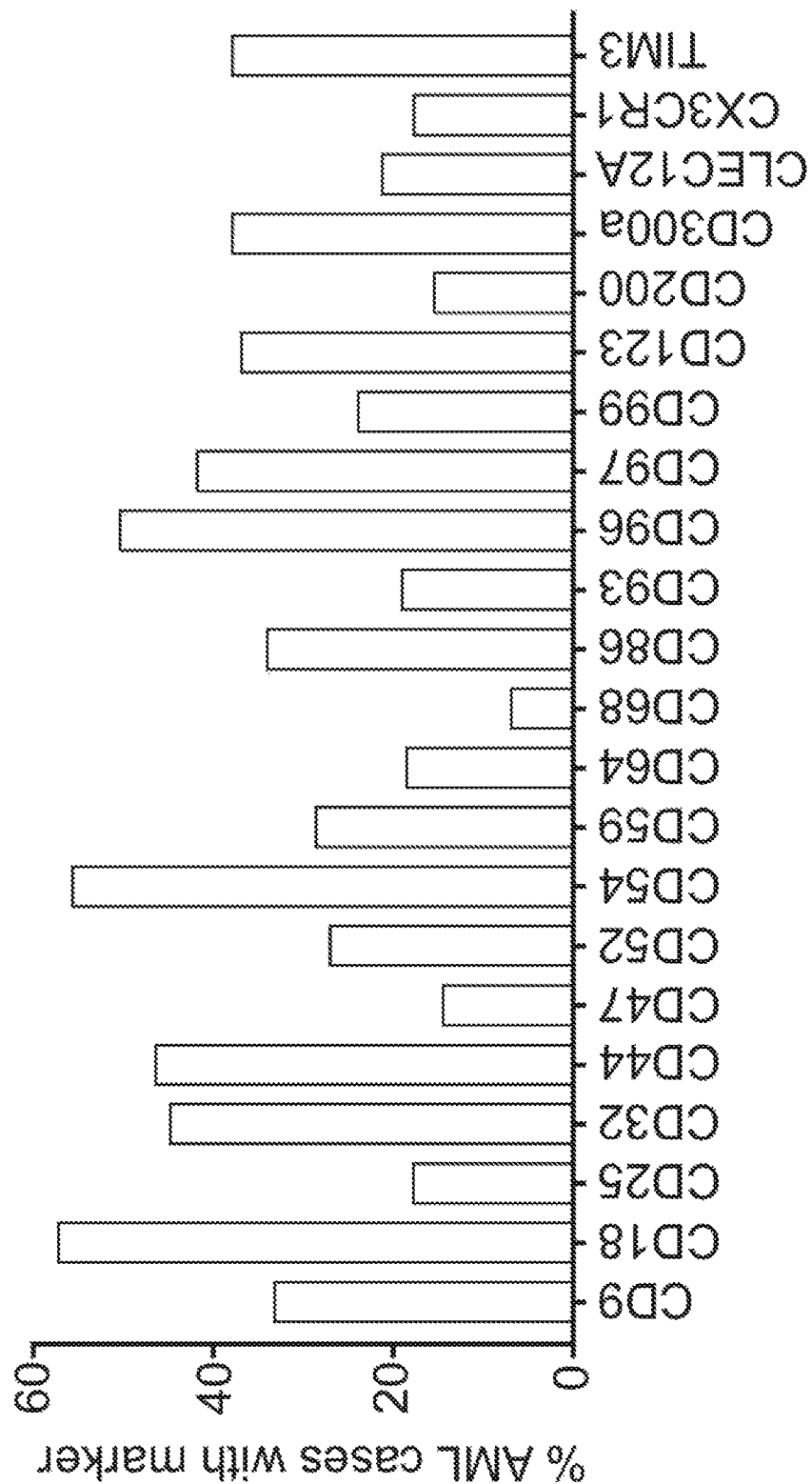
FIGS. 6A-C show marker expression in 129 consecutive cases of AML and sensitivity of MRD detection.
Figure 6B:
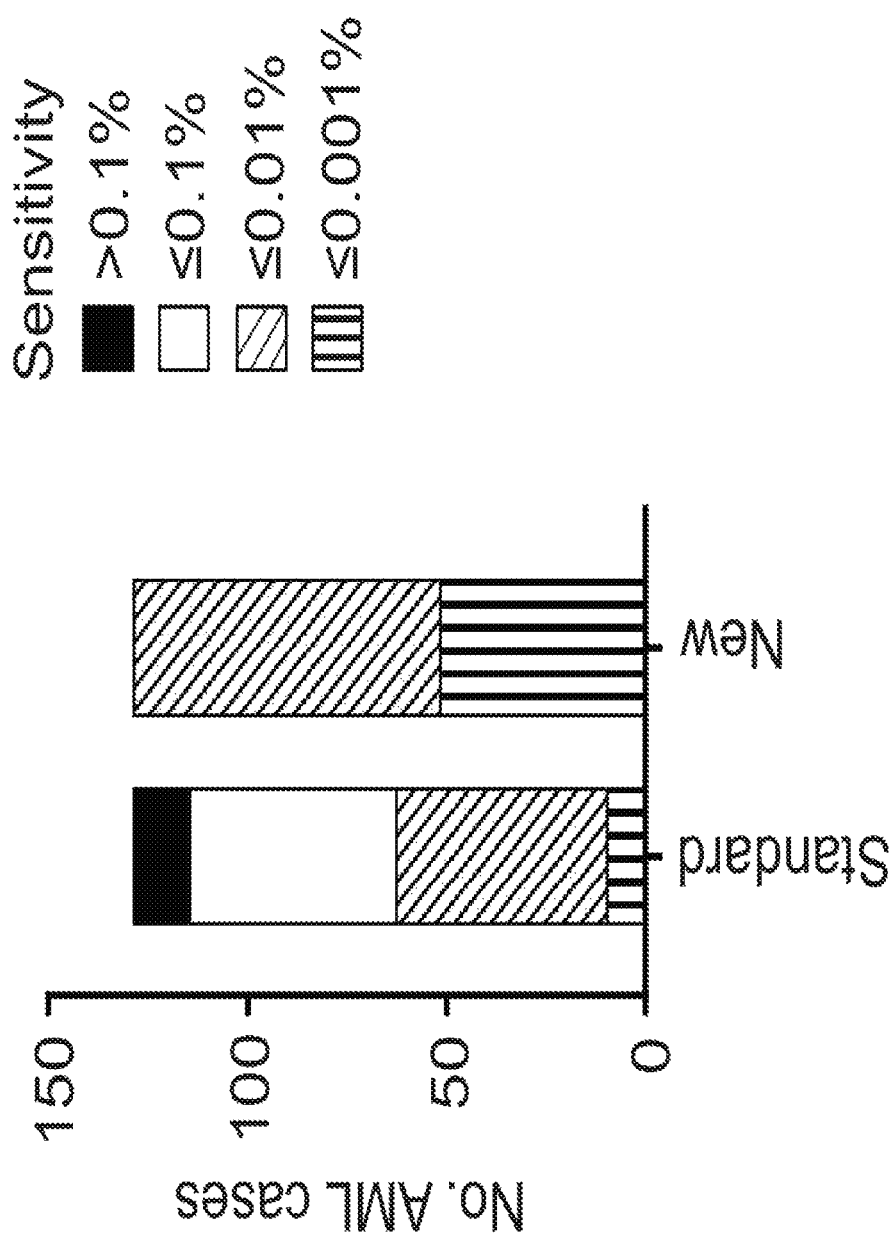
Figure 6C:
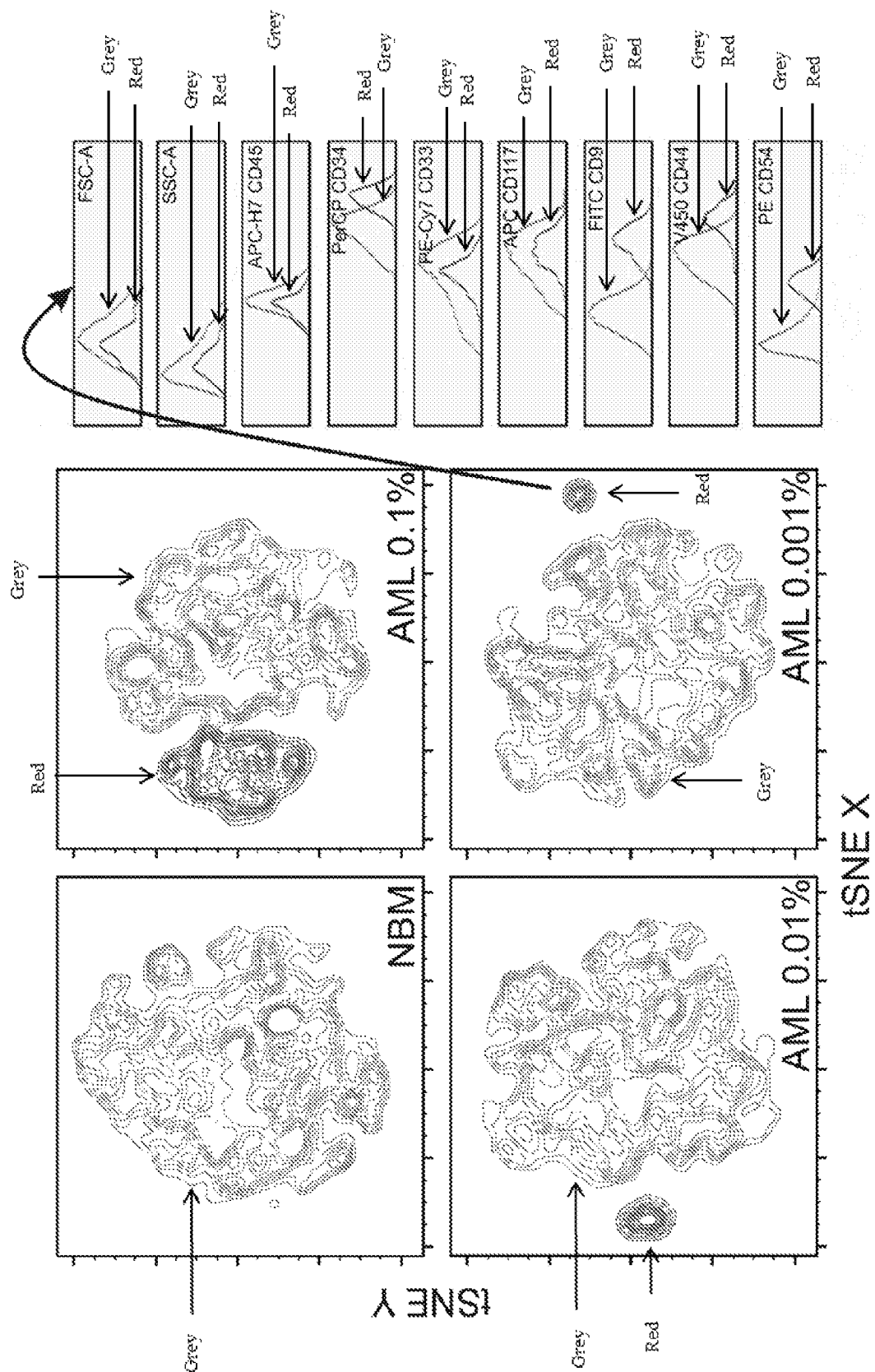
Figure 12:
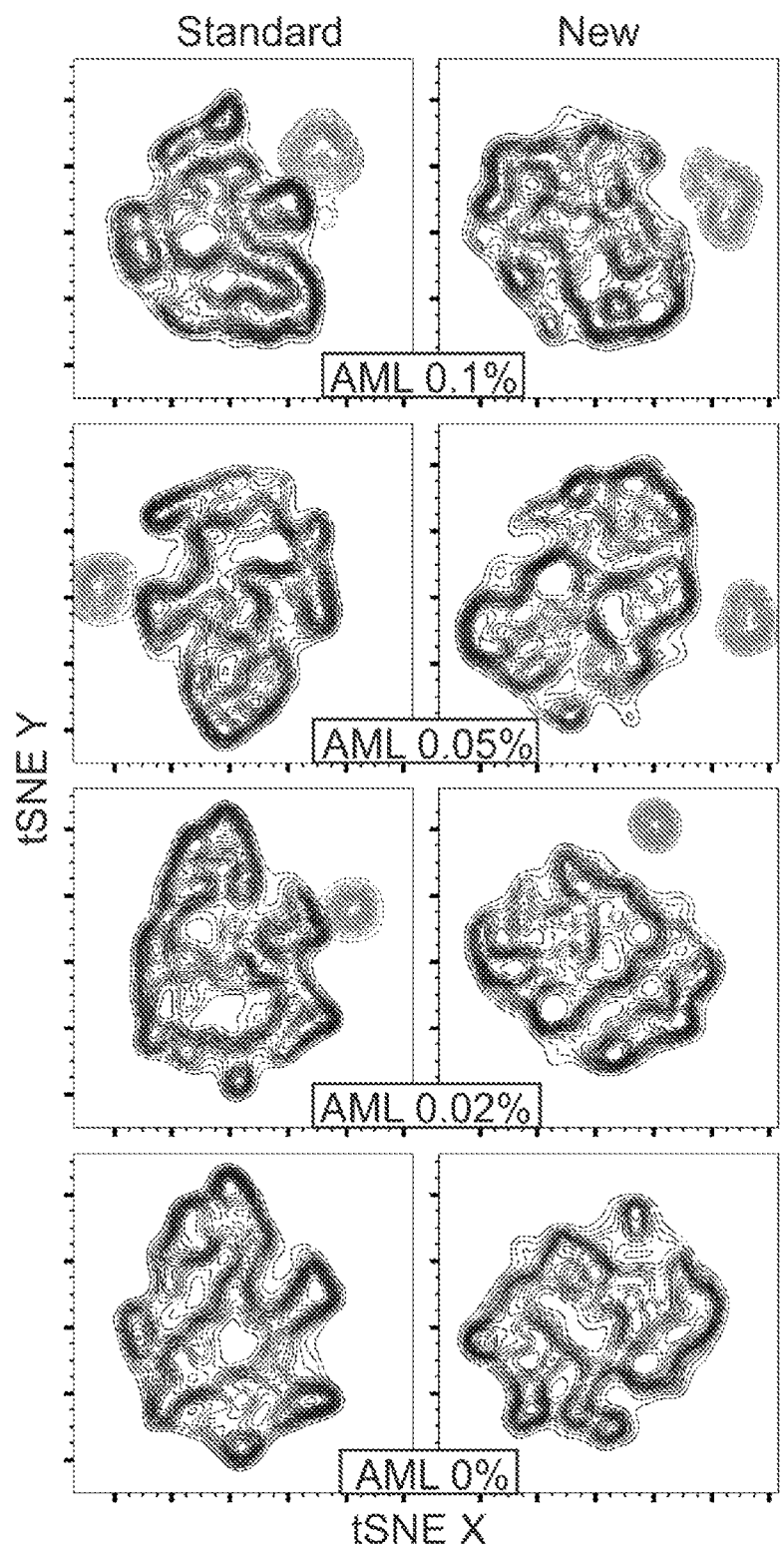
FIG. 12 shows improved discrimination of AML and normal cells with the new markers. t-SNE analysis of the cell profile of normal bone marrow CD34, CD117, CD45 and CD33 mononucleated cells from 4 donors (shown in blue) mixed with various proportions of AML cells (shown in red). Percentage of AML cells in each mixture is shown.

To visualize how the new leukemia-associated markers could improve the resolution of leukemic and normal cells, artificial mixtures containing various proportions of AML cells and normal bone marrow mononucleated cells (from 2 healthy donors and 2 MRD-negative children with ALL regenerating after chemotherapy) were prepared. The individual samples had been labelled with either the most distinctive set of standard markers (CD13, CD133 and CD38) or the most distinctive new markers (CD9, CD44, CD54) identified in the AML cells; both standard and new markers had been combined with CD34, CD117, CD45 and CD33, which identified immature myeloid cells. All flow cytometric files were merged, and analyzed by using t-Distributed Stochastic Neighbor Embedding (t-SNE) machine learning algorithm (48). As shown in FIG. 12, the new markers provided a clear separation between AML and normal cells, whereas these overlapped with the best standard markers. FIG. 6C illustrates an experiment in which data from 10 non-leukemic bone marrow samples were superimposed and either analyzed alone or with the addition of data from a diagnostic AML specimen at different concentrations. After conventional gating of CD34, CD33 and CD117 viable single cells, we applied t-SNE. Event at 1 in 100,000 frequency AML cells were clearly distinguishable as separate cluster; a subsequent analysis of the cluster demonstrated the predicted AML marker profile.

Figure 13:
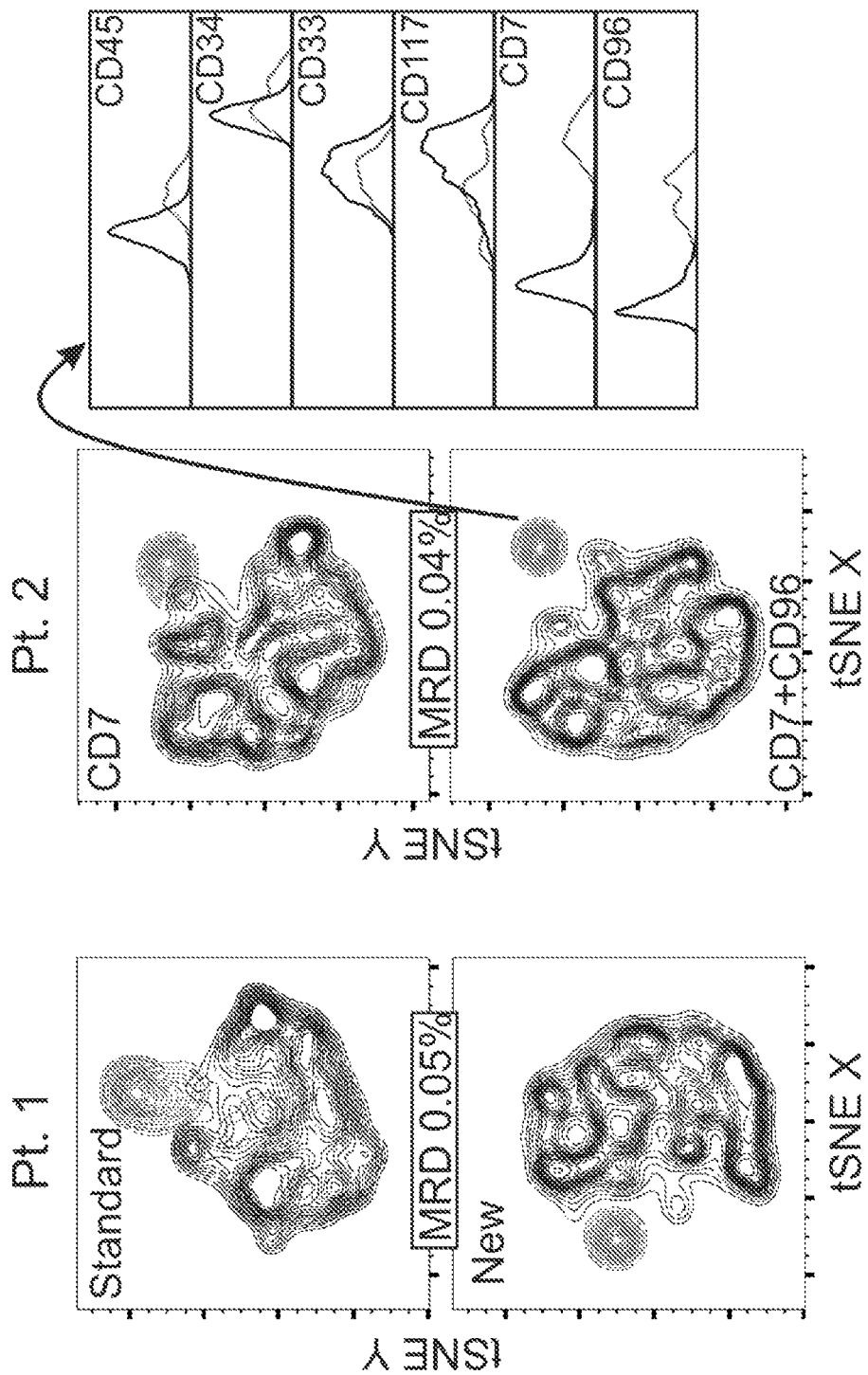
FIG. 13 shows MRD visualization in bone marrow mononucleated cells from 2 patients with AML after chemotherapy. In Pt. 1, cells were collected after the first cycle of remission induction chemotherapy. They were labelled with either the best available standard markers (CD38, CD133, CD7, and anti-HLA-Dr) or the new markers CD52 and CD47; both sample aliquots were also labelled with CD34, CD117, CD45 and CD33. tSNE was performed on gated myeloid CD34+ cells. Percent estimated MRD (red contour plots) according to the new markers is shown. In Pt. 2, cell were collected after the second cycle of remission induction chemotherapy. Cells were labelled with CD34, CD117, CD45 and CD33, in combination with CD7 (the best standard marker in this case) and the new marker CD96. Percent estimated MRD (gray contour plots) according to CD7 plus CD96 is shown; histograms illustrate the individual marker expression in normal (black) versus AML cells (gray).
Figure 14:
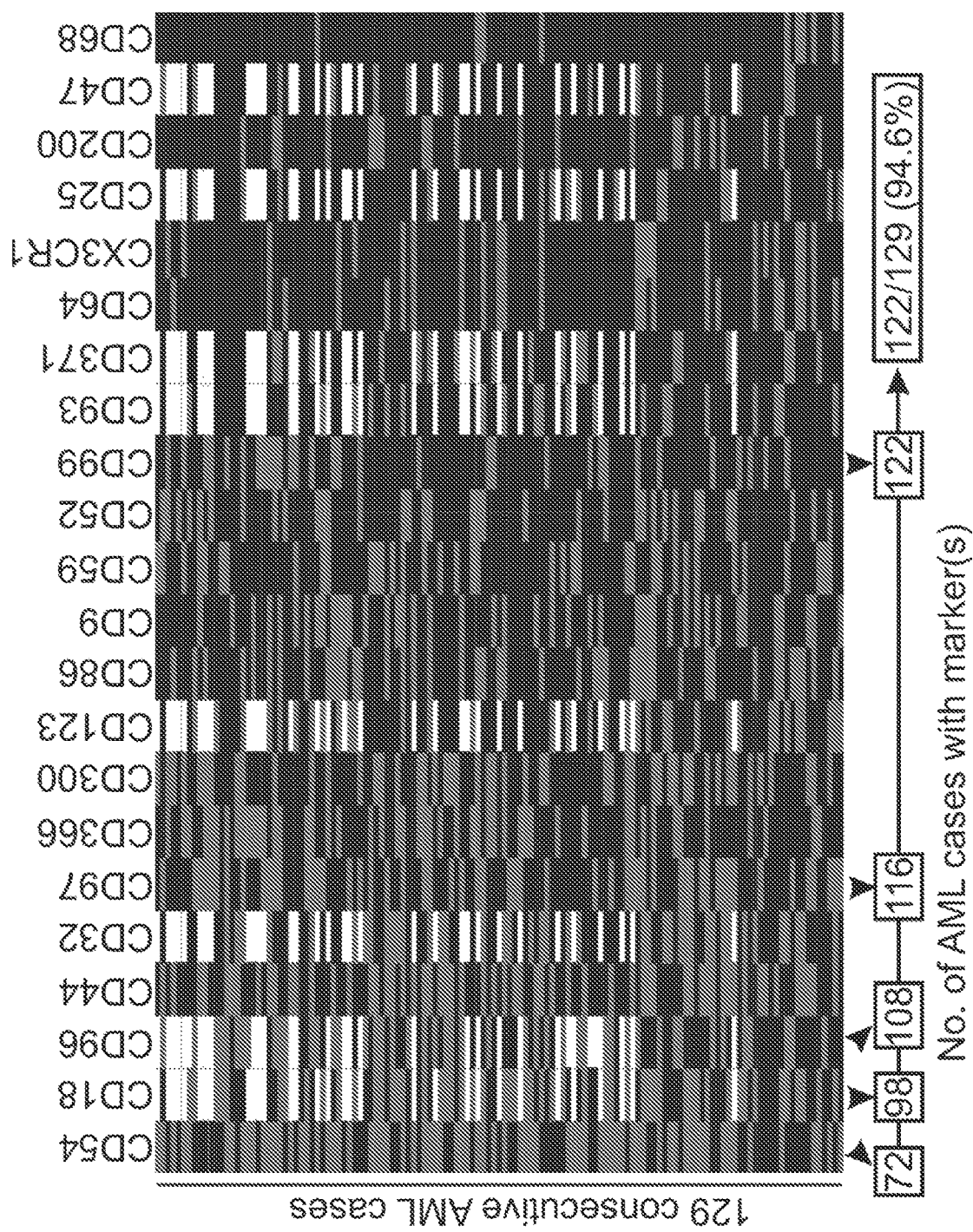
FIG. 14 shows marker expression in 129 consecutive cases of AML. Scale map showing the expression of the new markers in the 129 consecutive AML cases. Red cells indicate marker expression, and blue cells lack of expression; blank cells, not tested. A combination of 5 markers (CD54, CD18, CD96, CD97 and CD99) would be sufficient to study 122 of the 129 cases (94.6%).

Next, tSNE was used to visualize data from bone marrow samples collected during therapy from two patients with AML in morphologic remission. In one of the samples, one aliquot was labelled with the 4 best available standard markers (CD38, CD133, CD7, and anti-HLA-Dr) and the other with 2 new markers (CD52 and CD47), in addition to CD34, CD117, CD45 and CD33. As shown in FIG. 13, there was considerable overlap between the cells identified as AML and normal immature myeloid cells despite the use of 4 standard MRD markers. By contrast, the cell populations were clearly distinct with the new markers and MRD 0.05% could be unequivocally identified. The second sample illustrates the advantage of adding a new marker (CD96) to standard marker (CD7); addition of CD96 improved the discrimination of MRD, estimated at 0.04%.

The availability of additional markers should allow MRD studies in patients lacking suitable leukemia-associated immunophenotypes by traditional methods. By improving the resolution of leukemic and normal cells, the sensitivity of the test should also increase. To test these predictions, we applied 8-10-antibody panels including the new markers to 129 consecutive samples obtained from 118 patients with AML at diagnosis and 11 at relapse. FIG. 6A shows the percentage of cases studies with each marker. The immunophenotype of the individual cases is summarized in FIG.

14. The new markers allowed the definition of an aberrant profile for MRD monitoring in all 129 cases. By contrast, panels composed only by traditional markers (Table 7) could not identify an aberrant immunophenotype in 14 of the 129 cases (10.8%). Comparisons between the immunophenotype of AML cells to that of normal hematopoietic cells indicated that the new markers would allow a sensitivity of MRD detection of 0.01% or better in all 129 cases (0.001% in 52 cases, 40.3%). Sensitivity with the standard markers, however, was limited to 0.1% in 52 (40.3%); in 53 (41.1%) extended to 0.01%, and only in 10 (7.8%) 0.001% could be achieved (FIG. 6B). Hence, the new markers expand the possibility of MRD studies by flow cytometry and increase their sensitivity.

Figure 15:
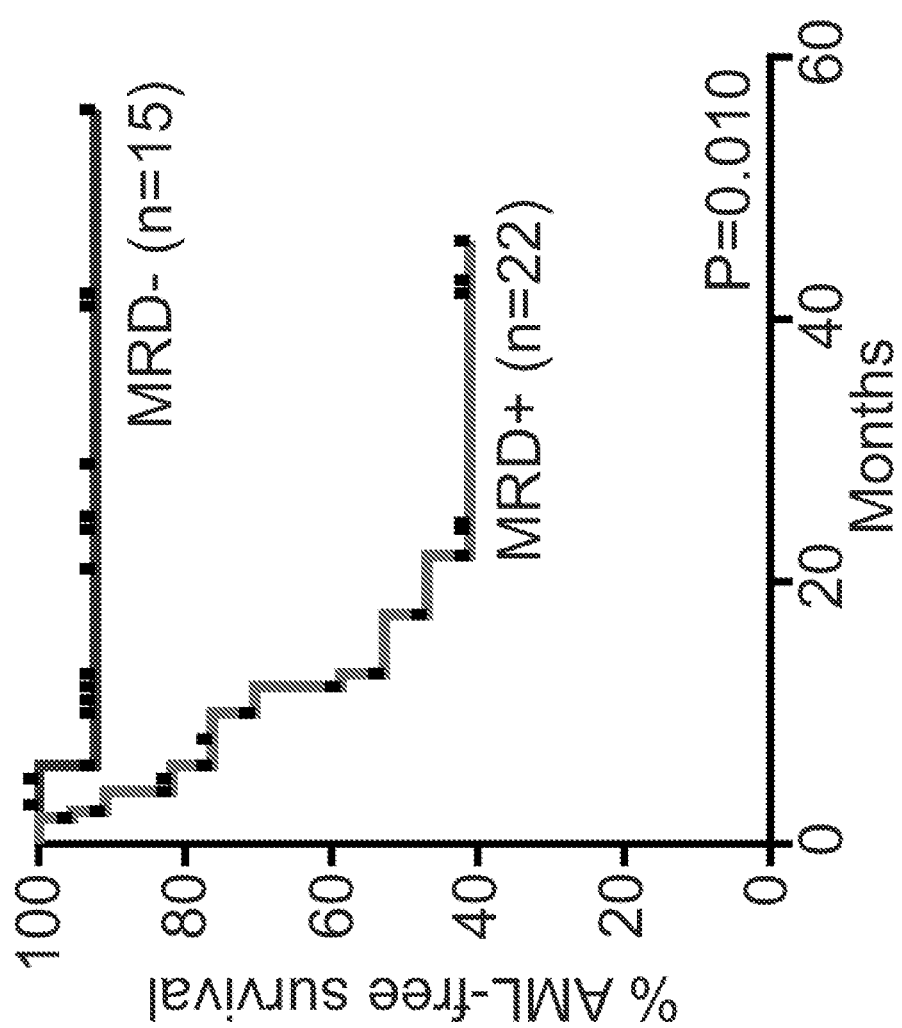
FIG. 15 shows leukemia-free survival of children with AML according to MRD at the end of the first course of remission induction chemotherapy. Patients received either chemotherapy alone according to the Ma-Spore AML 2006 study (n=26), or chemotherapy plus allogeneic hematopoietic stem cell transplant (2 in the MRD− group, 9 in the MRD+ group); P value by log-rank test.

In 37 children and adolescents with AML treated according to the Malaysia-Singapore AML 2006 protocol after the first course of remission induction therapy, the new markers were used to detect MRD (>0.01%) in 22 patients, while 15 were MRD negative. As shown in FIG. 15, absence of detectable MRD was associated with a significantly more favorable outcome (P=0.010).

Additional Marker Combinations

Table 8 identifies three panels that are combinations of markers.

depends entirely on the identification of cell marker profiles that are unequivocally distinct from those expressed by normal hematopoietic cells. In this study, we used genome-wide gene expression analysis to uncover differences between AML cells and CD34+ myeloid hematopoietic cells, which are the most challenging cells to distinguish from AML blasts by flow cytometry because of their close immunophenotypic resemblance (49). The results of this analysis, enriched by genes previously reported to be differentially expressed in leukemic and normal hematopoietic stem cells, led us to the identification of 22 promising markers which reliably detected MRD in follow-up samples of patients with AML. By expanding the range of markers, the identification of AML cells in the background of normal hematopoiesis was greatly improved. With antibodies panels targeting the new markers, unique leukemia profiles could be defined in all 129 consecutive diagnostic AML samples studied, and the potential sensitivity of MRD detection increased to 1 leukemic cell in 10,000 normal bone marrow cells or greater for all cases. Thus, it is now possible to implement highly sensitive and reliable assays to monitor MRD in all patients with AML.

Leukemia-associated markers currently used for MRD studies in AML had been identified empirically, primarily by

TABLE 8

| Antibody panel | Established markers to identify immature myeloid cells | | | | New markers to distinguish normal from AML | | | |
|---|---|---|---|---|---|---|---|---|
| 1 | CD34 | CD117 | CD33 | CD45 | CD52 | CD59 or CD96 or CD300a | TIM3 CD200 | CD123 |
| 2 | CD34 | CD117 | CD33 | CD45 | CD9 | CD93 or CD99 or CLEC12A | CD44 CD32 | CD25 |
| 3 | CD34 | CD117 | CD33 | CD45 | CD97 | CD54 or CD68 or CX3CR1 | CD64 CD86 | CD47 |

CD34 (8G12), PerCP Cy5.5, BD Biosciences
CD117 (A3C6E2), APC, Miltenyi Biotec
CD33 (P67.6), PE-Cy7, BD Biosciences
CD45 (2D1), APC-H7, Miltenyi Biotec
CD52 (CF1D12), FITC, Life Technologies
CD59 (P282; H19), PE, BD Biosciences
CD96 (6F9), PE, BD Biosciences
CD300a (E59.126), PE, Beckman Coulter
TIM3/CD366 (F38-2E2), BV421, Biolegend
CD200(MRC OX-104), BV510, BD Biosciences
CD123 (9F5), BV786, BD Biosciences
CD9 (M-L13), FITC, BD Biosciences
CD93 (VIMD2), PE, Biolegend
CD99 (Tü12), PE, BD Biosciences
CLEC12A/CD371 (50C1), PE, Biolegend
CD44 (G44-26), BV450, BD Biosciences
CD32 (FL18.26), BV510, BD Biosciences
CD25 (2A3), BV786, BD Biosciences
CD97 (VIM3b), FITC, BD Biosciences
CD54 (LB-2), PE, BD Biosciences
CD68 (Y1/82A), PE, BD Biosciences
CX3CR1/CD181 (2A9-1), PE, Medical & Biological Laboratories
CD64 (10.1), V450, BD Biosciences
CD86 (FUN-1), BV510, BD Biosciences
CD47 (B6H12), BV786, BD Biosciences
CD18, MEM-48, PE, GeneTex

DISCUSSION

Sequential measurement of treatment response and, hence, MRD monitoring are essential for a "precision medicine" approach to the clinical management of AML. The only option to monitor MRD in the majority of patients with AML is flow cytometric detection of markers aberrantly expressed in leukemic cells. The soundness of this approach observing flow cytometric data obtained during the process of leukemia diagnosis (49). Instead, our starting point was an unbiased and wide-ranging comparison of gene expression in normal and leukemic cells, an approach that had previously led us to discover new markers for MRD studies in ALL (30). It might be argued that differential expression at mRNA level cannot predict protein expression levels, but the flow cytometric data in our study generally reflected the differences emerging from the gene array comparisons. Mirkowska et al. (50) used mass spectrometry to study protein expression on the surface of ALL cells and amplified leukemic samples through xenograft models to obtain sufficient cell quantities. It is possible that this approach could also be used to discover new markers for AML. To this end, the database that we generated for gene expression of CD34+ normal myeloid cells could also be a useful reference for studies attempting to define the surfaceome of AML by mass spectrometry. Although our gene expression analysis relied on a database of pediatric AML, the immunophenotypic aberrations that we observed extended to adult AML cases. We noted, however, that some markers were particularly prevalent in cases with specific genetic features. For example, cases with RUNX1-RUNXT1, an abnormality more common in pediatric than adult AML (51, 52), often had abnormal expression of CD52, CD59, CD96, CD200, CD300a, CLEC12A and TIM3, whereas CD25 was more frequently over-expressed in cases with FLT3 ITD, more common in adults (53).

Gene expression differences between normal and leukemic stem cells had been previously noted (41, 42). Our gene-expression results and the immunophenotypic studies of cell subsets within the AML populations study suggest that these differences extend to most leukemic cells, regardless of their stem cell status. Saito et al. (41) used the immunophenotype CD34+CD38− to sort "leukemia stem cells" from 21 AML samples; corresponding cells from 5 cord blood or bone marrow samples served as a normal control. Using a similar approach, Kikushige et al. (42) analyzed gene expression of "leukemia stem cells" from 12 AML samples and 5 normal bone marrow samples. Collectively, the two studies identified 40 genes over-expressed in "leukemia stem cells", 35 of which were probed by our HG-U133 array. Surprisingly, all 35 were also found to be overexpressed in our analysis. We tested 5 of these by flow cytometry found that 3 (CD32, CD96 and CD97) were also significantly overexpressed at the protein level, while CD18 and CD25 were less consistently overexpressed. Another marker recently reported to be associated with leukemia stem cells, CD99 (54), was also over-expressed in AML cells according to both our gene expression analysis and subsequent flow cytometric validation. It is noteworthy that CD99 has been proposed to be a targetable marker for immunotherapy (54), and CD123, another marker overexpressed in our group, is being targeted by antibodies and chimeric antigen receptor-T cells for the treatment of AML (46, 55). While the focus of our study was the identification of new markers of AML to track MRD, our database warrant further exploration for targetable markers preferentially expressed in AML cells.

In patients with AML, a better assessment of treatment response should help predicting relapse and optimize therapy. Therefore, measuring MRD levels at key points during chemotherapy can help steering decisions about intensity of subsequent chemotherapy, eligibility for allogeneic hematopoietic stem cell transplantation, or experimental therapy (1, 56). The markers identified in this study were generally stable during chemotherapy and remained expressed at relapse. MRD levels measured using these markers correlated well with those detectable by standard methods, but the new approach significantly improved sensitivity and allowed MRD measurement in all patients. A limitation of MRD monitoring by flow cytometry has been the requirement for an expert operator to interpret the complex patterns. As demonstrated in this study, the combination of the new markers with contemporary analytical tools, should significantly clarify the distinction between normal and leukemic cells, mitigate the risk of incorrect interpretation, and facilitate the implementation of response-directed therapy in AML.

REFERENCES

1. Coustan-Smith E, and Campana D. Should evaluation for minimal residual disease be routine in acute myeloid leukemia? Curr Opin Hematol. 2013; 20(2):86-92.
2. Kayser S, et al. Minimal residual disease in acute myeloid leukemia—current status and future perspectives. Current Hematol Malign Reports. 2015; 10(2):132-44.
3. Araki D, et al. Allogeneic Hematopoietic cell transplantation for acute myeloid leukemia: time to move toward a minimal residual disease-based definition of complete remission? J Clin Oncol. 2016; 34(4):329-36.
4. Grimwade D, et al. Assessment of minimal residual disease in acute myeloid leukemia. Curr Opin Oncol. 2010; 22(6):656-63.
5. Kronke J, et al. Monitoring of minimal residual disease in NPM1-mutated acute myeloid leukemia: a study from the German-Austrian acute myeloid leukemia study group. J Clin Oncol. 2011; 29(19):2709-16.
6. Inaba H, et al. Comparative analysis of different approaches to measure treatment response in acute myeloid leukemia. J Clin Oncol. 2012; 30(29):3625-32.
7. Buccisano F, et al. Prognostic and therapeutic implications of minimal residual disease detection in acute myeloid leukemia. Blood. 2012; 119(2):332-41.
8. Terwijn M, et al. High prognostic impact of flow cytometric minimal residual disease detection in acute myeloid leukemia: data from the HOVON/SAKK AML 42A study. J Clin Oncol. 2013; 31(31):3889-97.
9. Walter R B, et al. Significance of minimal residual disease before myeloablative allogeneic hematopoietic cell transplantation for AML in first and second complete remission. Blood. 2013; 122(10):1813-21.
10. Ivey A, et al. Assessment of Minimal Residual Disease in Standard-Risk AML. N Engl J Med. 2016; 374(5):422-33.
11. Taub J W, et al. Improved outcomes for myeloid leukemia of Down syndrome: a report from the Children's Oncology Group AAML0431 trial. Blood. 2017; 129(25): 3304-13.
12. Hourigan C S, et al. Measurable residual disease testing in acute myeloid leukaemia. Leukemia. 2017; 31(7): 1482-90.
13. Harrison C J, et al. Cytogenetics of childhood acute myeloid leukemia: United Kingdom Medical Research Council Treatment trials AML 10 and 12. J Clin Oncol. 2010; 28(16):2674-81.
14. Falini B, et al. Acute myeloid leukemia with mutated nucleophosmin (NPM1): is it a distinct entity? Blood. 2010; 117(4):1109-20.
15. Hollink I H, et al. Favorable prognostic impact of NPM1 gene mutations in childhood acute myeloid leukemia, with emphasis on cytogenetically normal AML. Leukemia. 2009; 23(2):262-70.
16. Lane S, et al. A>or=1 log rise in RQ-PCR transcript levels defines molecular relapse in core binding factor acute myeloid leukemia and predicts subsequent morphologic relapse. Leuk Lymphoma. 2008; 49(3):517-23.
17. Yin J A, et al. Minimal residual disease monitoring by quantitative RT-PCR in core binding factor AML allows 18. Schnittger S, et al. Minimal residual disease levels assessed by NPM1 mutation-specific RQ-PCR provide important prognostic information in AML. Blood. 2009; 114(11):2220-31.
19. Corbacioglu A, et al. Prognostic impact of minimal residual disease in CBFB-MYH11-positive acute myeloid leukemia. J Clin Oncol. 2010; 28(23):3724-9.
20. San Miguel J F, et al. Early immunophenotypical evaluation of minimal residual disease in acute myeloid leukemia identifies different patient risk groups and may contribute to postinduction treatment stratification. Blood. 2001; 98(6):1746-51.
21. Coustan-Smith E, et al. Clinical significance of residual disease during treatment in childhood acute myeloid leukemia. Br J Haematol. 2003; 123:243-52.
22. Langebrake C, et al. Residual disease monitoring in childhood acute myeloid leukemia by multiparameter flow cytometry: the MRD-AML-BFM Study Group. J Clin Oncol. 2006; 24(22):3686-92.
23. Maurillo L, et al. Toward optimization of postremission therapy for residual disease-positive patients with acute myeloid leukemia. J Clin Oncol. 2008; 26(30):4944-51.
24. Rubnitz J E, et al. Minimal residual disease-directed therapy for childhood acute myeloid leukemia: results of the AML02 multicenter trial Lancet Oncol. 2010; 11(6): 543-52.
25. van der Velden V H, et al. Clinical significance of flowcytometric minimal residual disease detection in pediatric acute myeloid leukemia patients treated according to the DCOG ANLL97/MRC AML12 protocol. Leukemia. 2010; 24(9):1599-606.
26. Walter R B, et al. Impact of pretransplantation minimal residual disease, as detected by multiparametric flow cytometry, on outcome of myeloablative hematopoietic cell transplantation for acute myeloid leukemia. J Clin Oncol. 2011; 29(9):1190-7.
27. Inaba H, et al. Comparative analysis of different approaches to measure treatment response in acute myeloid leukemia. J Clin Oncol. 2012; 30(29):3625-32
28. Loken M R, et al. Residual disease detected by multidimensional flow cytometry signifies high relapse risk in patients with de novo acute myeloid leukemia: a report from Children's Oncology Group. Blood. 2012; 120(8): 1581-8.
29. Bjorklund E, et al. CD34+ cell subpopulations detected by 8-color flow cytometry in bone marrow and in peripheral blood stem cell collections: application for MRD detection in leukemia patients. Int J Hematol. 2009; 90(3):292-302.
30. Coustan-Smith E, et al. New markers for minimal residual disease detection in acute lymphoblastic leukemia. Blood. 2011; 117(23):6267-76.
31. Zeijlemaker W, et al. A simple one-tube assay for immunophenotypical quantification of leukemic stem cells in acute myeloid leukemia. Leukemia. 2016; 30(2): 439-46.
32. Ross M E, et al. Classification of pediatric acute lymphoblastic leukemia by gene expression profiling. Blood. 2003; 102:2951-9.
33. Inoue K, et al. Long-term follow-up of minimal residual disease in leukemia patients by monitoring WT1 (Wilms tumor gene) expression levels. Blood. 1996; 88(6):2267-78.
34. Cilloni D, et al. Real-time quantitative polymerase chain reaction detection of minimal residual disease by standardized WT1 assay to enhance risk stratification in acute myeloid leukemia: a European LeukemiaNet study. J Clin Oncol. 2009; 27(31):5195-201.
35. Coustan-Smith E, et al. N-CAM (CD56) expression by CD34+ malignant myeloblasts has implications for minimal residual disease detection in acute myeloid leukemia. Leukemia. 1993; 7(6):853-8.
36. Campana D, et al. The cytoplasmic expression of CD3 antigens in normal and malignant cells of the T lymphoid lineage. J Immunol. 1987; 138(2):648-55.
37. Terstappen L W, et al. Flow cytometric characterization of acute myeloid leukemia. Part II. Phenotypic heterogeneity at diagnosis. Leukemia. 1992; 6(1):70-80.
38. Macedo A, et al. Characterization of aberrant phenotypes in acute myeloblastic leukemia. Ann Hematol. 1995; 70(4):189-94.
39. Smith F O, et al. Expression of lymphoid-associated cell surface antigens by childhood acute myeloid leukemia cells lacks prognostic significance. Blood. 1992; 79(9): 2415-22.
40. Terstappen L W, et al. Flow cytometric characterization of acute myeloid leukemia: IV. Comparison to the differentiation pathway of normal hematopoietic progenitor cells. Leukemia. 1992; 6(10):993-1000.
41. Saito Y, et al. Identification of therapeutic targets for quiescent, chemotherapy-resistant human leukemia stem cells. Sci Transl Med. 2010; 2(17):17ra9.
42. Kikushige Y, et al. TIM-3 is a promising target to selectively kill acute myeloid leukemia stem cells. Cell Stem Cell. 2010; 7(6):708-17.
43. Campana D, et al. The immunologic detection of minimal residual disease in acute leukemia. Blood. 1990; 76(1):163-71.
44. Venditti A, et al. Level of minimal residual disease after consolidation therapy predicts outcome in acute myeloid leukemia. Blood. 2000; 96(12):3948-52.
45. Majeti R, et al. CD47 is an adverse prognostic factor and therapeutic antibody target on human acute myeloid leukemia stem cells. Cell. 2009; 138(2):286-99.
46. Jin L, et al. Monoclonal antibody-mediated targeting of CD123, IL-3 receptor alpha chain, eliminates human acute myeloid leukemic stem cells. Cell Stem Cell. 2009; 5(1):31-42.
47. van Rhenen A, et al. The novel AML stem cell associated antigen CLL-1 aids in discrimination between normal and leukemic stem cells. Blood. 2007; 110(7):2659-66.
48. van der Maaten L, and Hinton G. Visualizing data using t-SNE. Journal of Machine Learning Research. 2008; 9:2579-605.
49. Campana D, and Coustan-Smith E. Detection of minimal residual disease in acute leukemia by flow cytometry. Cytometry. 1999; 38:139-52.
50. Mirkowska P, et al. Leukemia surfaceome analysis reveals new disease-associated features. Blood. 2013; 121(25):e149-59.
51. Rubnitz J E, and Inaba H. Childhood acute myeloid leukaemia. Br J Haematol. 2012.
52. Dohner H, et al. Diagnosis and management of AML in adults: 2017 ELN recommendations from an international expert panel. Blood. 2017; 129(4):424-47.
53. Levis M. FLT3 mutations in acute myeloid leukemia: what is the best approach in 2013? Hematology 2013; 2013:220-6.

54. Chung S S, et al. CD99 is a therapeutic target on disease stem cells in myeloid malignancies. Science Transl Med. 2017; 9(374).
55. Mardiros A, et al. T cells expressing CD123 chimeric antigen receptors for treatment of acute myeloid leukemia. Curr Opin Hematol. 2015; 22(6):484-8.
56. Kayser S, et al. Minimal residual disease-directed therapy in acute myeloid leukemia. Blood. 2015; 125(15): 2331-5.

INCORPORATION BY REFERENCE AND EQUIVALENTS

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of treating minimal residual disease in acute myeloid leukemia in a subject who has been diagnosed previously with acute myeloid leukemia, the method comprising:
    a) contacting a bone marrow sample from the subject with a plurality of probes, wherein:
        i) each probe specifically binds to a single marker;
        ii) the markers are two or more of CD9, CD18, CD25, CD32, CD44, CD47, CD52, CD54, CD59, CD64, CD68, CD86, CD93, CD96, CD97, CD99, CD123, CD200, CD300a, CLEC12A, CX3CR1 and Tim-3; and
    b) detecting, by flow cytometry, a complex formed between each probe and corresponding marker in a), wherein a value is generated corresponding to an expression level of each of the markers;
    c) diagnosing whether the subject has minimal residual disease in acute myeloid leukemia based on the generated values corresponding to the expression level of the markers; and
    d) administering an effective amount of a chemotherapy for treating acute myeloid leukemia to the subject diagnosed previously with acute myeloid leukemia and identified as having minimal residual disease in acute myeloid leukemia, thereby treating minimal residual disease in acute myeloid leukemia.

2. The method of claim 1, wherein the markers are two or more of CD9, CD32, CD44, CD52, CD54, CD59, CD64, CD68, CD86, CD93, CD96, CD97, CD99, CD123, CX3CR1 and Tim-3.

3. The method of claim 1, wherein the markers are CD54, CD18, CD96, CD97 and CD99.

4. The method of claim 1, wherein the markers are CD44, CD54, CD18, CD96, CD97 and CD99.

5. The method of claim 1, wherein the plurality of probes is a first set of probes that specifically bind to:
    a) CD52;
    b) CD59, CD96, or CD300a;
    c) TIM3;
    d) CD200; and
    e) CD123; and
    further comprising a second set of probes that specifically bind to:
        a) CD34;
        b) CD117;
        c) CD33; and
        d) CD45.

6. The method of claim 1, wherein the plurality of probes is a first set of probes that specifically bind to:
    a) CD9;
    b) CD93, CD99, or CLEC12A;
    c) CD44;
    d) CD32; and
    e) CD25; and
    further comprising a second set of probes that specifically bind to:
        a) CD34;
        b) CD117;
        c) CD33; and
        d) CD45.

7. The method of claim 1, wherein the plurality of probes is a first set of probes that specifically bind to:
    a) CD97;
    b) CD54, CD68, or CX3CR1;
    c) CD64;
    d) CD86; and
    e) CD47; and
    further comprising a second set of probes that specifically bind to:
        a) CD34;
        b) CD117;
        c) CD33; and
        d) CD45.

8. The method of claim 1, wherein the plurality of probes is a first set of probes that specifically bind to:
    a) CD54;
    b) CD18;
    c) CD96;
    d) CD97; and
    e) CD99; and
    further comprising a second set of probes that specifically bind to:
        a) CD34;
        b) CD117;
        c) CD33; and
        d) CD45.

9. The method of claim 1, wherein the plurality of probes is a first set of probes that specifically bind to:
    a) CD44;
    b) CD54;
    c) CD18;
    d) CD96; and
    e) CD97 and CD99; and
    further comprising a second set of probes that specifically bind to:
        a) CD34;
        b) CD117;
        c) CD33; and
        d) CD45.

10. The method of claim 1, wherein one or more of the probes is an antibody that specifically binds to a single marker.

11. The method of claim 1, wherein the value generated is fluorescence intensity.

12. The method of claim 1, wherein the value generated is mean fluorescence intensity or median fluorescence intensity.

13. The method of claim 1, further comprising contacting the bone marrow sample with a phosphate buffered saline (PBS)-saponin-based permeabilization reagent to permeabilize a cell membrane prior to contacting the bone marrow sample from the subject with a plurality of probes.

14. The method of claim 1, wherein the bone marrow sample comprises one or more of blood cells, bone marrow, and cellular products derived from blood cells or bone marrow cells.

15. The method of claim 1, further comprising contacting the bone marrow sample with one or more probes that specifically detect one or more genes of Table 2 or Table 3.

16. A method of treating minimal residual disease in acute myeloid leukemia in a subject who has been diagnosed previously with acute myeloid leukemia, the method comprising:
   a) contacting a bone marrow sample from the subject with a plurality of probes, wherein:
      i) each probe specifically binds to a single marker;
      ii) the markers are two or more of CD9, CD18, CD25, CD32, CD44, CD47, CD52, CD54, CD59, CD64, CD68, CD86, CD93, CD96, CD97, CD99, CD123, CD200, CD300a, CLEC12A, CX3CR1 and Tim-3; and
   b) detecting, by flow cytometry, a complex formed between each probe and corresponding marker in a), wherein a value is generated corresponding to an expression level of each of the markers;
   c) diagnosing whether the subject has minimal residual disease in acute myeloid leukemia based on the generated values corresponding to the expression level of the markers; and
   d) administering an effective amount of a radiation therapy, a stem cell transplantation, or a biological therapy for treating acute myeloid leukemia to the subject diagnosed previously with acute myeloid leukemia and identified as having minimal residual disease in acute myeloid leukemia, thereby treating minimal residual disease in acute myeloid leukemia.

17. The method of claim 16, wherein the plurality of probes is a first set of probes that specifically bind to:
   a) CD52;
   b) CD59, CD96, or CD300a;
   c) TIM3;
   d) CD200; and
   e) CD123; and
   further comprising a second set of probes that specifically bind to:
   a) CD34;
   b) CD117;
   c) CD33; and
   d) CD45.

18. The method of claim 16, wherein the plurality of probes is a first set of probes that specifically bind to:
   a) CD9;
   b) CD93, CD99, or CLEC12A;
   c) CD44;
   d) CD32; and
   e) CD25; and
   further comprising a second set of probes that specifically bind to:
   a) CD34;
   b) CD117;
   c) CD33; and
   d) CD45.

19. The method of claim 16, wherein the plurality of probes is a first set of probes that specifically bind to:
   a) CD97;
   b) CD54, CD68, or CX3CR1;
   c) CD64;
   d) CD86; and
   e) CD47; and
   further comprising a second set of probes that specifically bind to:
   a) CD34;
   b) CD117;
   c) CD33; and
   d) CD45.

20. The method of claim 16, wherein the plurality of probes is a first set of probes that specifically bind to:
   a) CD54;
   b) CD18;
   c) CD96;
   d) CD97; and
   e) CD99; and
   further comprising a second set of probes that specifically bind to:
   a) CD34;
   b) CD117;
   c) CD33; and
   d) CD45.

* * * * *